United States Patent
Engelhardt et al.

(10) Patent No.: US 12,064,421 B2
(45) Date of Patent: Aug. 20, 2024

(54) SUBSTITUTED 1H-PYRAZOLO[4,3-c]PYRIDINES AND DERIVATIVES AS EGFR INHIBITORS

(71) Applicant: Boehringer Ingelheim International GmbH, Ingelheim am Rhein (DE)

(72) Inventors: Harald Engelhardt, Ebreichsdorf (AT); Mark Petronczki, Vienna (AT); Juergen Ramharter, Vienna (AT); Ulrich Reiser, Vienna (AT); Heinz Stadtmueller, Weigelsdorf (DE); Dirk Scharn, Berlin (DE); Tobias Wunberg, Hinterbruehl (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 335 days.

(21) Appl. No.: 17/514,145

(22) Filed: Oct. 29, 2021

(65) Prior Publication Data

US 2022/0133734 A1 May 5, 2022

(30) Foreign Application Priority Data

Nov. 2, 2020 (EP) .................... 20205297

(51) Int. Cl.

| | | |
|---|---|---|
| C07D 211/04 | (2006.01) | |
| A61K 31/437 | (2006.01) | |
| A61K 31/4545 | (2006.01) | |
| A61K 31/4995 | (2006.01) | |
| A61K 31/553 | (2006.01) | |
| A61P 35/00 | (2006.01) | |
| C07D 519/00 | (2006.01) | |
| A61K 31/496 | (2006.01) | |
| A61K 31/5377 | (2006.01) | |
| A61K 31/5386 | (2006.01) | |
| A61K 31/541 | (2006.01) | |

(52) U.S. Cl.
CPC ........ *A61K 31/437* (2013.01); *A61K 31/4545* (2013.01); *A61K 31/4995* (2013.01); *A61K 31/553* (2013.01); *A61P 35/00* (2018.01); *C07D 211/04* (2013.01); *C07D 519/00* (2013.01); *A61K 31/496* (2013.01); *A61K 31/5377* (2013.01); *A61K 31/5386* (2013.01); *A61K 31/541* (2013.01)

(58) Field of Classification Search
CPC ...... A61P 35/00; A61K 31/437; C07D 211/04
See application file for complete search history.

(56) References Cited

FOREIGN PATENT DOCUMENTS

| WO | 2016133935 A1 | 8/2016 |
|---|---|---|
| WO | 2017120429 A1 | 7/2017 |

OTHER PUBLICATIONS

International Search Report and Written Opinion for corresponding application, PCT/EP2021/080151, date of mailing Jan. 24, 2022.

*Primary Examiner* — Jeffrey S Lundgren
*Assistant Examiner* — Chris E Simmons
(74) *Attorney, Agent, or Firm* — Philip I. Datlow

(57) ABSTRACT

The present invention encompasses compounds of formula (I)

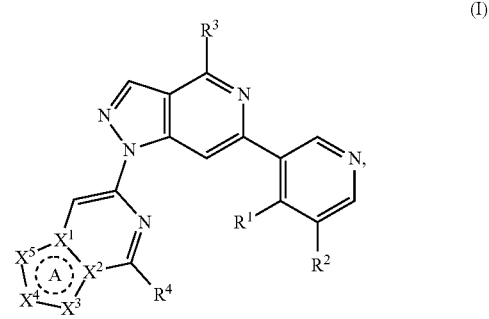

wherein the groups $R^1$ to $R^4$ and $X^1$ to $X^5$ have the meanings given in the claims and specification, their use as inhibitors of mutant EGFR, pharmaceutical compositions which contain compounds of this kind and their use as medicaments/medical uses, especially as agents for treatment and/or prevention of oncological diseases.

23 Claims, No Drawings

SUBSTITUTED 1H-PYRAZOLO[4,3-c]PYRIDINES AND DERIVATIVES AS EGFR INHIBITORS

FIELD OF THE INVENTION

The present invention relates to new substituted 1H-pyrazolo[4,3-c]pyridines and derivatives of formula (I)

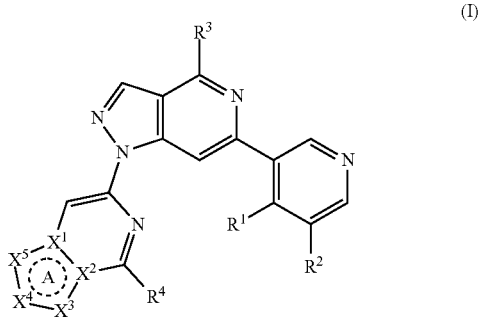

wherein the groups $R^1$ to $R^4$ and $X^1$ to $X^5$ have the meanings given in the claims and specification, their use as inhibitors of mutant EGFR, pharmaceutical compositions which contain compounds of this kind and their use as medicaments/medical uses, especially as agents for treatment and/or prevention of oncological diseases.

BACKGROUND OF THE INVENTION

The epidermal growth factor receptor (EGFR) is a receptor tyrosine kinase that transduces mitogenic signals. Mutations in the EGFR gene are found in approximately 12% to 47% of non-small cell lung cancer (NSCLC) tumors with adenocarcinoma histology (Midha, 2015). The two most frequent EGFR alterations found in NSCLC tumors are short in-frame deletions in exon 19 (del19) of the EGFR gene and L858R, a single missense mutation in exon 21 (Konduri, 2016). These two mutations cause ligand-independent EGFR activation and are collectively referred to as EGFR M+. Del19 and L858R mutations in EGFR sensitize NSCLC tumors to the treatment with EGFR tyrosine kinase inhibitors (TKIs). Clinical experience shows an objective response rate of approximately 60-85% in EGFR M+ NSCLC patients treated in $1^{st}$ line with the $1^{st}$, $2^{nd}$ and $3^{rd}$ generation EGFR TKIs erlotinib, gefitinib, afatinib and osimertinib (Mitsudomi, 2010; Park, 2016; Soria, 2017; Zhou, 2011). These responses demonstrate that EGFR M+ NSCLC cells and tumors depend on oncogenic EGFR activity for survival and proliferation, establishing del19 or L858R mutated EGFR as a validated drug target and predictive biomarker for the treatment of NSCLC. The $1^{st}$ generation EGFR TKIs erlotinib and gefitinib as well as the $2^{nd}$ generation TKI afatinib are FDA-approved for the $1^{st}$ line treatment of EGFR M+ NSCLC patients.

While tumor responses are accompanied by marked tumor shrinkage in patients, the response is usually not durable and most patients relapse within 10 to 12 months of treatment with $1^{st}$ and $2^{nd}$ generation EGFR TKIs (Mitsudomi, 2010; Park, 2016; Soria, 2017; Zhou, 2011). The most prominent molecular mechanism underlying progression is the acquisition of a secondary mutation in EGFR, namely T790M (Blakely, 2012; Kobayashi, 2005), in 50% to 70% of patients progressing on $1^{st}$ and $2^{nd}$ generation EGFR inhibitors. This mutation attenuates the inhibitory activity of $1^{st}$ and $2^{nd}$ generation TKIs in cellular assays (see e.g. data in Table A).

Mutant selective and covalent $3^{rd}$ generation EGFR TKIs, such as osimertinib, have been developed that effectively inhibit the primary EGFR mutations del19 and L858R with and without the secondary T790M resistance mutation (Cross, 2014; Wang, 2016). The efficacy observed with the $3^{rd}$ generation EGFR TKI osimertinib in the $2^{nd}$ line treatment of EGFR M+ T790M-positive NSCLC demonstrates clinically that tumor cell survival and proliferation is dependent on the mutated EGFR allele (Jänne, 2015; Mok, 2016). Approximately 70% of EGFR M+ T790M-positive patients that were previously treated with earlier generation EGFR TKI respond to osimertinib treatment in $2^{nd}$ line. However, disease progression occurs after an average duration of 10 months (Mok, 2016). The mechanisms underlying acquired resistance to $3^{rd}$ generation EGFR TKIs have been studied and are beginning to emerge (Ou, 2017). Recent data suggest that one major resistance mechanism is the acquisition of the tertiary EGFR mutation C797S in about 20-40% of $2^{nd}$ line patients relapsing on osimertinib TKI (Ortiz-Cuaran, 2016; Ou, 2017; Song, 2016; Thress, 2015; Yu, 2015). $3^{rd}$ generation TKIs, such as osimertinib, covalently attach to EGFR via the residue C797 (Cross, 2014; Wang, 2016). In cellular models the C797S mutation abolishes the activity of $3^{rd}$ generation TKIs tested (Thress, 2015) (see e.g. data in Table A). In $2^{nd}$ line patients, the mutation C797S is preferentially found in conjunction with the EGFR del19 genotype and on the same allele as the T790M mutation (cis configuration) (82% of C797S+ patients) (Piotrowska, 2017). Crucially, the EGFR del19/L858R T790M C797S cis mutant kinase variant that emerges in $2^{nd}$ line patients progressing on osimertinib (Ortiz-Cuaran, 2016; Ou, 2017; Song, 2016; Thress, 2015; Yu, 2015) can no longer be inhibited by $1^{st}$, $2^{nd}$ or $3^{rd}$ generation EGFR TKIs (Thress, 2015) (see e.g. data in Table A). Based on the fact that the C797S mutation is detected at progression on osimertinib (Ortiz-Cuaran, 2016; Ou, 2017; Song, 2016; Thress, 2015; Yu, 2015), it is likely that tumor cell survival and proliferation in EGFR del19/L858R T790M C797S patients is dependent on this mutant allele and can be inhibited by targeting this allele. Additional EGFR resistance mutations with a lower incidence than C797S were recently described in $2^{nd}$ line EGFR M+ NSCLC patients progressing on osimertinib: L718Q, L792F/H/Y and C797G/N (Bersanelli, 2016; Chen, 2017; Ou, 2017).

The $3^{rd}$ generation EGFR TKI osimertinib has recently also shown efficacy in previously untreated EGFR M+ NSCLC patients (Soria, 2017). Disease progression occurs after an average duration of 19 months. While the EGFR resistance mutation spectrum after $1^{st}$ line osimertinib treatment has not been extensively studied yet, first available data also suggest the emergence of the mutation C797S that abrogates osimertinib activity (Ramalingam, 2017). Based on the efficacy of osimertinib in untreated EGFR M+ NSCLC patients and T790M-positive $2^{nd}$ line patients, the drug has been approved in both settings.

The fact that no approved EGFR TKI can inhibit the EGFR del19/L858R T790M C797S variant, an allele occurring after progression of patients on $1^{st}$ or $2^{nd}$ line osimertinib treatment, highlights the medical need for a next generation EGFR TKI, a "$4^{th}$ generation EGFR TKI". This $4^{th}$ generation EGFR TKI should potently inhibit EGFR del19 or L858R irrespective of the presence of the two common resistance mutations T790M and C797S, especially EGFR del19 T790M C797S. The utility of such a $4^{th}$ generation EGFR TKI would be enhanced by activity of the compound on additional resistance mutations, such as the potential osimertinib resistance mutations C797X (X=S, G, N) and L792F/H/Y. The broad activity of the molecule on the EGFR del19 or L858R variants also without T790M and/or C797S mutations would ensure that the new compound can effectively cope with the expected allelic complexity in patient tumors as a monotherapy agent. A $4^{th}$ generation EGFR TKI molecule that has activity on EGFR del19 and EGFR L858R primary activating mutations irrespective of the presence of the resistance mutations T790M and C797S would allow the treatment and prevention of resistance disease. In particular, it would be useful to treat EGFR M+ NSCLC patients that have progressed on prior EGFR TKI therapy with $1^{st}$, $2^{nd}$ or $3^{rd}$ generation TKIs as well as EGFR TKI-naïve $1^{st}$ line patients. To facilitate efficacious dosing and reduce EGFR-mediated on-target toxicities, a $4^{th}$ generation EGFR TKI should not inhibit wild-type EGFR. High selectivity across the human kinome would reduce off-target toxicity of the compound. Another desirable property of a $4^{th}$ generation EGFR TKI is the ability to efficiently penetrate into the brain (blood-brain barrier penetration) in order to be able to prevent ans/or treat brain metastasis and leptomeningeal disease.

The aforementioned properties of a $4^{th}$ generation EGFR TKI would allow to treat patients progressing on $2^{nd}$ line treatment with a $3^{rd}$ generation TKI, such as osimertinib, (e.g. with the genotype EGFR del19/L858R T790M C797S), who have currently no targeted therapy treatment option. Furthermore, these properties also have the potential to allow a $4^{th}$ generation EGFR TKI to provide a longer duration of response in earlier treatment line patients, such as patients progressing on $1^{st}$ line osimertinib treatment with EGFR C797S mutations as well as in $1^{st}$ line patients. The activity of a $4^{th}$ generation EGFR TKI on resistance mutations such as T790M, C797X (X=S, G, N) and L792X (X=F, H, Y) has the potential to delay the development of resistance through EGFR intra target mutations in NSCLC tumors. The characteristics outlined above define a $4^{th}$ generation EGFR TKI as the first EGFR TKI able to effectively target patients with NSCLC tumors carrying the EGFR del19 or L858R genotype as well as the EGFR del19/L858R T790M C797X/L792X variants. Furthermore, a $4^{th}$ generation EGFR TKI will be the first C797S active compound that also inhibits T790M-positive alleles, possesses EGFR wild-type sparing activity and effectively penetrates into the brain.

Over the past years, selective targeting of mutated EGFR has gained increasing attention. Until today several efforts to identify and optimize inhibitors, which target either the catalytic site of EGFR mutants or an allosteric site of the EGFR protein, have been made, most with only limited success in respect of the above mentioned characteristics. Benzimidazole compounds which come close to the desired properties are disclosed in WO 2019/162323.

Additionally, a number of EGFR inhibitors which can overcome EGFR resistance mutations including the mutation T790M, as well as the C797S mutation and combinations of both have been published (Zhang, 2017; Park, 2017; Chen, 2017; Bryan 2016; Juchum, 2017; Gunther, 2017; WO 2017/004383). Most of the published molecules are non-covalent variants of quinazoline based $2^{nd}$ generation EGFR inhibitors. (Patel, 2017; Park, 2017; Chen, 2017). However, these published molecules are either weak inhibitors with low selectivity over EGFR wt (Patel, 2017; Chen, 2017) or were designed to specifically bind only to the del19/T790M/C797S mutant without activity to other EGFR variant combinations and mutations (Park, 2017). Other published compound classes show activity only against the T790M and T790M/C797S resistance mutation in the L858R activation background (Bryan 2016; Juchum, 2017; Gunther, 2017). However, since these mutations and mutation combinations were only observed in a small fraction of the patient population and since allelic complexity in metastatic tumors is likely high, they are very unlikely to fulfill the necessary criteria in order to be developed towards effective EGFR inhibitors.

The following prior art documents disclose non-covalent compounds as mutant selective EGFR inhibitors with activity toward T790M bearing EGFR: WO 2014/210354; WO 2014/081718; Heald, 2015; Hanan, 2014; Lelais, 2016; Chan, 2016.

Although the compounds from the above mentioned documents are claimed to be active against the two most common EGFR activation/resistance mutation combinations del19/T790M and L858/T790M, most of them display only weak activity against the more prevalent del19/T790M mutation, they also display no affinity towards EGFR harboring the primary activation mutations del19 and L858R alone. Such a selective inhibition of the double mutated EGFR over the activity against the single activation mutations is highly unfavorable due to the heterogeneity of EGFR mutations in patients and would likely lead to a limited efficacy. Additionally, most of the compounds show only a small selectivity towards EGFR wt which is known to be the major factor for common side effects in EGFR targeted therapies (diarrhea, skin-rash) leading to a target specific toxicity. This specific cytotoxic component is undesirable, because it potentially leads to adverse events in treated patients.

The following prior art documents disclose aminobenzimidazole based compounds as EGFR selective inhibitors with activity toward both oncogenic driver mutations L858R and del19 as well as activity against the T790M resistance mutation and combination of them: WO 2013/184757; WO 2013/184766, WO 2015/143148, WO 2015/143161, WO 2016/185333; Lelais, 2016; Jia, 2016.

In summary, compounds (I) according to the invention show a broad activity on EGFR del19 or EGFR L858R variants, with or without T790M and/or C797S mutations, which ensures that the compounds may effectively cope with the expected allelic complexity in patient tumors as a monotherapy agent. To facilitate efficacious dosing and reduce EGFR-mediated on-target toxicities, the compounds according to the invention have a reduced inhibitory potential regarding wild-type EGFR. Compounds (I) show a high selectivity across the human kinome, which may reduce off-target toxicity of the compounds. Another property of the compounds (I) according to the invention is the ability to potentially penetrate into the brain (blood-brain barrier penetration) in order to be used to prevent and/or treat brain metastasis and leptomeningeal disease. In addition to the inhibitory effect and potency, the compounds disclosed herein show good solubility and suitable DMPK properties for use in organismal settings.

REFERENCES

Bersanelli, B. et al. (2016). L718Q Mutation as New Mechanism of Acquired Resistance to AZD9291 in EGFR-Mutated NSCLC. Journal of Thoracic Oncology 11, e121-e123.

Blakely, C. M. et al. (2012). Resiliency of lung cancers to EGFR inhibitor treatment unveiled, offering opportunities to divide and conquer EGFR inhibitor resistance. Cancer Discov. 2, 872-875.

Bryan, M. C. et al.; Pyridones as Highly Selective, Noncovalent Inhibitors of T790M Double Mutants of EGFR. ACS Med. Chem. Lett. 2016, 7, 100-104.

Bryan, M. C. et al.; Preparation of azaindazole compounds as inhibitors of T790M containing EGFR mutants. WO 2014/210354

Chan, B. K. et al. (2016). Discovery of a Noncovalent, Mutant-Selective Epidermal Growth Factor Receptor Inhibitor. J. Med. Chem. 2016, 59, 9080-9093.

Chen, K. et al. (2017). Novel Mutations on EGFR Leu792 Potentially Correlate to Acquired Resistance to Osimertinib in Advanced NSCLC. Journal of Thoracic Oncology 12, e65-e68.

Chen, L. et al.; Novel 4-arylaminoquinazoline derivatives with (E)-propen-1-yl moiety as potent EGFR inhibitors with enhanced antiproliferative activities against tumor cells. Eu. J. Med. Chem. 2017, 138, 689-697.

Cross, D. A. E. et al. (2014). AZD9291, an Irreversible EGFR TKI, Overcomes T790M-Mediated Resistance to EGFR Inhibitors in Lung Cancer. Cancer Discovery. 2014 September; 4(9):1046-61. doi: 10.1158/2159-8290.CD-14-0337.

Engel, J. et al.; Insight into the Inhibition of Drug-Resistant Mutants of the Receptor Tyrosine Kinase EGFR. Angew. Chem. Int. Ed. 2016, 55, 10909-10912.

Günther, M. et al.; Trisubstituted Pyridinylimidazoles as Potent Inhibitors of the Clinically Resistant L858R/T790M/C797S EGFR Mutant: Targeting of Both Hydrophobic Regions and the Phosphate Binding Site. J. Med. Chem. 2017, 60, 5613-5637.

Hanan, E. J. et al.; Discovery of Selective and Noncovalent Diaminopyrimidine-Based Inhibitors of Epidermal Growth Factor Receptor Containing the T790M Resistance Mutation. J. Med. Chem. 2014, 57, 10176-10191.

Heald, R. et al. (2015). Noncovalent Mutant Selective Epidermal Growth Factor Receptor Inhibitors: A Lead Optimization Case Study. J. Med. Chem. 58, 8877-8895.

Jänne, P. A et al. (2015). AZD9291 in EGFR Inhibitor-Resistant Non-Small-Cell Lung Cancer. N. Engl. J. Med. 372, 1689-1699.

Jia, Y. et al.; EGF816 Exerts Anticancer Effects in Non-Small Cell Lung Cancer by Irreversibly and Selectively Targeting Primary and Acquired Activating Mutations in the EGF Receptor. Cancer Research 2016, 76, 1591-1602.

Juchum, M. et al.; Trisubstituted Imidazoles with a Rigidized Hinge Binding Motif Act As Single Digit nM Inhibitors of Clinically Relevant EGFR L858R/T790M and L858R/T790M/C797S Mutants: An Example of Target Hopping. J. Med. Chem. 2017, 60, 4636-4656.

Kobayashi, S. et al. (2005). EGFR mutation and resistance of non-small-cell lung cancer to gefitinib. N. Engl. J. Med. 352, 786-792.

Konduri, K. et al. (2016). EGFR Fusions as Novel Therapeutic Targets in Lung Cancer. Cancer Discovery. 2016 June; 6(6):601-11. doi: 10.1158/2159-8290.CD-16-0075.

Le, N.; Methods for treating epidermal growth factor receptor (EGFR) mutant cancers. WO 2016/185333.

Lelais, G. et al.; Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a Novel, Potent, and WT Sparing Covalent Inhibitor of Oncogenic (L858R, ex19del) and Resistant (T790M) EGFR Mutants for the Treatment of EGFR Mutant Non-Small-Cell Lung Cancers. J. Med. Chem. 2016, 59, 6671-6689.

Lelais, G. et al.; Preparation of fused imidazole compounds and compositions for modulating EGFR activity. WO 2013/184757.

Midha, A. et al. (2015). EGFR mutation incidence in non-small-cell lung cancer of adenocarcinoma histology: a systematic review and global map by ethnicity (mutMapII). Am J Cancer Res. 2015; 5(9): 2892-2911.

Mitsudomi, T. et al. (2010). Gefitinib versus cisplatin plus docetaxel in patients with non-small-cell lung cancer harbouring mutations of the epidermal growth factor receptor (WJTOG3405): an open label, randomised phase 3 trial. Lancet Oncol. 11, 121-128.

Mok, T. S. et al. (2016). Osimertinib or Platinum-Pemetrexed in EGFR T790M-Positive Lung Cancer. N. Engl. J. Med. 367, 629-640.

Ortiz-Cuaran, S. et al. (2016). Heterogeneous Mechanisms of Primary and Acquired Resistance to Third-Generation EGFR Inhibitors. Clin. Cancer Res. 22, 4837-4847.

Ou, Q. et al. (2017). Investigating novel resistance mechanisms to third generation EGFR TKI osimertinib in non-small cell lung cancer patients using next generation sequencing. 2017 ASCO Annual Meeting; Abstract No: 2572; J Clin Oncol 35, 2017 (suppl; abstr 2572)

Park, H. et al.; Discovery of EGF Receptor Inhibitors That Are Selective for the d746-750/T790M/C797S Mutant through Structure-Based de Novo Design. Angew. Chem. Int. Ed. 2017, 56, 7634-7638.

Park, K. et al. (2016). Afatinib versus gefitinib as first-line treatment of patients with EGFR mutation-positive non-small-cell lung cancer (LUX-Lung 7): a phase 2B, open-label, randomised controlled trial. Lancet Oncol. 17, 577-589.

Patel, H. M. et al.; Design and synthesis of quinazolinones as EGFR inhibitors to overcome EGFR resistance obstacle. Biorg. Med. Chem. 2017, 25, 2713-2723.

Piotrowska, Z. et al. (2017). Characterizing the genomic landscape of EGFR C797S in lung cancer using ctDNA next-generation sequencing. Presented at IASLC 18$^{th}$ World Conference on Lung Cancer.

Ramalingam, S. S. et al. (2017). Osimertinib As First-Line Treatment of EGFR Mutation-Positive Advanced Non-Small-Cell Lung Cancer. Journal of Clinical Oncology, 2017 Aug. 25:JCO2017747576. doi: 10.1200/JCO.2017.74.7576. [Epub ahead of print]

Song, H. N. et al. (2016). Acquired C797S Mutation upon Treatment with a T790M-Specific Third-Generation EGFR Inhibitor (HM61713) in Non-Small Cell Lung Cancer. J. Thorac. Oncol. 11:e45-47.

Soria, J. C. et al. (2017). Osimertinib in Untreated EGFR-Mutated Advanced Non-Small-Cell Lung Cancer. N. Engl. J. Med. 2017 Nov. 18. doi: 10.1056/NEJMoa1713137.

Thress, K. S. et al. (2015). Acquired EGFR C797S mutation mediates resistance to AZD9291 in non-small cell lung cancer harboring EGFR T790M. Nat. Med. 21, 560-562.

Wang, S. et al. (2016). Third-generation inhibitors targeting EGFR T790M mutation in advanced non-small cell lung cancer. J Hematol Oncol. 2016 Apr. 12; 9:34.

Yu, H. A. et al. (2015). Acquired Resistance of EGFR-Mutant Lung Cancer to a T790M-Specific EGFR Inhibitor: Emergence of a Third Mutation (C797S) in the EGFR Tyrosine Kinase Domain. JAMA Oncol. 1, 982-984.

Zhang, Y. et al.; Quinazoline-1-deoxynojirimycin hybrids as high active dual inhibitors of EGFR and α-glucosidase. *Bioorg. Med. Chem. Lett.* 2017, 27, 4309-4313.

Zhou, C. et al. (2011). Erlotinib versus chemotherapy as first-line treatment for patients with advanced EGFR mutation-positive non-small-cell lung cancer (OPTIMAL, CTONG-0802): a multicentre, open-label, randomised, phase 3 study. Lancet Oncol. 12, 735-742.

DETAILED DESCRIPTION OF THE INVENTION

Compounds

It has now been found that, surprisingly, compounds of formula (I) wherein the groups $R^1$ to $R^4$ and $X^1$ to $X^5$ have the meanings given hereinafter act as inhibitors of mutant EGFR which is involved in controlling cell proliferation. Thus, the compounds according to the invention may be used for example for the treatment of diseases characterised by excessive or abnormal cell proliferation.

The present invention therefore relates to a compound of formula (I)

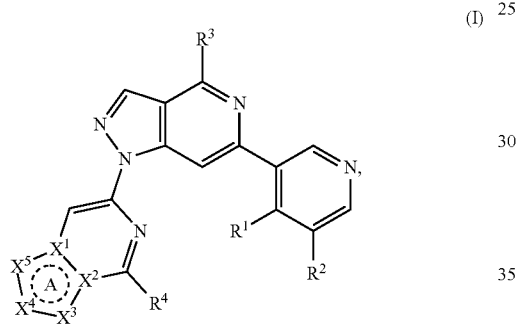

wherein

[A0]

$R^1$ is selected from the group consisting of hydrogen, $C_{1-6}$alkyl, $C_{1-6}$haloalkyl, $C_{1-6}$alkoxy, $C_{1-6}$haloalkoxy, halogen, —OH, —NH$_2$, —NH($C_{1-6}$alkyl), —N($C_{1-6}$alkyl)$_2$, $C_{3-6}$cycloalkyl, $C_{3-6}$cycloalkoxy, 3-6 membered heterocyclyloxy and 3-6 membered heterocyclyl;

$R^2$ is selected from the group consisting of hydrogen, $C_{1-6}$alkyl, $C_{1-6}$haloalkyl, $C_{1-6}$alkoxy, $C_{1-6}$haloalkoxy, halogen, —OH, —NH$_2$, —NH($C_{1-6}$alkyl), —N($C_{1-6}$alkyl)$_2$, $C_{3-6}$cycloalkyl, $C_{3-6}$cycloalkoxy, 3-6 membered heterocyclyloxy and 3-6 membered heterocyclyl; or $R^1$ and $R^2$ together with the carbon atoms they are attached form a 5-6 membered heterocyle or a 5-6 membered heteroaromatic ring;

[B0]

$R^3$ is selected from the group consisting of hydrogen, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, halogen, —CN, —OH, —NH$_2$, —NH($C_{1-6}$alkyl), —N($C_{1-6}$alkyl)$_2$, $C_{3-6}$cycloalkyl, $C_{3-6}$cycloalkoxy, 3-6 membered heterocyclyloxy and 3-6 membered heterocyclyl;

[C0]

$R^4$ is selected from the group consisting of $R^{a1}$ and $R^{b1}$;

$R^{a1}$ is selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b1}$ and/or $R^{c1}$;

each $R^{b1}$ is independently selected from the group consisting of —$OR^{c1}$, —$N(R^{c1})R^{c1}$, halogen, —CN, —C(=O)$R^{c1}$, —C(=O)O$R^{c1}$, —C(=O)N($R^{c1}$)$R^{c1}$, —C(=O)N(H)O$R^{c1}$, —C(=O)N($C_{1-4}$alkyl)O$R^{c1}$, —S(=O)$_2R^{c1}$, —S(=O)$_2$N($R^{c1}$)$R^{c1}$, —N(H)C(=O)$R^{c1}$, —N($C_{1-4}$alkyl)C(=O)$R^{c1}$, —N(H)C(=O)O$R^{c1}$, —N($C_{1-4}$alkyl)C(=O)O$R^{c1}$, —N(H)S(=O)$_2R^{c1}$, —N($C_{1-4}$alkyl)S(=O)$_2R^{c1}$ and the bivalent substituent =O;

each $R^{c1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d1}$ and/or $R^{e1}$;

each $R^{d1}$ is independently selected from the group consisting of —$OR^{e1}$, —$N(R^{e1})R^{e1}$, halogen, —CN, —C(=O)$R^{e1}$, —C(=O)O$R^{e1}$, —C(=O)N($R^{e1}$)$R^{e1}$, —C(=O)N(H)O$R^{e1}$, —C(=O)N($C_{1-4}$alkyl)O$R^{e1}$, —S(=O)$_2R^{e1}$, —S(=O)$_2$N($R^{e1}$)$R^{e1}$, —N(H)C(=O)$R^{e1}$, —N($C_{1-4}$alkyl)C(=O)$R^{e1}$, —N(H)C(=O)O$R^{e1}$, —N($C_{1-4}$alkyl)C(=O)O$R^{e1}$, —N(H)S(=O)$_2R^{e1}$, —N($C_{1-4}$alkyl)S(=O)$_2R^{e1}$ and the bivalent substituent =O;

each $R^{e1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —NH$_2$, —C(=O)$C_{1-4}$alkyl, —NH($C_{1-4}$alkyl), —N($C_{1-4}$alkyl)$_2$ and the bivalent substituent =O;

[D0]

$X^1$ is selected from the group consisting of carbon (C) and nitrogen (N);

$X^2$ is selected from the group consisting of carbon (C) and nitrogen (N);

at least one of $X^1$ and $X^2$ is carbon (C);

$X^3$ is selected from the group consisting of nitrogen (N), $C(R^5)$, $N(R^6)$, $C(R^5)(R^5)$, oxygen (O), sulphur (S), S(=O), S(=O)$_2$, and C(=O);

$X^4$ is selected from the group consisting of nitrogen (N), $C(R^7)$, $N(R^8)$, $C(R^7)(R^7)$, oxygen (O), sulphur (S), S(=O), S(=O)$_2$, and C(=O);

$X^5$ is selected from the group consisting of nitrogen (N), $C(R^9)$, $N(R^{10})$, $C(R^9)(R^9)$, oxygen (O), sulphur (S), S(=O), S(=O)$_2$, and C(=O);

each bond between ring members in ring A is independently selected from a single bond, a double bond or a (hetero)aromatic bond;

each $R^5$ is independently selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-4}$alkyl, $C_{1-6}$haloalkoxy-$C_{1-6}$alkyl, halogen, —NH$_2$, —NH($C_{1-6}$alkyl), —N($C_{1-6}$ alkyl)$_2$, $C_{3-6}$cycloalkyl and 3-6 membered heterocyclyl;

each $R^6$ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

each $R^7$ is independently selected from the group consisting of $R^{a2}$ and $R^{b2}$;

$R^{a2}$ is selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of —O$R^{c2}$, —N($R^{c2}$)$R^{c2}$, halogen, —CN, —C(=O)$R^{c2}$, —C(=O)O$R^{c2}$, —C(=O)N($R^{c2}$)$R^{c2}$, —C(=O)N(H)O$R^{c2}$, —C(=O)N($C_{1-4}$alkyl)O$R^{c2}$, —S(=O)$_2R^{c2}$, —S(=O)$_2$N($R^{c2}$)$R^{c2}$, —N(H)C(=O)$R^{c2}$, —N($C_{1-4}$alkyl)C(=O)$R^{c2}$, —N(H)C(=O)O$R^{c2}$, —N($C_{1-4}$alkyl)C(=O)O$R^{c2}$, —N(H)S(=O)$_2R^{c2}$, —N($C_{1-4}$alkyl)S(=O)$_2R^{c2}$ and the bivalent substituent =O;

each $R^{c2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d2}$ and/or $R^{e2}$;

each $R^{d2}$ is independently selected from the group consisting of —O$R^{e2}$, —N($R^{e2}$)$R^{e2}$, halogen, —CN, —C(=O)$R^{e2}$, —C(=O)O$R^{e2}$, —C(=O)N($R^{e2}$)$R^{e2}$, —C(=O)N(H)O$R^{e2}$, —C(=O)N($C_{1-4}$alkyl)O$R^{e2}$, —S(=O)$_2R^{e2}$, —S(=O)$_2$N($R^{e2}$)$R^{e2}$, —N(H)C(=O)$R^{e2}$, —N($C_{1-4}$alkyl)C(=O)$R^{e2}$, —N(H)C(=O)O$R^{e2}$, —N($C_{1-4}$alkyl)C(=O)O$R^{e2}$, —N(H)S(=O)$_2R^{e2}$, —N($C_{1-4}$alkyl)S(=O)$_2R^{c2}$ and the bivalent substituent =O;

each $R^{e2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —NH$_2$, —C(=O)$C_{1-4}$alkyl, —NH($C_{1-4}$alkyl), —N($C_{1-4}$alkyl)$_2$ and the bivalent substituent =O;

each $R^8$ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

each $R^9$ is independently selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-6}$alkyl, $C_{1-6}$haloalkoxy-$C_{1-6}$alkyl, halogen, —NH$_2$, —NH($C_{1-6}$alkyl), —N($C_{1-6}$ alkyl)$_2$, $C_{3-6}$cycloalkyl and 3-6 membered heterocyclyl; each $R^{10}$ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

or a salt thereof.

The following structural aspects represent preferred embodiments [A1] to [A9], [B1] to [B4], [C1] to [C16] and [D1] to [D9] of the corresponding structural aspects [A0], [B0], [C0] and [D0], respectively:

In one aspect [A1] the invention relates to a compound of formula (I) or a salt thereof, wherein
$R^1$ is selected from the group consisting of hydrogen, $C_{1-6}$alkyl, $C_{1-6}$haloalkyl, $C_{1-6}$alkoxy, $C_{1-6}$haloalkoxy, halogen, —OH, —NH$_2$, —NH($C_{1-6}$alkyl), —N($C_{1-6}$ alkyl)$_2$, $C_{3-6}$cycloalkyl, $C_{3-6}$cycloalkoxy, 3-6 membered heterocyclyloxy and 3-6 membered heterocyclyl;
$R^2$ is selected from the group consisting of hydrogen, $C_{1-6}$alkyl, $C_{1-6}$haloalkyl, $C_{1-6}$alkoxy, $C_{1-6}$haloalkoxy, halogen, —OH, —NH$_2$, —NH($C_{1-6}$alkyl), —N($C_{1-6}$ alkyl)$_2$, $C_{3-6}$cycloalkyl, $C_{3-6}$cycloalkoxy, 3-6 membered heterocyclyloxy and 3-6 membered heterocyclyl.

In another aspect [A2] the invention relates to a compound of formula (I) or a salt thereof, wherein
$R^1$ is selected from the group consisting of hydrogen, $C_{1-6}$alkyl, $C_{1-6}$haloalkyl, $C_{1-6}$alkoxy, $C_{1-6}$haloalkoxy, halogen, —OH, —NH$_2$, —NH($C_{1-6}$alkyl), —N($C_{1-6}$ alkyl)$_2$, $C_{3-6}$cycloalkyl, $C_{3-6}$cycloalkoxy, 3-6 membered heterocyclyloxy and 3-6 membered heterocyclyl;
$R^2$ is hydrogen.

In another aspect [A3] the invention relates to a compound of formula (I) or a salt thereof, wherein
$R^1$ is selected from the group consisting of $C_{1-6}$alkoxy, $C_{1-6}$haloalkoxy, halogen, —OH, $C_{3-6}$cycloalkyl and $C_{3-6}$cycloalkoxy;
$R^2$ is hydrogen.

In another aspect [A4] the invention relates to a compound of formula (I) or a salt thereof, wherein
$R^1$ is selected from the group consisting of methoxy, isopropyloxy, —OH, cyclopropyl and cyclopropyloxy;
$R^2$ is hydrogen.

In another aspect [A5] the invention relates to a compound of formula (I) or a salt thereof, wherein
$R^1$ is selected from the group consisting of $C_{1-4}$alkoxy and —OH;
$R^2$ is hydrogen.

In another aspect [A6] the invention relates to a compound of formula (I) or a salt thereof, wherein
$R^1$ is methoxy;
$R^2$ is hydrogen.

In another aspect [A7] the invention relates to a compound of formula (I) or a salt thereof, wherein
$R^1$ is —OH;
$R^2$ is hydrogen.

In another aspect [A8] the invention relates to a compound of formula (I) or a salt thereof, wherein R$^1$ and R$^2$ together with the carbon atoms they are attached form a 5-6 membered heterocyle or a 5-6 membered heteroaromatic ring.

In another aspect [A9] the invention relates to a compound of formula (I) or a salt thereof, wherein
R$^1$ and R$^2$ together with the carbon atoms they are attached form a ring selected from the group consisting of pyrrole, 2,3-dihydrofuran and furan.

In another aspect [B1] the invention relates to a compound of formula (I) or a salt thereof, wherein
R$^3$ is selected from the group consisting of hydrogen, C$_{1-6}$alkyl, C$_{1-6}$haloalkyl, C$_{1-6}$alkoxy, C$_{1-6}$haloalkoxy and halogen.

In another aspect [B2] the invention relates to a compound of formula (I) or a salt thereof, wherein
R$^3$ is selected from the group consisting of hydrogen, C$_{1-4}$alkyl, C$_{1-4}$haloalkyl and halogen.

In another aspect [B3] the invention relates to a compound of formula (I) or a salt thereof, wherein
R$^3$ is C$_{1-4}$alkyl.

In another aspect [B4] the invention relates to a compound of formula (I) or a salt thereof, wherein
R$^3$ is methyl.

In another aspect [C$_1$] the invention relates to a compound of formula (I) or a salt thereof, wherein
R$^4$ is selected from the group consisting of R$^{a1}$ and R$^{b1}$;
R$^{a1}$ is selected from the group consisting of C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl, wherein the C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl are all optionally substituted with one or more, identical or different R$^{b1}$ and/or R$^{c1}$;
each R$^{b1}$ is independently selected from the group consisting of —OR$^{c1}$, —N(R$^{c1}$)R$^{c1}$, halogen, —CN, —C(=O)R$^{c1}$, —C(=O)OR$^{c1}$, —C(=O)N(R$^{c1}$)R$^{c1}$, —C(=O)N(H)OR$^{c1}$, —C(=O)N(C$_{1-4}$alkyl)OR$^{c1}$, —S(=O)$_2$R$^{c1}$, —S(=O)$_2$N(R$^{c1}$)R$^{c1}$, —N(H)C(=O)R$^{c1}$, —N(C$_{1-4}$alkyl)C(=O)R$^{c1}$, —N(H)C(=O)OR$^{c1}$, —N(C$_{1-4}$alkyl)C(=O)OR$^{c1}$, —N(H)S(=O)$_2$R$^{c1}$, —N(C$_{1-4}$alkyl)S(=O)$_2$R$^{c1}$ and the bivalent substituent =O;
each R$^{c1}$ is independently selected from the group consisting of hydrogen, C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl, wherein the C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl are all optionally substituted with one or more, identical or different R$^{d1}$ and/or R$^{e1}$;
each R$^{d1}$ is independently selected from the group consisting of —OR$^{e1}$, —N(R$^{e1}$)R$^{e1}$, halogen, —CN, —C(=O)R$^{e1}$, —C(=O)OR$^{e1}$, —C(=O)N(R$^{e1}$)R$^{e1}$, —C(=O)N(H)OR$^{e1}$, —C(=O)N(C$_{1-4}$alkyl)OR$^{e1}$, —S(=O)$_2$R$^{e1}$, —S(=O)$_2$N(R$^{e1}$)R$^{e1}$, —N(H)C(=O)R$^{e1}$, —N(C$_{1-4}$alkyl)C(=O)R$^{e1}$, —N(H)C(=O)OR$^{e1}$, —N(C$_{1-4}$alkyl)C(=O)OR$^{e1}$, —N(H)S(=O)$_2$R$^{e1}$, —N(C$_{1-4}$alkyl)S(=O)$_2$R$^{e1}$ and the bivalent substituent =O;
each R$^{e1}$ is independently selected from the group consisting of hydrogen, C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl, wherein the C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl are all optionally substituted with one or more, identical or different substituent(s) selected from the group consisting of C$_{1-6}$alkyl, C$_{1-6}$haloalkyl, C$_{3-10}$cycloalkyl, 3-11 membered heterocyclyl, C$_{6-10}$aryl, 5-10 membered heteroaryl, —OH, C$_{1-6}$alkoxy, C$_{1-4}$alkoxy-C$_{1-4}$alkyl, hydroxy-C$_{1-4}$alkyl, halogen, —CN, —NH$_2$, —C(=O)C$_{1-4}$alkyl, —NH(C$_{1-4}$alkyl), —N(C$_{1-4}$alkyl)$_2$ and the bivalent substituent =O.

In another aspect [C$_2$] the invention relates to a compound of formula (I) or a salt thereof, wherein
R$^4$ is selected from the group consisting of R$^{a1}$ and R$^{b1}$;
R$^{a1}$ is selected from the group consisting of C$_{1-6}$alkyl, C$_{1-6}$haloalkyl, C$_{3-10}$cycloalkyl, 3-11 membered heterocyclyl, C$_{6-10}$aryl and 5-10 membered heteroaryl, wherein the C$_{1-6}$alkyl, C$_{1-6}$haloalkyl, C$_{3-10}$cycloalkyl, 3-11 membered heterocyclyl, C$_{6-10}$aryl and 5-10 membered heteroaryl are all optionally substituted with one or more, identical or different R$^{b1}$ and/or R$^{c1}$;
each R$^{b1}$ is independently selected from the group consisting of —OR$^{c1}$, —N(R$^{c1}$)R$^{c1}$, halogen, —CN, —C(=O)N(R$^{c1}$)R$^{c1}$, —S(=O)$_2$N(R$^{c1}$)R$^{c1}$, —N(H)C(=O)R$^{c1}$, —N(C$_{1-4}$alkyl)C(=O)R$^{c1}$, —N(H)C(=O)OR$^{c1}$, —N(C$_{1-4}$alkyl)C(=O)OR$^{c1}$, —N(H)S(=O)$_2$R$^{c1}$, —N(C$_{1-4}$alkyl)S(=O)$_2$R$^{c1}$ and the bivalent substituent =O;
each R$^{c1}$ is independently selected from the group consisting of hydrogen, C$_{1-6}$alkyl, C$_{1-6}$haloalkyl, C$_{3-10}$cycloalkyl, 3-11 membered heterocyclyl, C$_{6-10}$aryl and 5-10 membered heteroaryl, wherein the C$_{1-6}$alkyl, C$_{1-6}$haloalkyl, C$_{3-10}$cycloalkyl, 3-11 membered heterocyclyl, C$_{6-10}$aryl and 5-10 membered heteroaryl are all optionally substituted with one or more, identical or different R$^{d1}$ and/or R$^{e1}$;
each R$^{d1}$ is independently selected from the group consisting of —OR$^{e1}$, —N(R$^{e1}$)R$^{e1}$, halogen, —CN, —C(=O)N(R$^{e1}$)R$^{e1}$, —S(=O)$_2$N(R$^{e1}$)R$^{e1}$, —N(H)C(=O)R$^{e1}$, —N(C$_{1-4}$alkyl)C(=O)R$^{e1}$, —N(H)C(=O)OR$^{e1}$, —N(C$_{1-4}$alkyl)C(=O)OR$^{e1}$, —N(H)S(=O)$_2$R$^{e1}$, —N(C$_{1-4}$alkyl)S(=O)$_2$R$^{e1}$ and the bivalent substituent =O;
each R$^{e1}$ is independently selected from the group consisting of hydrogen, C$_{1-6}$alkyl, C$_{1-6}$haloalkyl, C$_{3-10}$cycloalkyl, 3-11 membered heterocyclyl, C$_{6-10}$aryl and 5-10 membered heteroaryl, wherein the C$_{1-6}$alkyl, C$_{1-6}$haloalkyl, C$_{3-10}$cycloalkyl, 3-11 membered heterocyclyl, C$_{6-10}$aryl and 5-10 membered heteroaryl are all optionally substituted with one or more, identical or different substituent(s) selected from the group consisting of C$_{1-6}$alkyl, C$_{1-6}$haloalkyl, C$_{3-10}$cycloalkyl, 3-11 membered heterocyclyl, C$_{6-10}$aryl, 5-10 membered heteroaryl, —OH, C$_{1-6}$alkoxy, C$_{1-4}$alkoxy-C$_{1-4}$alkyl, hydroxy-C$_{1-4}$alkyl, halogen, —CN, —NH$_2$, —C(=O)C$_{1-4}$alkyl, —NH(C$_{1-4}$alkyl), —N(C$_{1-4}$alkyl)$_2$ and the bivalent substituent =O.

In another aspect [C$_3$] the invention relates to a compound of formula (I) or a salt thereof, wherein
R$^4$ is selected from the group consisting of R$^{a1}$ and R$^{b1}$;
R$^{a1}$ is selected from the group consisting of C$_{1-6}$alkyl, C$_{3-10}$cycloalkyl, 3-11 membered heterocyclyl, phenyl and 5-6 membered heteroaryl, wherein the $C_{1-6}$alkyl, $C_{3-10}$cycloalkyl, 3-11 membered heterocyclyl, phenyl and 5-6 membered heteroaryl are all optionally substituted with one or more, identical or different $R^{b1}$ and/or $R^{c1}$;

each $R^{b1}$ is independently selected from the group consisting of —$OR^{c1}$, —$N(R^{c1})R^{c1}$, halogen and the bivalent substituent =O;

each $R^{c1}$ is independently selected from the group consisting of hydrogen, $C_{1-6}$alkyl, $C_{1-6}$haloalkyl, $C_{3-10}$cycloalkyl, 3-11 membered heterocyclyl, phenyl and 5-6 membered heteroaryl, wherein the $C_{1-6}$alkyl, $C_{1-6}$haloalkyl, $C_{3-10}$cycloalkyl, 3-11 membered heterocyclyl, phenyl and 5-6 membered heteroaryl are all optionally substituted with one or more, identical or different $R^{d1}$ and/or $R^{e1}$;

each $R^{d1}$ is independently selected from the group consisting of —$OR^{e1}$, —$N(R^{e1})R^{e1}$, halogen and the bivalent substituent =O;

each $R^{e1}$ is independently selected from the group consisting of hydrogen, $C_{1-6}$alkyl, $C_{1-6}$haloalkyl, $C_{3-10}$cycloalkyl, 3-11 membered heterocyclyl, phenyl and 5-6 membered heteroaryl, wherein the $C_{1-6}$alkyl, $C_{1-6}$haloalkyl, $C_{3-10}$cycloalkyl, 3-11 membered heterocyclyl, phenyl and 5-6 membered heteroaryl are all optionally substituted with one or more, identical or different substituent(s) selected from the group consisting of halogen and the bivalent substituent =O.

In another aspect [C4] the invention relates to a compound of formula (I) or a salt thereof, wherein
$R^4$ is selected from the group consisting of $R^{a1}$ and $R^{b1}$;
$R^{a1}$ is selected from the group consisting of $C_{1-6}$alkyl, $C_{3-10}$cycloalkyl and 3-11 membered heterocyclyl, wherein the $C_{1-6}$alkyl, $C_{3-10}$cycloalkyl, 3-11 membered heterocyclyl are all optionally substituted with one or more, identical or different $R^{b1}$ and/or $R^{c1}$;
each $R^{b1}$ is independently selected from the group consisting of —$OR^{c1}$, —$N(R^{c1})R^{c1}$ and halogen;
each $R^{c1}$ is independently selected from the group consisting of hydrogen, $C_{1-6}$alkyl, $C_{1-6}$haloalkyl, 3-11 membered heterocyclyl and 5-6 membered heteroaryl, wherein the $C_{1-6}$alkyl, $C_{1-6}$haloalkyl, 3-11 membered heterocyclyl and 5-6 membered heteroaryl are all optionally substituted with one or more, identical or different $R^{d1}$ and/or $R^{e1}$;
each $R^{d1}$ is independently selected from the group consisting of —$OR^{e1}$, —$N(R^{e1})R^{e1}$ and halogen;
each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

In another aspect [C5] the invention relates to a compound of formula (I) or a salt thereof, wherein
$R^4$ is $R^{a1}$;
$R^{a1}$ is 3-11 membered heterocyclyl optionally substituted with one or more, identical or different $R^{b1}$ and/or $R^{c1}$;
each $R^{b1}$ is independently selected from the group consisting of —$OR^{c1}$, —$N(R^{c1})R^{c1}$ and halogen;
each $R^{c1}$ is independently selected from the group consisting of hydrogen, $C_{1-6}$alkyl, $C_{1-6}$haloalkyl, 3-11 membered heterocyclyl and 5-6 membered heteroaryl, wherein the $C_{1-6}$alkyl, $C_{1-6}$haloalkyl, 3-11 membered heterocyclyl and 5-6 membered heteroaryl are all optionally substituted with one or more, identical or different $R^{d1}$ and/or $R^{e1}$;
each $R^{d1}$ is independently selected from the group consisting of —$OR^{e1}$, —$N(R^{e1})R^{e1}$ and halogen;
each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

In another aspect [C6] the invention relates to a compound of formula (I) or a salt thereof, wherein
$R^4$ is $R^{a1}$;
$R^{a1}$ is selected from the group consisting of

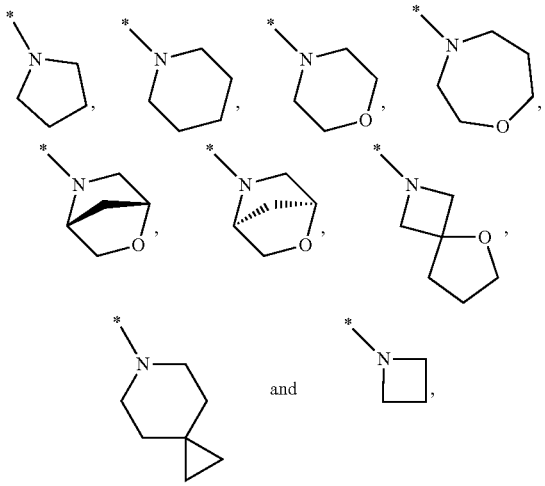

wherein each $R^{a1}$ is optionally substituted with one or more, identical or different $R^{b1}$ and/or $R^{c1}$;
each $R^{b1}$ is independently selected from the group consisting of —$OR^{c1}$, —$N(R^{c1})R^{c1}$ and halogen;
each $R^{c1}$ is independently selected from the group consisting of hydrogen, $C_{1-6}$alkyl, $C_{1-6}$haloalkyl, 3-11 membered heterocyclyl and 5-6 membered heteroaryl, wherein the $C_{1-6}$alkyl, $C_{1-6}$haloalkyl, 3-11 membered heterocyclyl and 5-6 membered heteroaryl are all optionally substituted with one or more, identical or different $R^{d1}$ and/or $R^{e1}$;
each $R^{d1}$ is independently selected from the group consisting of —$OR^{e1}$, —$N(R^{e1})R^{e1}$ and halogen;
each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

In another aspect [C7] the invention relates to a compound of formula (I) or a salt thereof, wherein
$R^4$ is $R^{a1}$;
$R^{a1}$ is selected from the group consisting of

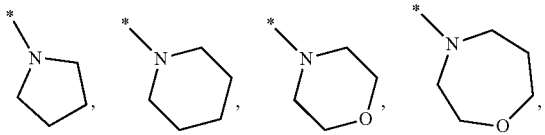

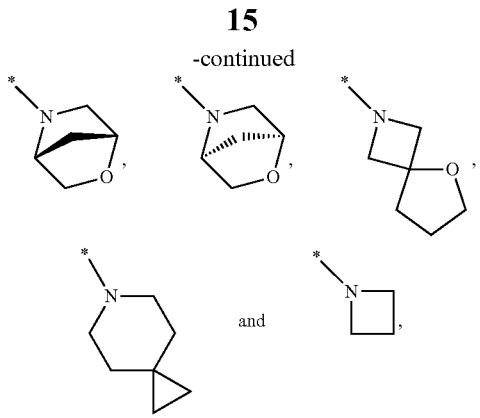

wherein each $R^{a1}$ is optionally substituted with one or more, identical or different $R^{b1}$ and/or $R^{c1}$;
each $R^{b1}$ is independently selected from the group consisting of —$OR^{c1}$ and halogen;
each $R^{c1}$ is independently selected from the group consisting of hydrogen, $C_{1-6}$alkyl, $C_{1-6}$haloalkyl and 5-6 membered heteroaryl, wherein the $C_{1-6}$alkyl, $C_{1-6}$haloalkyl and 5-6 membered heteroaryl are all optionally substituted with one or more, identical or different $R^{d1}$ and/or $R^{e1}$;
each $R^{d1}$ is independently selected from the group consisting of —$OR^{e1}$ and halogen; each $R^{e1}$ is independently selected from the group consisting of hydrogen and $C_{1-6}$alkyl.

In another aspect [C8] the invention relates to a compound of formula (I) or a salt thereof, wherein
$R^4$ is selected from the group consisting of

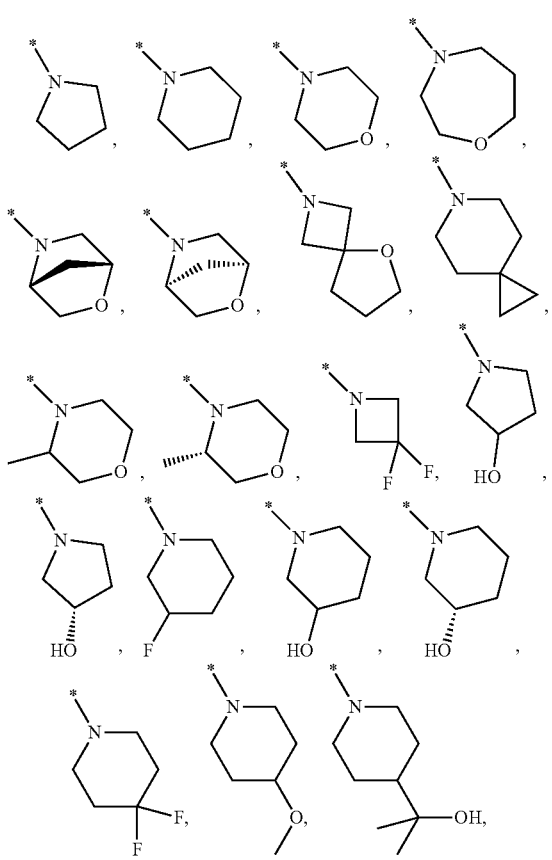

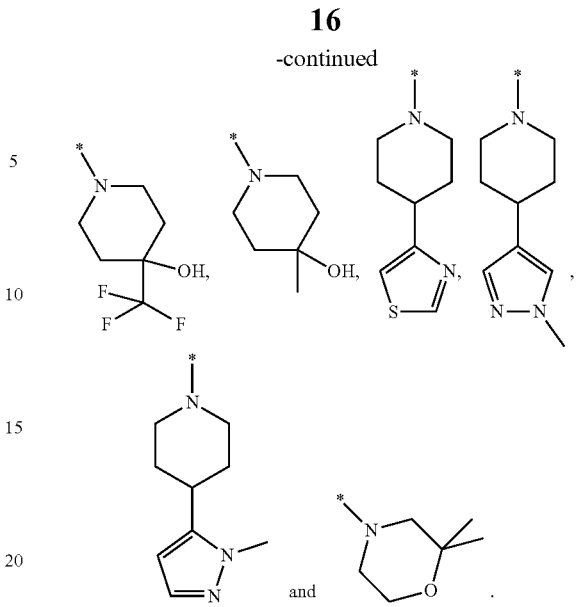

In another aspect [C9] the invention relates to a compound of formula (I) or a salt thereof, wherein
$R^4$ is selected from the group consisting of —$NH_2$, —$NH(C_{1-4}$alkyl) and —$N(C_{1-4}$alkyl)$_2$.

In another aspect [C10] the invention relates to a compound of formula (I) or a salt thereof, wherein
$R^4$ is —$N(C_{1-4}$alkyl)$_2$.

In another aspect [C11] the invention relates to a compound of formula (I) or a salt thereof, wherein
$R^4$ is —$OR^{c1}$;
$R^{c1}$ is independently selected from the group consisting of hydrogen, $C_{1-6}$alkyl, $C_{1-6}$haloalkyl, 3-11 membered heterocyclyl and 5-6 membered heteroaryl, wherein the $C_{1-6}$alkyl, $C_{1-6}$haloalkyl, 3-11 membered heterocyclyl and 5-6 membered heteroaryl are all optionally substituted with one or more, identical or different $R^{d1}$ and/or $R^{e1}$;
each $R^{d1}$ is independently selected from the group consisting of —$OR^{e1}$, —$N(R^{e1})R^{e1}$ and halogen;
each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

In another aspect [C12] the invention relates to a compound of formula (I) or a salt thereof, wherein
$R^4$ is —$OR^{c1}$;
$R^{c1}$ is independently selected from the group consisting of $C_{1-6}$alkyl, $C_{1-6}$haloalkyl and 3-11 membered heterocyclyl, wherein the $C_{1-6}$alkyl, $C_{1-6}$haloalkyl and 3-11 membered heterocyclyl are all optionally substituted with one or more, identical or different $R^{d1}$ and/or $R^{e1}$;
each $R^{d1}$ is halogen;
each $R^{e1}$ is independently selected from the group consisting of $C_{3-10}$cycloalkyl and 3-11 membered heterocyclyl, wherein the $C_{3-10}$cycloalkyl and 3-11 membered heterocyclyl are all optionally substituted with one or more, identical or different halogen.

In another aspect [C13] the invention relates to a compound of formula (I) or a salt thereof, wherein

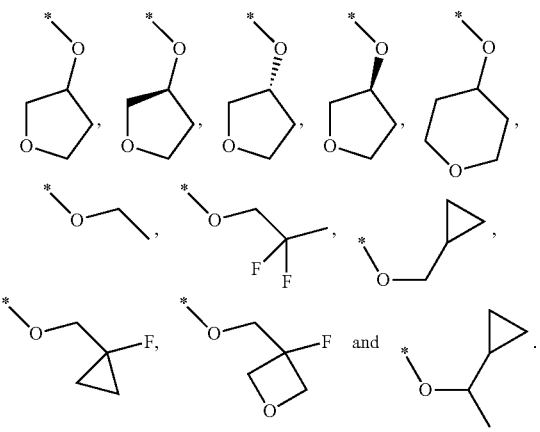

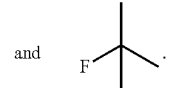 and 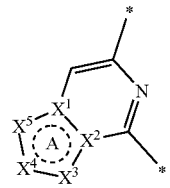

In another aspect [D1] the invention relates to a compound of formula (I) or a salt thereof, wherein

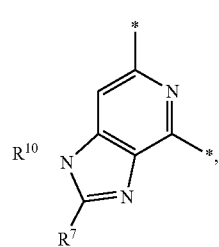

is selected from the group consisting of (i)

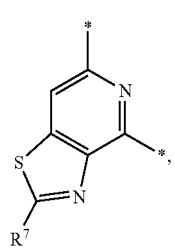

(ii)

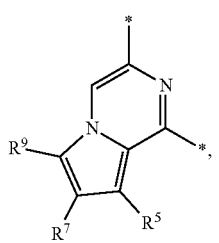

(iii)

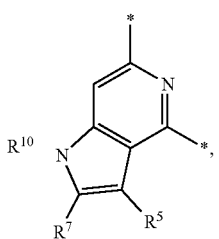

(iv)

In another aspect [C14] the invention relates to a compound of formula (I) or a salt thereof, wherein $R^4$ is selected from the group consisting $C_{1-6}$alkyl, $C_{3-10}$cycloalkyl and 3-11 membered heterocyclyl, wherein the $C_{1-6}$alkyl, $C_{3-10}$cycloalkyl, 3-11 membered heterocyclyl are all optionally substituted with one or more, identical or different $R^{b1}$ and/or $R^{c1}$;

each $R^{b1}$ is independently selected from the group consisting of —$OR^{c1}$, —$N(R^{c1})R^{c1}$ and halogen;

each $R^{c1}$ is independently selected from the group consisting of hydrogen, $C_{1-6}$alkyl, $C_{1-6}$haloalkyl, 3-11 membered heterocyclyl and 5-6 membered heteroaryl, wherein the $C_{1-6}$alkyl, $C_{1-6}$haloalkyl, 3-11 membered heterocyclyl and 5-6 membered heteroaryl are all optionally substituted with one or more, identical or different $R^{d1}$ and/or $R^{e1}$;

each $R^{d1}$ is independently selected from the group consisting of —$OR^{e1}$, —$N(R^{e1})R^{e1}$ and halogen;

each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

In another aspect [C15] the invention relates to a compound of formula (I) or a salt thereof, wherein $R^4$ is selected from the group consisting $C_{1-6}$alkyl, $C_{3-10}$cycloalkyl and 3-11 membered heterocyclyl, wherein the $C_{1-6}$alkyl, $C_{3-10}$cycloalkyl, 3-11 membered heterocyclyl are all optionally substituted with one or more, identical or different $R^{b1}$ and/or $R^{c1}$;

each $R^{b1}$ is independently selected from the group consisting of —$OR^{c1}$ and halogen;

each $R^{c1}$ is independently selected from the group consisting of hydrogen and $C_{1-6}$alkyl.

In another aspect [C16] the invention relates to a compound of formula (I) or a salt thereof, wherein $R^4$ is selected from the group consisting of

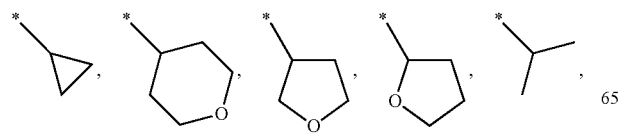

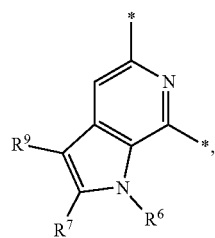
(v)
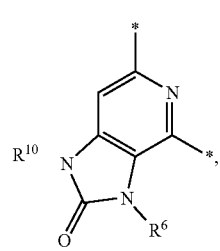
(vi)
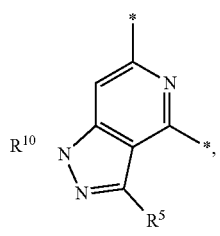
(vii)
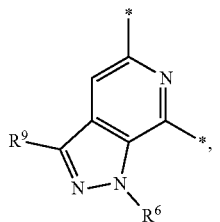
(viii)
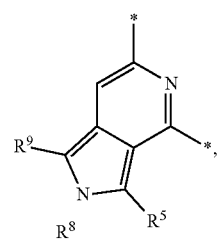
(ix)
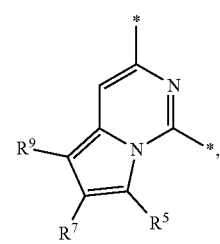
(x)
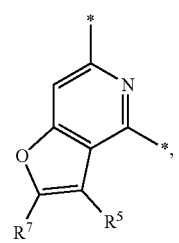
(xi)
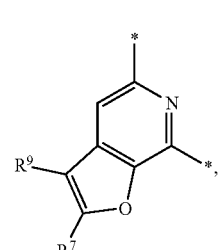
(xii)
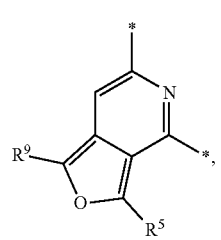
(xiii)
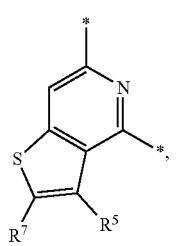
(xiv)
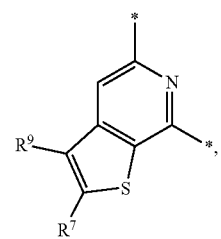
(xv)
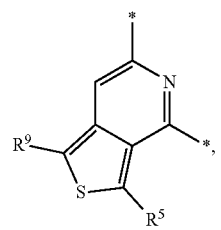
(xvi)

(xvii)
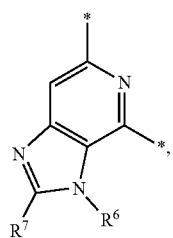
(xviii)
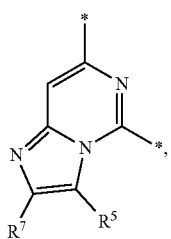
(xix)
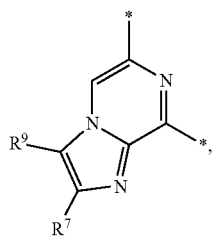
(xx)
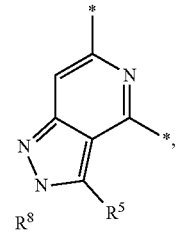
(xxi)
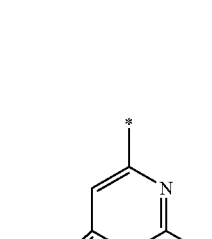
(xxii)
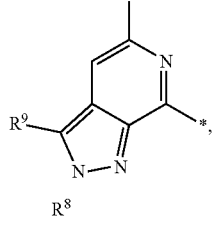
(xxiii)
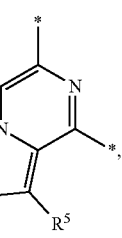
(xxiv)
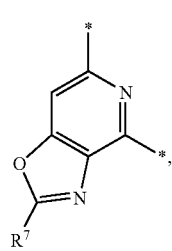
(xxv)
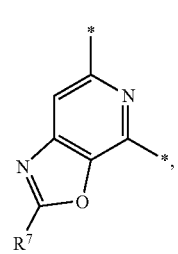
(xxvi)
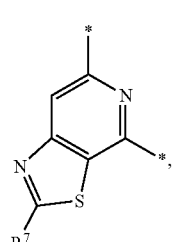
(xxvii)
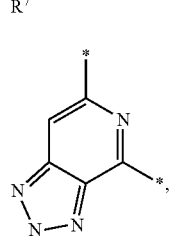
(xxviii)
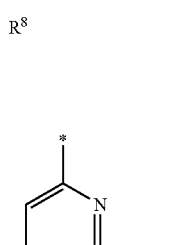 and (xxix)

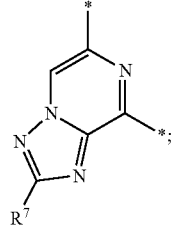

each R⁵ is independently selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-4}$alkyl, $C_{1-6}$haloalkoxy-$C_{1-6}$alkyl, halogen, —NH₂, —NH($C_{1-6}$alkyl), —N($C_{1-6}$ alkyl)₂, $C_{3-6}$cycloalkyl and 3-6 membered heterocyclyl;

each R⁶ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

each R⁷ is independently selected from the group consisting of $R^{a2}$ and $R^{b2}$;

each $R^{a2}$ is selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of —$OR^{c2}$, —$N(R^{c2})R^{c2}$, halogen, —CN, —C(=O)$R^{c2}$, —C(=O)$OR^{c2}$, —C(=O)N($R^{c2}$)$R^{c2}$, —C(=O)N(H)$OR^{c2}$, —C(=O)N($C_{1-4}$alkyl)$OR^{c2}$, —S(=O)₂$R^{c2}$, —S(=O)₂N($R^{c2}$)$R^{c2}$, —N(H)C(=O)$R^{c2}$, —N($C_{1-4}$alkyl)C(=O)$R^{c2}$, —N(H)C(=O)$OR^{c2}$, —N($C_{1-4}$alkyl)C(=O)$OR^{c2}$, —N(H)S(=O)₂$R^{c2}$, —N($C_{1-4}$alkyl)S(=O)₂$R^{c2}$ and the bivalent substituent =O;

each $R^{c2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d2}$ and/or $R^{e2}$;

each $R^{d2}$ is independently selected from the group consisting of —$OR^{e2}$, —$N(R^{e2})R^{e2}$, halogen, —CN, —C(=O)$R^{e2}$, —C(=O)$OR^{e2}$, —C(=O)N($R^{e2}$)$R^{e2}$, —C(=O)N(H)$OR^{e2}$, —C(=O)N($C_{1-4}$alkyl)$OR^{e2}$, —S(=O)₂$R^{e2}$, —S(=O)₂N($R^{e2}$)$R^{e2}$, —N(H)C(=O)$R^{e2}$, —N($C_{1-4}$alkyl)C(=O)$R^{e2}$, —N(H)C(=O)$OR^{e2}$, —N($C_{1-4}$alkyl)C(=O)$OR^{e2}$, —N(H)S(=O)₂$R^{e2}$, —N($C_{1-4}$alkyl)S(=O)₂$R^{e2}$ and the bivalent substituent =O;

each $R^{e2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —NH₂, —C(=O)$C_{1-4}$alkyl, —NH($C_{1-4}$alkyl), —N($C_{1-4}$alkyl)₂ and the bivalent substituent =O;

each R⁸ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

each R⁹ is independently selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-6}$alkyl, $C_{1-6}$haloalkoxy-$C_{1-6}$alkyl, halogen, —NH₂, —NH($C_{1-6}$alkyl), —N($C_{1-6}$ alkyl)₂, $C_{3-6}$cycloalkyl and 3-6 membered heterocyclyl;

each R¹⁰ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl.

In another aspect [D2] the invention relates to a compound of formula (I) or a salt thereof, wherein

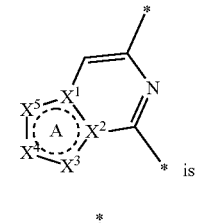 is (i)

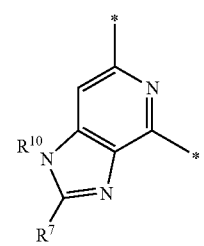

R⁷ is selected from the group consisting of $R^{a2}$ and $R^{b2}$;
$R^{a2}$ is selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of —$OR^{c2}$, —$N(R^{c2})R^{c2}$, halogen, —CN, —C(=O)$R^{c2}$, —C(=O)$OR^{c2}$, —C(=O)N($R^{c2}$)$R^{c2}$, —C(=O)N(H)$OR^{c2}$, —C(=O)N($C_{1-4}$alkyl)$OR^{c2}$, —S(=O)₂$R^{c2}$, —S(=O)₂N($R^{c2}$)$R^{c2}$, —N(H)C(=O)$R^{c2}$, —N($C_{1-4}$alkyl)C(=O)$R^{c2}$, —N(H)C (=O)OR$^{c2}$, —N(C$_{1-4}$alkyl)C(=O)OR$^{c2}$, —N(H)S(=O)$_2$R$^{c2}$, —N(C$_{1-4}$alkyl)S(=O)$_2$R$^{c2}$ and the bivalent substituent =O;

- each R$^{c2}$ is independently selected from the group consisting of hydrogen, C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl, wherein the C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl are all optionally substituted with one or more, identical or different R$^{d2}$ and/or R$^{e2}$;
- each R$^{d2}$ is independently selected from the group consisting of —OR$^{e2}$, —N(R$^{e2}$)R$^{e2}$, halogen, —CN, —C(=O)R$^{e2}$, —C(=O)OR$^{e2}$, —C(=O)N(R$^{e2}$)R$^{e2}$, —C(=O)N(H)OR$^{e2}$, —C(=O)N(C$_{1-4}$alkyl)OR$^{e2}$, —S(=O)$_2$R$^{e2}$, —S(=O)$_2$N(R$^{e2}$)R$^{e2}$, —N(H)C(=O)R$^{e2}$, —N(C$_{1-4}$alkyl)C(=O)R$^{e2}$, —N(H)C(=O)OR$^{e2}$, —N(C$_{1-4}$alkyl)C(=O)OR$^{e2}$, —N(H)S(=O)$_2$R$^{e2}$, —N(C$_{1-4}$alkyl)S(=O)$_2$R$^{e2}$ and the bivalent substituent =O;
- each R$^{e2}$ is independently selected from the group consisting of hydrogen, C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl, wherein the C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl are all optionally substituted with one or more, identical or different substituent(s) selected from the group consisting of C$_{1-6}$alkyl, C$_{1-6}$haloalkyl, C$_{3-10}$cycloalkyl, 3-11 membered heterocyclyl, C$_{6-10}$aryl, 5-10 membered heteroaryl, —OH, C$_{1-6}$alkoxy, C$_{1-4}$alkoxy-C$_{1-4}$alkyl, hydroxy-C$_{1-4}$alkyl, halogen, —CN, —NH$_2$, —C(=O)C$_{1-4}$alkyl, —NH(C$_{1-4}$alkyl), —N(C$_{1-4}$alkyl)$_2$ and the bivalent substituent =O;

R$^{10}$ is selected from the group consisting of hydrogen, C$_{1-6}$alkyl, C$_{1-6}$haloalkyl, C$_{1-6}$alkoxy-C$_{1-6}$alkyl, C$_{1-6}$haloalkoxy-C$_{1-6}$alkyl, C$_{3-6}$cycloalkyl and 3-6 membered heterocyclyl.

In another aspect [D3] the invention relates to a compound of formula (I) or a salt thereof, wherein

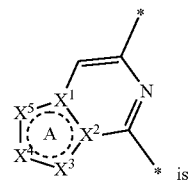

(ii)

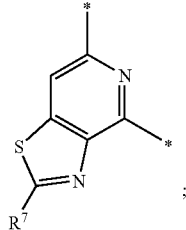

;

R$^7$ is selected from the group consisting of R$^{a2}$ and R$^{b2}$;

R$^{a2}$ is selected from the group consisting of hydrogen, C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl, wherein the C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl are all optionally substituted with one or more, identical or different R$^{b2}$ and/or R$^{c2}$;

- each R$^{b2}$ is independently selected from the group consisting of —OR$^{c2}$, —N(R$^{c2}$)R$^{c2}$, halogen, —CN, —C(=O)R$^{c2}$, —C(=O)OR$^{c2}$, —C(=O)N(R$^{c2}$)R$^{c2}$, —C(=O)N(H)OR$^{c2}$, —C(=O)N(C$_{1-4}$alkyl)OR$^{c2}$, —S(=O)$_2$R$^{c2}$, —S(=O)$_2$N(R$^{c2}$)R$^{c2}$, —N(H)C(=O)R$^{c2}$, —N(C$_{1-4}$alkyl)C(=O)R$^{c2}$, —N(H)C(=O)OR$^{c2}$, —N(C$_{1-4}$alkyl)C(=O)OR$^{c2}$, —N(H)S(=O)$_2$R$^{c2}$, —N(C$_{1-4}$alkyl)S(=O)$_2$R$^{c2}$ and the bivalent substituent =O;
- each R$^{c2}$ is independently selected from the group consisting of hydrogen, C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl, wherein the C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl are all optionally substituted with one or more, identical or different R$^{d2}$ and/or R$^{e2}$;
- each R$^{d2}$ is independently selected from the group consisting of —OR$^{e2}$, —N(R$^{e2}$)R$^{e2}$, halogen, —CN, —C(=O)R$^{e2}$, —C(=O)OR$^{e2}$, —C(=O)N(R$^{e2}$)R$^{e2}$, —C(=O)N(H)OR$^{e2}$, —C(=O)N(C$_{1-4}$alkyl)OR$^{e2}$, —S(=O)$_2$R$^{e2}$, —S(=O)$_2$N(R$^{e2}$)R$^{e2}$, —N(H)C(=O)R$^{e2}$, —N(C$_{1-4}$alkyl)C(=O)R$^{e2}$, —N(H)C(=O)OR$^{e2}$, —N(C$_{1-4}$alkyl)C(=O)OR$^{e2}$, —N(H)S(=O)$_2$R$^{e2}$, —N(C$_{1-4}$alkyl)S(=O)$_2$R$^{e2}$ and the bivalent substituent =O;
- each R$^{e2}$ is independently selected from the group consisting of hydrogen, C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl, wherein the C$_{1-6}$alkyl, C$_{1-6}$haloalkyl, C$_{2-6}$alkenyl, C$_{2-6}$alkynyl, C$_{3-10}$cycloalkyl, C$_{4-10}$cycloalkenyl, 3-11 membered heterocyclyl, C$_{6-10}$aryl and 5-10 membered heteroaryl are all optionally substituted with one or more, identical or different substituent(s) selected from the group consisting of C$_{1-6}$alkyl, C$_{1-6}$haloalkyl, C$_{3-10}$cycloalkyl, 3-11 membered heterocyclyl, C$_{6-10}$aryl, 5-10 membered heteroaryl, —OH, C$_{1-6}$alkoxy, C$_{1-4}$alkoxy-C$_{1-4}$alkyl, hydroxy-C$_{1-4}$alkyl, halogen, —CN, —NH$_2$, —C(=O)C$_{1-4}$alkyl, —NH(C$_{1-4}$alkyl), —N(C$_{1-4}$alkyl)$_2$ and the bivalent substituent =O.

In another aspect [D4] the invention relates to a compound of formula (I) or a salt thereof, wherein

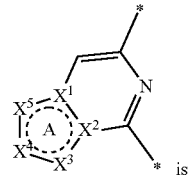

is

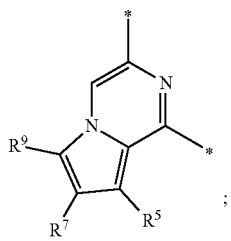
(iii)

R⁵ is selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-4}$alkyl, $C_{1-6}$haloalkoxy-$C_{1-6}$alkyl, halogen, —NH$_2$, —NH($C_{1-6}$alkyl), —N($C_{1-6}$alkyl)$_2$, $C_{3-6}$cycloalkyl and 3-6 membered heterocyclyl;

R⁷ is selected from the group consisting of $R^{a2}$ and $R^{b2}$;

$R^{a2}$ is selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of —OR$^{c2}$, —N(R$^{c2}$)R$^{c2}$, halogen, —CN, —C(=O)R$^{c2}$, —C(=O)OR$^{c2}$, —C(=O)N(R$^{c2}$)R$^{c2}$, —C(=O)N(H)OR$^{c2}$, —C(=O)N($C_{1-4}$alkyl)OR$^{c2}$, —S(=O)$_2$R$^{c2}$, —S(=O)$_2$N(R$^{c2}$)R$^{c2}$, —N(H)C(=O)R$^{c2}$, —N($C_{1-4}$alkyl)C(=O)R$^{c2}$, —N(H)C(=O)OR$^{c2}$, —N($C_{1-4}$alkyl)C(=O)OR$^{c2}$, —N(H)S(=O)$_2$R$^{c2}$, —N($C_{1-4}$alkyl)S(=O)$_2$R$^{c2}$ and the bivalent substituent =O;

each $R^{c2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d2}$ and/or $R^{e2}$;

each $R^{d2}$ is independently selected from the group consisting of —OR$^{e2}$, —N(R$^{e2}$)R$^{e2}$, halogen, —CN, —C(=O)R$^{e2}$, —C(=O)OR$^{e2}$, —C(=O)N(R$^{e2}$)R$^{e2}$, —C(=O)N(H)OR$^{e2}$, —C(=O)N($C_{1-4}$alkyl)OR$^{e2}$, —S(=O)$_2$R$^{e2}$, —S(=O)$_2$N(R$^{e2}$)R$^{e2}$, —N(H)C(=O)R$^{e2}$, —N($C_{1-4}$alkyl)C(=O)R$^{e2}$, —N(H)C(=O)OR$^{e2}$, —N($C_{1-4}$alkyl)C(=O)OR$^{e2}$, —N(H)S(=O)$_2$R$^{e2}$, —N($C_{1-4}$alkyl)S(=O)$_2$R$^{e2}$ and the bivalent substituent =O;

each $R^{e2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —NH$_2$, —C(=O)$C_{1-4}$alkyl, —NH($C_{1-4}$alkyl), —N($C_{1-4}$alkyl)$_2$ and the bivalent substituent =O;

R⁹ is selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-6}$alkyl, $C_{1-6}$haloalkoxy-$C_{1-6}$alkyl, halogen, —NH$_2$, —NH($C_{1-6}$alkyl), —N($C_{1-6}$alkyl)$_2$, $C_{3-6}$cycloalkyl and 3-6 membered heterocyclyl.

In another aspect [D5] the invention relates to a compound of formula (I) or a salt thereof, wherein

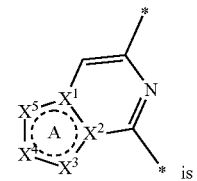
is

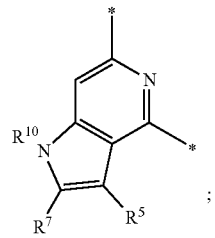
(iv)

R⁵ is selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-4}$alkyl, $C_{1-6}$haloalkoxy-$C_{1-6}$alkyl, halogen, —NH$_2$, —NH($C_{1-6}$alkyl), —N($C_{1-6}$alkyl)$_2$, $C_{3-6}$cycloalkyl and 3-6 membered heterocyclyl;

R⁷ is selected from the group consisting of $R^{a2}$ and $R^{b2}$;

$R^{a2}$ is selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of —OR$^{c2}$, —N(R$^{c2}$)R$^{c2}$, halogen, —CN, —C(=O)R$^{c2}$, —C(=O)OR$^{c2}$, —C(=O)N(R$^{c2}$)R$^{c2}$, —C(=O)N(H)OR$^{c2}$, —C(=O)N($C_{1-4}$alkyl)OR$^{c2}$, —S(=O)$_2$R$^{c2}$, —S(=O)$_2$N(R$^{c2}$)R$^{c2}$, —N(H)C(=O)R$^{c2}$, —N($C_{1-4}$alkyl)C(=O)R$^{c2}$, —N(H)C(=O)OR$^{c2}$, —N($C_{1-4}$alkyl)C(=O)OR$^{c2}$, —N(H)S(=O)$_2$R$^{c2}$, —N($C_{1-4}$alkyl)S(=O)$_2$R$^{c2}$ and the bivalent substituent =O;

each $R^{c2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d2}$ and/or $R^{e2}$;

each $R^{d2}$ is independently selected from the group consisting of —$OR^{e2}$, —$N(R^{e2})R^{e2}$, halogen, —CN, —C(=O)$R^{e2}$, —C(=O)$OR^{e2}$, —C(=O)N($R^{e2}$)$R^{e2}$, —C(=O)N(H)$OR^{e2}$, —C(=O)N($C_{1-4}$alkyl)$OR^{e2}$, —S(=O)$_2R^{e2}$, —S(=O)$_2$N($R^{e2}$)$R^{e2}$, —N(H)C(=O)$R^{e2}$, —N($C_{1-4}$alkyl)C(=O)$R^{e2}$, —N(H)C(=O)$OR^{e2}$, —N($C_{1-4}$alkyl)C(=O)$OR^{e2}$, —N(H)S(=O)$_2R^{e2}$, —N($C_{1-4}$alkyl)S(=O)$_2R^{e2}$ and the bivalent substituent =O;

each $R^{e2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —$NH_2$, —C(=O)$C_{1-4}$alkyl, —NH($C_{1-4}$alkyl), —N($C_{1-4}$alkyl)$_2$ and the bivalent substituent =O;

$R^{10}$ is selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl.

In another aspect [D6] the invention relates to a compound of formula (I) or a salt thereof, wherein

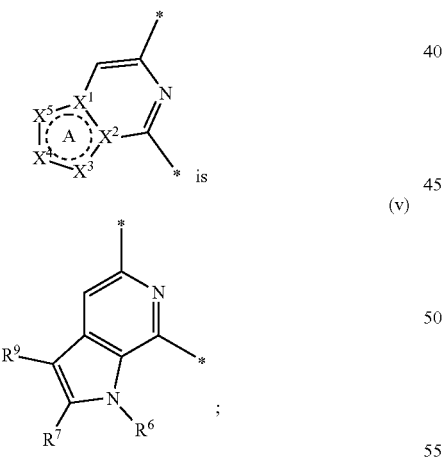

is (v)

$R^6$ is selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

$R^7$ is selected from the group consisting of $R^{a2}$ and $R^{b2}$;

$R^{a2}$ is selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of —$OR^{c2}$, —$N(R^{c2})R^{c2}$, halogen, —CN, —C(=O)$R^{c2}$, —C(=O)$OR^{c2}$, —C(=O)N($R^{c2}$)$R^{c2}$, —C(=O)N(H)$OR^{c2}$, —C(=O)N($C_{1-4}$alkyl)$OR^{c2}$, —S(=O)$_2R^{c2}$, —S(=O)$_2$N($R^{c2}$)$R^{c2}$, —N(H)C(=O)$R^{c2}$, —N($C_{1-4}$alkyl)C(=O)$R^{c2}$, —N(H)C(=O)$OR^{c2}$, —N($C_{1-4}$alkyl)C(=O)$OR^{c2}$, —N(H)S(=O)$_2R^{c2}$, —N($C_{1-4}$alkyl)S(=O)$_2R^{c2}$ and the bivalent substituent =O;

each $R^{c2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d2}$ and/or $R^{e2}$;

each $R^{d2}$ is independently selected from the group consisting of —$OR^{e2}$, —$N(R^{e2})R^{e2}$, halogen, —CN, —C(=O)$R^{e2}$, —C(=O)$OR^{e2}$, —C(=O)N($R^{e2}$)$R^{e2}$, —C(=O)N(H)$OR^{e2}$, —C(=O)N($C_{1-4}$alkyl)$OR^{e2}$, —S(=O)$_2R^{e2}$, —S(=O)$_2$N($R^{e2}$)$R^{e2}$, —N(H)C(=O)$R^{e2}$, —N($C_{1-4}$alkyl)C(=O)$R^{e2}$, —N(H)C(=O)$OR^{e2}$, —N($C_{1-4}$alkyl)C(=O)$OR^{e2}$, —N(H)S(=O)$_2R^{e2}$, —N($C_{1-4}$alkyl)S(=O)$_2R^{e2}$ and the bivalent substituent =O;

each $R^{e2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —$NH_2$, —C(=O)$C_{1-4}$alkyl, —NH($C_{1-4}$alkyl), —N($C_{1-4}$alkyl)$_2$ and the bivalent substituent =O;

$R^9$ is selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-6}$alkyl, $C_{1-6}$haloalkoxy-$C_{1-6}$alkyl, halogen, —$NH_2$, —NH($C_{1-6}$alkyl), —N($C_{1-6}$alkyl)$_2$, $C_{3-6}$cycloalkyl and 3-6 membered heterocyclyl.

In another aspect [D7] the invention relates to a compound of formula (I) or a salt thereof, wherein

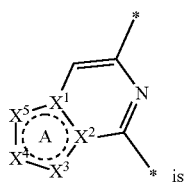

is

-continued (vi)

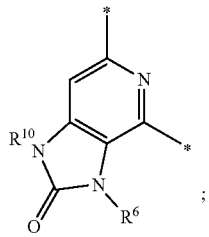

-continued (viii)

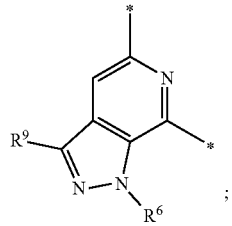

$R^6$ is selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

$R^{10}$ is selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl.

In another aspect [D8] the invention relates to a compound of formula (I) or a salt thereof, wherein

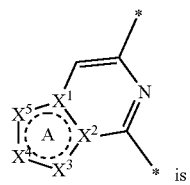 is (vii)

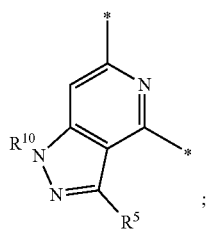

$R^5$ is selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-4}$alkyl, $C_{1-6}$haloalkoxy-$C_{1-6}$alkyl, halogen, —NH$_2$, —NH($C_{1-6}$alkyl), —N($C_{1-6}$alkyl)$_2$, $C_{3-6}$cycloalkyl and 3-6 membered heterocyclyl;

$R^{10}$ is selected from the group consisting of hydrogen, $C_{1-6}$alkyl, $C_{1-6}$haloalkyl, $C_{1-6}$alkoxy-$C_{1-6}$-alkyl, $C_{1-6}$haloalkoxy-$C_{1-6}$alkyl, $C_{3-6}$cycloalkyl and 3-6 membered heterocyclyl.

In another aspect [D9] the invention relates to a compound of formula (I) or a salt thereof, wherein

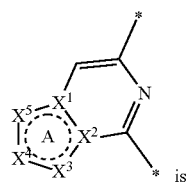 is $R^6$ is selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

$R^9$ is selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-6}$alkyl, $C_{1-6}$haloalkoxy-$C_{1-6}$alkyl, halogen, —NH$_2$, —NH($C_{1-6}$alkyl), —N($C_{1-6}$alkyl)$_2$, $C_{3-6}$cycloalkyl and 3-6 membered heterocyclyl.

The following aspects [E1] to [E3] are sub-aspects of aspects [D0], [D1], [D4], [D5] and [D8] in respect of residue $R^1$:

In one sub-aspect [E1] the invention relates to a compound of formula (I) or a salt thereof according to aspects [D0], [D1], [D4], [D5] and [D8], wherein
  each $R^5$ is independently selected from the group consisting of hydrogen, $C_{1-4}$alkyl, $C_{1-4}$haloalkyl, $C_{1-4}$alkoxy, $C_{1-4}$haloalkoxy.

In another sub-aspect [E2] the invention relates to a compound of formula (I) or a salt thereof according to aspects [D0], [D1], [D4], [D5] and [D8], wherein
  each $R^5$ is $C_{1-4}$alkyl.

In another sub-aspect [E3] the invention relates to a compound of formula (I) or a salt thereof according to aspects [D0], [D1], [D4], [D5] and [D8], wherein
  each $R^5$ is methyl.

The following aspects [F1] to [F3] are sub-aspects of aspects [D0], [D1], [D6], [D7] and [D9] in respect of residue $R^6$:

In one sub-aspect [F1] the invention relates to a compound of formula (I) or a salt thereof according to aspects [D0], [D1], [D6], [D7] and [D9], wherein
  each $R^6$ is independently selected from the group consisting of hydrogen, $C_{1-4}$alkyl and $C_{1-4}$haloalkyl.

In another sub-aspect [F2] the invention relates to a compound of formula (I) or a salt thereof according to aspects [D0], [D1], [D6], [D7] and [D9], wherein
  each $R^6$ is $C_{1-4}$alkyl.

In another sub-aspect [F3] the invention relates to a compound of formula (I) or a salt thereof according to aspects [D0], [D1], [D6], [D7] and [D9], wherein
  each $R^6$ is methyl.

The following aspects [G1] and [G2] are sub-aspects of aspects [D0] and [D1] in respect of residue $R^8$:

In one sub-aspect [G1] the invention relates to a compound of formula (I) or a salt thereof according to aspects [D0] and [D1], wherein
  each $R^8$ is $C_{1-4}$alkyl.

In another sub-aspect [G2] the invention relates to a compound of formula (I) or a salt thereof according to aspects [D0] and [D1], wherein
  each $R^8$ is methyl.

The following aspects [H1] to [H3] are sub-aspects of aspects [D0], [D1], [D4], [D6] and [D9] in respect of residue $R^9$:

In one sub-aspect [H1] the invention relates to a compound of formula (I) or a salt thereof according to aspects [D0], [D1], [D4], [D6] and [D9], wherein
  each $R^9$ is independently selected from the group consisting of hydrogen, $C_{1-4}$alkyl, $C_{1-4}$haloalkyl.

In another sub-aspect [H2] the invention relates to a compound of formula (I) or a salt thereof according to aspects [D0], [D1], [D4], [D6] and [D9], wherein
  each $R^9$ is $C_{1-4}$alkyl.

In another sub-aspect [H3] the invention relates to a compound of formula (I) or a salt thereof according to aspects [D0], [D1], [D4], [D6] and [D9], wherein
  each $R^9$ is methyl.

The following aspects [I1] to [I3] are sub-aspects of aspects [D0], [D1], [D2], [D5], [D7] and [D8] in respect of residue $R^{10}$:

In one sub-aspect [I1] the invention relates to a compound of formula (I) or a salt thereof according to aspects [D0], [D1], [D2], [D5], [D7] and [D8], wherein
  each $R^{10}$ is independently selected from the group consisting of hydrogen, $C_{1-4}$alkyl, $C_{1-4}$haloalkyl, $C_{3-6}$cycloalkyl and 3-6 membered heterocyclyl.

In another sub-aspect [I2] the invention relates to a compound of formula (I) or a salt thereof according to aspects [D0], [D1], [D2], [D5], [D7] and [D8], wherein
  each $R^{10}$ is $C_{1-4}$alkyl.

In another sub-aspect [I3] the invention relates to a compound of formula (I) or a salt thereof according to aspects [D0], [D1], [D2], [D5], [D7] and [D8], wherein
  each $R^{10}$ is independently selected from the group consisting of methyl, ethyl and isopropyl.

The following aspects [J1] to [J9] are sub-aspects of aspects [D0], [D1], [D2], [D3], [D4], [D5] and [D6] in respect of residue $R^7$:

In one sub-aspect [J1] the invention relates to a compound of formula (I) or a salt thereof according to aspects [D0], [D1], [D2], [D3], [D4], [D5] and [D6], wherein
  each $R^7$ is independently selected from the group consisting of $R^{a2}$ and $R^{b2}$;
    $R^{a2}$ is selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different $R^{b2}$ and/or $R^{c2}$;
    each $R^{b2}$ is independently selected from the group consisting of —$OR^{c2}$, —$N(R^{c2})R^{c2}$, halogen, —CN, —C(=O)$R^{c2}$, —C(=O)O$R^{c2}$, —C(=O)N($R^{c2}$)$R^{c2}$, —C(=O)N(H)O$R^{c2}$, —C(=O)N($C_{1-4}$alkyl)O$R^{c2}$, —S(=O)$_2$N($R^{c2}$)$R^{c2}$, —N(H)C(=O)$R^{c2}$, —N($C_{1-4}$alkyl)C(=O)$R^{c2}$, —N(H)C(=O)O$R^{c2}$, —N($C_{1-4}$alkyl)C(=O)O$R^{c2}$, —N(H)S(=O)$_2$$R^{c2}$, —N($C_{1-4}$alkyl)S(=O)$_2$$R^{c2}$ and the bivalent substituent =O;
    each $R^{c2}$ is independently selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different $R^{d2}$ and/or $R^{e2}$;
    each $R^{d2}$ is independently selected from the group consisting of —$OR^{e2}$, —$N(R^{e2})R^{e2}$, halogen, —CN, —C(=O)$R^{e2}$, —C(=O)O$R^{e2}$, —C(=O)N($R^{e2}$)$R^{e2}$, —C(=O)N(H)O$R^{e2}$, —C(=O)N($C_{1-4}$alkyl)O$R^{e2}$, —S(=O)$_2$N($R^{e2}$)$R^{e2}$, —N(H)C(=O)$R^{e2}$, —N($C_{1-4}$alkyl)C(=O)$R^{e2}$, —N(H)C(=O)O$R^{e2}$, —N($C_{1-4}$alkyl)C(=O)O$R^{e2}$, —N(H)S(=O)$_2$$R^{e2}$, —N($C_{1-4}$alkyl)S(=O)$_2$$R^{e2}$ and the bivalent substituent =O;
    each $R^{e2}$ is independently selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —$NH_2$, —C(=O)$C_{1-4}$alkyl, —NH($C_{1-4}$alkyl), —N($C_{1-4}$alkyl)$_2$ and the bivalent substituent =O.

In another sub-aspect [J2] the invention relates to a compound of formula (I) or a salt thereof according to aspects [D0], [D1], [D2], [D3], [D4], [D5] and [D6], wherein
  each $R^7$ is independently selected from the group consisting of $R^{a2}$ and $R^{b2}$;
    $R^{a2}$ is selected from the group consisting of hydrogen, $C_{1-6}$alkyl, $C_{1-6}$haloalkyl, $C_{3-10}$cycloalkyl, 3-11 membered heterocyclyl, phenyl and 5-6 membered heteroaryl, wherein the $C_{1-6}$alkyl, $C_{1-6}$haloalkyl, $C_{3-10}$cycloalkyl, 3-11 membered heterocyclyl, phenyl and 5-6 membered heteroaryl are all optionally substituted with one or more, identical or different $R^{b2}$ and/or $R^{c2}$;
    each $R^{b2}$ is independently selected from the group consisting of —$OR^{c2}$, —$N(R^{c2})R^{c2}$, halogen, —C(=O)$R^{c2}$, —C(=O))O$R^{c2}$, —C(=O)N($R^{c2}$)$R^{c2}$, —C(=O)N(H)O$R^{c2}$, —C(=O)N($C_{1-4}$alkyl)O$R^{c2}$ and the bivalent substituent =O;
    each $R^{c2}$ is independently selected from the group consisting of hydrogen, $C_{1-6}$alkyl, $C_{1-6}$haloalkyl, $C_{3-10}$cycloalkyl, 3-11 membered heterocyclyl, phenyl and 5-6 membered heteroaryl, wherein the $C_{1-6}$alkyl, $C_{1-6}$haloalkyl, $C_{3-10}$cycloalkyl, 3-11 membered heterocyclyl, phenyl and 5-6 membered heteroaryl are all optionally substituted with one or more, identical or different $R^{d2}$ and/or $R^{e2}$;
    each $R^{d2}$ is independently selected from the group consisting of —$OR^{e2}$, —$N(R^{e2})R^{e2}$, halogen, —C(=O)$R^{e2}$, —C(=O)O$R^{e2}$, —C(=O)N($R^{e2}$)$R^{e2}$, —C(=O)N(H)O$R^{e2}$, —C(=O)N($C_{1-4}$alkyl)O$R^{e2}$ and the bivalent substituent =O;
    each $R^{e2}$ is independently selected from the group consisting of hydrogen, $C_{1-6}$alkyl, $C_{1-6}$haloalkyl, $C_{3-10}$cycloalkyl, 3-11 membered heterocyclyl, phenyl and 5-6 membered heteroaryl, wherein the $C_{1-6}$alkyl, $C_{1-6}$haloalkyl, $C_{3-10}$cycloalkyl, 3-11 membered heterocyclyl, phenyl and 5-6 membered heteroaryl are all optionally substituted with one or more, identical or different substituent(s) selected from the group consisting of halogen and the bivalent substituent =O.

In another sub-aspect [J3] the invention relates to a compound of formula (I) or a salt thereof according to aspects [D0], [D1], [D2], [D3], [D4], [D5] and [D6], wherein each $R^7$ is independently selected from the group consisting of $R^{a2}$ and $R^{b2}$;
  $R^{a2}$ is selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different $R^{b2}$ and/or $R^{c2}$;
  each $R^{b2}$ is independently selected from the group consisting of —$OR^{c2}$, —$N(R^{c2})R^{c2}$, halogen, —$C(\!=\!O)R^{c2}$, —$C(\!=\!O)OR^{c2}$, —$C(\!=\!O)N(R^{c2})R^{c2}$, —$C(\!=\!O)N(H)OR^{c2}$ and —$C(\!=\!O)N(C_{1-4}$alkyl$)OR^{c2}$;
  each $R^{c2}$ is independently selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different $R^{d2}$ and/or $R^{e2}$;
  each $R^{d2}$ is independently selected from the group consisting of —$OR^{e2}$, —$N(R^{e2})R^{e2}$, halogen, —$C(\!=\!O)R^{e2}$, —$C(\!=\!O)OR^{e2}$ and the bivalent substituent =O;
  each $R^{e2}$ is independently selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different halogen.

In another sub-aspect [J3a] the invention relates to a compound of formula (I) or a salt thereof according to aspects [D0], [D1], [D2], [D3], [D4], [D5] and [D6], wherein
  each $R^7$ is independently selected from the group consisting of $R^{a2}$ and $R^{b2}$;
  $R^{a2}$ is selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different $R^{b2}$ and/or $R^{c2}$;
  each $R^{b2}$ is independently selected from the group consisting of —$OR^{c2}$, —$N(R^{c2})R^{c2}$, halogen, —$C(\!=\!O)R^{c2}$, —$C(\!=\!O)OR^{c2}$, —$C(\!=\!O)N(R^{c2})R^{c2}$, —$C(\!=\!O)N(H)OR^{c2}$ and —$C(\!=\!O)N(C_{1-4}$alkyl$)OR^{c2}$;
  each $R^{c2}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different $R^{d2}$ and/or $R^{e2}$;
  each $R^{d2}$ is independently selected from the group consisting of —$OR^{e2}$, —$N(R^{e2})R^{e2}$, halogen, —$C(\!=\!O)R^{e2}$, —$C(\!=\!O)OR^{e2}$ and the bivalent substituent =O;
  each $R^{e2}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

In another sub-aspect [J4] the invention relates to a compound of formula (I) or a salt thereof according to aspects [D0], [D1], [D2], [D3], [D4], [D5] and [D6], wherein
  each $R^7$ is independently selected from the group consisting of $R^{a2}$ and $R^{b2}$;
  $R^{a2}$ is selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different $R^{b2}$ and/or $R^{c2}$;
  each $R^{b2}$ is independently selected from the group consisting of —$N(R^{c2})R^{c2}$, halogen, —$C(\!=\!O)R^{c2}$ and —$C(\!=\!O)OR^{c2}$;
  each $R^{c2}$ is independently selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different $R^{d2}$ and/or $R^{e2}$;
  each $R^{d2}$ is independently selected from the group consisting of —$OR^{e2}$ and —$C(\!=\!O)OR^{e2}$;
  each $R^{e2}$ is independently selected from the group consisting of hydrogen and $C_{1-6}$alkyl.

In another sub-aspect [J4a] the invention relates to a compound of formula (I) or a salt thereof according to aspects [D0], [D1], [D2], [D3], [D4], [D5] and [D6], wherein
  each $R^7$ is independently selected from the group consisting of $R^{a2}$ and $R^{b2}$;
  $R^{a2}$ is selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different $R^{b2}$ and/or $R^{c2}$;
  each $R^{b2}$ is independently selected from the group consisting of —$N(R^{c2})R^{c2}$, halogen, —$C(\!=\!O)R^{c2}$ and —$C(\!=\!O)OR^{c2}$;
  each $R^{c2}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different $R^{d2}$ and/or $R^{e2}$;
  each $R^{d2}$ is independently selected from the group consisting of —$OR^{e2}$ and —$C(\!=\!O)OR^{e2}$;
  each $R^{e2}$ is independently selected from the group consisting of hydrogen, $C_{3-10}$cycloalkyl and $C_{1-6}$alkyl.

In another sub-aspect [J5] the invention relates to a compound of formula (I) or a salt thereof according to aspects [D0], [D1], [D2], [D3], [D4], [D5] and [D6], wherein
  each $R^7$ is $R^{a2}$;
  $R^{a2}$ is 3-11 membered heterocyclyl optionally substituted with one or more, identical or different $R^{b2}$ and/or $R^{c2}$;
  each $R^{b2}$ is independently selected from the group consisting of halogen, —$C(\!=\!O)R^{c2}$ and —$C(\!=\!O)OR^{c2}$;
  each $R^{c2}$ is $C_{1-6}$alkyl optionally substituted with one or more, identical or different $R^{d2}$ and/or $R^{e2}$;
  each $R^{d2}$ is independently selected from the group consisting of —$OR^{e2}$ and —$C(\!=\!O)OR^{e2}$;
  each $R^{e2}$ is independently selected from the group consisting of hydrogen and $C_{1-6}$alkyl.

In another sub-aspect [J6] the invention relates to a compound of formula (I) or a salt thereof according to aspects [D0], [D1], [D2], [D3], [D4], [D5] and [D6], wherein
  each $R^7$ is independently selected from the group consisting of hydrogen, $C_{1-4}$alkyl,

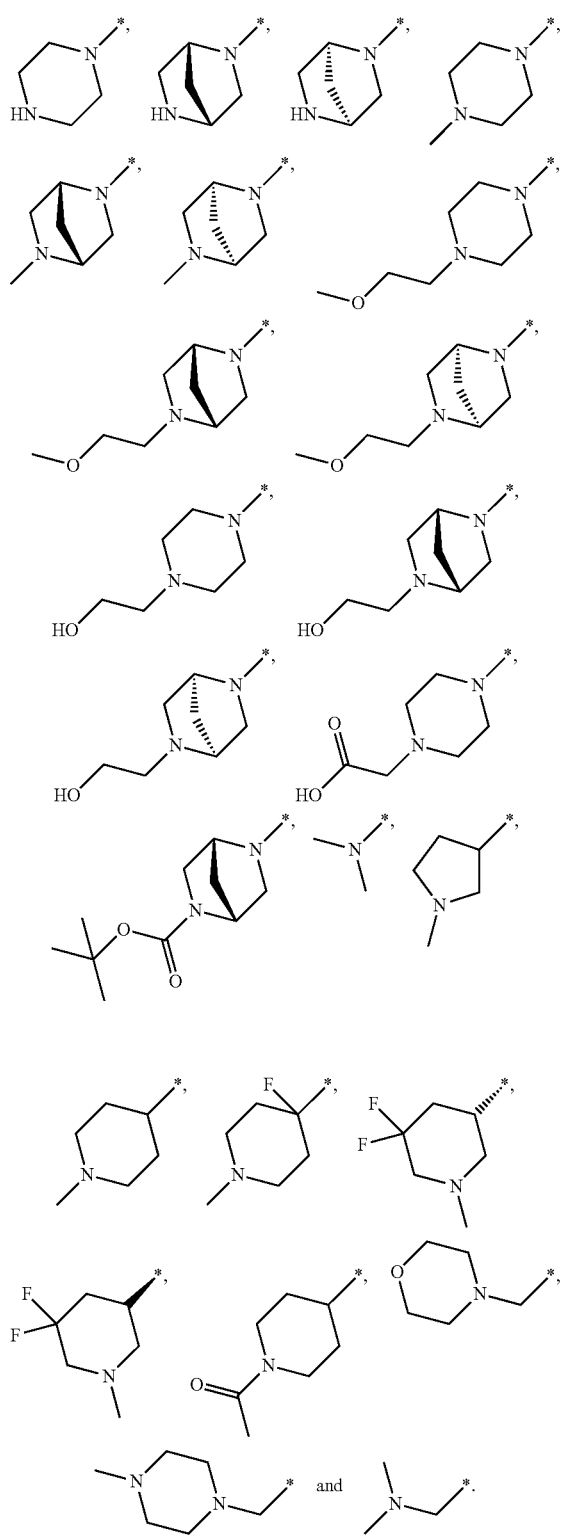
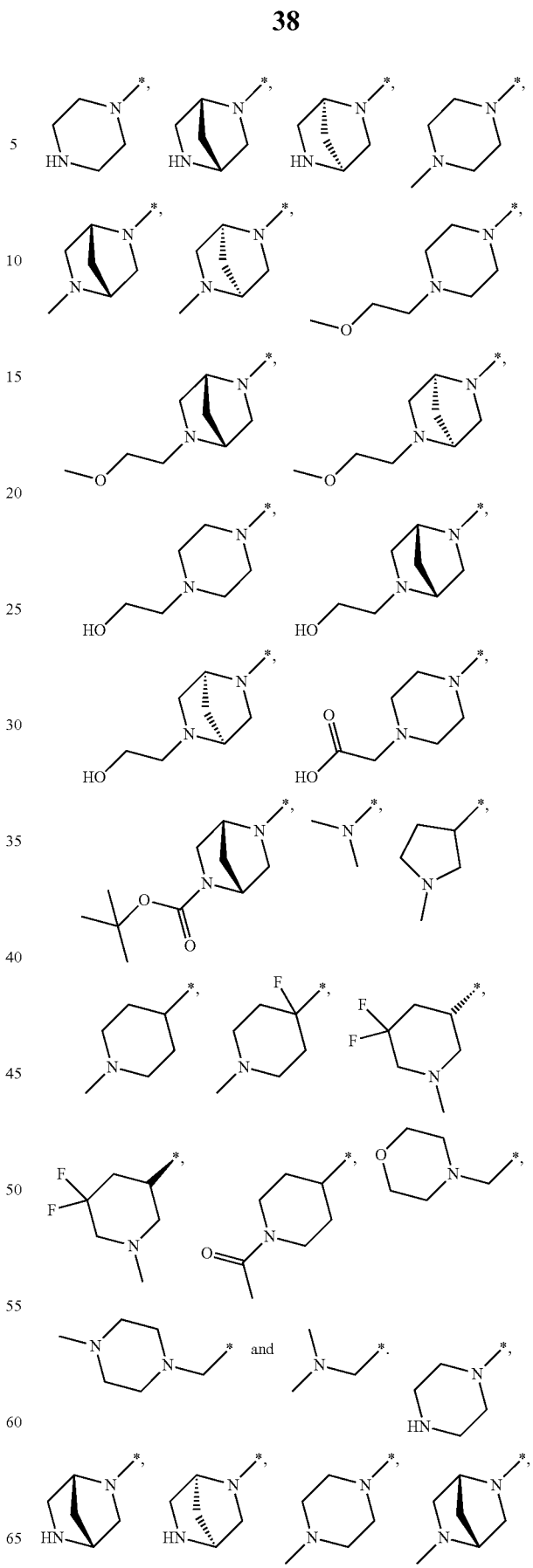
In another sub-aspect [J6a] the invention relates to a compound of formula (I) or a salt thereof according to aspects [D0], [D1], [D2], [D3], [D4], [D5] and [D6], wherein
each $R^7$ is independently selected from the group consisting of hydrogen, $C_{1-4}$alkyl,

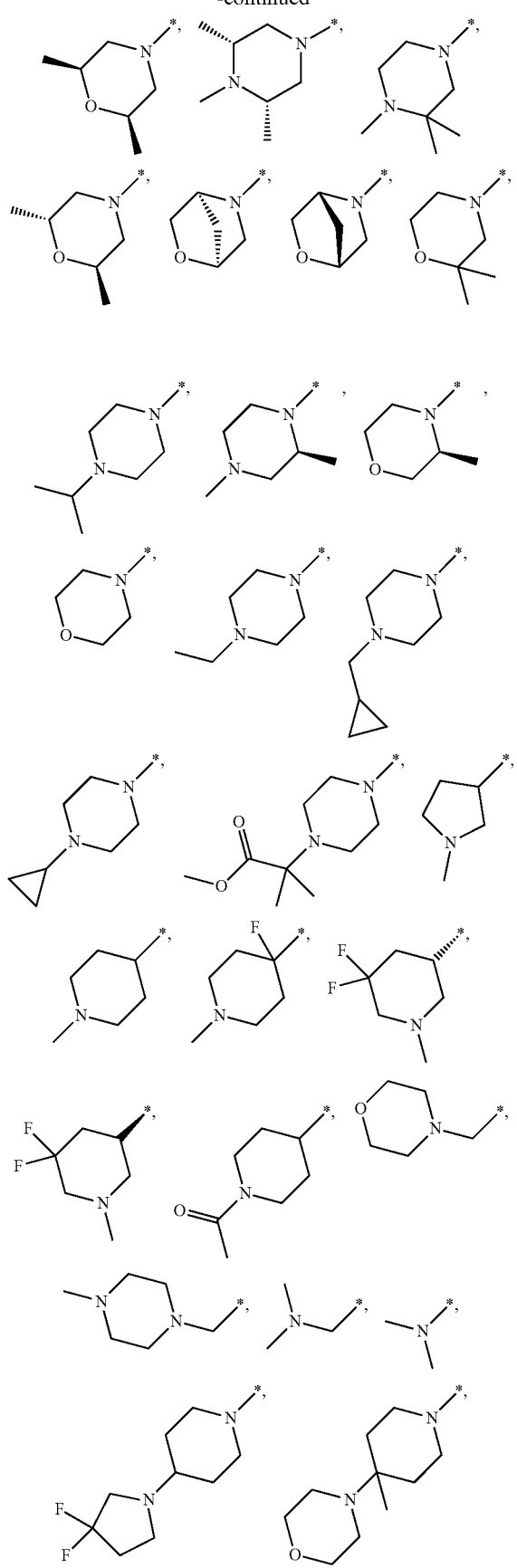
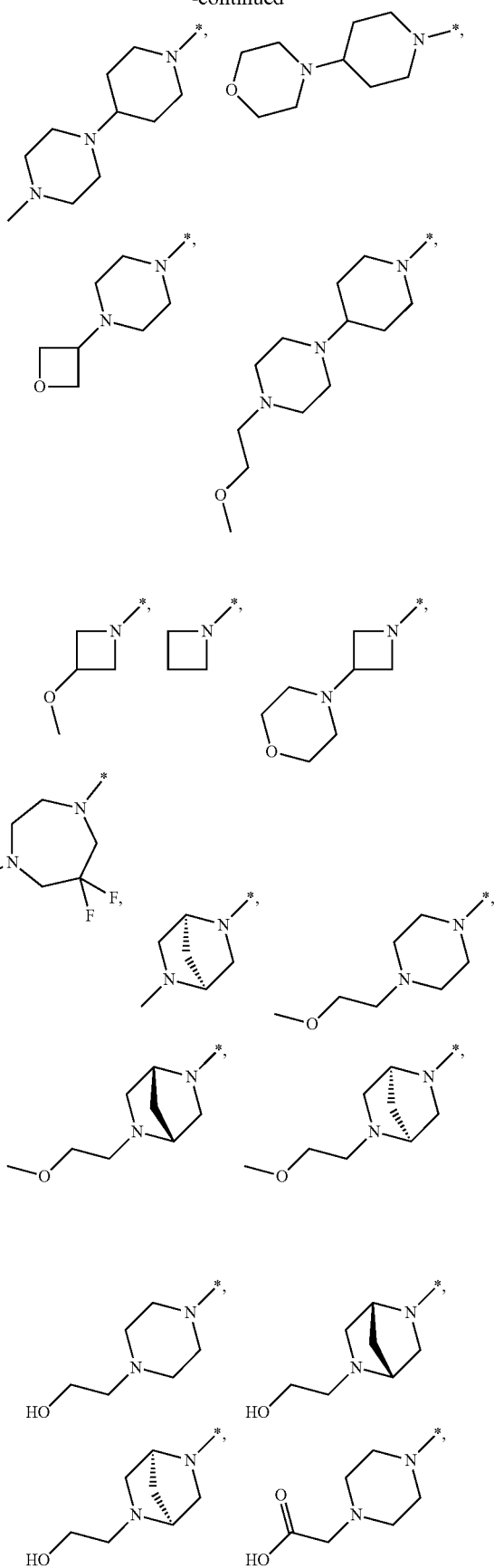

41
-continued
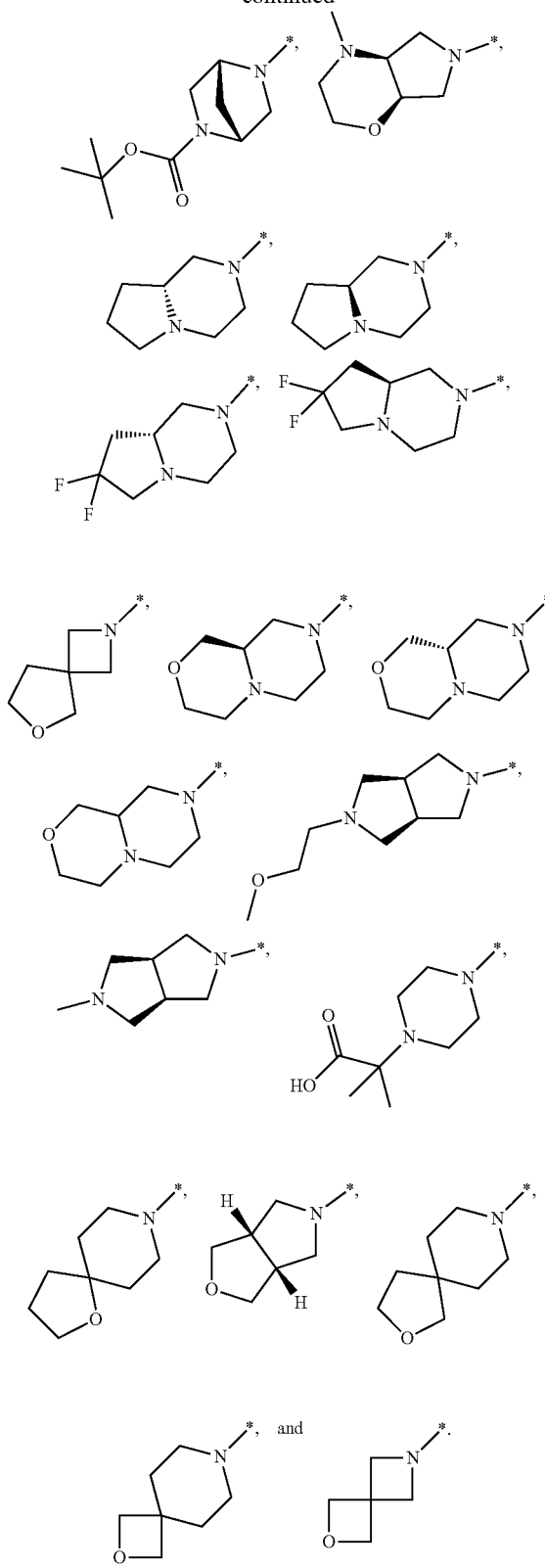
In another sub-aspect [J6b] the invention relates to a compound of formula (I) or a salt thereof according to aspects [D0], [D1], [D2], [D3], [D4], [D5] and [D6], wherein
42
each $R^7$ is independently selected from the group consisting of
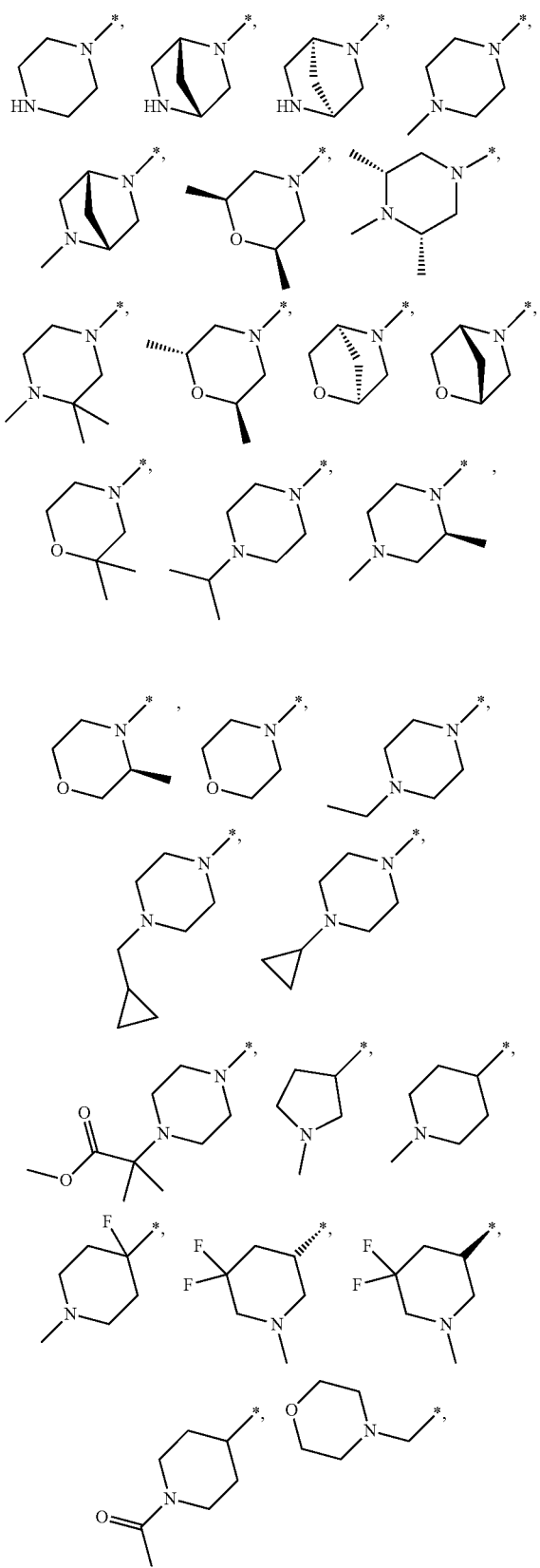

43
-continued
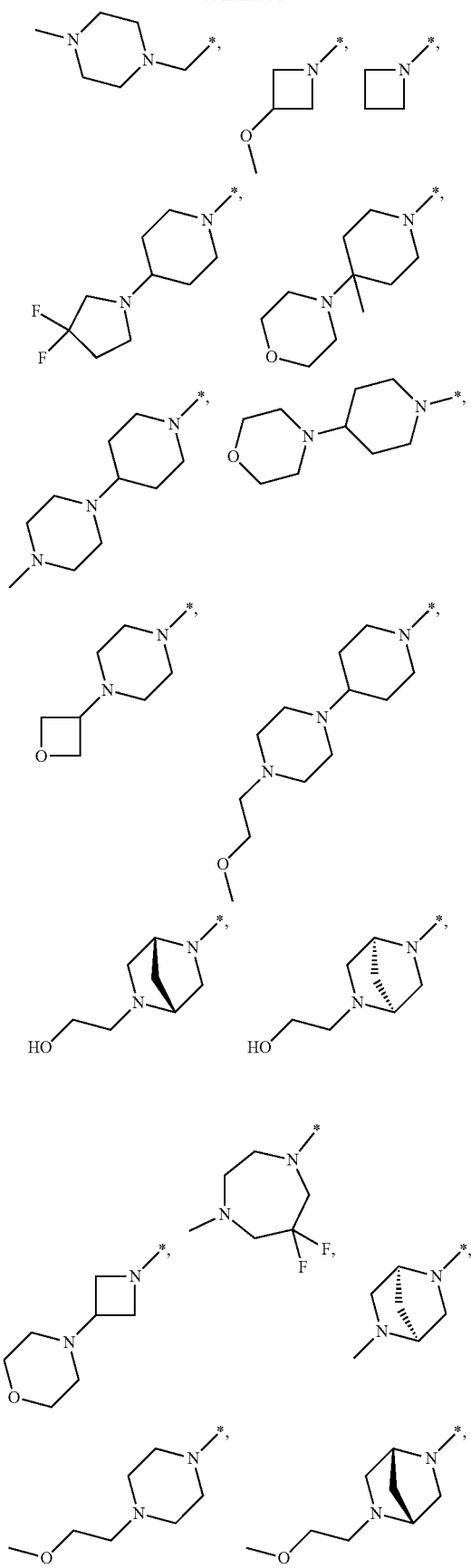
44
-continued
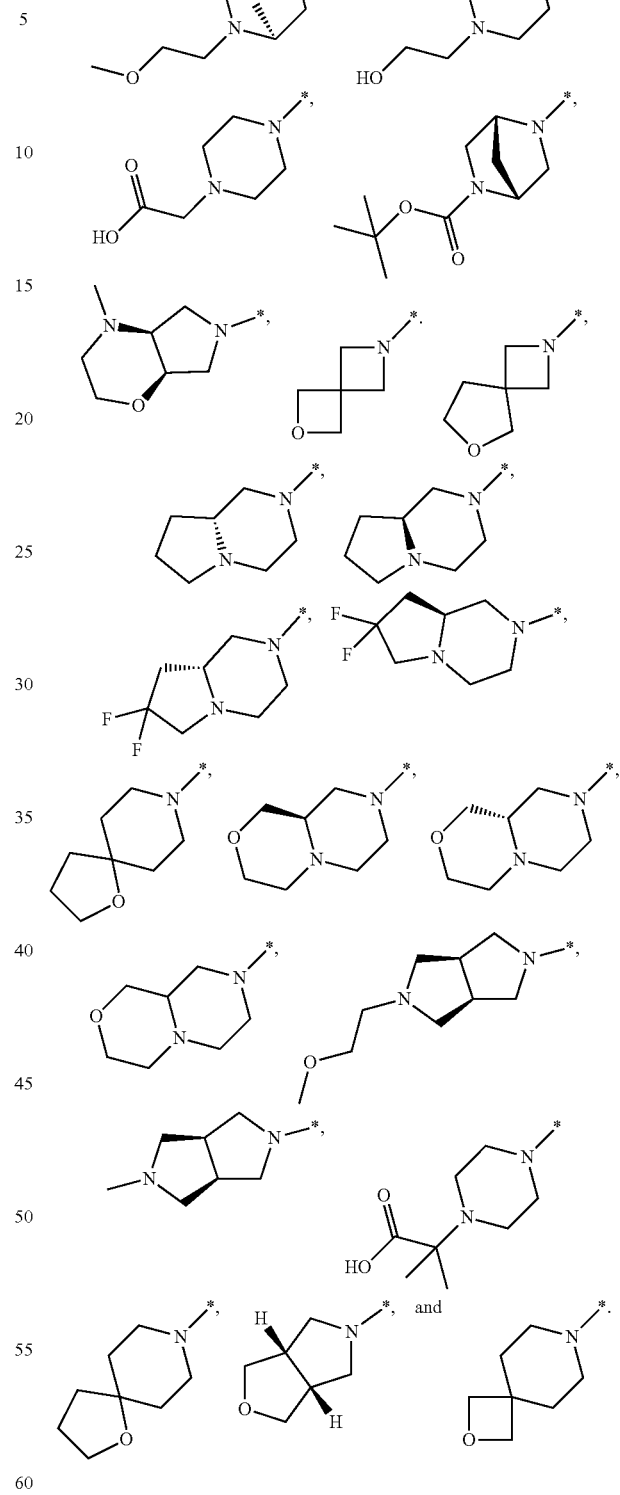
In another sub-aspect [J7] the invention relates to a compound of formula (I) or a salt thereof according to aspects [D0], [D1], [D2], [D3], [D4], [D5] and [D6], wherein
 each $R^7$ is $R^{b2}$;
 each $R^{b2}$ is independently selected from the group consisting of —C(=O)$R^{c2}$, —C(=O)O$R^{c2}$, —C(=O)N(R$^{c2}$)R$^{c2}$, —C(=O)N(H)OR$^{c2}$ and —C(=O)N(C$_{1-4}$alkyl)OR$^{c2}$;

each R$^{c2}$ is independently selected from the group consisting of hydrogen, C$_{1-6}$alkyl and 3-11 membered heterocyclyl, wherein the C$_{1-6}$alkyl and 3-11 membered heterocyclyl are all optionally substituted with one or more, identical or different R$^{d2}$ and/or R$^{e2}$;

each R$^{d2}$ is independently selected from the group consisting of —OR$^{e2}$, —N(R$^{e2}$)R$^{e2}$, halogen, —C(=O)R$^{e2}$, —C(=O)OR$^{e2}$ and the bivalent substituent =O;

each R$^{e2}$ is independently selected from the group consisting of hydrogen, C$_{1-6}$alkyl and 3-11 membered heterocyclyl, wherein the C$_{1-6}$alkyl and 3-11 membered heterocyclyl are all optionally substituted with one or more, identical or different halogen.

In another sub-aspect [J8] the invention relates to a compound of formula (I) or a salt thereof according to aspects [D0], [D1], [D2], [D3], [D4], [D5] and [D6], wherein each R$^7$ is R$^{b2}$;

each R$^{b2}$ is independently selected from the group consisting of —C(=O)R$^{c2}$, —C(=O)OR$^{c2}$, —C(=O)N(R$^{c2}$)R$^{c2}$ and —C(=O)N(C$_{1-4}$alkyl) OR$^{c2}$;

each R$^{c2}$ is independently selected from the group consisting of hydrogen, C$_{1-6}$alkyl and 3-11 membered heterocyclyl, wherein the C$_{1-6}$alkyl and 3-11 membered heterocyclyl are all optionally substituted with one or more, identical or different R$^{d2}$ and/or R$^{e2}$;

each R$^{d2}$ is independently selected from the group consisting of —OR$^{e2}$, halogen, —C(=O)R$^{e2}$ and the bivalent substituent =O;

each R$^{e2}$ is independently selected from the group consisting of hydrogen, C$_{1-6}$alkyl and 3-11 membered heterocyclyl.

In another sub-aspect [J9] the invention relates to a compound of formula (I) or a salt thereof according to aspects [D0], [D1], [D2], [D3], [D4], [D5] and [D6], wherein each R$^7$ is independently selected from the group consisting of

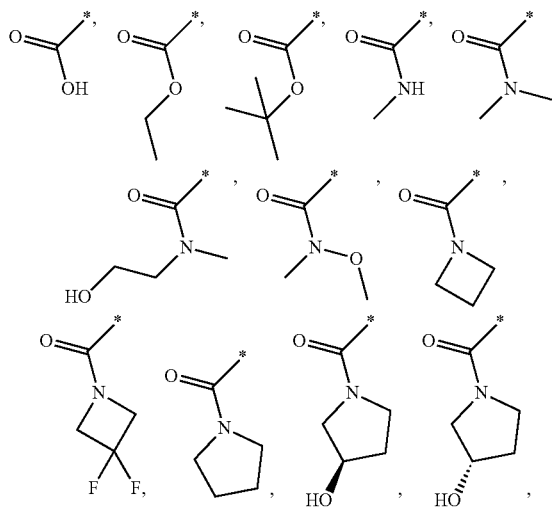

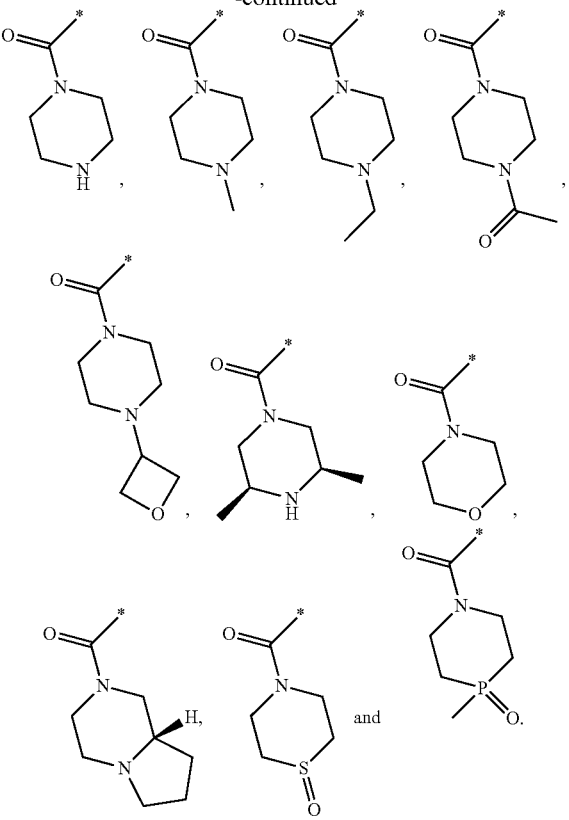

-continued

In another aspect [L1] the invention relates to a compound of formula (I) or a salt thereof according to aspect [D2] in combination with aspects [A5] or [A6].

In another aspect [L2] the invention relates to a compound of formula (I) or a salt thereof according to aspect [D2] or to aspect [L1] each of which is taken in combination with aspects [B3] or [B4].

In another aspect [L3] the invention relates to a compound of formula (I) or a salt thereof according to aspect [D2] or to aspects [L1] or [L2] each of which is taken in combination with aspects [I2] or [I3].

In another aspect [L4] the invention relates to a compound of formula (I) or a salt thereof according to anyone of aspects [D2] or [L1]-[L3] each of which is taken in combination with anyone of aspects [C5]-[C8]

In another aspect [L5] the invention relates to a compound of formula (I) or a salt thereof, according to anyone of aspects [D2] or [L1]-[L4] each of which is taken in combination with anyone of aspects [J1]-[J7], [J3a], [J4a], [J6a] and [J6b].

In another aspect [L6] the invention relates to a compound of formula (I) or a salt thereof, according to anyone of aspects [D2] or [L1]-[L5], each of which is taken in combination with R$^4$ is a 3-11 membered heterocyclyl or R$^4$ is a 7 membered heterocyclyl.

It is to be understood that all sub-aspects [E1] to [E3] (in respect of residue R$^5$), [F1] to [F3](in respect of residue R$^6$), [G1] and [G2] (in respect of residue R$^8$), [H1] to [H3] (in respect of residue R$^9$), [I1] to [I3] (in respect of residue R$^{10}$) and [J1] to [J9] (in respect of residue R$^7$) can be combined with one another based on aspects [D0] to [D9] as applicable to form additional aspects [D] which shall all also be included.

All above-mentioned structural aspects [A1] to [A9], [B1] to [B4], [C1] to [C16] and [D1] to [D9] (including additional aspects [D] based on combinations of [D1] to [D9] with sub-aspects [E1] to [E3], [F1] to [F3], [G1] and [G2], [H1] to [H3], [I1] to [I3] and [J1] to [J9] as applicable and as described above) are preferred embodiments of the corresponding structural aspects [A0], [B0], [C0] and [D0], respectively. The structural aspects [A0] to [A9], [B0] to [B4], [C0] to [C16] and [D0] to [D9] (including additional aspects [D] as described above) relating to different molecular parts of the compounds (I) according to the invention may be combined with one another as desired in combinations [A][B][C][D] to obtain preferred compounds (I). Each such combination [A][B][C][D] represents and defines individual embodiments or generic subsets of compounds (I) according to the invention.

Preferred embodiments of the invention with structure (I) are example compounds I-1 to I-225 and any subset thereof.

All synthetic intermediates generically defined as well as specifically disclosed herein and their salts are also part of the invention.

All individual synthetic reaction steps as well as reaction sequences comprising these individual synthetic reaction steps, both generically defined or specifically disclosed herein, are also part of the invention.

The present invention further relates to hydrates, solvates, polymorphs, metabolites, derivatives, stereoisomers and prodrugs of a compound of formula (I) (including all individual embodiments and generic subsets disclosed herein).

The present invention further relates to a hydrate of a compound of formula (I) (including all individual embodiments and generic subsets disclosed herein).

The present invention further relates to a solvate of a compound of formula (I) (including all individual embodiments and generic subsets disclosed herein).

Compounds of formula (I) (including all individual embodiments and generic subsets disclosed herein) which e.g. bear ester groups are potential prodrugs the ester being cleaved under physiological conditions and are also part of the invention.

The present invention further relates to a pharmaceutically acceptable salt of a compound of formula (I) (including all individual embodiments and generic subsets disclosed herein).

The present invention further relates to a pharmaceutically acceptable salt of a compound of formula (I) (including all individual embodiments and generic subsets disclosed herein) with anorganic or organic acids or bases.

Pharmaceutical Compositions

Suitable pharmaceutical compositions for administering the compounds of formula (I) according to the invention will be apparent to those with ordinary skill in the art and include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the compounds (I) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day, e.g. twice daily.

Suitable tablets may be obtained, for example, by mixing the compounds (I) with known pharmaceutically acceptable excipients, for example inert diluents, carriers, disintegrants, adjuvants, surfactants, binders and/or lubricants. The tablets may also comprise several layers.

Coated tablets may be prepared accordingly by coating cores produced analogously to the tablets with excipients normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing one or more compounds (I) or combinations with one or more other pharmaceutically active substance(s) may additionally contain excipients like a sweetener such as saccharine, cyclamate, glycerol or sugar and a flavour enhancer, e.g. a flavouring such as vanillin or orange extract. They may also contain excipients like suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of excipients like isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more compounds (I) or combinations with one or more other pharmaceutically active substance(s) may for example be prepared by mixing the compounds/active substance(s) with inert excipients such as lactose or sorbitol and packing them into gelatine capsules.

Suitable suppositories may be made for example by mixing with excipients provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The pharmaceutical compositions are administered by the usual methods, preferably by oral or transdermal route, most preferably by oral route. For oral administration the tablets may of course contain, apart from the above-mentioned excipients, additional excipients such as sodium citrate, calcium carbonate and dicalcium phosphate together with various excipients such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid excipients may be used.

The dosage range of the compounds of formula (I) applicable per day is usually from 1 mg to 2000 mg, preferably from 250 mg to 2000 mg.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

Thus, in a further aspect the invention relates to a pharmaceutical composition comprising at least one (preferably one) compound of formula (I)—or a pharmaceutically acceptable salt thereof—(including all individual embodiments and generic subsets disclosed herein) and one or more pharmaceutically acceptable excipient(s).

The compounds of formula (I)—or the pharmaceutically acceptable salts thereof—and the pharmaceutical compositions comprising such compound and salts may also be co-administered with other pharmacologically active substances, e.g. with other anti-neoplastic compounds (e.g. chemotherapy), i.e. used in combination (see combination treatment further below).

The elements of such combinations may be administered (whether dependently or independently) by methods customary to the skilled person and as they are used in monotherapy, e.g. by oral, enterical, parenteral (e.g., intramuscular, intraperitoneal, intravenous, transdermal or subcutaneous injection, or implant), nasal, vaginal, rectal, or topical routes of administration and may be formulated, alone or together, in suitable dosage unit formulations containing conventional non-toxic pharmaceutically acceptable excipients appropriate for each route of administration.

The combinations may be administered at therapeutically effective single or divided daily doses. The active components of the combinations may be administered in such doses which are therapeutically effective in monotherapy, or in such doses which are lower than the doses used in monotherapy, but when combined result in a desired (joint) therapeutically effective amount.

However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Thus, in a further aspect the invention also relates to a pharmaceutical composition comprising a compound of formula (I)—or a pharmaceutically acceptable salt thereof—(including all individual embodiments and generic subsets disclosed herein) and one or more (preferably one or two, most preferably one) other pharmacologically active substance(s).

In a further aspect the invention also relates to a pharmaceutical preparation comprising a compound of formula (I)—or a pharmaceutically acceptable salt thereof—(including all individual embodiments and generic subsets disclosed herein) and one or more (preferably one or two, most preferably one) other pharmacologically active substance(s).

Pharmaceutical compositions to be co-administered or used in combination can also be provided in the form of a kit.

Thus, in a further aspect the invention also relates to a kit comprising
- a first pharmaceutical composition or dosage form comprising a compound of formula (I)—or a pharmaceutically acceptable salt thereof—(including all individual embodiments and generic subsets disclosed herein) and, optionally, one or more pharmaceutically acceptable excipient(s), and
- a second pharmaceutical composition or dosage form comprising another pharmacologically active substance and, optionally, one or more pharmaceutically acceptable excipient(s).

In one aspect such kit comprises a third pharmaceutical composition or dosage form comprising still another pharmacologically active substance and, optionally, one or more pharmaceutically acceptable excipient(s).

Medical Uses—Methods of Treatment

Indications—Patient Populations

The present invention is mainly directed to EGFR inhibitors, in particular compounds of formula (I) (including all individual embodiments and generic subsets disclosed herein), which are potentially useful in the treatment and/or prevention of diseases and/or conditions associated with or modulated/mediated by mutant EGFR, especially wherein the inhibition of the mutant EGFR is of therapeutic benefit, including but not limited to the treatment and/or prevention of cancer.

In one aspect the invention relates to a compound of formula (I) (including all individual embodiments and generic subsets disclosed herein)—or a pharmaceutically acceptable salt thereof—for use as a medicament.

In another aspect the invention relates to a compound of formula (I) (including all individual embodiments and generic subsets disclosed herein)—or a pharmaceutically acceptable salt thereof—for use in a method of treatment of the human or animal body.

In another aspect the invention relates to a compound of formula (I) (including all individual embodiments and generic subsets disclosed herein)—or a pharmaceutically acceptable salt thereof—for use in the treatment and/or prevention of a disease and/or condition mediated by mutant EGFR.

In another aspect the invention relates to the use of a compound of formula (I) (including all individual embodiments and generic subsets disclosed herein)—or a pharmaceutically acceptable salt thereof—in the manufacture of a medicament for the treatment and/or prevention of a disease and/or condition mediated by mutant EGFR.

In another aspect the invention relates to a method for the treatment and/or prevention of a disease and/or condition mediated by mutant EGFR comprising administering a therapeutically effective amount of a compound of formula (I) (including all individual embodiments and generic subsets disclosed herein)—or a pharmaceutically acceptable salt thereof—to a human being.

In another aspect the invention relates to a compound of formula (I) (including all individual embodiments and generic subsets disclosed herein)—or a pharmaceutically acceptable salt thereof—for use in the treatment and/or prevention of cancer.

In another aspect the invention relates to a compound of formula (I) (including all individual embodiments and generic subsets disclosed herein)—or a pharmaceutically acceptable salt thereof—for use in a method of treatment and/or prevention of cancer in the human or animal body.

In another aspect the invention relates to the use of a compound of formula (I) (including all individual embodiments and generic subsets disclosed herein)—or a pharmaceutically acceptable salt thereof—in the manufacture of a medicament for the treatment and/or prevention of cancer.

In another aspect the invention relates to a method for the treatment and/or prevention of cancer comprising administering a therapeutically effective amount of a compound of formula (I) (including all individual embodiments and generic subsets disclosed herein)—or a pharmaceutically acceptable salt thereof—to a human being.

In another aspect the invention relates to a compound of formula (I) (including all individual embodiments and generic subsets disclosed herein)—or a pharmaceutically acceptable salt thereof—for use in providing an inhibitory effect on mutant EGFR.

In another aspect the invention relates to the use of a compound of formula (I) (including all individual embodiments and generic subsets disclosed herein)—or a pharmaceutically acceptable salt thereof—in the manufacture of a medicament for use in providing an inhibitory effect on mutant EGFR.

In another aspect the invention relates to a method for providing an inhibitory effect on mutant EGFR comprising administering a therapeutically effective amount of a compound of formula (I) (including all individual embodiments and generic subsets disclosed herein)—or a pharmaceutically acceptable salt thereof—to a human being.

Another aspect is based on identifying a link between the EGFR mutation status of a patient and potential susceptibility to treatment with a compound of formula (I) (including all individual embodiments and generic subsets disclosed herein). An EGFR inhibitor, such as a compound of formula (I) (including all individual embodiments and generic subsets disclosed herein) may then advantageously be used to treat patients with EGFR mutations who may be resistant to other therapies. This therefore provides opportunities, methods and tools for selecting patients for treatment with a compound of formula (I) (including all individual embodiments and generic subsets disclosed herein), particularly cancer patients. The selection is based on whether the tumor cells to be treated possess wild-type or mutant EGFR gene. The EGFR gene status could therefore be used as a biomarker to indicate that selecting treatment with a compound of formula (I) (including all individual embodiments and generic subsets disclosed herein) may be advantageous.

According to one aspect, there is provided a method for selecting a patient for treatment with a compound of formula (I) (including all individual embodiments and generic subsets disclosed herein) the method comprising providing a tumor cell-containing sample, preferably a tumor DNA-containing sample, from a patient;

determining whether the EGFR gene in the patient's sample encodes for wild-type or a mutant EGFR protein; and selecting a patient for treatment with a compound of formula (I) (including all individual embodiments and generic subsets disclosed herein) based thereon.

The method may include or exclude the actual patient sample isolation step.

"Mutant EGFR" as used herein in disclosing and defining the aspects of the invention refers to both a mutant EGFR gene and/or the corresponding protein derived from such mutant EGFR gene, and includes, but is not limited to:

[K1]
EGFR comprising a deletion in exon 19 (=del 19)
e.g.
delE746_A750 (most common),
delE746_S752insV,
delL747_A750insP,
delL747_P753insS,
delS752_I759;
EGFR comprising mutation L858R in exon 21(=L858R);
EGFR comprising mutation T790M in exon 20 (=T790M)
EGFR comprising a mutation in residue C797 in exon 20 (=C797mut)
e.g.
C797S,
C797G,
C797N,
EGFR comprising a mutation in residue L792 in exon 20 (=L792mut)
e.g.
L792F,
L792H,
L792Y,
or any mutant EGFR comprising a combination of two or more mutations, e.g.
del19 T790M
del19 C797mut
  del19 C797S
  del19 C797G
  del19 C797N
del19 T790M C797mut
  del19 T790M C797S
  del19 T790M C797G
  del19 T790M C797N
del19 L792mut
  del19 L792F
  del19 L792H
  del19 L792Y
del19 T790M L792mut
  del19 T790M L792F
  del19 T790M L792H
  del19 T790M L792Y
L858R T790M
L858R C797mut
  L858R C797S
  L858R C797G
  L858R C797N
L858R T790M C797mut
  L858R T790M C797S
  L858R T790M C797G
  L858R T790M C797N
L858R L792mut
  L858R L792F
  L858R L792H
  L858R L792Y
L858R T790M L792mut
  L858R T790M L792F
  L858R T790M L792H
  L858R T790M L792Y Thus, in one aspect of the invention [K2] the mutant EGFR comprises a deletion in exon 19 (=del 19).

In another aspect of the invention [K3] the mutant EGFR comprises mutation L858R in exon 21 (=L858R).

In another aspect of the invention [K4] the mutant EGFR comprises mutation T790M in exon 20 (=T790M).

In another aspect of the invention [K5] the mutant EGFR comprises a mutation in residue C797 in exon 20 (=C797mut).

In another aspect of the invention [K6] the mutant EGFR comprises mutation C797S in exon 20 (=C797S).

In another aspect of the invention [K7] the mutant EGFR comprises mutation C797G in exon 20 (=C797G).

In another aspect of the invention [K8] the mutant EGFR comprises mutation C797N in exon 20 (=C797N).

In another aspect of the invention [K9] the mutant EGFR comprises a mutation in residue L792 in exon 20 (=L792mut).

In another aspect of the invention [K10] the mutant EGFR comprises mutation L792F in exon 20 (=L792F).

In another aspect of the invention [K11] the mutant EGFR comprises mutation L792H in exon 20 (=L792H).

In another aspect of the invention [K12] the mutant EGFR comprises mutation L792Y in exon 20 (=L792Y).

In another aspect of the invention [K13] the mutant EGFR comprises mutations del19 T790M.

In another aspect of the invention [K14] the mutant EGFR comprises mutations del19 C797mut.

In another aspect of the invention [K15] the mutant EGFR comprises mutations del19 C797S.

In another aspect of the invention [K16] the mutant EGFR comprises mutations del19 C797G.

In another aspect of the invention [K17] the mutant EGFR comprises mutations del19 C797N.

In another aspect of the invention [K18] the mutant EGFR comprises mutations del19 T790M C797mut.

In another aspect of the invention [K19] the mutant EGFR comprises mutations del19 T790M C797S.

In another aspect of the invention [K20] the mutant EGFR comprises mutations del19 T790M C797G.

In another aspect of the invention [K21] the mutant EGFR comprises mutations del19 T790M C797N.

In another aspect of the invention [K22] the mutant EGFR comprises mutations del19 L792mut.

In another aspect of the invention [K23] the mutant EGFR comprises mutations del19 L792F.

In another aspect of the invention [K24] the mutant EGFR comprises mutations del19 L792H.

In another aspect of the invention [K25] the mutant EGFR comprises mutations del19 L792Y.

In another aspect of the invention [K26] the mutant EGFR comprises mutations del19 T790M L792mut.

In another aspect of the invention [K27] the mutant EGFR comprises mutations del19 T790M L792F.

In another aspect of the invention [K28] the mutant EGFR comprises mutations del19 T790M L792H.

In another aspect of the invention [K29] the mutant EGFR comprises mutations del19 T790M L792Y.

In another aspect of the invention [K30] the mutant EGFR comprises EGFR L858R T790M.

In another aspect of the invention [K31] the mutant EGFR comprises EGFR L858R C797mut.

In another aspect of the invention [K32] the mutant EGFR comprises mutations L858R C797S.

In another aspect of the invention [K33] the mutant EGFR comprises mutations L858R C797G.

In another aspect of the invention [K34] the mutant EGFR comprises mutations L858R C797N.

In another aspect of the invention [K35] the mutant EGFR comprises mutations L858R T790M C797mut.

In another aspect of the invention [K36] the mutant EGFR comprises mutations L858R T790M C797S.

In another aspect of the invention [K37] the mutant EGFR comprises mutations L858R T790M C797G.

In another aspect of the invention [K38] the mutant EGFR comprises mutations L858R T790M C797N.

In another aspect of the invention [K39] the mutant EGFR comprises mutations L858R L792mut.

In another aspect of the invention [K40] the mutant EGFR comprises mutations L858R L792F.

In another aspect of the invention [K41] the mutant EGFR comprises mutations L858R L792H.

In another aspect of the invention [K42] the mutant EGFR comprises mutations L858R L792Y.

In another aspect of the invention [K43] the mutant EGFR comprises mutations L858R T790M L792mut.

In another aspect of the invention [K44] the mutant EGFR comprises mutations L858R T790M L792F.

In another aspect of the invention [K45] the mutant EGFR comprises mutations L858R T790M L792H.

In another aspect of the invention [K46] the mutant EGFR comprises mutations L858R T790M L792Y.

In one aspect, the patient is selected for treatment with a compound of formula (I) (including all individual embodiments and generic subsets disclosed herein) if the tumor cell DNA harbours a mutant EGFR gene, wherein the mutant EGFR gene is preferably selected from any one of [K1] to [K46].

In another aspect, there is provided a compound of formula (I) (including all individual embodiments and generic subsets disclosed herein)—or a pharmaceutically acceptable salt thereof—for use in treating a cancer with tumor cells harbouring a mutant EGFR gene, wherein the mutant EGFR gene is preferably selected from any one of [K1] to [K46].

In another aspect, there is provided a method of treating a cancer with tumor cells harbouring a mutant EGFR gene comprising administering a therapeutically effective amount of a compound of formula (I) (including all individual embodiments and generic subsets disclosed herein)—or a pharmaceutically acceptable salt thereof—to a human being, wherein the mutant EGFR gene is preferably selected from any one of [K1] to [K46].

In another aspect the invention relates to the use of a compound of formula (I) (including all individual embodiments and generic subsets disclosed herein)—or a pharmaceutically acceptable salt thereof—in the manufacture of a medicament for use in treating a cancer with tumor cells harbouring a mutant EGFR gene, wherein the mutant EGFR gene is preferably selected from any one of [K1] to [K46].

Determining whether a tumor or cancer comprises a mutant EGFR can be undertaken by assessing the nucleotide sequence encoding the EGFR protein at DNA or RNA level, by assessing the amino acid sequence of the EGFR protein, or by assessing the characteristics of a putative EGFR mutant protein. The sequence of wild-type human EGFR is known in the art. Methods for detecting a mutation in an EGFR nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, digital droplet PCR, direct sequencing, primer extension reactions, electrophoresis, oligonucleotide ligation assays, hybridization assays, TaqMan assays, SNP genotyping assays, high resolution melting assays, microarray analyses, and next generation sequencing. In some embodiments, samples are evaluated for EGFR mutations by real-time PCR. In real-time PCR, fluorescent probes specific for the EGFR mutation are used. When a mutation is present, the probe binds and fluorescence is detected. In some embodiments, the EGFR mutation is identified using a direct sequencing method of specific regions in the EGFR gene. This technique will identify all possible mutations in the region sequenced. Methods for detecting a mutation in an EGFR protein are known by those of skill in the art. These methods include, but are not limited to, detection of an EGFR mutant using a binding agent (e.g. an antibody) specific for the mutant protein, protein electrophoresis, Western blotting and direct peptide sequencing.

Methods for determining whether a tumor or cancer comprises an EGFR mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA. In some embodiments the sample is a liquid biopsy and the test is done on a sample of blood, urine, sputum or other body fluid to look for cancer cells from a tumor that are contained within these samples or for pieces of DNA from tumor cells that are contained within these samples.

In another aspect the disease/condition/cancer to be treated/prevented with the compound of formula (I) (including all individual embodiments and generic subsets disclosed herein), or in the medical uses, uses, methods of treatment and/or prevention as herein disclosed is selected from the group consisting of lung cancer, brain cancers, colorectal cancer, bladder cancer, urothelial cancer, breast cancer, prostate cancer, ovarian cancer, head and neck cancer, pancreatic cancer, gastric cancer and mesothelioma, including metastasis (in particular brain metastasis) of all cancers listed.

In another aspect the disease/condition/cancer to be treated/prevented with the compound of formula (I) (including all individual embodiments and generic subsets disclosed herein), or in the medical uses, uses, methods of treatment and/or prevention as herein disclosed is lung cancer. Preferably, the lung cancer to be treated is non-small cell lung cancer (NSCLC) including, e.g., locally advanced or metastatic NSCLC, NSCLC adenocarcinoma, NSCLC with squamous histology and NSCLC with non-squamous histology. Most preferably, the lung cancer to be treated is NSCLC adenocarcinoma.

In another aspect the cancer (including all embodiments as disclosed herein) to be treated is a cancer with tumor cells harbouring a mutant EGFR gene, wherein the mutant EGFR gene comprises a deletion in exon 19 (=del19). Preferably, the cancer patients to be treated and suffering from such a cancer have the compound of formula (I) (including all individual embodiments and generic subsets disclosed herein) administered as a first line treatment (in respect of treatment with EGFR TKIs), i.e. the patients are treatment naïve in respect of EGFR TKIs.

In another aspect the cancer (including all embodiments as disclosed herein) to be treated is a cancer with tumor cells harbouring a mutant EGFR gene, wherein the mutant EGFR gene comprises mutations del19 T790M. Preferably, the cancer patients to be treated and suffering from such a cancer have the compound of formula (I) (including all individual embodiments and generic subsets disclosed herein) administered as a second line treatment (in respect of treatment with EGFR TKIs), i.e. the patients are progressing on earlier therapy with a $1^{st}$ or $2^{nd}$ generation EGFR TKI (i.e. the patients are progressing after prior treatment with gefitinib, erlotinib, icotinib, afatinib, or dacomitinib).

In another aspect the cancer (including all embodiments as disclosed herein) to be treated is a cancer with tumor cells harbouring a mutant EGFR gene, wherein the mutant EGFR gene comprises mutations del19 $C_{797}S$. Preferably, the cancer patients to be treated and suffering from such a cancer have the compound of formula (I) (including all individual embodiments and generic subsets disclosed herein) administered as a second line treatment (in respect of treatment with EGFR TKIs), i.e. the patients are progressing on earlier therapy with a $3^{rd}$ generation EGFR TKI (i.e. the patients are progressing after prior treatment with, e.g., osimertinib, olmutinib, nazartinib, lazertinib, almonertinib or avitinib).

In another aspect the cancer (including all embodiments as disclosed herein) to be treated is a cancer with tumor cells harbouring a mutant EGFR gene, wherein the mutant EGFR gene comprises mutations del19 C797mut (preferably C797G or C797N). Preferably, the cancer patients to be treated and suffering from such a cancer have the compound of formula (I) (including all individual embodiments and generic subsets disclosed herein) administered as a second line treatment (in respect of treatment with EGFR TKIs), i.e. the patients are progressing on earlier therapy with a $3^{rd}$ generation EGFR TKI (i.e. the patients are progressing after prior treatment with, e.g., osimertinib, olmutinib, nazartinib, lazertinib, almonertinib or avitinib).

In another aspect the cancer (including all embodiments as disclosed herein) to be treated is a cancer with tumor cells harbouring a mutant EGFR gene, wherein the mutant EGFR gene comprises mutations del19 T790M $C_{797}S$. Preferably, the cancer patients to be treated and suffering from such a cancer have the compound of formula (I) (including all individual embodiments and generic subsets disclosed herein) administered as a third line treatment (in respect of treatment with EGFR TKIs), i.e. the patients progressed on earlier therapy with a $1^{st}$ or $2^{nd}$ generation EGFR TKI (i.e. progressed after earlier treatment with gefitinib, erlotinib, icotinib, afatinib, or dacomitinib) upon T790M acquisition and are progressing on additional therapy with a $3^{rd}$ generation EGFR TKI (i.e. the patients are progressing after additional treatment with, e.g., osimertinib, olmutinib, nazartinib, lazertinib, almonertinib or avitinib) upon C797S acquisition.

In another aspect the cancer (including all embodiments as disclosed herein) to be treated is a cancer with tumor cells harbouring a mutant EGFR gene, wherein the mutant EGFR gene comprises mutations del19 T790M C797mut (preferably C797G or C797N). Preferably, the cancer patients to be treated and suffering from such a cancer have the compound of formula (I) (including all individual embodiments and generic subsets disclosed herein) administered as a third line treatment (in respect of treatment with EGFR TKIs), i.e. the patients progressed on earlier therapy with a $1^{st}$ or $2^{nd}$ generation EGFR TKI (i.e. the patients progressed after earlier treatment with gefitinib, erlotinib, icotinib, afatinib or dacomitinib) upon T790M acquisition and are progressing on additional therapy with a $3^{rd}$ generation EGFR TKI (i.e. the patients are progressing after additional treatment with, e.g., osimertinib, olmutinib, nazartinib, lazertinib, almonertinib or avitinib) upon C797mut (preferably C797G or C797N) acquisition.

In another aspect the cancer (including all embodiments as disclosed herein) to be treated is a cancer with tumor cells harbouring a mutant EGFR gene, wherein the mutant EGFR gene comprises mutations del19 L792mut (preferably L792F, L792H or L792Y). Preferably, the cancer patients to be treated and suffering from such a cancer have the compound of formula (I) (including all individual embodiments and generic subsets disclosed herein) administered as a second line treatment (in respect of treatment with EGFR TKIs), i.e. the patients are progressing on earlier therapy with a $3^{rd}$ generation EGFR TKI (i.e. the patients are progressing after prior treatment with, e.g., osimertinib, olmutinib, nazartinib, lazertinib, almonertinib or avitinib).

In another aspect the cancer (including all embodiments as disclosed herein) to be treated is a cancer with tumor cells harbouring a mutant EGFR gene, wherein the mutant EGFR gene comprises mutations del19 T790M L792mut (preferably L792F, L792H or L792Y). Preferably, the cancer patients to be treated and suffering from such a cancer have the compound of formula (I) (including all individual embodiments and generic subsets disclosed herein) administered as a third line treatment (in respect of treatment with EGFR TKIs), i.e. the patients progressed on earlier therapy with a $1^{st}$ or $2^{nd}$ generation EGFR TKI (i.e. the patients progressed after earlier treatment with gefitinib, erlotinib, icotinib, afatinib or dacomitinib) upon T790M acquisition and are progressing on additional therapy with a $3^{rd}$ generation EGFR TKI (i.e. the patients are progressing after additional treatment with, e.g., osimertinib, olmutinib, nazartinib, lazertinib, almonertinib or avitinib) upon L792mut (preferably L792F, L792H or L792Y) acquisition.

In another aspect the cancer (including all embodiments as disclosed herein) to be treated is a cancer with tumor cells harbouring a mutant EGFR gene, wherein the mutant EGFR gene comprises L858R mutation. Preferably, the cancer patients to be treated and suffering from such a cancer have the compound of formula (I) (including all individual embodiments and generic subsets disclosed herein) administered as a first line treatment (in respect of treatment with EGFR TKIs), i.e. the patients are treatment naïve in respect of EGFR TKIs.

In another aspect the cancer (including all embodiments as disclosed herein) to be treated is a cancer with tumor cells harbouring a mutant EGFR gene, wherein the mutant EGFR gene comprises mutations L858R T790M. Preferably, the cancer patients to be treated and suffering from such a cancer have the compound of formula (I) (including all individual embodiments and generic subsets disclosed herein) administered as a second line treatment (in respect of treatment with EGFR TKIs), i.e. the patients are progressing on earlier therapy with a $1^{st}$ or $2^{nd}$ generation EGFR TKI (i.e. the patients are progressing after prior treatment with gefitinib, erlotinib, icotinib, afatinib or dacomitinib).

In another aspect the cancer (including all embodiments as disclosed herein) to be treated is a cancer with tumor cells harbouring a mutant EGFR gene, wherein the mutant EGFR gene comprises mutations L858R $C_{797}$S. Preferably, the cancer patients to be treated and suffering from such a cancer have the compound of formula (I) (including all individual embodiments and generic subsets disclosed herein) administered as a second line treatment (in respect of treatment with EGFR TKIs), i.e. the patients are progressing on earlier therapy with a $3^{rd}$ generation EGFR TKI (i.e. the patients are progressing after treatment with, e.g., osimertinib, olmutinib, nazartinib, lazertinib, almonertinib or avitinib).

In another aspect the cancer (including all embodiments as disclosed herein) to be treated is a cancer with tumor cells harbouring a mutant EGFR gene, wherein the mutant EGFR gene comprises mutations L858R C797mut (preferably C797G or C797N). Preferably, the cancer patients to be treated and suffering from such a cancer have the compound of formula (I) (including all individual embodiments and generic subsets disclosed herein) administered as a second line treatment (in respect of treatment with EGFR TKIs), i.e. the patients are progressing on earlier therapy with a $3^{rd}$ generation EGFR TKI (i.e. the patients are progressing after prior treatment with, e.g., osimertinib, olmutinib, nazartinib, lazertinib, almonertinib or avitinib).

In another aspect the cancer (including all embodiments as disclosed herein) to be treated is a cancer with tumor cells harbouring a mutant EGFR gene, wherein the mutant EGFR gene comprises mutations L858R T790M C797S. Preferably, the cancer patients to be treated and suffering from such a cancer have the compound of formula (I) (including all individual embodiments and generic subsets disclosed herein) administered as a third line treatment (in respect of treatment with EGFR TKIs), i.e. the patients progressed on earlier therapy with a $1^{st}$ or $2^{nd}$ generation EGFR TKI (i.e. progressed after earlier treatment with gefitinib, erlotinib, icotinib, afatinib or dacomitinib) upon T790M acquisition and are progressing on additional therapy with a $3^{rd}$ generation EGFR TKI (i.e. the patients are progressing after additional treatment with, e.g., osimertinib, olmutinib, nazartinib, lazertinib, almonertinib or avitinib) upon C797S acquisition.

In another aspect the cancer (including all embodiments as disclosed herein) to be treated is a cancer with tumor cells harbouring a mutant EGFR gene, wherein the mutant EGFR gene comprises mutations L858R T790M C797mut (preferably C797G or C797N). Preferably, the cancer patients to be treated and suffering from such a cancer have the compound of formula (I) (including all individual embodiments and generic subsets disclosed herein) administered as a third line treatment (in respect of treatment with EGFR TKIs), i.e. the patients progressed on earlier therapy with a $1^{st}$ or $2^{nd}$ generation EGFR TKI (i.e. the patients progressed after earlier treatment with gefitinib, erlotinib, icotinib, afatinib or dacomitinib) upon T790M acquisition and are progressing on additional therapy with a $3^{rd}$ generation EGFR TKI (i.e. the patients are progressing after additional treatment with, e.g., osimertinib, olmutinib, nazartinib, lazertinib, almonertinib or avitinib) upon C797mut (preferably C797G or C797N) acquisition.

In another aspect the cancer (including all embodiments as disclosed herein) to be treated is a cancer with tumor cells harbouring a mutant EGFR gene, wherein the mutant EGFR gene comprises mutations L858R L792mut (preferably L792F, L792H or L792Y). Preferably, the cancer patients to be treated and suffering from such a cancer have the compound of formula (I) (including all individual embodiments and generic subsets disclosed herein) administered as a second line treatment (in respect of treatment with EGFR TKIs), i.e. the patients are progressing on earlier therapy with a $3^{rd}$ generation EGFR TKI (i.e. the patients are progressing after prior treatment with, e.g., osimertinib, olmutinib, nazartinib, lazertinib, almonertinib or avitinib).

In another aspect the cancer (including all embodiments as disclosed herein) to be treated is a cancer with tumor cells harbouring a mutant EGFR gene, wherein the mutant EGFR gene comprises mutations L858R T790M L792mut (preferably L792F, L792H or L792Y). Preferably, the cancer patients to be treated and suffering from such a cancer have the compound of formula (I) (including all individual embodiments and generic subsets disclosed herein) administered as a third line treatment (in respect of treatment with EGFR TKIs), i.e. the patients progressed on earlier therapy with a $1^{st}$ or $2^{nd}$ generation EGFR TKI (i.e. the patients progressed after earlier treatment with gefitinib, erlotinib, icotinib, afatinib or dacomitinib) upon T790M acquisition and are progressing on additional therapy with a $3^{rd}$ generation EGFR TKI (i.e. the patients are progressing after additional treatment with, e.g., osimertinib, olmutinib, nazartinib, lazertinib, almonertinib or avitinib) upon L792mut (preferably L792F, L792H or L792Y) acquisition.

In another aspect the cancer (including all embodiments as disclosed herein) to be treated is a cancer which is progressing after earlier treatment with a $3^{rd}$ generation EGFR TKI (i.e. the cancer is progressing after prior treatment with, e.g., osimertinib, olmutinib, nazartinib, lazertinib, almonertinib or avitinib). In one aspect, the cancer patients to be treated and suffering from such a cancer have the compound of formula (I) (including all individual embodiments and generic subsets disclosed herein) administered as a second line treatment (in respect of treatment with EGFR TKIs). In another aspect, the cancer patients to be treated and suffering from such a cancer have the compound of formula (I) (including all individual embodiments and generic subsets disclosed herein) administered as a third line treatment (in respect of treatment with EGFR TKIs). Preferred treatment in these settings is treatment after prior treatment with osimertinib.

The compounds of the invention may be used for the prevention, short-term or long-term treatment of the above-mentioned diseases/conditions/cancers/tumors, optionally also in combination with radiotherapy and/or surgery.

The methods of treatment, methods, uses and compounds for use as disclosed herein (above and below) can be performed with any compound of formula (I)—or a pharmaceutically acceptable salt thereof—(including all individual embodiments and generic subsets disclosed herein) and with any pharmaceutical composition or kit comprising a compound of formula (I)—or a pharmaceutically acceptable salt thereof (including all individual embodiments and generic subsets disclosed herein).

Combination Treatment

The compounds of formula (I)—or the pharmaceutically acceptable salts thereof—(including all individual embodiments and generic subsets disclosed herein) and the pharmaceutical compositions comprising such compound and salts may also be co-administered with other pharmacologically active substances, e.g. with other anti-neoplastic compounds (e.g. chemotherapy), or used in combination with other treatments, such as radiation or surgical intervention, either as an adjuvant prior to surgery or post-operatively. Preferably, the pharmacologically active substance(s) for co-administration is/are (an) anti-neoplastic compound(s).

Thus, in a further aspect the invention relates to a compound of formula (I)—or a pharmaceutically acceptable salt thereof—(including all individual embodiments and generic subsets disclosed herein) for use as hereinbefore disclosed, wherein said compound is administered before, after or together with one or more other pharmacologically active substance(s).

In a further aspect the invention relates to a compound of formula (I)—or a pharmaceutically acceptable salt thereof—(including all individual embodiments and generic subsets disclosed herein) for use as hereinbefore disclosed, wherein said compound is administered in combination with one or more other pharmacologically active substance(s).

In a further aspect the invention relates to the use of a compound of formula (I)—or a pharmaceutically acceptable salt thereof—(including all individual embodiments and generic subsets disclosed herein) as hereinbefore disclosed wherein said compound is to be administered before, after or together with one or more other pharmacologically active substance(s).

In a further aspect the invention relates to a method (e.g. a method for the treatment and/or prevention) as hereinbefore disclosed wherein the compound of formula (I)—or a pharmaceutically acceptable salt thereof—(including all individual embodiments and generic subsets disclosed herein) is administered before, after or together with a therapeutically effective amount of one or more other pharmacologically active substance(s).

In a further aspect the invention relates to a method (e.g. a method for the treatment and/or prevention) as hereinbefore disclosed wherein the compound of formula (I)—or a pharmaceutically acceptable salt thereof—(including all individual embodiments and generic subsets disclosed herein) is administered in combination with a therapeutically effective amount of one or more other pharmacologically active substance(s).

In a further aspect the invention relates to a method for the treatment and/or prevention of cancer comprising administering to a patient in need thereof a therapeutically effective amount of a compound of formula (I)—or a pharmaceutically acceptable salt thereof—(including all individual embodiments and generic subsets disclosed herein) and a therapeutically effective amount of one or more other pharmacologically active substance(s), wherein the compound of formula (I)—or the pharmaceutically acceptable salt thereof—is administered simultaneously, concurrently, sequentially, successively, alternately or separately with the one or more other pharmacologically active substance(s).

In a further aspect the invention relates to a compound of formula (I)—or a pharmaceutically acceptable salt thereof—(including all individual embodiments and generic subsets disclosed herein) for use in the treatment and/or prevention of cancer, wherein the compound of formula (I)—or the pharmaceutically acceptable salt thereof—is administered simultaneously, concurrently, sequentially, successively, alternately or separately with the one or more other pharmacologically active substance(s).

In a further aspect the invention relates to a kit comprising
- a first pharmaceutical composition or dosage form comprising a compound of formula (I)—or a pharmaceutically acceptable salt thereof—(including all individual embodiments and generic subsets disclosed herein) and, optionally, one or more pharmaceutically acceptable excipient(s), and
- a second pharmaceutical composition or dosage form comprising another pharmacologically active substance, and, optionally, one or more pharmaceutically acceptable excipient(s), for use in the treatment and/or prevention of cancer, wherein the first pharmaceutical composition is to be administered simultaneously, concurrently, sequentially, successively, alternately or separately with the second and/or additional pharmaceutical composition or dosage form.

In one aspect such kit for said use comprises a third pharmaceutical composition or dosage form comprising a third pharmaceutical composition or dosage form comprising still another pharmacologically active substance, and, optionally, one or more pharmaceutically acceptable excipient(s).

In a further embodiment of the invention the components (i.e. the combination partners) of the combinations, kits, uses, methods and compounds for use according to the invention (including all embodiments) are administered simultaneously.

In a further embodiment of the invention the components (i.e. the combination partners) of the combinations, kits, uses, methods and compounds for use according to the invention (including all embodiments) are administered concurrently.

In a further embodiment of the invention the components (i.e. the combination partners) of the combinations, kits, uses, methods and compounds for use according to the invention (including all embodiments) are administered sequentially.

In a further embodiment of the invention the components (i.e. the combination partners) of the combinations, kits, uses, methods and compounds for use according to the invention (including all embodiments) are administered successively.

In a further embodiment of the invention the components (i.e. the combination partners) of the combinations, kits, uses, methods and compounds for use according to the invention (including all embodiments) are administered alternately.

In a further embodiment of the invention the components (i.e. the combination partners) of the combinations, kits, uses, methods and compounds for use according to the invention (including all embodiments) are administered separately.

The pharmacologically active substance(s) to be used together/in combination with the compound of formula (I)—or a pharmaceutically acceptable salt thereof—(including all individual embodiments or generic subsets of compounds (I)) or in the medical uses, uses, methods of treatment and/or prevention as herein (above and below) disclosed can be selected from any one or more of the following (preferably there is one or two additional pharmacologically active substance used in all these embodiments):

1. an inhibitor of EGFR and/or ErbB2 (HER2) and/or ErbB3 (HER3) and/or ErbB4 (HER4) or of any mutants thereof
   a. irreversible inhibitors: e.g. afatinib, dacomitinib, canertinib, neratinib, avitinib, poziotinib, AV 412, PF-6274484, HKI 357, olmutinib, osimertinib, almonertinib, nazartinib, lazertinib, pelitinib;
   b. reversible inhibitors: e.g. erlotinib, gefitinib, icotinib, sapitinib, lapatinib, varlitinib, vandetanib, TAK-285, AEE788, BMS599626/AC-480, GW 583340;
   c. anti-EGFR antibodies: e.g. necitumumab, panitumumab, cetuximab, amivantanab;
   d. anti-HER2 antibodies: e.g. pertuzumab, trastuzumab, trastuzumab emtansine;
   e. inhibitors of mutant EGFR;
   f. an inhibitor of HER2 with exon 20 mutations;
   g. preferred irreversible inhibitor is afatinib;
   h. preferred anti-EGFR antibody is cetuximab;
2. an inhibitor of MEK and/or of mutants thereof
   a. e.g. trametinib, cobimetinib, binimetinib, selumetinib, refametinib, BI 3011441;
   b. preferred are trametinib and BI 3011441;
   c. most preferred is BI 3011441;
3. an inhibitor of c-MET and/or of mutants thereof
   a. e.g. savolitinib, cabozantinib, foretinib;
   b. MET antibodies, e.g. emibetuzumab, amivantanab;
4. an inhibitor of SOS1 and/or of any mutants thereof (i.e. a compound that modulates/inhibits the GEF functionality of SOS1, e.g. by binding to SOS1 and preventing protein-protein interaction between SOS1 and a (mutant) Ras protein, e.g. KRAS)
   a. e.g. BAY-293, BI-3406, BI 1701963;
   b. most preferred is BI 1701963;
5. an inhibitor of GDP-loaded or GTP-loaded RAS and/or of any mutants thereof (i.e. a compound that modulates/inhibits the functionality of (mutant) RAS protein by, e.g., binding to GDP-loaded or GTP-loaded (mutant) RAS protein, e.g. KRAS, NRAS and/or HRAS, preferably KRAS)
   a. an irreversible inhibitor of KRAS G12C;
      i. e.g. AMG-510, MRTX849, ARS-324, GDC-6036;
   b. a reversible or irreversible binder to GDP-loaded (mutant) KRAS;
   c. a reversible or irreversible binder to GTP-loaded (mutant) KRAS;
6. an immunotherapeutic agent
   a. e.g. an immune checkpoint inhibitor
      i. e.g. an anti-CTLA4 mAb, anti-PD1 mAb, anti-PD-L1 mAb, anti-PD-L2 mAb, anti-LAG3 mAb, anti-TIM3 mAb;
      ii. preferred is an anti-PD1 mAb;
      iii. e.g. ipilimumab, nivolumab, pembrolizumab, tislelizumab, atezolizumab, avelumab, durvalumab, pidilizumab, PDR-001 (=spartalizumab), AMG-404, ezabenlimab;
      iv. preferred are nivolumab, pembrolizumab, PDR-001 (=spartalizumab) and ezabenlimab;
      v. most preferred is pembrolizumab, nivolumab and ezabenlimab.
   b. e.g. an immuno modulator
      i. e.g. CD73 inhibitors or CD73 inhibitory antibodies
7. an inhibitor of ALK and/or of any mutants thereof
   a. e.g. crizotinib, alectinib, entrectinib, brigatinib, ceritinib;
   b. preferred are crizotinib and alectinib;
   c. most preferred is crizotinib;
8. a taxane
   a. e.g. paclitaxel, nab-paclitaxel, docetaxel;
   b. preferred is paclitaxel;
9. a platinum-containing compound
   a. e.g. cisplatin, carboplatin, oxaliplatin
   b. preferred is carboplatin;
10. an anti-metabolite
    a. e.g. 5-fluorouracil, capecitabine, floxuridine, cytarabine, gemcitabine, pemetrexed, combination of trifluridine and tipiracil (=TAS102);
    b. preferred is pemetrexed;
11. a cell cycle inhibitor
    a. e.g. inhibitors of CDK4/6 and/or of any mutants thereof
       i. e.g. palbociclib, ribociclib, abemaciclib, trilaciclib, PF-06873600;
       ii. preferred are palbociclib and abemaciclib;
       iii. most preferred is abemaciclib.
    b. e.g. vinca alkaloids
       i. e.g. vinorelbine.
    c. e.g. inhibitors of Aurora kinase and/or of any mutants thereof
       i. e.g. alisertib, barasertib.
12. an inhibitor of mTOR
    a. e.g. rapamycin, temsirolimus, everolimus, ridaforolimus, zotarolimus, sapanisertib, Torin 1, dactolisib, GDC-0349, VS-5584, vistusertib, AZD8055.
13. an inhibitor of a Src family kinase and/or of any mutants thereof
    a. e.g. an inhibitor of a kinase of the SrcA subfamily and/or of any mutants thereof, i.e. an inhibitor of Src, Yes, Fyn, Fgr and/or of any mutants thereof;
    b. e.g. an inhibitor of a kinase of the SrcB subfamily and/or of any mutants thereof, i.e. an inhibitor of Lck, Hck, Blk, Lyn and/or of any mutants thereof;

c. e.g. an inhibitor of a kinase of the Frk subfamily and/or of any mutants thereof, i.e. an inhibitor of Frk and/or of any mutants thereof;
d. e.g. dasatinib, ponatinib, bosutinib, vandetanib, KX-01, saracatinib, KX2-391, SU 6656, WH-4-023.
14. an apoptosis inducing agent
    a. e.g. an MCL-1 inhibitor;
        i. e.g. AZD-5991, AMG-176, AMG-397, S64315, S63845, A-1210477;
    b. e.g. a Bcl-2 inhibitor;
        i. e.g. venetoclax, obatoclax, navitoclax, oblimersen;
    c. e.g. a Bcl-xL inhibitor
15. an anti-angiogenic agent
    a. e.g. bevacizumab, nintedanib;
    b. most preferred is bevacizumab;
    c. e.g. an anti-VEGF/Ang2 bispecific antibody
        i. e.g. bispecific binding molecules as disclosed and described in WO 2012/131078 and WO 2018/220169;
16. an inhibitor of PI3 kinase (=PI3K) and/or of any mutants thereof
    a. e.g. inhibitors of PI3Kα and/or of any mutants thereof
        i. e.g. alpelisib, serabelisib, GDC-0077, HH-CYH33, AMG 511, buparlisib, dactolisib, pictilisib, taselisib;
17. an inhibitor of histone deacetylase
18. an inhibitor of IL6
19. an inhibitor of JAK and/or of any mutants thereof
20. an inhibitor of A-Raf and/or B-Raf and/or C-Raf and/or of any mutants thereof
    a. e.g. encorafenib, dabrafenib, vemurafenib, PLX-8394, RAF-709 (=example 131 in WO 2014/151616), LXH254, sorafenib, LY-3009120 (=example 1 in WO 2013/134243), lifirafenib, TAK-632, agerafenib, CCT196969, RO5126766, RAF265;
21. an inhibitor of a receptor tyrosine kinase (RTK) and/or of any mutants thereof
22. an inhibitor of SHP2 and/or of any mutants thereof
    a. e.g. SHP099, TNO155, RMC-4550, RMC-4630, IACS-13909.

In a further embodiment of the (combined) use and method (e.g. method for the treatment and/or prevention) as hereinbefore described one other pharmacologically active substance is to be administered before, after or together with the compound of formula (I)—or a pharmaceutically acceptable salt thereof—(including all individual embodiments and generic subsets disclosed herein) wherein said one other pharmacologically active substance is
    a SOS1 inhibitor; or
    BI 1701963; or
    a MEK inhibitor; or
    trametinib, or
    BI 3011441, or
    an anti-PD-1 antibody; or
    ezabenlimab, or
    cetuximab; or
    afatinib; or
    an inhibitor of GDP-loaded or GTP-loaded mutant KRAS; or
    an MCL1 inhibitor; or
    a PI3K inhibitor.

In a further embodiment of the (combined) use and method (e.g. method for the treatment and/or prevention) as hereinbefore described one other pharmacologically active substance is to be administered in combination with the compound of formula (I)—or a pharmaceutically acceptable salt thereof—(including all individual embodiments and generic subsets disclosed herein) wherein said one other pharmacologically active substance is
    a SOS1 inhibitor; or
    BI 1701963
    a MEK inhibitor; or
    trametinib, or
    BI 3011441, or
    an anti-PD-1 antibody; or
    ezabenlimab, or
    cetuximab; or
    afatinib; or
    an inhibitor of GDP-loaded or GTP-loaded mutant KRAS; or
    an MCL1 inhibitor; or
    a PI3K inhibitor.

In a further aspect of the (combined) use and method (e.g. method for the treatment and/or prevention) as hereinbefore described two other pharmacologically active substances are to be administered before, after or together with the compound of formula (I)—or a pharmaceutically acceptable salt thereof—(including all individual embodiments and generic subsets disclosed herein) wherein said two other pharmacologically active substances are
    a MEK inhibitor and a SOS1 inhibitor; or
    trametinib and a SOS1 inhibitor; or
    trametinib and BI 1701963, or
    BI 3011441 and BI 1701963, or
    an anti-PD-1 antibody and an anti-LAG-3 antibody; or
    an anti-PD-1 antibody and an anti-CTLA-4 antibody; or
    an anti-PD-1 antibody and a SOS1 inhibitor; or
    ezabenlimab and BI 1701963; or
    a MEK inhibitor and an inhibitor selected from the group consisting of an EGFR inhibitor and/or ErbB2 (HER2) inhibitor and/or inhibitor of any mutants thereof; or
    BI 3011441 and an inhibitor selected from the group consisting of an EGFR inhibitor and/or ErbB2 (HER2) inhibitor and/or inhibitor of any mutants thereof; or
    a SOS1 inhibitor and an inhibitor selected from the group consisting of an EGFR inhibitor and/or ErbB2 (HER2) inhibitor and/or inhibitor of any mutants thereof; or
    BI 1701963 and an inhibitor selected from the group consisting of an EGFR inhibitor and/or ErbB2 (HER2) inhibitor and/or inhibitor of any mutants thereof; or
    a MEK inhibitor and afatinib; or
    BI 3011441 and afatinib; or
    a MEK inhibitor and cetuximab; or
    BI 3011441 and cetuximab; or
    trametinib and afatinib; or
    trametinib and cetuximab; or
    a SOS1 inhibitor and afatinib; or
    BI 1701963 and afatinib; or
    a SOS1 inhibitor and cetuximab; or
    BI 1701963 and cetuximab; or
    a SOS1 inhibitor and an inhibitor of GDP-loaded or GTP-loaded mutant KRAS; or
    BI 1701963 and an inhibitor of GDP-loaded or GTP-loaded mutant KRAS; or
    cisplatin and pemetrexed; or
    carboplatin and pemetrexed.

In a further aspect of the (combined) use and method (e.g. method for the treatment and/or prevention) as hereinbefore described two other pharmacologically active substances are to be administered in combination with the compound of formula (I)—or a pharmaceutically acceptable salt thereof—

(including all individual embodiments and generic subsets disclosed herein) wherein said two other pharmacologically active substances are
- a MEK inhibitor and a SOS1 inhibitor; or
- trametinib and a SOS1 inhibitor; or
- trametinib and BI 1701963, or
- BI 3011441 and BI 1701963, or
- an anti-PD-1 antibody and an anti-LAG-3 antibody; or
- an anti-PD-1 antibody and an anti-CTLA-4 antibody; or
- an anti-PD-1 antibody and a SOS1 inhibitor; or
- ezabenlimab and BI 1701963; or
- a MEK inhibitor and an inhibitor selected from the group consisting of an EGFR inhibitor and/or ErbB2 (HER2) inhibitor and/or inhibitor of any mutants thereof; or
- BI 3011441 and an inhibitor selected from the group consisting of an EGFR inhibitor and/or ErbB2 (HER2) inhibitor and/or inhibitor of any mutants thereof; or
- a SOS1 inhibitor and an inhibitor selected from the group consisting of an EGFR inhibitor and/or ErbB2 (HER2) inhibitor and/or inhibitor of any mutants thereof; or
- BI 1701963 and an inhibitor selected from the group consisting of an EGFR inhibitor and/or ErbB2 (HER2) inhibitor and/or inhibitor of any mutants thereof; or
- a MEK inhibitor and afatinib; or
- BI 3011441 and afatinib; or
- a MEK inhibitor and cetuximab; or
- BI 3011441 and cetuximab; or
- trametinib and afatinib; or
- trametinib and cetuximab; or
- a SOS1 inhibitor and afatinib; or
- BI 1701963 and afatinib; or
- a SOS1 inhibitor and cetuximab; or
- BI 1701963 and cetuximab; or
- a SOS1 inhibitor and an inhibitor of GDP-loaded or GTP-loaded mutant KRAS; or
- BI 1701963 and an inhibitor of GDP-loaded or GTP-loaded mutant KRAS; or
- cisplatin and pemetrexed; or
- carboplatin and pemetrexed.

Additional pharmacologically active substance(s) which can also be used together/in combination with the compound of formula (I)—or a pharmaceutically acceptable salt thereof—(including all individual embodiments or generic subsets of compounds (I)) or in the medical uses, uses, methods of treatment and/or prevention as herein (above and below) disclosed include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumor antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP inhibitors/SMAC mimetics, Mcl-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors (e.g. venetoclax), Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors (e.g. carfilzomib), immunotherapeutic agents such as immune checkpont inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19), PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

It is to be understood that the combinations, compositions, kits, methods, uses or compounds for use according to this invention may envisage the simultaneous, concurrent, sequential, successive, alternate or separate administration of the active ingredients or components. It will be appreciated that the compound of formula (I)—or a pharmaceutically acceptable salt thereof—and the one or more other pharmacologically active substance(s) can be administered formulated either dependently or independently, such as e.g. the compound of formula (I)—or a pharmaceutically acceptable salt thereof—and the one or more other pharmacologically active substance(s) may be administered either as part of the same pharmaceutical composition/dosage form or, preferably, in separate pharmaceutical compositions/dosage forms.

In this context, "combination" or "combined" within the meaning of this invention includes, without being limited, a product that results from the mixing or combining of more than one active ingredient and includes both fixed and non-fixed (e.g. free) combinations (including kits) and uses, such as e.g. the simultaneous, concurrent, sequential, successive, alternate or separate use of the components or ingredients. The term "fixed combination" means that the active ingredients are administered to a patient simultaneously in the form of a single entity or dosage. The term "non-fixed combination" means that the active ingredients are administered to a patient as separate entities either simultaneously, concurrently or sequentially with no specific time limits, wherein such administration provides therapeutically effective levels of the compounds in the body of the patient.

The administration of the compound of formula (I)—or a pharmaceutically acceptable salt thereof—and the one or more other pharmacologically active substance(s) may take place by co-administering the active components or ingredients, such as e.g. by administering them simultaneously or concurrently in one single or in two or more separate formulations or dosage forms. Alternatively, the administration of the compound of formula (I)—or a pharmaceutically acceptable salt thereof—and the one or more other pharmacologically active substance(s) may take place by administering the active components or ingredients sequentially or in alternation, such as e.g. in two or more separate formulations or dosage forms.

For example, simultaneous administration includes administration at substantially the same time. This form of administration may also be referred to as "concomitant" administration.

Concurrent administration includes administering the active agents within the same general time period, for example on the same day(s) but not necessarily at the same time. Alternate administration includes administration of one agent during a time period, for example over the course of a few days or a week, followed by administration of the other agent(s) during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent(s) during a second and/or additional time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g. according to the agents used and the condition of the subject.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a positive integer (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroaryl, heteroarylalkyl, heterocyclyl, heterocycylalkyl) relates to the total number of atoms of all the ring members or the total of all the ring and carbon chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl or the like) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

In groups like HO, $H_2N$, (O)S, $(O)_2S$, NC (cyano), HOOC, $F_3C$ or the like, the skilled artisan can see the radical attachment point(s) to the molecule from the free valences of the group itself.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me, —$CH_3$), ethyl (Et, —$CH_2CH_3$), 1-propyl (n-propyl, n-Pr, —$CH_2CH_2CH_3$), 2-propyl (i-Pr, iso-propyl, —$CH(CH_3)_2$), 1-butyl (n-butyl, n-Bu, —$CH_2CH_2CH_2CH_3$), 2-methyl-1-propyl (iso-butyl, i-Bu, —$CH_2CH(CH_3)_2$), 2-butyl (sec-butyl, sec-Bu, —$CH(CH_3)CH_2CH_3$), 2-methyl-2-propyl (tert-butyl, t-Bu, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl, —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl, —$CH_2C(CH_3)_3$), 2-methyl-1-butyl (—$CH_2CH(CH_3)CH_2CH_3$), 1-hexyl (n-hexyl, —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the generic terms propyl, butyl, pentyl, hexyl, heptyl, octyl, nonyl, decyl or the like without any further definition are meant saturated hydrocarbon groups with the corresponding number of carbon atoms, wherein all isomeric forms are included.

The above definition for alkyl also applies if alkyl is a part of another (combined) group like, e.g., $C_{x-y}$alkylamino or $C_{x-y}$alkyloxy.

The term alkylene is derived from alkyl. Alkylene is bivalent, unlike alkyl, and requires two binding partners. Formally, the second valency is generated by removing a hydrogen atom from an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CH(CH(CH$_3$))$_2$)— and —C(CH$_3$)(CH$_2$CH$_3$)—. Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene or the like without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group like, e.g., in HO—$C_{x-y}$alkyleneamino or H$_2$N—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl or the like without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies if alkenyl is part of another (combined) group like, e.g., in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene or the like without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies if alkenylene is a part of another (combined) group like for example in HO—$C_{x-y}$alkenyleneamino or H$_2$N—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl, etc.

By the generic terms propynyl, butynyl, pentynyl, hexynyl, heptynyl, octynyl, nonynyl, decynyl or the like without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, like, e.g., in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene or the like without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group like, e.g., in HO—$C_{x-y}$alkynyleneamino or $H_2N$—$C_{x-y}$alkynyleneoxy.

By heteroatoms are meant oxygen, nitrogen, phosphor and sulphur atoms. Preferably, heteroatoms are selected from oxygen, nitrogen and sulphur.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic cycloalkyl (=monocyclic hydrocarbon rings), bicyclic cycloalkyl (=bicyclic hydrocarbon rings) and spiro cycloalkyl (=spiro hydrocarbon rings). The ring systems are saturated. In bicyclic hydrocarbon rings two rings are joined together so that they have at least two carbon atoms in common. In spiro hydrocarbon rings one carbon atom (spiroatom) belongs to two rings together.

If a cycloalkyl is to be substituted, the substitutions may take place independently of one another, in the form of mono or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group like, e.g., in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained (with all definitions for cycloalkyl applying accordingly to the alicyclic group).

The term cycloalkylene is derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

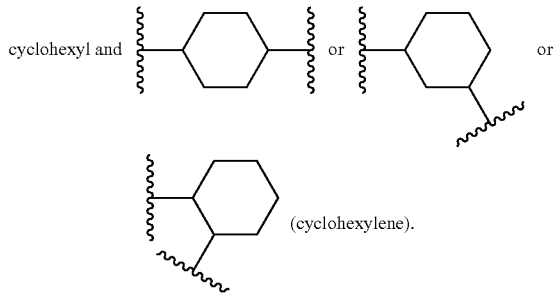

(cyclohexylene).

The above definition for cycloalkylene also applies if cycloalkylene is part of another (combined) group like, e.g., in HO—$C_{x-y}$cycloalkyleneamino or $H_2N$—$C_{x-y}$cycloalkyleneoxy.

Cycloalkenyl is also made up of the subgroups monocyclic cycloalkenyl (=monocyclic hydrocarbon rings, bicyclic cycloalkenyl (=bicyclic hydrocarbon rings) and spiro cycloalkenyl (=spiro hydrocarbon rings). However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group like, e.g., in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained (with all definitions for cycloalkenyl applying accordingly to the unsaturated alicyclic group).

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:

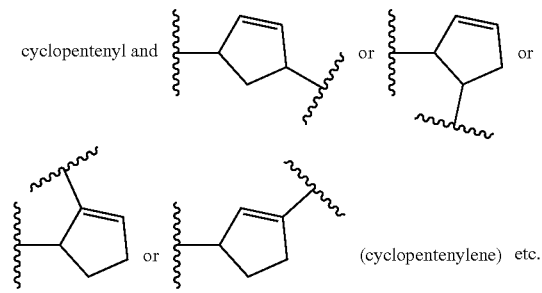

(cyclopentenylene) etc.

The above definition for cycloalkenylene also applies if cycloalkenylene is part of another (combined) group like, e.g., in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or may also be partially saturated.

If an aryl is to be substituted, the substitutions may take place independently of one another, in the form of mono or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group like, e.g., in arylamino, aryloxy or arylalkyl.

If the free valency of an aryl is saturated, then an aromatic group is obtained (with all definitions for aryl applying accordingly to the aromatic group).

The term arylene can also be derived from the previously defined aryl. Arylene, unlike aryl, is bivalent and requires two binding partners. Formally, the second valency is formed by removing a hydrogen atom from an aryl. Corresponding groups are for example:

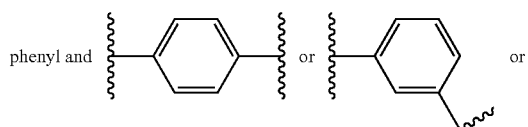

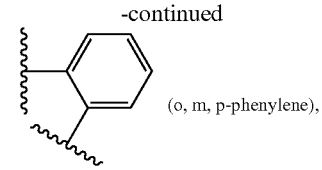

(o, m, p-phenylene),

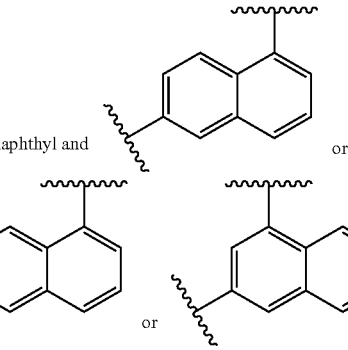

The above definition for arylene also applies if arylene is part of another (combined) group like, e.g., in HO-aryleneamino or $H_2N$-aryleneoxy.

Heterocyclyl denotes ring systems, which are derived from the previously defined cycloalkyl, cycloalkenyl and aryl by replacing one or more carbon atom(s) by heteroatom(s), e.g. replacing the groups —$CH_2$— independently of one another in the hydrocarbon rings by, e.g., the groups —O—, —S—, —NH— or —PH—, or by, e.g., replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (e.g., sulphur→sulphoxide —SO—, sulphone —$SO_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the sub-groups monocyclic heterocyclyl (=monocyclic heterorings), bicyclic heterocyclyl (=bicyclic heterorings), tricyclic heterocyclyl (=tricyclic heterorings) and spiro heterocyclyl (=spiro heterorings), which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro heterorings one carbon atom (spiro atom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. Substituents on heterocyclyl do not count for the number of members of a heterocyclyl, i.e. a given number of members of a heterocyclyl only refers to the number of atoms forming the ring/ring system of the heterocyclyl.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl, 2-oxa-6-azaspiro[3.3]heptyl, 5-oxa-2-azaspiro[3.4]octyl, 6-oxa-2-azaspiro[3.4]octyl etc.

Further examples are the structures illustrated below, which may be attached via each hydrogen-carrying atom (exchanged for hydrogen):

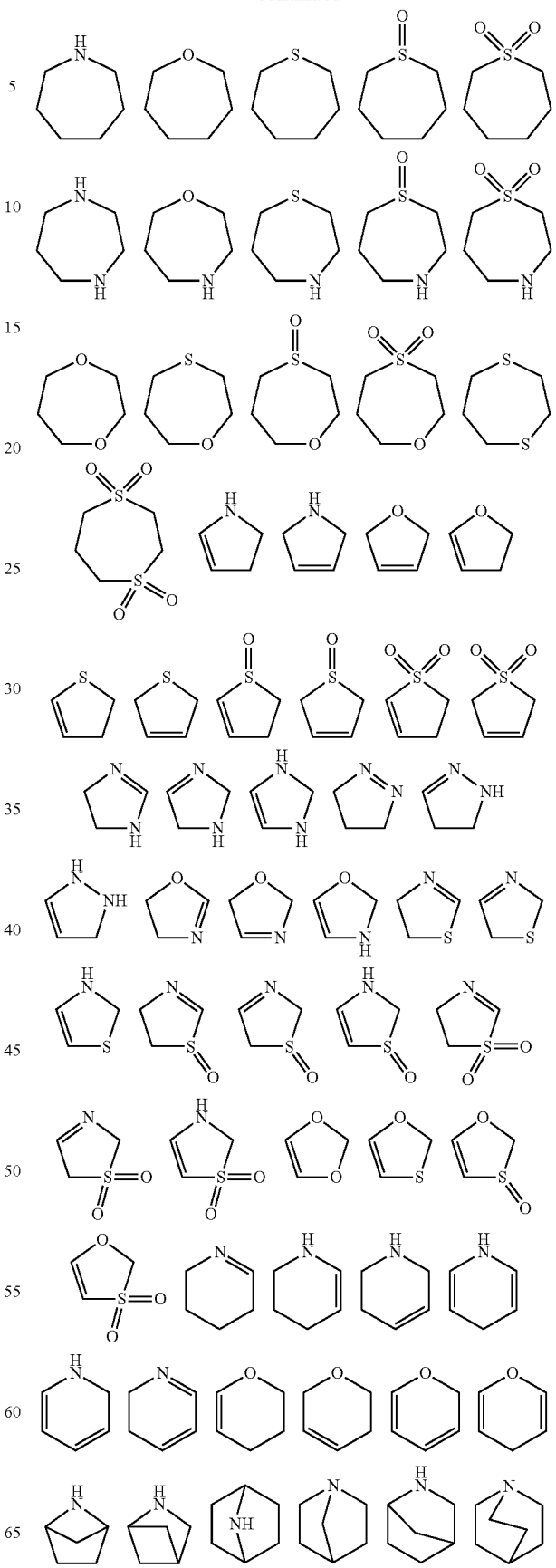

-continued

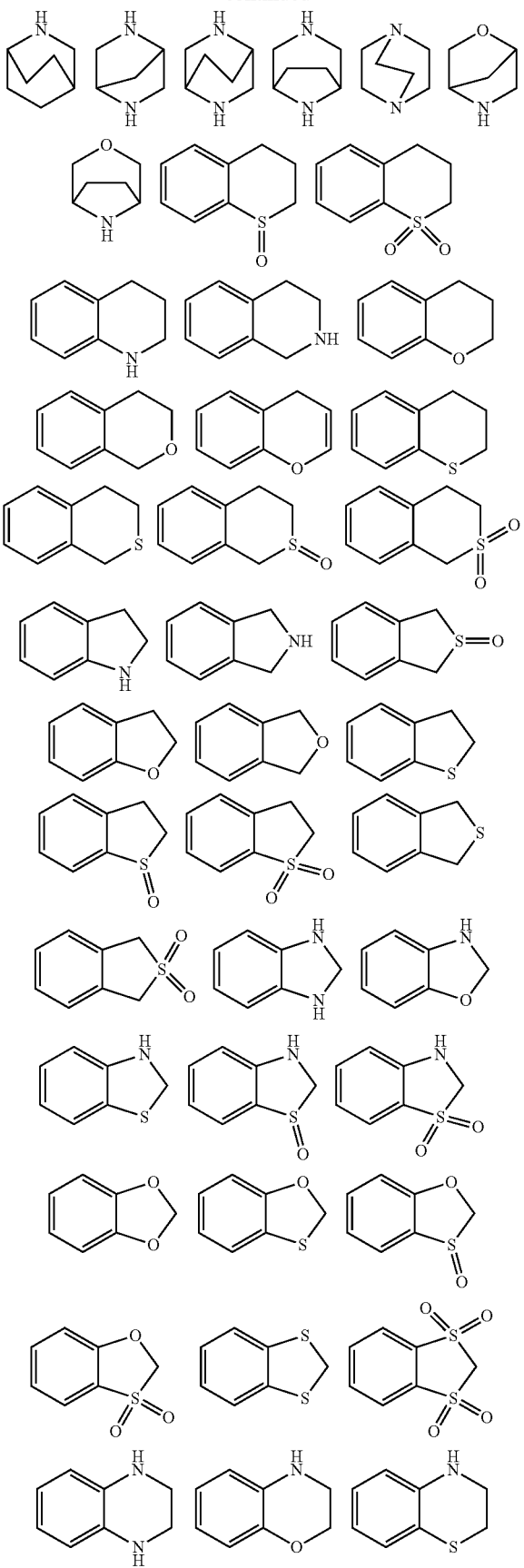

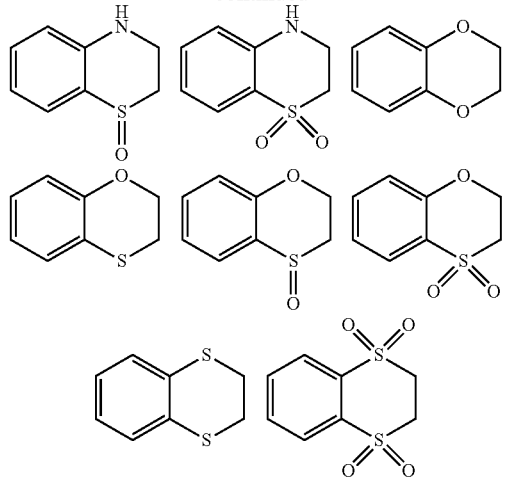

Preferably, heterocyclyls are 4 to 8 membered, monocyclic and have one or two heteroatoms independently selected from oxygen, nitrogen and sulfur.

Preferred heterocyclyls are: piperazinyl, piperidinyl, morpholinyl, homomorpholinyl, pyrrolidinyl, azetidinyl, oxetanyl, tetrahydropyranyl, tetrahydrofuranyl, 2-oxa-6-azaspiro[3.3]heptyl, 5-oxa-2-azaspiro[3.4]octyl, 6-oxa-2-azaspiro[3.4]octyl, 2-oxa-5-azabicyclo[2.2.1]heptyl, 2,5-diazabicyclo[2.2.1]heptyl.

Preferred monocyclic heterocyclyl is 4 to 7 membered and has one or two heteroatoms independently selected from oxygen, nitrogen and sulfur.

Preferred monocyclic heterocyclyls are: piperazinyl, piperidinyl, morpholinyl, pyrrolidinyl, and azetidinyl.

Preferred bicyclic heterocyclyl is 6 to 10 membered and has one or two heteroatoms independently selected from oxygen, nitrogen and sulfur.

Preferred tricyclic heterocyclyl is 9 membered and has one or two heteroatoms independently selected from oxygen, nitrogen and sulfur.

Preferred spiro heterocyclyl is 7 to 11 membered and has one or two heteroatoms independently selected from oxygen, nitrogen and sulfur.

The above definition of heterocyclyl also applies if heterocyclyl is part of another (combined) group like, e.g., in heterocyclylamino, heterocyclyloxy or heterocyclylalkyl.

If the free valency of a heterocyclyl is saturated, then a heterocycle is obtained (with all definitions for heterocyclyl applying accordingly to the heterocycle).

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

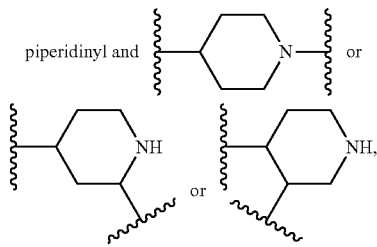

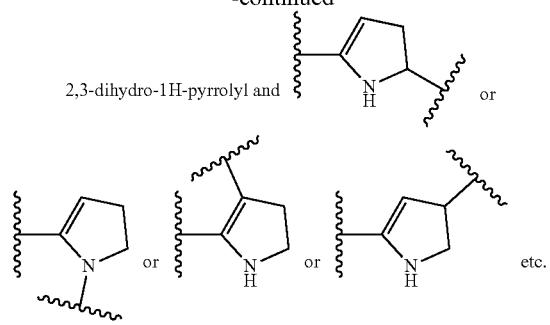

2,3-dihydro-1H-pyrrolyl and ... or ... or ... or ... etc.

The above definition of heterocyclylene also applies if heterocyclylene is part of another (combined) group like, e.g., in HO-heterocyclyleneamino or H₂N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen. Substituents on heteroaryl do not count for the number of members of a heteroaryl, i.e. a given number of members of a heteroaryl only refers to the number of atoms forming the ring/ring system of the heteroaryl.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

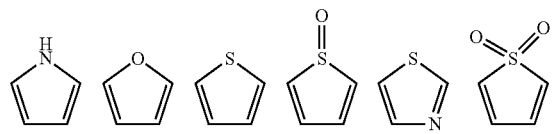

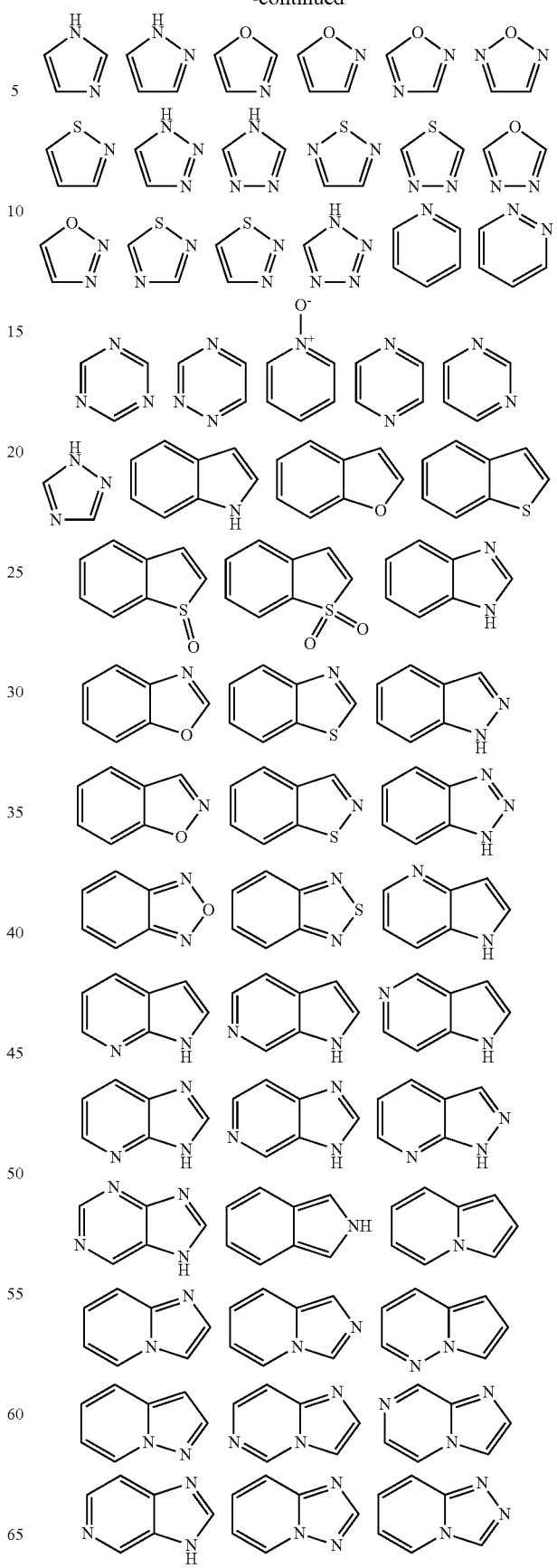

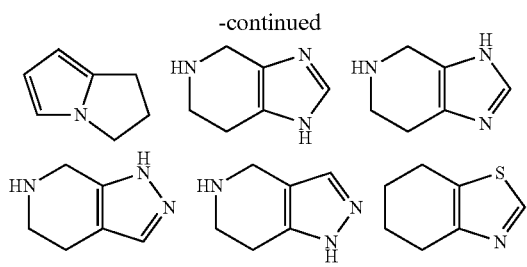

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group like, e.g., in heteroarylamino, heteroaryloxy or heteroarylalkyl.

If the free valency of a heteroaryl is saturated, a heteroaromatic ring is obtained (with all definitions for heteroaryl applying accordingly to the heteroaromatic ring).

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:

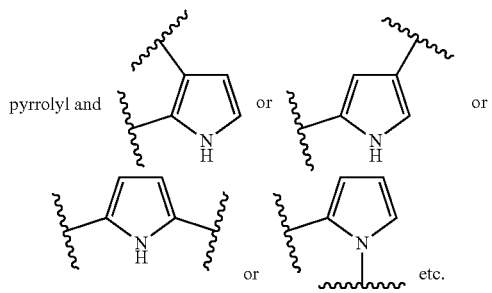

The above definition of heteroarylene also applies if heteroarylene is part of another (combined) group like, e.g., in HO-heteroaryleneamino or $H_2N$-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, whereas the bivalent substituents =O and =NR may also be a substituent on sulphur and phosphor. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$—, sulphur and phosphor atoms (=O group or =NR group only, one or two =O groups possible or, e.g., one =O group and one =NR group, each group replacing a free electron pair) of a ring system.

Stereochemistry/Solvates/Hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), are also part of the invention.

In a representation such as for example

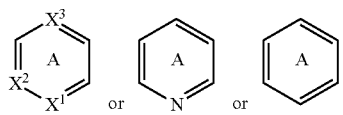

the letter A has the function of a ring designation in order to make it easier, for example, to indicate the attachment of the ring in question to other rings.

In a representation such as for example

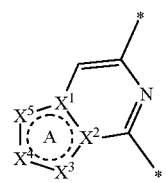

the dotted circle in ring A denotes that each bond between ring members in ring A can be independently selected from a single bond, a double bond or a (hetero)aromatic bond. A (hetero)aromatic bond is a bond comprising delocalized binding electrons with a bond order between a single and a double bond. Preferably, ring A is a (hetero)aromatic ring.

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

| List of abbreviations | |
|---|---|
| Ac | acetyl |
| AcCN | acetonitrile |
| aq. | aquatic, aqueous |
| ATP | adenosine triphosphate |
| Bn | benzyl |
| Boc | tert-butyloxycarbonyl |
| Bu | butyl |
| c | concentration |
| CSA | camphorsulfonic acid |
| d | day(s) |
| dba | dibenzylideneacetone |
| TLC | thin layer chromatography |
| Davephos | 2-dimethylamino-2'-dicyclohexylaminophosphinobiphenyl |
| DBA | dibenzylideneacetone |
| DCM | dichloromethane |
| DEA | diethylamine |
| DEAD | diethyl azodicarboxylate |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| EDTA | ethylenediaminetetraacetic acid |
| EGTA | ethyleneglycoltetraacetic acid |
| eq. | equivalent(s) |
| ESI | electron spray ionization |
| Et | ethyl |
| $Et_2O$ | diethyl ether |
| EtOAc | ethyl acetate |
| EtOH | ethanol |
| h | hour |
| HATU | O-(7-azabenzotriazol-1-yl)-N,N,N,N-tetramethyl-uronium hexafluorophosphate |
| HPLC | high performance liquid chromatography |
| IBX | 2-iodoxy benzoic acid |
| i | iso |
| conc. | concentrated |
| LAH | lithium aluminium hydride |
| LC | liquid chromatography |
| LiHMDS | lithium bis(trimethylsilyl)amide |
| sln. | solution |
| Me | methyl |
| MeOH | methanol |
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf ($R_f$) | retention factor |
| RP | reversed phase |
| rt | ambient temperature |
| SEM | trimethylsilyl ethoxymethyl |
| SFC | supercritical fluid chromatography |
| $S_N$ | nucleophilic substitution |
| T3P | propylphosphonic anhydride |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |

-continued

| List of abbreviations | |
|---|---|
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the principles of the invention by way of example without restricting its scope:
Preparation of the Compounds According to the Invention
General Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with IUPAC rules using the software ChemDraw. If a compound is to be represented both by a structural formula and by its nomenclature, in the event of a conflict the structural formula prevails.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.
Chromatography Thin layer chromatography is carried out on ready-made TLC plates of silica gel 60 on glass (with fluorescence indicator F-254) made by Merck.

The preparative high pressure chromatography (HPLC) of the example compounds according to the invention is carried out with, e.g., columns made by Waters (names: Sunfire C18 OBD, 10 µm, 30×100 mm Part. No. 186003971; X-Bridge C18 OBD, 10 µm, 30×100 mm Part. No. 186003930). The compounds are eluted using, e.g., different gradients of $H_2O$/AcCN wherein 0.2% HCOOH is added to the water (acidic conditions). For chromatography under basic conditions the water is, e.g., made basic according to the following recipe: 5 mL of ammonium hydrogen carbonate solution (158 g to 1 L $H_2O$) and 2 mL 32% $ammonia_{(aq)}$ are made up to 1 L with $H_2O$.

The supercritical fluid chromatography (SFC) of the intermediates and example compounds according to the invention is, e.g., carried out on a JASCO SFC-system with the following columns: Chiralcel OJ (250×20 mm, 5 µm), Chiralpak AD (250×20 mm, 5 µm), Chiralpak AS (250×20 mm, 5 µm), Chiralpak IC (250×20 mm, 5 µm), Chiralpak IA (250×20 mm, 5 µm), Chiralcel OJ (250×20 mm, 5 µm), Chiralcel OD (250×20 mm, 5 µm), Phenomenex Lux $C_2$ (250×20 mm, 5 µm).

The analytical HPLC (reaction monitoring) of intermediate compounds is carried out with, e.g., columns made by Waters and Phenomenex. The analytical equipment is also provided with a mass detector in each case.
HPLC Mass Spectroscopy/UV Spectrometry The retention times/MS-ESI⁺ for characterizing the example compounds according to the invention are produced using an HPLC-MS apparatus (high performance liquid chromatography with mass detector) made by Agilent. Compounds that elute at the injection peak are given the retention time $t_{Ret.}$=0.00.
HPLC-methods (Preparative)
NP 1
   NP purification: GLASS COLUMN
   Column: 100-200 mesh size silica gel
   Solvent: A: DCM; B: MeOH
   Detection: $KMnO_4$
   Flow: 100 mL/min
   Gradient: 0-60 min: 1% B
      60-100 min: varying
      100-200 min: 10% B
Prep. HPLC 1
   HPLC: 333 and 334 Pumps
   Column: Waters XBridge C18 OBD, 10 µm, 30×100 mm, Part. No. 186003930
   Solvent: A: 10 mM $NH_4HCO_3$ in $H_2O$; B: AcCN (HPLC grade)
   Detection: UV/Vis-155
   Flow: 50 mL/min
   Gradient: 0.00-1.50 min: 1.5% B
      1.50-7.50 min: varying
      7.50-9.00 min: 100% B
Prep. HPLC 3
   HPLC/MS: semi prep HPLC Agilent
   Column: Triart Prep C18, 10 µm, 30×100 mm, Part. No. 3010000120
   Solvent: A: $H_2O$+0.2% HCOOH; B: AcCN (HPLC grade)+0.2% HCOOH
   Detection: UV/Vis-155
   Mass: Agilent G6120B MSD—API-ES, positive mode range 120-820
   Flow: 50 mL/min
   Gradient: 0.00-0.80 min: 28% B
      0.80-6.80 min: varying
      6.80-9.00 min: 98% B
HPLC-Methods (Analytic)
LCMS3, basisch_1
   HPLC: Agilent 1100 Series
   MS: Agilent LC/MSD (API-ES+/−3000 V, Quadrupol, G6140)
   Column: Waters, XBridge C18, 2.5 µm, 2.1×20 mm column
   Solvent: A: 20 mM $NH_4HCO_3/NH_3$ in $H_2O$ pH 9; B: AcCN (HPLC grade)
   Detection: MS: positive and negative mode
   Mass range: 120-900 m/z
   Flow: 1.00 mL/min
   Column temperature: 60° C.
   Gradient: 0.00-1.50 min: 10%→95% B
      1.50-2.00 min: 95% B
      2.00-2.10 min: 95%→10% B
VAB
   HPLC: Agilent 1100/1200 Series
   MS: Agilent LC/MSD SL
   Column: Waters XBridge BEH C18, 2.5 µm, 2.1×30 mm XP
   Solvent: A: 5 mM $NH_4HCO_3$/19 mM $NH_3$ in $H_2O$; B: AcCN (HPLC grade)
   Detection: MS: positive and negative mode
   Mass range: 100-1200 m/z
   Flow: 1.40 mL/min
   Column temperature: 45° C.
   Gradient: 0.00-1.00 min: 5% B→100% B
      1.00-1.37 min: 100% B
      1.37-1.40 min: 100%→5% B VAS
 HPLC: Agilent 1100/1200 Series
 MS: Agilent LC/MSD SL
 Column: YMC TriART C18 2.0×30 mm, 3 μm
 Solvent: A: H2O+0.2% formic acid; B: AcCN (HPLC grade)
 Detection: MS: positive and negative mode
 Mass range: 105-1200 m/z
 Flow: 1.40 mL/min
 Column temperature: 35° C.
 Gradient: 0.0 min: 5% B
  0.0-1.00 min: 5% B à 100% B
  1.00-1.37 min: 100% B
  1.37-1.40 min: 100% B à 5% B TCG_LCMS, basisch_1
 HPLC: Waters ACQUITY UPLC
 MS: ACQUITY SQD Mass Spectrometer from Waters
 Column: YMC triart Waters, 1.8 μm, 2.1×33 mm
 Solvent: A: 10 mM NH$_4$OAc pH 6.5; B: AcCN (HPLC grade)
 Detection: MS: positive and negative mode
 Mass range: 100-1000 m/z
 Flow: 1.00 mL/min
 Column temperature: 50° C.
 Gradient: 0.00-0.75 min: 2% B
  0.75-1.00 min: 2%→10% B
  1.00-2.00 min: 10%→98% B
  2.00-2.50 min: 98% B
  2.50-2.90 min: 98% B
  2.90-3.00 min: 98%→2% B TCG_LCMS, basisch_2
 HPLC: Shimadzu Prominance
 MS: LCMS/MS-API Q trap
 Column: Waters XBridge C18; 4.6×50 mm, 5 μm
 Solvent: A: 10 mM NH$_4$OAc pH 6.5; B: AcCN (HPLC grade)
 Detection: MS: positive and negative mode
 Mass range: 100-800 m/z
 Flow: 1.20 mL/min
 Column temperature: 25° C.
 Gradient: 0.00-0.01 min: 0%→10% B
  0.01-1.50 min: 10%→30% B
  1.50-3.00 min: 30%→90% B
  3.00-4.00 min: 90% B
  4.00-5.00 min: 90%→10% B GVK_LCMS_19
 HPLC: Agilent RRLC
 MS: Agilent Technologies—6130 Quadrupole LC/MS
 Column: Waters XBridge C18, 4.6×75 mm, 3.5 μm
 Solvent: A: 10 mM NH$_4$OAc; B: AcCN (HPLC grade)
 Detection: MS: positive and negative mode
 Mass range: 70-1200 m/z
 Flow: 2.0 mL/min
 Column temperature: 35° C.
 Gradient: 0.00-0.20 min: 10% B
  0.20-2.50 min: 10%→75% B
  2.50-3.00 min: 75%→100% B
  3.00-4.80 min: 100% B
  4.80-5.00 min: 100%→5% B GVK_LCMS_41
 UPLC/MS: Waters Acquity-UPLC-SQ Detector-2
 Column: AQUITY UPLC BEH C18 1.7 μm, 2.1×50 mm
 Solvent: A: 0.07% formic acid in AcCN; B: 0.07% formic acid in water
 Detection: MS: positive and negative mode
 Mass range: 100-1500 m/z
 Flow: 0.6 mL/min
 Column temperature: 35° C.
 Gradient: 0.00-0.30 min: 97% B
  0.30-2.20 min: 97%→2% B
  2.20-3.30 min: 2% B
  3.30-4.50 min: 2%→97% B
  4.50-4.51 min: 97% B GVK_LCMS_61
 UPLC/MS: Waters Acquity-Binary Solvent Manager-UPLC-SQ Detector-2
 Column: AQUITY UPLC BEH C18 1.7 μm, 2.1×50 mm
 Solvent: A: 0.07% formic acid in AcCN; B: 0.07% formic acid in water
 Detection: MS: positive and negative mode
 Mass range: 100-1500 m/z
 Flow: 0.6 mL/min
 Column temperature: 35° C.
 Gradient: 0.00-0.40 min: 97% B
  0.40-2.50 min: 97%→2% B
  2.50-3.40 min: 2% B
  3.40-3.50 min: 2%→97% B
  3.50-4.00 min: 97% B XB5A
 HPLC: Agilent HPLC 1100/1200
 Column: Waters XBridge BEH C18, 4.6×50 mm, p/n 186006037
 Solvent: A: H$_2$O+0.01% HClO$_4$; B: 100% AcCN (HPLC grade)
 Flow: 1.50 mL/min
 Column temperature: 30° C.
 Gradient: 0.00-3.50: 10% B
  3.50-4.50 min: 10%→95% B
  4.50-5.00 min: 10% B The compounds according to the invention and intermediates are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or their synthesis is described in the prior art or they may be prepared analogously to known prior art compounds or methods described herein, i.e. it is within the skills of an organic chemist to synthesize these compounds. Substances described in the literature can be prepared according to the published methods of synthesis.

General Reaction Scheme and Summary of the Synthesis Route

Compounds (I) according to the invention can be synthesized using a BUCHWALD-HARTWIG cross coupling reaction (→scheme 1) starting from the 1H-pyrazolo[4,3-c]pyridines A-1 and different halogenated building blocks B-1 using a palladium source (e.g. tris-(dibenzylideneacetone)-dipalladium(0)) and a phosphine ligand (e.g. tert-butyl XPhos) (see e.g. WO 2019/105886).

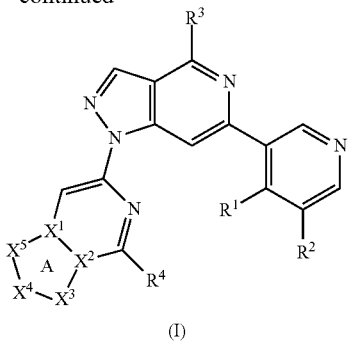

(I)

The A-1 building blocks needed can be synthesized (→scheme 2) starting from pyridine derivatives A-7. A reduction of the ester group followed by an oxidation leads to the carbaldehydes A-5. The ring closure reaction with hydrazine monohydrate (see e.g. WO 2015/94929) followed by protection of the indazole nitrogen in A-4 (e.g. with a Boc or THP group) results in protected indazole A-3. A SUZUKI coupling with boronate esters C-1 (see e.g. J. Org. Chem. 2007, 72, 4067-4072; Org. Lett., 2011, 13, 252-255; J. Org. Chem. 2004, 69, 7779-7782) or a STILLE coupling (see e.g. WO 2003/87037) with the corresponding stannane C-2 followed by deprotection leads to 1H-pyrazolo[4,3-c]pyridines A-1. Alternatively, carbaldehydes A-5 can be obtained starting from malonyl chloride and nitriles (D-4). Resultant dihydroxypyridine D-3 is then subjected to chlorination conditions to give dichloride D-2 (see e.g. WO 2018/93569, WO 2014/52563, J. Med. Chem. 2009, 52, 7473-7487). Reduction of the nitrile group followed by hydrolysis gives aldehyde A-5.

Scheme 1

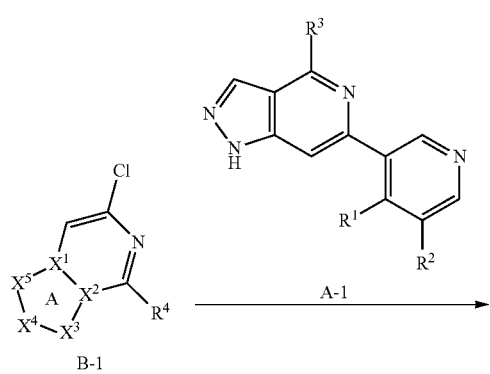

Scheme 2

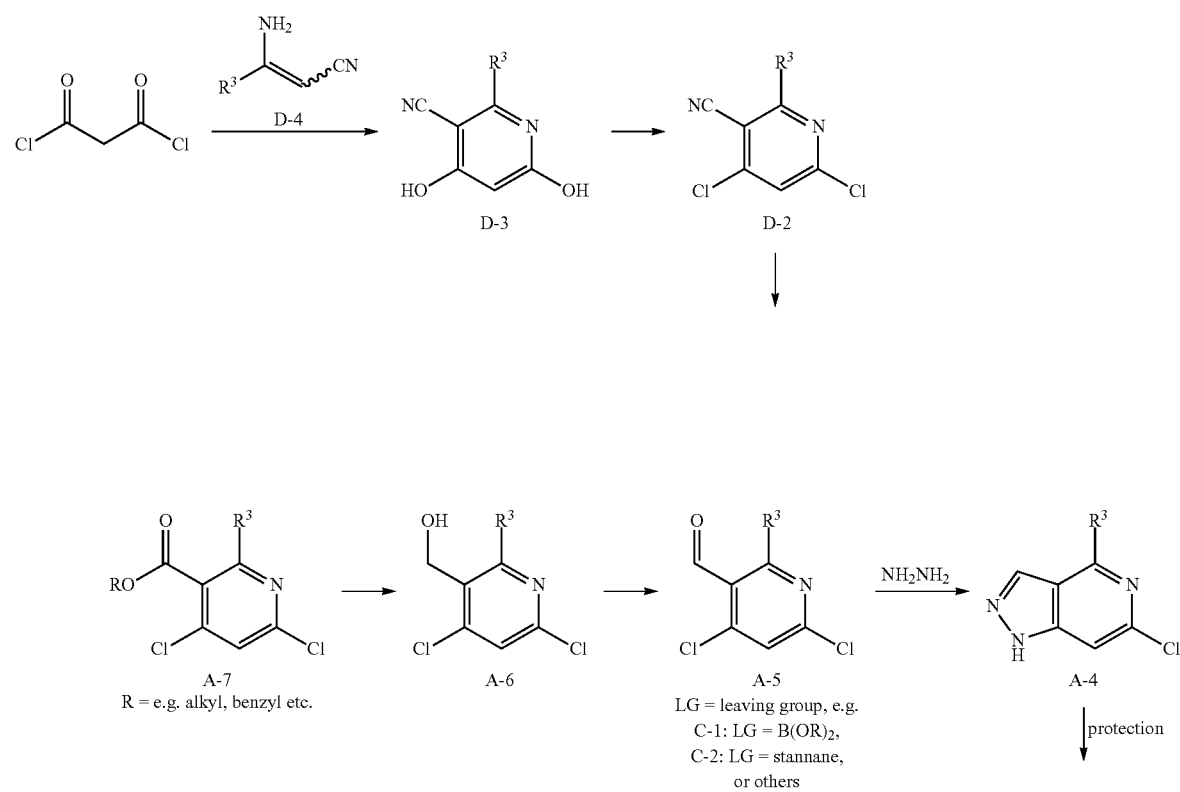

-continued

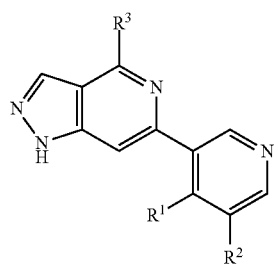
A-1

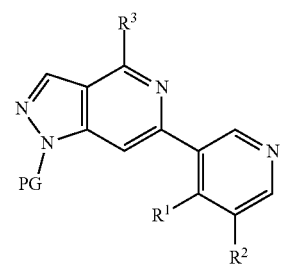
A-2

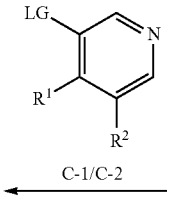

C-1/C-2

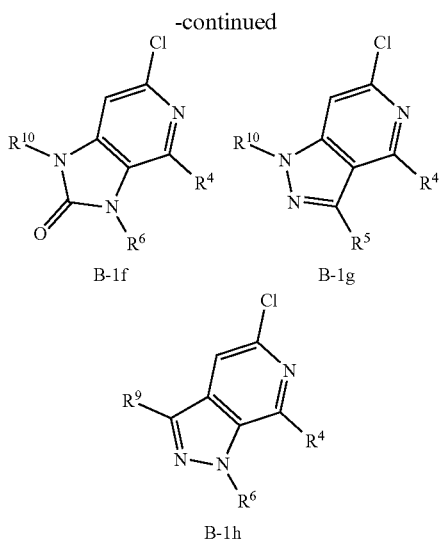
A-3
PG = protecting group,
e.g. Boc, 2-tetrahydropyranyl etc.

The key building blocks B-1 are, e.g., accessible via three different synthetic strategies starting from B-3 (→scheme 3a):

Building blocks B-1 with N-linked residues $R^4$ are available through a nucleophilic aromatic substitution with an excess of the corresponding N-nucleophile/amine B-2 under neat conditions.

Building blocks B-1 with O-linked residues $R^4$ are available through a nucleophilic aromatic substitution carried out with an excess of the O-nucleophile/alcohol B-2 and a strong base, e.g. sodium hydride in a suitable solvent (see e.g. US 2016/207924).

C—C-coupling of $R^4$ can be achieved with a SUZUKI coupling of a boronic acid derivative B-2 of residue $R^4$ using a palladium catalyst (e.g. [1,1'-bis (diphenylphosphino)ferrocene]di-chloropalladium(II)).

Scheme 3a

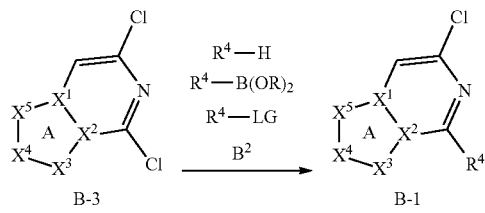

Exemplary more specific embodiments of building blocks B-1 are as follows (→scheme 3b):

Scheme 3b

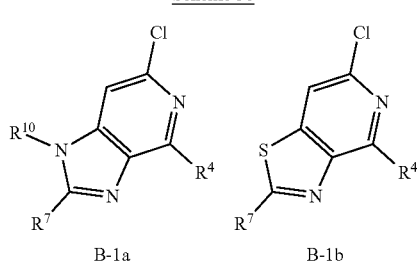
B-1a      B-1b

-continued

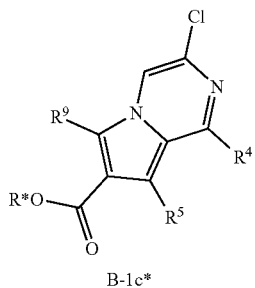
B-1f      B-1g

B-1h $R^*$ = e.g. alkyl, benzyl etc.

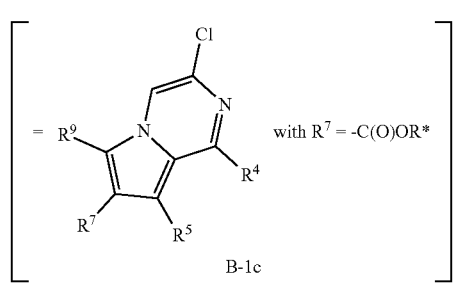
B-1c* with $R^7$ = -C(O)OR*

B-1c

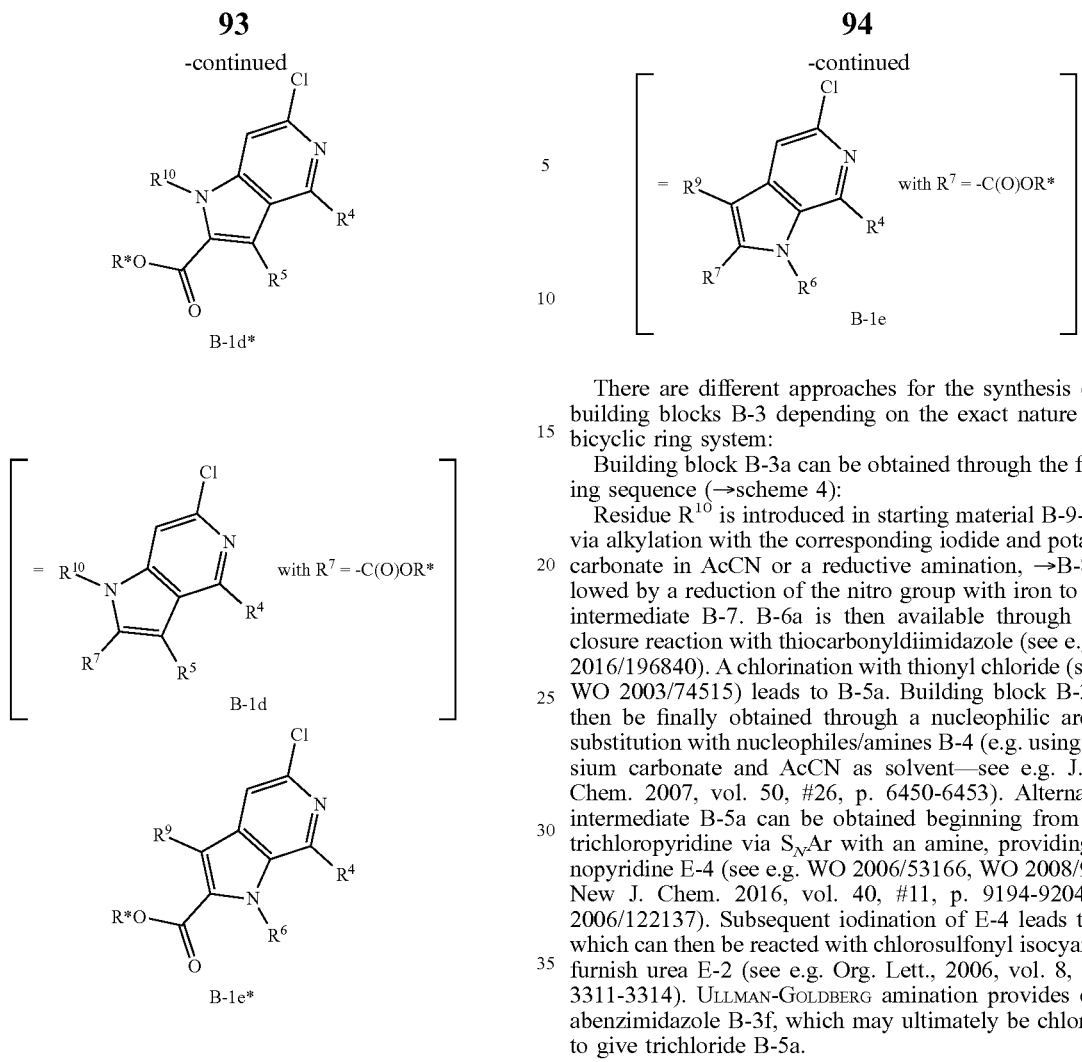

There are different approaches for the synthesis of key building blocks B-3 depending on the exact nature of the bicyclic ring system:

Building block B-3a can be obtained through the following sequence (→scheme 4):

Residue $R^{10}$ is introduced in starting material B-9-a (e.g. via alkylation with the corresponding iodide and potassium carbonate in AcCN or a reductive amination, →B-8) followed by a reduction of the nitro group with iron to obtain intermediate B-7. B-6a is then available through a ring closure reaction with thiocarbonyldiimidazole (see e.g. WO 2016/196840). A chlorination with thionyl chloride (see e.g. WO 2003/74515) leads to B-5a. Building block B-3a can then be finally obtained through a nucleophilic aromatic substitution with nucleophiles/amines B-4 (e.g. using potassium carbonate and AcCN as solvent—see e.g. J. Med. Chem. 2007, vol. 50, #26, p. 6450-6453). Alternatively, intermediate B-5a can be obtained beginning from 2,4,6-trichloropyridine via $S_NAr$ with an amine, providing aminopyridine E-4 (see e.g. WO 2006/53166, WO 2008/92942, New J. Chem. 2016, vol. 40, #11, p. 9194-9204, WO 2006/122137). Subsequent iodination of E-4 leads to E-3, which can then be reacted with chlorosulfonyl isocyanate to furnish urea E-2 (see e.g. Org. Lett., 2006, vol. 8, #15, p 3311-3314). ULLMAN-GOLDBERG amination provides oxoazabenzimidazole B-3f, which may ultimately be chlorinated to give trichloride B-5a.

Scheme 4

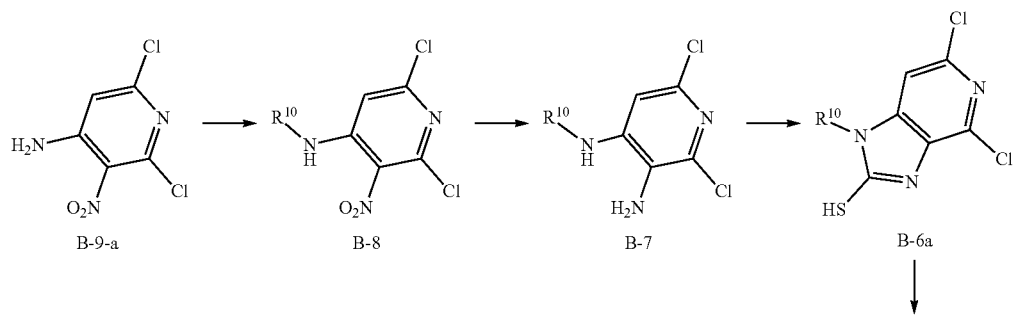

-continued

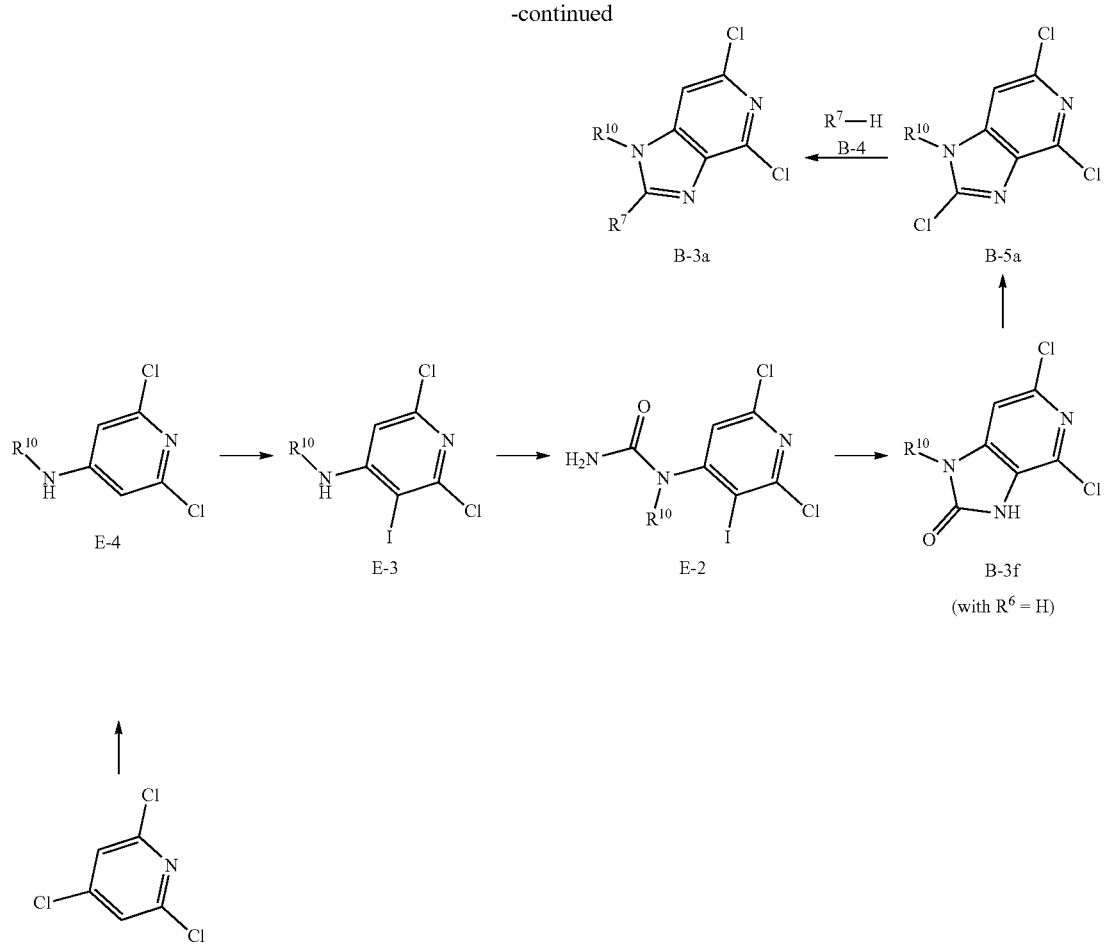

In an alternative approach (→scheme 5) the ring closure on intermediate B-7 is performed via amidation with carboxylic acid B-11 to intermediate B-10 and ring condensation under acidic conditions (see e.g. Bioorg. Med. Chem. Lett., 2011, vol. 21, #14, p. 4197-4202). In still another variation carboxylic acid B-11 is activated, e.g. with polyphosphoric acid, and ring closure/condensation to B-3a can be achieved in a one-step/one-pot reaction. In case of $R^7$=H the ring closure can also be performed with trimethyl orthoformate (TMOF) as C1 acid equivalent.

Scheme 5

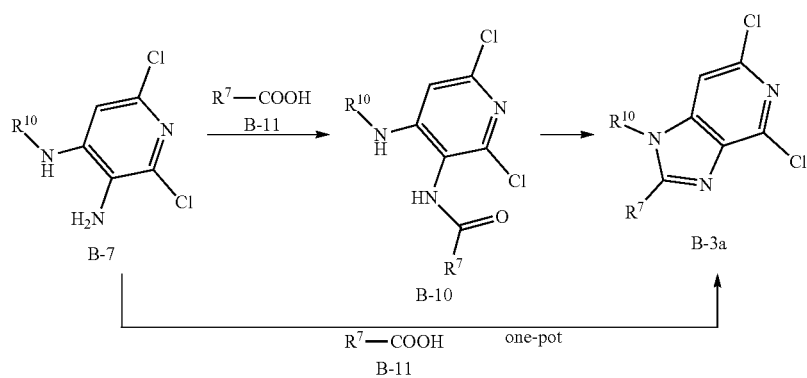

Building block B-3b can be obtained through the following sequence (→scheme 6):

One potential reaction sequence starts with a reduction of the nitro group of starting material B-13-a (e.g. with iron). The ring closure reaction on B-12 can be carried out with, e.g., potassium ethylxanthate (→B-6b; see e.g. WO 2015/104688). A chlorination with sulfuryl chloride (see e.g. WO 2013/56679) leads to B-5b. Building block B-3b can then be finally obtained through a nucleophilic aromatic substitution with nucleophiles/amines B-4 (e.g. using potassium carbonate and AcCN as solvent—see e.g. J. Med. Chem. 2007, vol. 50, #26, p. 6450-6453).

Scheme 6

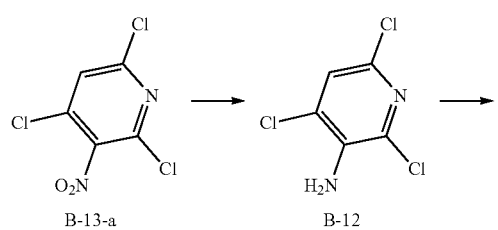

B-13-a → B-12 →

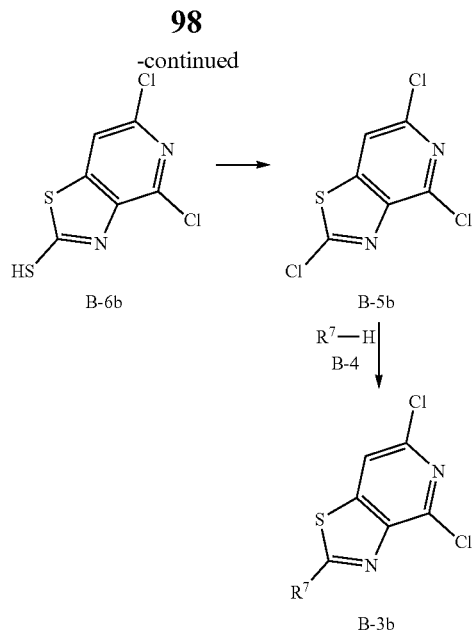

B-6b → B-5b

R$^7$—H
B-4

↓

B-3b

Building block B-3c* can be obtained through the following sequence (→scheme 7):

Starting material B-18 is alkylated on the pyrrole ring to give B-17 which is then treated with hydrazine hydrate leading to B-16. A ring closure reaction under acetic conditions leads to B-15 which is then treated with sodium nitrite and hydrochloric acid resulting in B-14 (see e.g. Monatshefte für Chemie 2016, vol. 147, #4, p. 783-789). In the final step B-3c* is available by a chlorination reaction with a mixture of phosphorus oxychloride and phosphorus pentachloride.

Scheme 7

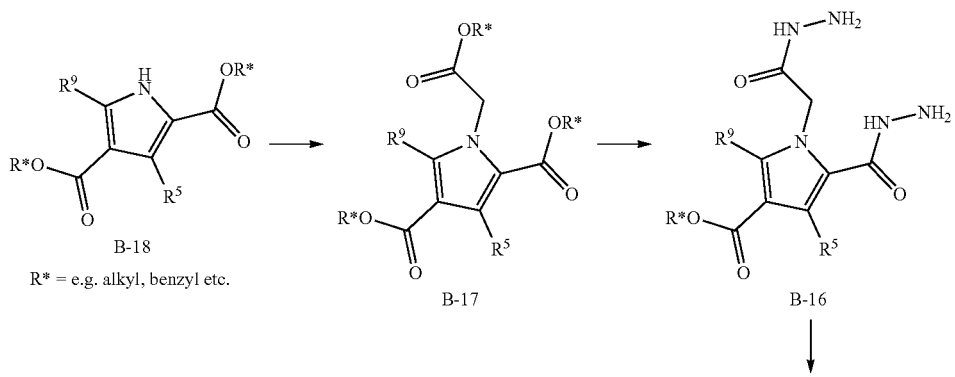

B-18
R* = e.g. alkyl, benzyl etc.

B-17

B-16

↓

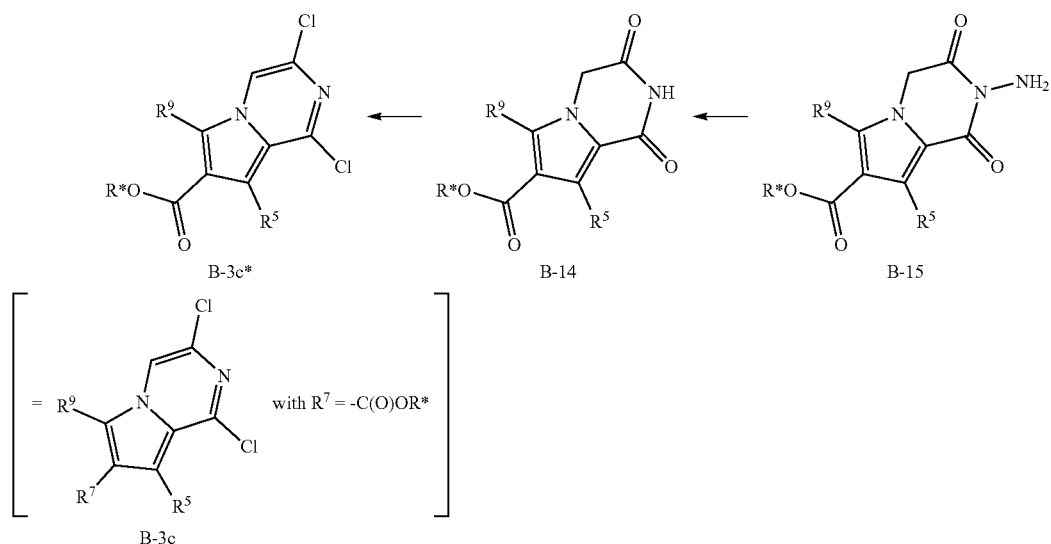

Building block B-3d* can be obtained through the following sequence (→scheme 8):

The reaction sequence leading to building blocks B-3d* starts with the formylation of B-24 with, e.g., n-BuLi and ethylformate to obtain the carbaldehyde B-23 (see e.g. WO 2015/25026). A GRIGNARD reaction followed by an oxidation leads to the intermediate B-21 (see e.g. WO 2017/42100). B-19 can be obtained through a nucleophilic aromatic substitution with the corresponding glycinate B-20 with, e.g., DIPEA in EtOH. The concluding ring closure reaction under basic conditions leads to B-3d*.

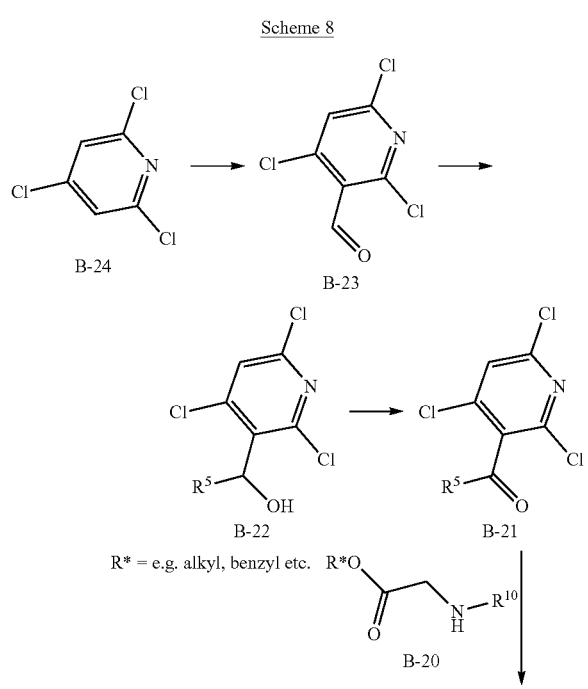

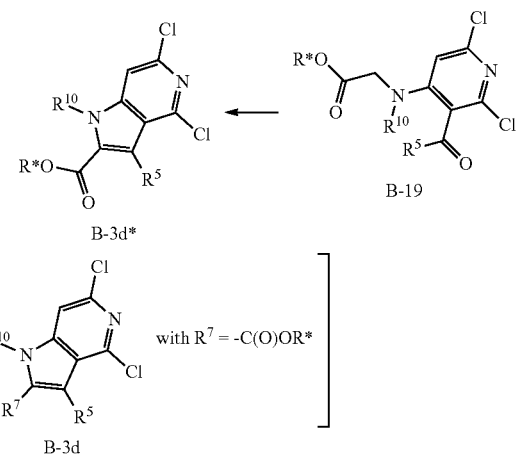

Building block B-3e* can be obtained through the following sequence (→scheme 9):

The multi-step reaction sequence to building blocks B-3e* starts with a nitration of B-31 followed by the reaction of B-30 with oxalic acid diester B-29 to give B-28 (see e.g. WO 2004/104001). The reduction of the nitro group results in the ring closure to B-27 (see e.g. WO 2012/80450). An iodination with N-iodsuccinimide in DCM gives B-26 followed by an alkylation with the corresponding alkyl halide to obtain B-25. The sequence concludes with a SUZUKI coupling to introduce the $R^9$ moieties resulting in B-3e* (see e.g. US 2013/210818).

Scheme 9
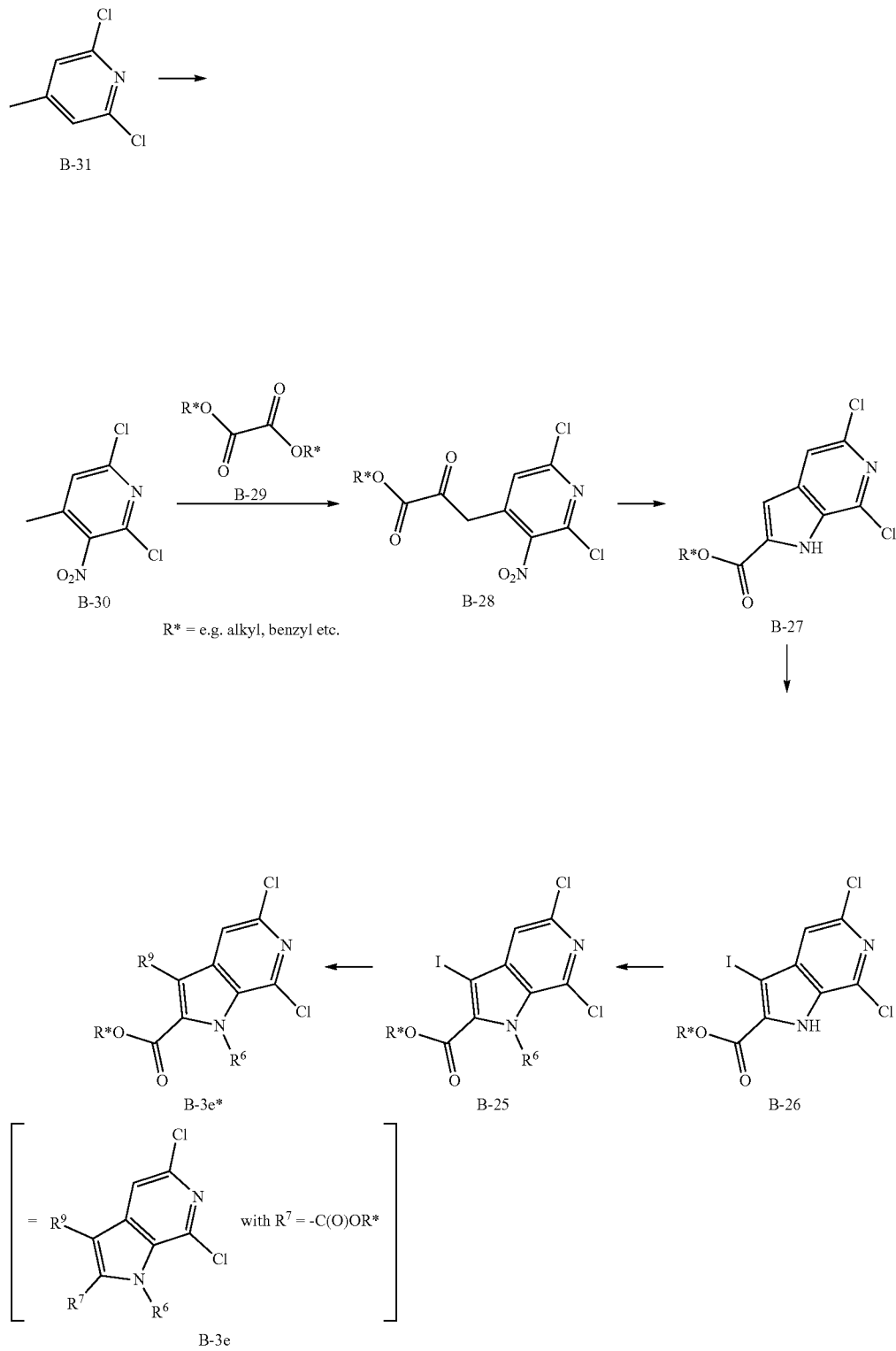

Building blocks B-3c*, B-3d* and B-3e* are embodiments of more general building blocks B-3c, B-3d und B-3e, respectively, with $R^7=-C(=O)OR^*$, which can be transformed to intermediates B-1 and then coupled with intermediates A-1. Compounds (I) according the invention thus obtained can then be further modified by saponification and derivatization/amidation of the free carboxyl group.

Building block B-3f can be obtained through the following sequence (→scheme 10):

Starting again with dichloro pyridine B-7 (see scheme 4 and 5) intermediate B-32 is available through a ring closure. Introduction of residue $R^6$, e.g. by alkylation with a corresponding alkylating agent like an alkyl iodide and a base (e.g. sodium hydride) in a solvent like DMF, leads to B-3f.

Scheme 10

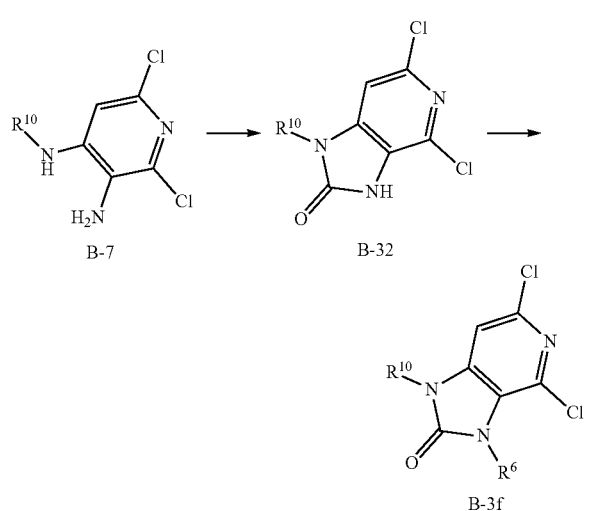

Building block B-3a can be obtained through the following sequence (→scheme 11):

Starting with trichloropyridin compounds B-34 the ring closure and introduction of residue $R^{10}$ is achieved by using a corresponding hydrazine B-33, e.g. in a solvent like MeOH.

Scheme 11

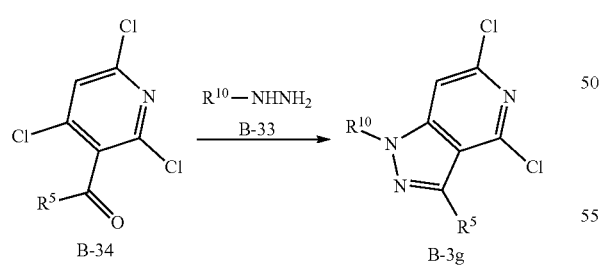

Building block B-3h can be obtained through the following sequence (→scheme 12):

Starting with a diazotation of B-36 followed by a ring closure intermediates B-3h (see e.g. WO 2007/117778) can be obtained. Introduction of other residues $R^6$, e.g. by alkylation with a corresponding alkylating agent B-35 like, e.g., sulfuric acid dimethyl ester and a base (e.g. potassium carbonate) in a solvent like AcCN, leads to further intermediates B-3h.

Scheme 12

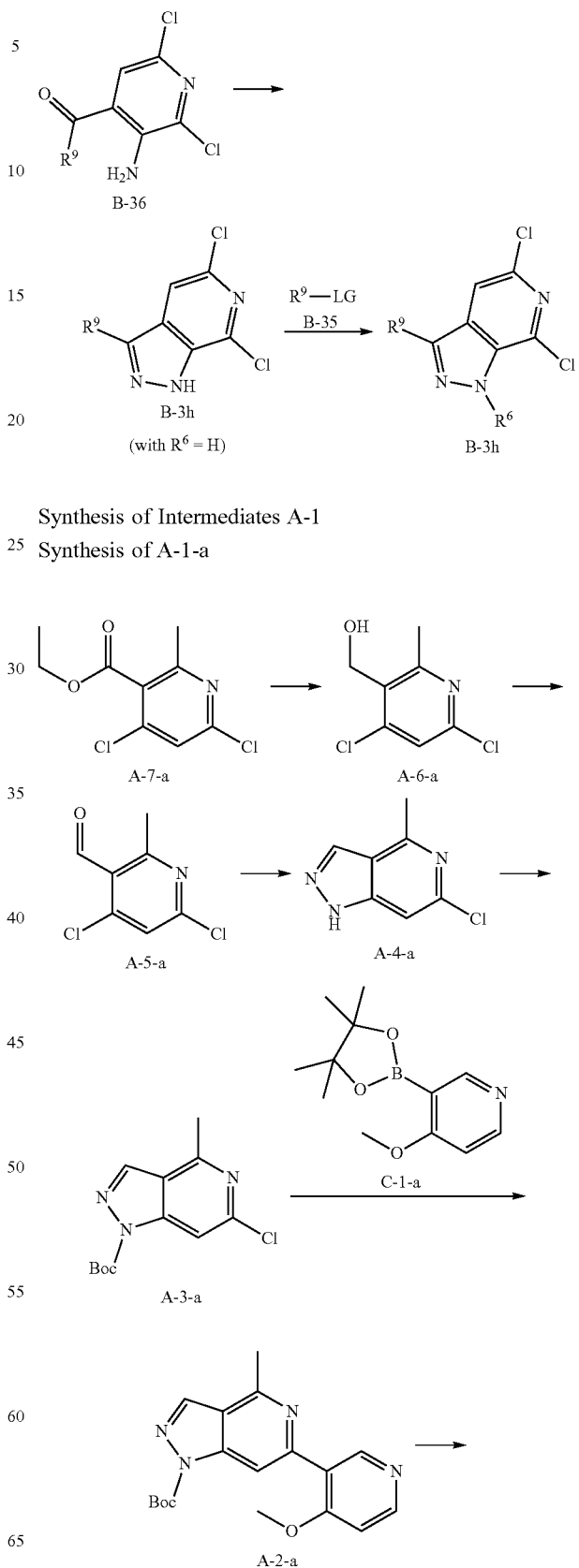

Synthesis of Intermediates A-1

Synthesis of A-1-a

-continued

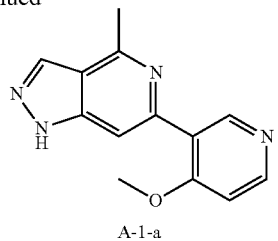

A-1-a

Experimental Procedure for the Synthesis of A-6-a

To a stirred solution of A-7-a (100.0 g; 42.70 mmol) in THF (100.0 mL) is added DIBAL-H (854.0 mL; 85.40 mmol) at 0° C. The reaction mixture is stirred at rt for 4 h. The reaction is quenched with Rochelle salt (1000 mL) and then EtOAc (1000 mL) is added. The reaction mixture is filtered through a pad of Celite and washed with EtOAc (1000 mL). The organic layer is dried over MgSO$_4$, filtered and the solvent is evaporated under reduced pressure. The crude product is purified by normal phase chromatography (EtOAc/petroleum ether 20:80) to afford the desired product A-6-a (HPLC-MS: (M+H)$^+$=192.1, $t_{Ret.}$=1.60 min, method GVK_LCMS_41).

Experimental Procedure for the Synthesis of A-5-a

To a stirred solution of A-6-a (70.0 g; 36.50 mmol) in DCM (100.0 mL) is added DESS-Martin periodinane (170.0 g; 40.1 mmol) at rt. The reaction mixture is stirred at rt for 3 h. The reaction mixture is quenched with saturated NaHCO$_3$ solution (2000 mL) and is stirred for 15 min. The reaction mixture is filtered through a pad of Celite and washed with DCM (1000 mL). The organic layer is dried over MgSO$_4$, filtered and the solvent is evaporated under reduced pressure. The crude product is purified by normal phase chromatography (EtOAc/petroleum ether 10:80) to afford the desired product A-5-a (HPLC-MS: (M+H)$^+$=190.0, $t_{Ret.}$=2.00 min, method GVK_LCMS_41).

Experimental Procedure for the Synthesis of A-4-a

To a stirred solution of A-5-a (46.0 g, 24.2 mmol) in DMA (460.0 mL) is added hydrazine monohydrate (63.7 mL; 121.0 mmol) at 0° C. The reaction mixture is stirred at 80° C. for 3 h.

The reaction mixture is poured into ice water (800 mL) and extracted with EtOAc (3×). The combined organic layers are dried over MgSO$_4$, filtered and the solvent is evaporated under reduced pressure. The crude product is purified by normal phase chromatography (EtOAc/petroleum ether 85:15) to afford the desired product A-4-a (HPLC-MS: (M+H)$^+$=168.1, $t_{Ret.}$=1.54 min, method GVK_LCMS_19).

Experimental Procedure for the Synthesis of A-3-a

To a stirred solution of A-4-a (25.0 g; 14.9 mmol) in THF (250.0 mL) is added TEA (24.5 mL, 17.9 mmol) and Boc anhydride (41.11 mL; 17.9 mmol) at rt. The reaction mixture is stirred at rt for 16 h. The reaction mixture is poured into ice water (500 mL) and extracted with EtOAc (3×). The combined organic layers are dried over Na$_2$SO$_4$, filtered and the solvent is evaporated under reduced pressure. The crude product is purified by normal phase chromatography (EtOAc/petroleum ether 20:80) to afford the desired product A-3-a (HPLC-MS: (M+H)$^+$=268, $t_{Ret.}$=1.31 min, method LCMS3, basisch_1).

Experimental Procedure for the Synthesis of A-2-a

To a stirred solution of A-3-a (34.0 g; 12.7 mmol) in 1,4-dioxane (340.0 mL) are added C-1-a (35.83 g; 15.2 mmol), cesium carbonate (2.0 M in water; 124.14 g; 38.1 mmol), PdCl$_2$(dppf) (10.37 g; 1.13 mmol, 0.1 eq.). The reaction mixture is stirred at 100° C. for 1 h. The reaction mixture is filtered through a pad of Celite and washed with EtOAc (2×250 mL). The combined organic layers are dried over Na$_2$SO$_4$, filtered and the solvent is evaporated under reduced pressure to afford the desired product A-2-a (HPLC-MS: (M+H)$^+$=341, $t_{Ret.}$=1.14 min, method LCMS3, basisch_1)

Experimental Procedure for the Synthesis of A-1-a

To a stirred solution of A-2-a (50.0 g; 14.7 mmol) in 1,4-dioxane (500.0 mL) is added 4.0 M HCl in dioxane (250.0 mL) at 0° C. The reaction mixture is stirred at rt for 6 h. The reaction mixture is filtered off and washed with EtOAc (2×200 mL). The obtained solid is dissolved in water (400 mL) and is cooled to 0° C. and the pH is adjusted to 9 by using 1 N aqueous NaOH solution. The precipitate is filtered off, washed with diethylether (2×250 mL) to give A-1-a (HPLC-MS: (M+H)$^+$=241, $t_{Ret.}$=0.59 min, method LCMS3, basisch_1)

Alternative Synthesis of Building Block A-4-a

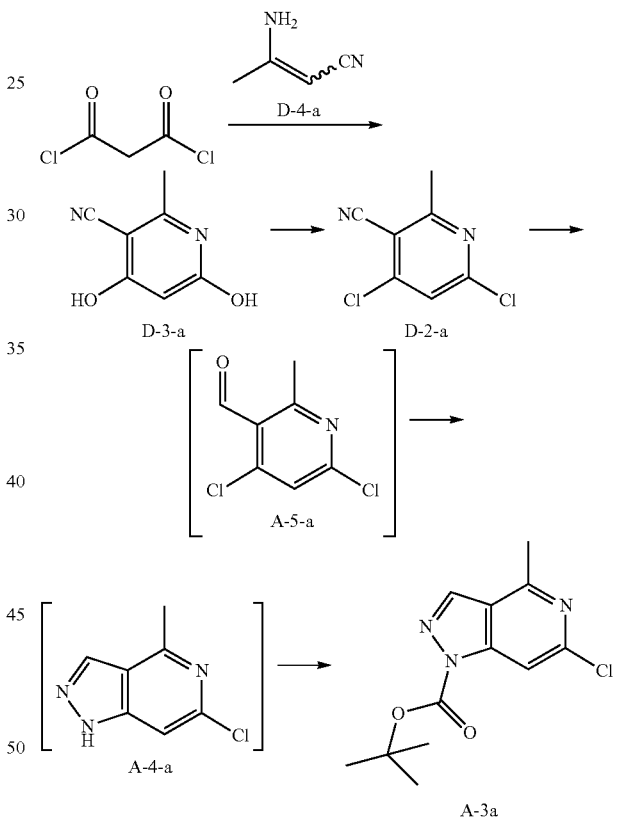

Experimental Procedure for the Synthesis of D-3-a

To a solution of malonyl chloride (5.00 g, 34.409 mmol, 1.0 eq.) in acetonitrile (37.5 mL) is added a solution of D-4-a (2.825 g, 34.409 mmol, 1.0 eq.) in acetonitrile (21.0 mL) at a rate to control the internal temperature below 15° C. The reaction mixture is stirred under nitrogen for 15 h at 20° C., then filtered and rinsed with acetonitrile (19.5 mL). The resulting solid is dried under vacuum with a nitrogen bleed at 50° C. to afford the desired product D-3-a ($^1$H-NMR (500 MHz, DMSO-d6) δ 5.77 (1H, s), 2.37 (3H, s)).

Experimental Procedure for the Synthesis of D-2-a

To a suspension of D-3-a (6.61 g, 19.752 mmol, 1.0 eq.) and benzyltriethylammonium chloride (4.50 g, 19.752 mmol, 1.0 eq) in acetonitrile (13.2 mL) is added phosphorus oxychloride (10.0 g, 65.181 mmol, 3.3 eq.) at 20° C. The mixture is stirred at 20° C. for 3 h, then heated to 78° C. for 8 h. The mixture is cooled to 22° C., and toluene (46.3 mL) is added. The mixture is cooled to 15° C., then water (15.8 mL) is added at a rate to control the internal temperature below 25° C. A solution of sodium hydroxide (50% in water, 12.64 g, 158.015 mmol, 8.0 eq.) in water (9.9 mL) is added at a rate to keep the temperature below 25° C. to reach pH 7.4. The mixture is filtered through Celite, rinsing with toluene (27.8 mL). The aqueous phase is removed, and the organic phase is washed with water (9.9 mL). The organic phase is circulated through a carbon filter, then the toluene is removed by vacuum distillation. Methylcyclohexane (66 mL) is added, and the vacuum distillation is continued. The mixture is heated to 70° C. until a clear solution is obtained, then the mixture is cooled to 20° C. The mixture is filtered and the solid rinsed with heptane (13.2 mL) to give the desired product D-2-a ($^1$H-NMR (500 MHz, DMSO-d6) δ 8.01 (1H, s), 2.70 (3H, s)).

Experimental Procedure for the Synthesis of A-3-a (Via A-4-a and A-5-a)

To a solution of D-2-a (3.04 g, 15.622 mmol, 1.0 eq.) in heptane (30.4 mL) at −30° C. is added 1 M diisobutylaluminum hydride in heptane (12.1 g, 17.184 mmol, 1.1 eq.) at a rate to control the internal temperature below −20° C. The mixture is stirred at −25° C. for 50 min, then EtOAc (1.1 g, 12.497 mmol, 0.8 eq.) is added at a rate to control the internal temperature below −20° C. The mixture is warmed to −10° C. and stirred for 15 min. A solution of tartaric acid (2.58 g, 17.184 mmol, 1.1 eq.) in water (11.4 mL) is added at a rate to control the internal temperature below 5° C. The mixture is warmed to 5° C. and stirred for 15 min. A solution of potassium sodium tartrate tetrahydrate (4.41 g, 15.622 mmol, 1.0 eq.) in water (11.4 mL) is added to bring the pH to 6.5, allowing the mixture to warm to rt. Isopropyl acetate (18 mL) is added, and the mixture is stirred at rt for 1.5 h. The aqueous phase is removed, and heptane/isopropyl acetate is removed by vacuum distillation until about 9 mL remain, then EtOH (30 mL) is added and distillation continued until about 12 mL remain (→A-5-a). To this solution of A-5-a in EtOH is added hydrazine hydrate (55% in water, 4.24 g, 46.865 mmol, 3.0 eq.), and the mixture is heated at 78° C. for 12 h. The mixture is cooled to rt, then 2-methyltetrahydrofuran (30 mL) and water (15 mL) are added, stirred for 15 min, then the aqueous phase is removed. 2-Methyltetrahydrofuran is removed by vacuum distillation until about 6 mL remain, then acetonitrile (30 mL) is added and distillation continued until about 6 mL remain (→A-4-a). The mixture is cooled to rt, and then TEA (4.74 g, 46.865 mmol, 3.0 eq.) is added, followed by DMAP (0.191 g, 1.562 mmol, 0.1 eq.) in acetonitrile (1.5 mL), and di-tert-butyldicarbonate (4.43 g, 20.308 mmol, 1.3 eq.) in acetonitrile (6.0 mL). The mixture is aged at rt for 40 min, then water (24 mL) is added over 1 h. The mixture is stirred at rt for 1 h, then filtered to collect A-3-a. The solid was rinsed with water (6 mL), then dried at 40° C. under vacuum ($^1$H-NMR (500 MHz, CDCl$_3$) δ 8.22 (s, 1H), 7.93 (s, 1H), 2.83 (s, 3H), 1.73 (s, 9H)).

Synthesis of A-1-b

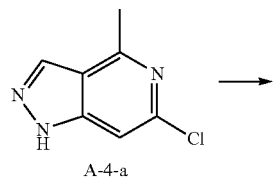

A-4-a

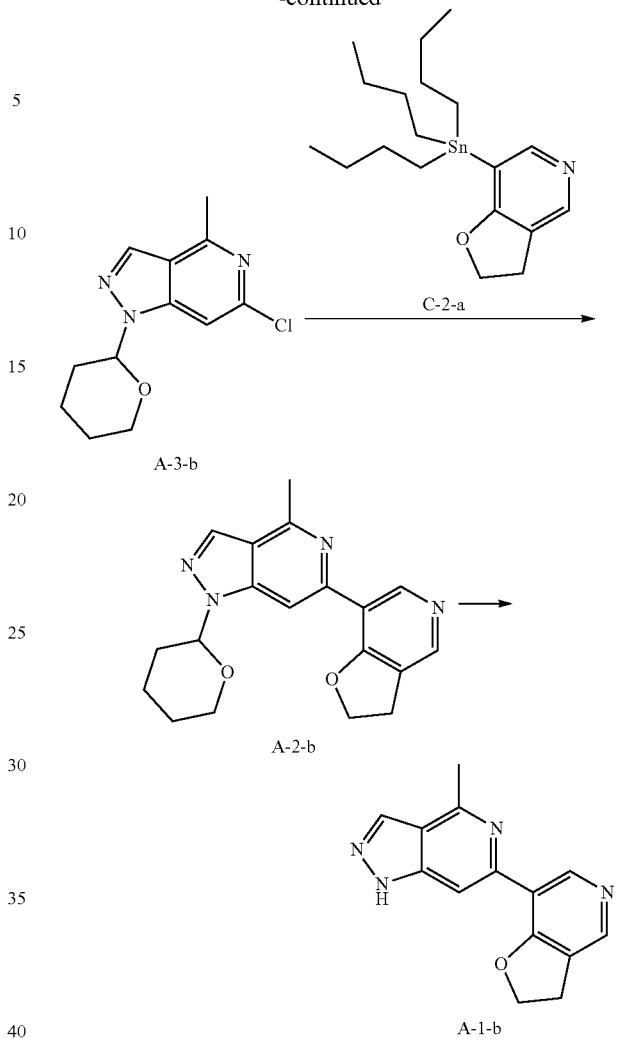

Experimental Procedure for the Synthesis of A-3-b

To a suspension of A-4-a (3.0 g; 167.6 mmol) in EtOAc (70.0 mL) are added p-TsOH (0.3 g; 172.1 mmol) and 2,3-dihydro-4H-pyran (4.5 g; 84 mmol) and stirred for 3 h at 60° C. The reaction mixture is diluted with water and extracted with EtOAc. The organic layers are dried over MgSO$_4$, filtered and the solvent is evaporated under reduced pressure. The crude product is purified by normal phase chromatography (cyclohexan/EtOAc 10:50) to afford the desired product A-3-b (HPLC-MS: (M+H)$^+$=252.0, t$_{Ret.}$=0.850 min, method VAB).

Experimental Procedure for the Synthesis of A-2-b

To a stirred solution of A-3-b (179.3 mg; 0.44 mmol) in DMF (4.0 mL) are added C-2-a (100.0 mg; 0.39 mmol), copper(I) iodide (3.0 mg; 0.02 mmol), cesium fluoride (120.7 mg; 0.80 mmol), PdCl$_2$(dppf) (30.6 mg; 0.04 mmol). The reaction mixture is stirred under argon at 100° C. for 3 h. The reaction mixture is poured into water and extracted with DCM. The organic layers are dried over MgSO$_4$, filtered and the solvent is evaporated under reduced pressure. The crude product is purified by reversed phase chromatography HPLC 1 to afford the desired product A-2-b (HPLC-MS: (M+H)$^+$=337, t$_{Ret.}$=0.852 min, method VAB).

Experimental Procedure for the Synthesis of A-1-b

To a stirred solution of A-2-b (54.0 mg; 0.16 mmol) in DCM (1.5 mL) is added 4.0 M HCl in dioxane (0.8 mL) at rt. The reaction mixture is stirred at rt for 3 h. The reaction mixture is concentrated under reduced pressure to give A-1-b (HPLC-MS: (M+H)$^+$=253.3, $t_{Ret.}$=0.623 min, method VAB).

Synthesis of C-2-a

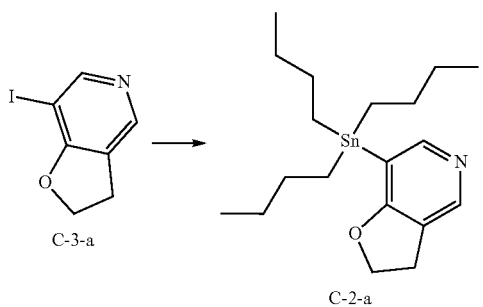 [SMILES: Ic1cncc2c1OCC2 ; CCC[CH2][Sn]([CH2]CCC)([CH2]CCC)[c]1cncc2c1OCC2]

To a stirred solution of C-3-a (400.0 mg; 1.62 mmol) in degassed toluene is added hexabutyl ditin (4.7 g; 8.1 mmol), DIPEA (1.49 mL, 8.1 mmol) and Pd(PPh$_3$)$_4$ at rt and stirred at 130° C. for 2 h in a microwave reactor. The reaction mixture is concentrated under reduced pressure and crude material is dissolved in EtOAc, washed with water (2×10 mL). The organic layers are dried over Na$_2$SO$_4$, filtered and the solvent is evaporated under reduced pressure. The crude product is purified by normal phase chromatography (hexane/EtOAc) to afford the desired product C-2-a (HPLC-MS: (M+H)$^+$=412.2, $t_{Ret.}$=2.33 min, method GVK_LCMS_41)

The following intermediates A-1 (table 1) are available in an analogous manner starting from different building blocks A-7, A-3, C-1 and C-2.

TABLE 1

| # | structure | MS (M + H)$^+$; $t_{Ret.}$ HPLC [min] | HPLC-MS method |
|---|---|---|---|
| A-1-a | 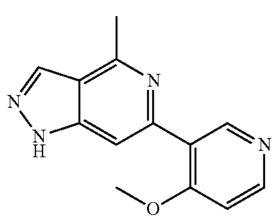 [SMILES: COc1ccncc1-c1cc2[nH]ncc2c(C)n1] | (M + H)$^+$ = 241; $t_{Ret.}$ = 0.59 | LCMS3, basisch_1 |
| A-1-b | 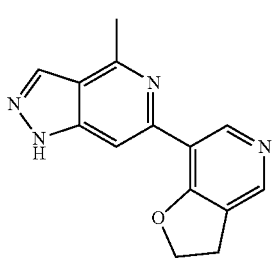 [SMILES: Cc1nc(-c2cncc3c2OCC3)cc2[nH]ncc12] | (M + H)$^+$ = 253; $t_{Ret.}$ = 0.623 | VAB |

TABLE 1-continued

| # | structure | MS (M + H)$^+$; $t_{Ret.}$ HPLC [min] | HPLC-MS method |
|---|---|---|---|
| A-1-c | 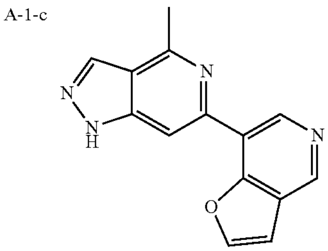 | (M + H)$^+$ = 251; $t_{Ret.}$ = 0.78 | LCMS3, basisch_1 |
| A-1-d | 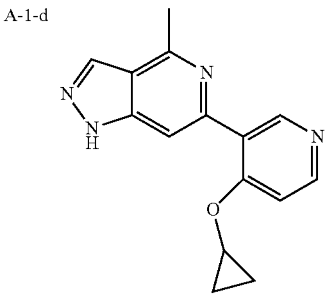 | (M + H)$^+$ = 267; $t_{Ret.}$ = 0.81 | LCMS3, basisch_1 |
| A-1-e | 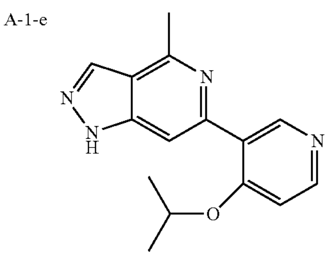 | (M + H)$^+$ = 269; $t_{Ret.}$ = 0.69 | VAB |
| A-1-f | 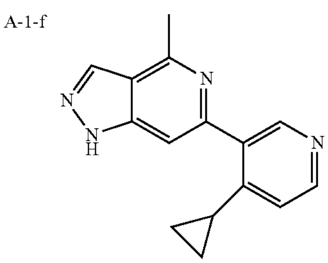 | (M + H)$^+$ = 251; $t_{Ret.}$ = 0.67 | VAB |

Synthesis of Intermediates B-1

Synthesis of B-1a-a

-continued

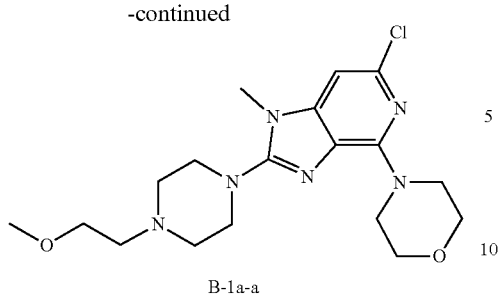

B-1a-a

To the starting material B-3a-a (1.5 g, 4.36 mmol) is added B-2-a (3.84 mL, 43.6 mmol). The reaction mixture is stirred under microwave irradiation at 140° C. for 1 h. Purification by normal phase chromatography using DCM/MeOH affords the pure product B-1a-a.

The following intermediates B-1a, B-1b, B-1c*, B-1d* and B-1e* (table 2) are available in an analogous manner starting from different building blocks B-3a, B-3b, B-3c*, B-3d* and B-3e*.

TABLE 2

| # | structure | MS (M + H)+; $t_{Ret.}$ HPLC [min] | HPLC-MS method |
|---|---|---|---|
| B-1a-a | 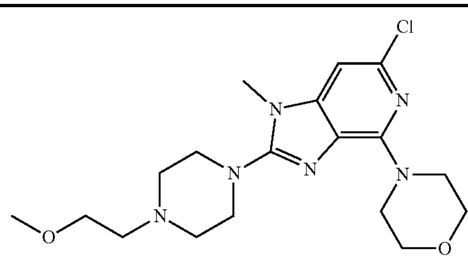 | (M + H)+ = 395; $t_{Ret.}$ = 0.899 | VAB |
| B-1a-b | 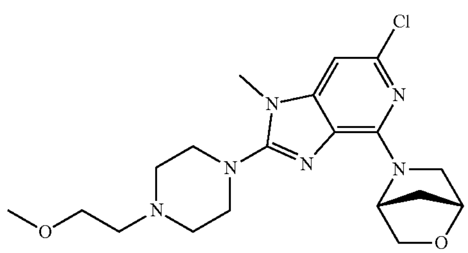 [SMILES: COCCN1CCN(c2nc3c(N4C[C@H]5C[C@@H]4CO5)nc(Cl)cc3n2C)CC1] | (M + H)+ = 407; $t_{Ret.}$ = 0.859 | VAB |
| B-1a-c | 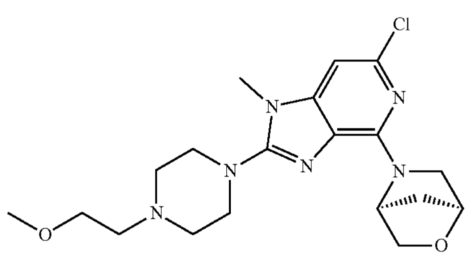 [SMILES: COCCN1CCN(c2nc3c(N4C[C@@H]5C[C@H]4CO5)nc(Cl)cc3n2C)CC1] | (M + H)+ = 407; $t_{Ret.}$ = 0.861 | VAB |
| B-1a-d | 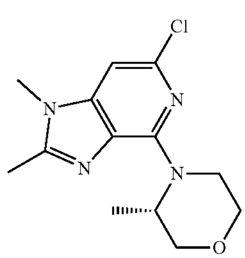 [SMILES: Cc1nc2c(N3CCOC[C@@H]3C)nc(Cl)cc2n1C] | (M + H)+ = 281; $t_{Ret.}$ = 0.857 | VAB |

TABLE 2-continued

| # | structure | MS (M + H)⁺; t$_{Ret.}$ HPLC [min] | HPLC-MS method |
|---|---|---|---|
| B-1a-e | 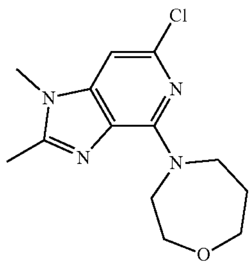 [SMILES: Cc1nc2c(N3CCCOCC3)nc(Cl)cc2n1C] | (M + H)⁺ = 281; t$_{Ret.}$ = 0.848 | VAB |
| B-1a-f | 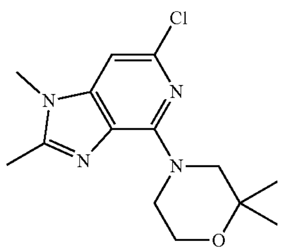 | (M + H)⁺ = 295; t$_{Ret.}$ = 0.890 | VAB |
| B-1a-g | 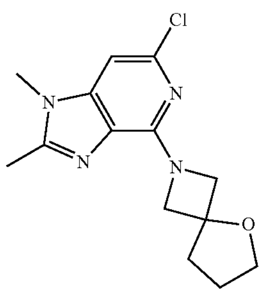 [SMILES: Cc1nc2c(N3CC4(CCCO4)C3)nc(Cl)cc2n1C] | (M + H)⁺ = 293; t$_{Ret.}$ = 0.777 | VAB |
| B-1a-h | 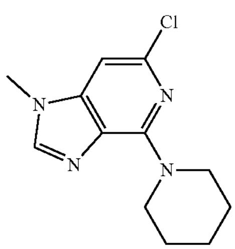 [SMILES: Cn1cnc2c(N3CCCCC3)nc(Cl)cc21] | (M + H)⁺ = 251; t$_{Ret.}$ = 0.957 | VAB |
| B-1a-i | 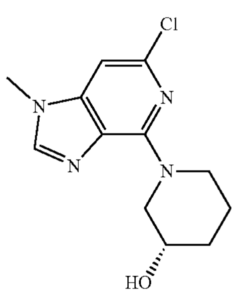 [SMILES: Cn1cnc2c(N3CCC[C@H](O)C3)nc(Cl)cc21] | (M + H)⁺ = 267; t$_{Ret.}$ = 0.734 | VAB |
| B-1a-j | 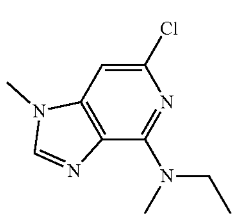 | (M + H)⁺ = 225; t$_{Ret.}$ = 0.882 | VAB |

TABLE 2-continued

| # | structure | MS (M + H)⁺; $t_{Ret.}$ HPLC [min] | HPLC-MS method |
|---|---|---|---|
| B-1a-k | 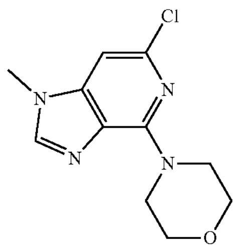 [SMILES: Cn1cnc2c(N3CCOCC3)nc(Cl)cc21] | (M + H)⁺ = 253; $t_{Ret.}$ = 0.780 | VAB |
| B-1a-l | 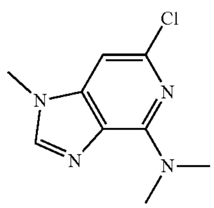 | (M + H)⁺ = 211; $t_{Ret.}$ = 0.806 | VAB |
| B-1a-m | 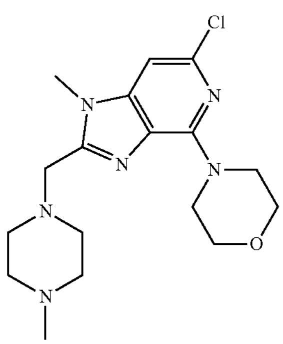 [SMILES: CN1CCN(Cc2nc3c(N4CCOCC4)nc(Cl)cc3n2C)CC1] | (M + H)⁺ = 365; $t_{Ret.}$ = 0.838 | VAB |
| B-1a-n | 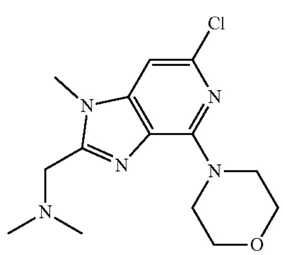 [SMILES: CN(C)Cc1nc2c(N3CCOCC3)nc(Cl)cc2n1C] | (M + H)⁺ = 310; $t_{Ret.}$ = 0.862 | VAB |
| B-1a-o | 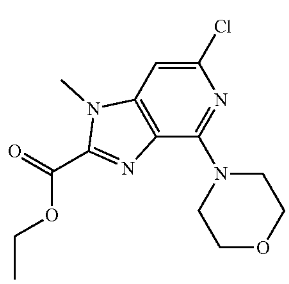 [SMILES: CCOC(=O)c1nc2c(N3CCOCC3)nc(Cl)cc2n1C] | (M + H)⁺ = 325; $t_{Ret.}$ = 0.939 | VAB |

TABLE 2-continued

| # | structure | MS (M + H)⁺; t_Ret. HPLC [min] | HPLC-MS method |
|---|---|---|---|
| B-1a-p | 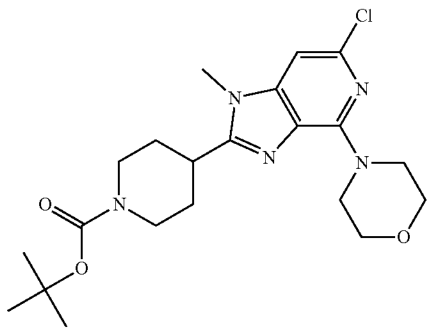 [SMILES: Cn1c(C2CCN(C(=O)OC(C)(C)C)CC2)nc2c(N3CCOCC3)nc(Cl)cc21] | (M + H)⁺ = 436; t_Ret. = 1.049 | VAB |
| B-1a-q | 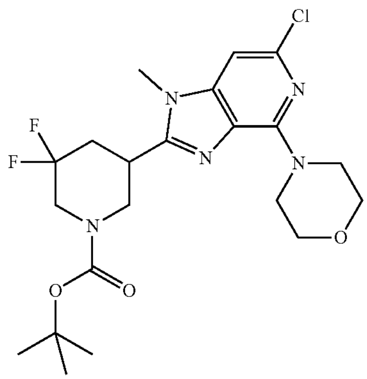 [SMILES: Cn1c(C2CN(C(=O)OC(C)(C)C)CC(F)(F)C2)nc2c(N3CCOCC3)nc(Cl)cc21] | (M + H)⁺ = 472; t_Ret. = 1.091 | VAB |
| B-1a-r | 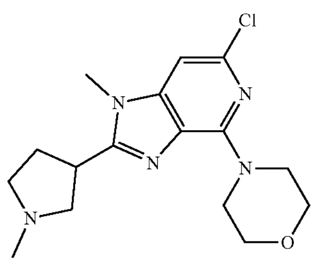 [SMILES: CN1CCC(c2nc3c(N4CCOCC4)nc(Cl)cc3n2C)C1] | (M + H)⁺ = 336; t_Ret. = 0.854 | VAB |
| B-1a-ap | 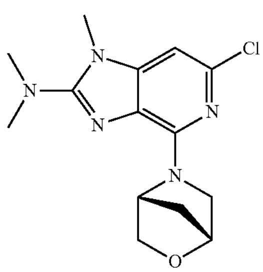 [SMILES: CN(C)c1nc2c(N3C[C@H]4C[C@@H]3CO4)nc(Cl)cc2n1C] | (M + H)⁺ = 308; t_Ret. = 0.86 | VAB |
| B-1a-aq | 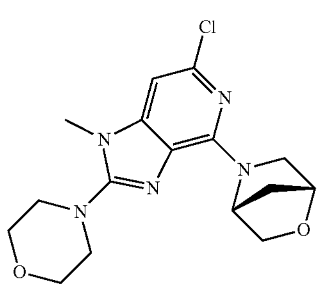 [SMILES: Cn1c(N2CCOCC2)nc2c(N3C[C@H]4C[C@@H]3CO4)nc(Cl)cc21] | (M + H)⁺ = 350; t_Ret. = 1.12 | LCMS3, basisch_1 |

TABLE 2-continued

| # | structure | MS (M + H)+; t_Ret. HPLC [min] | HPLC-MS method |
|---|---|---|---|
| B-1a-ar | 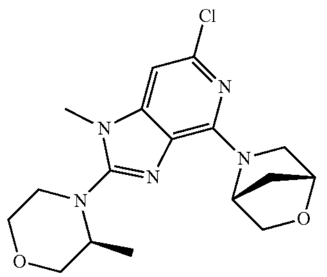 [SMILES: C[C@H]1COCCN1c1nc2c(N3C[C@H]4C[C@@H]3CO4)nc(Cl)cc2n1C] | (M + H)+ = 364.3; t_Ret. = 0.880 | VAB |
| B-1a-as | 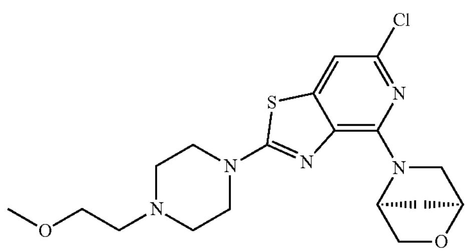 | (M + H)+ = 378; t_Ret. = 0.91 | VAB |
| B-1a-at | 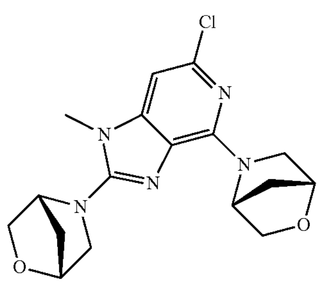 [SMILES: Cn1c(N2C[C@H]3C[C@@H]2CO3)nc2c(N3C[C@H]4C[C@@H]3CO4)nc(Cl)cc21] | (M + H)+ = 362; t_Ret. = 0.80 | VAB |
| B-1a-au | 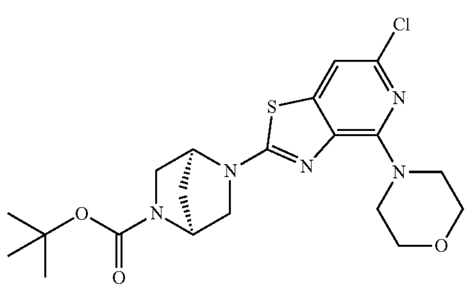 | (M + H)+ = 362; t_Ret. = 0.80 | VAB |
| B-1a-av | 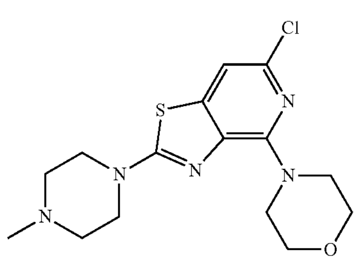 | (M + H)+ = 378; t_Ret. = 0.91 | VAB |

TABLE 2-continued

| # | structure | MS (M + H)+; $t_{Ret.}$ HPLC [min] | HPLC-MS method |
|---|---|---|---|
| B-1a-aw | 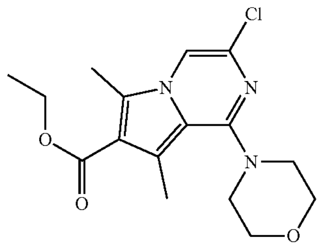 | (M + H)+ = 378; $t_{Ret.}$ = 0.91 | VAB |
| B-1a-ax | 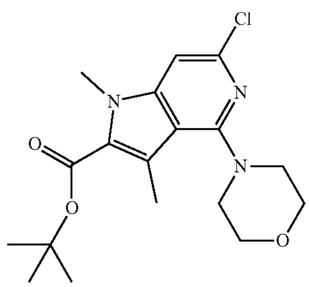 | (M + H)+ = 378; $t_{Ret.}$ = 0.93 | VAB |
| B-1a-ay | 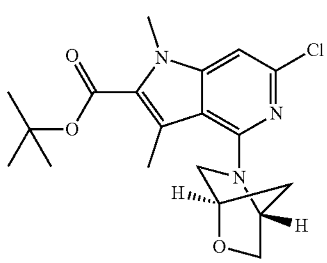 [SMILES: Cc1c(C(=O)OC(C)(C)C)n(C)c2cc(Cl)nc(N3C[C@H]4C[C@@H]3CO4)c12] | (M + H)+ = 377; $t_{Ret.}$ = 1.23 | LCMS3, basisch_1 |
| B-1a-az | 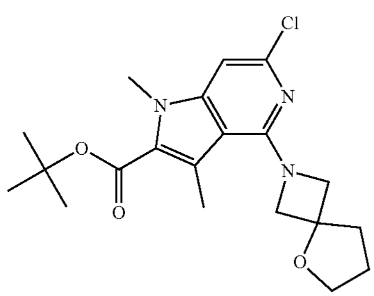 [SMILES: Cc1c(C(=O)OC(C)(C)C)n(C)c2cc(Cl)nc(N3CC4(CCCO4)C3)c12] | (M + H)+ = 391; $t_{Ret.}$ = 0.90 | VAB |
| B-1a-ba | 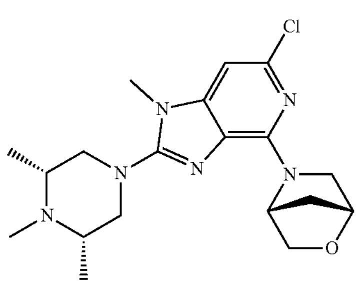 [SMILES: C[C@@H]1CN(c2nc3c(N4C[C@H]5C[C@@H]4CO5)nc(Cl)cc3n2C)C[C@H](C)N1C] | (M + H)+ = 391; $t_{Ret.}$ = 0.90 | VAB |

TABLE 2-continued

| # | structure | MS (M + H)+; t_Ret. HPLC [min] | HPLC-MS method |
|---|---|---|---|
| B-1a-bb | 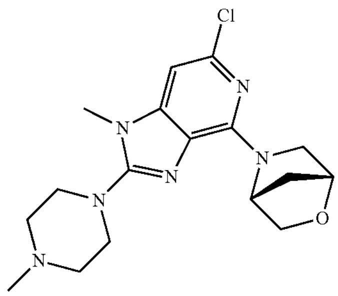 [SMILES: CN1CCN(c2nc3c(N4C[C@H]5C[C@@H]4CO5)nc(Cl)cc3n2C)CC1] | (M + H)+ = 363; t_Ret. = 0.82 | VAB |
| B-1a-bc | 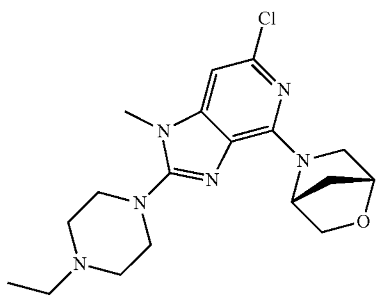 [SMILES: CCN1CCN(c2nc3c(N4C[C@H]5C[C@@H]4CO5)nc(Cl)cc3n2C)CC1] | (M + H)+ = 377; t_Ret. = 0.86 | VAB |
| B-1a-bd | 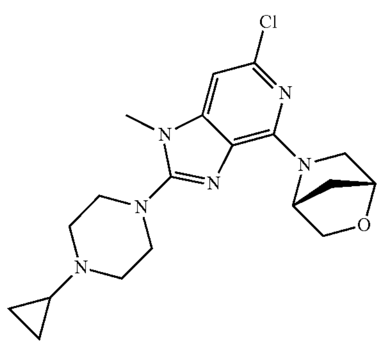 [SMILES: Cn1c(N2CCN(C3CC3)CC2)nc2c(N3C[C@H]4C[C@@H]3CO4)nc(Cl)cc21] | (M + H)+ = 389; t_Ret. = 0.95 | VAB |
| B-1a-be | 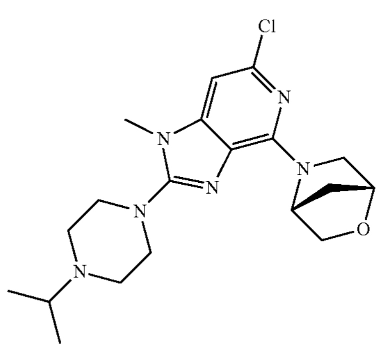 [SMILES: CC(C)N1CCN(c2nc3c(N4C[C@H]5C[C@@H]4CO5)nc(Cl)cc3n2C)CC1] | (M + H)+ = 391; t_Ret. = 0.91 | VAB |

TABLE 2-continued

| # | structure | MS (M + H)+; t_Ret. HPLC [min] | HPLC-MS method |
|---|---|---|---|
| B-1a-bf | 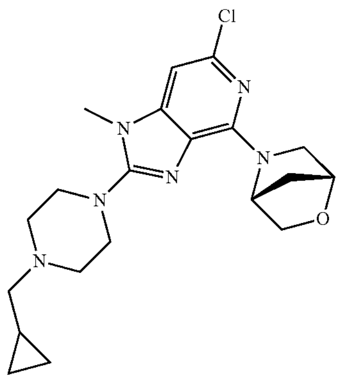 [SMILES: Cn1c(N2CCN(CC3CC3)CC2)nc2c(N3C[C@H]4C[C@@H]3CO4)nc(Cl)cc21] | t_Ret. = 5.54 | XB5A |
| B-1a-bg | 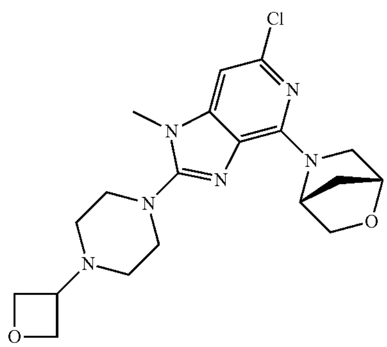 [SMILES: Cn1c(N2CCN(C3COC3)CC2)nc2c(N3C[C@H]4C[C@@H]3CO4)nc(Cl)cc21] | (M + H)+ = 405; t_Ret. = 0.79 | VAB |
| B-1a-bh | 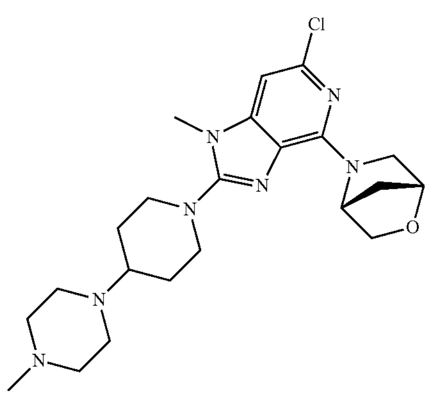 [SMILES: CN1CCN(C2CCN(c3nc4c(N5C[C@H]6C[C@@H]5CO6)nc(Cl)cc4n3C)CC2)CC1] | (M + H)+ = 446; t_Ret. = 0.780 | VAB |
| B-1a-bi | 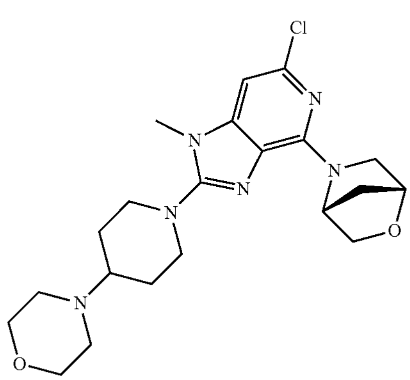 [SMILES: Cn1c(N2CCC(N3CCOCC3)CC2)nc2c(N3C[C@H]4C[C@@H]3CO4)nc(Cl)cc21] | (M + H)+ = 433; t_Ret. = 1.15 | LCMS3, basisch_1 |

TABLE 2-continued

| # | structure | MS (M + H)+; $t_{Ret.}$ HPLC [min] | HPLC-MS method |
|---|---|---|---|
| B-1a-bj | 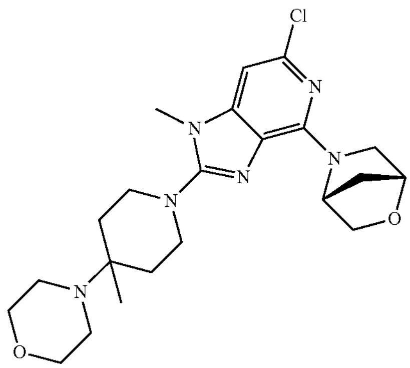 [SMILES: Cn1c(N2CCC(C)(N3CCOCC3)CC2)nc2c(N3C[C@H]4C[C@@H]3CO4)nc(Cl)cc21] | (M + H)+ = 447; $t_{Ret.}$ = 0.94 | VAB |
| B-1a-bk | 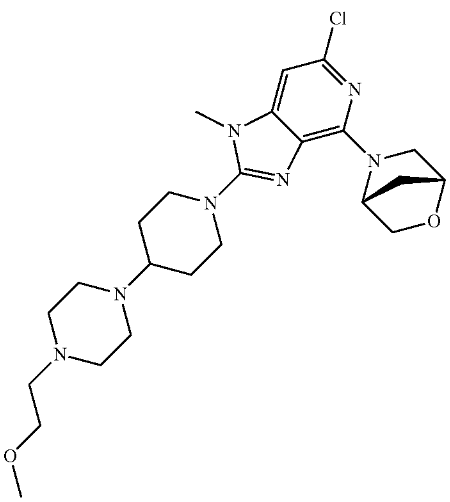 [SMILES: COCCN1CCN(C2CCN(c3nc4c(N5C[C@H]6C[C@@H]5CO6)nc(Cl)cc4n3C)CC2)CC1] | (M + H)+ = 490; $t_{Ret.}$ = 0.81 | VAB |
| B-1a-bl | 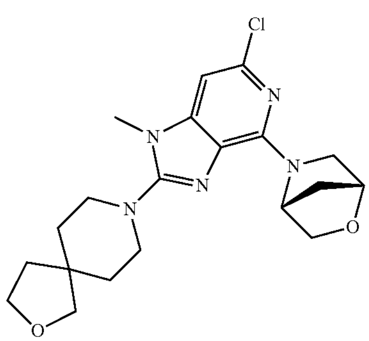 [SMILES: Cn1c(N2CCC3(CCOC3)CC2)nc2c(N3C[C@H]4C[C@@H]3CO4)nc(Cl)cc21] | (M + H)+ = 404; $t_{Ret.}$ = 1.28 | LCMS3, basisch_1 |
| B-1a-bm | 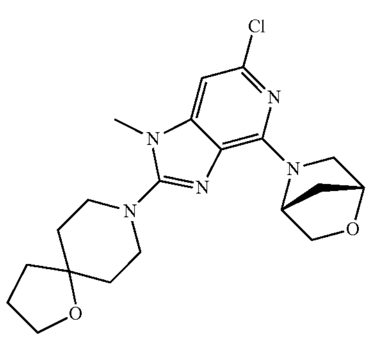 [SMILES: Cn1c(N2CCC3(CCCO3)CC2)nc2c(N3C[C@H]4C[C@@H]3CO4)nc(Cl)cc21] | (M + H)+ = 404; $t_{Ret.}$ = 0.96 | VAB |

TABLE 2-continued
| # | structure | MS (M + H)+; $t_{Ret.}$ HPLC [min] | HPLC-MS method |
|---|---|---|---|
| B-1a-bn | 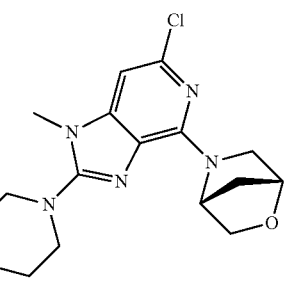 | (M + H)+ = 390; $t_{Ret.}$ = 1.19 | LCMS3, basisch_1 |
| B-1a-bo | 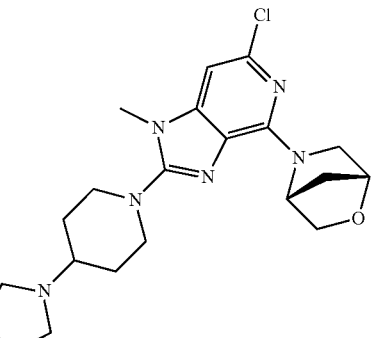 | (M + H)+ = 453; $t_{Ret.}$ = 0.98 | VAB |
| B-1a-bp | 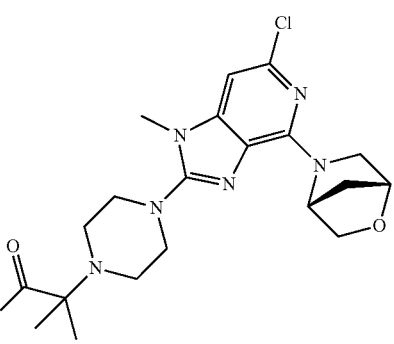 | (M + H)+ = 449; $t_{Ret.}$ = 0.94 | VAB |
| B-1a-bq | 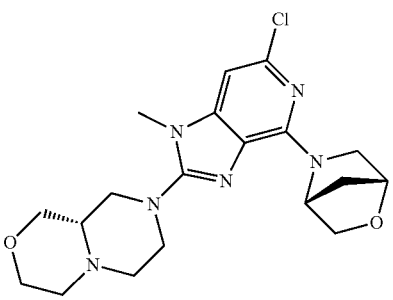 [SMILES: Cn1c(N2CCN3CCOC[C@@H]3C2)nc2c(N3C[C@H]4C[C@@H]3CO4)nc(Cl)cc21] | (M + H)+ = 405; $t_{Ret.}$ = 1.09 | LCMS3, basisch_1 |

TABLE 2-continued

| # | structure | MS (M + H)+; $t_{Ret.}$ HPLC [min] | HPLC-MS method |
|---|---|---|---|
| B-1a-br | 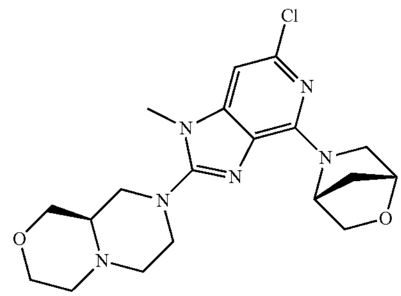 [SMILES: Cn1c(N2CCN3CCOC[C@H]3C2)nc2c(N3C[C@H]4C[C@@H]3CO4)nc(Cl)cc21] | (M + H)+ = 405; $t_{Ret.}$ = 1.09 | LCMS3, basisch_1 |
| B-1a-bs | 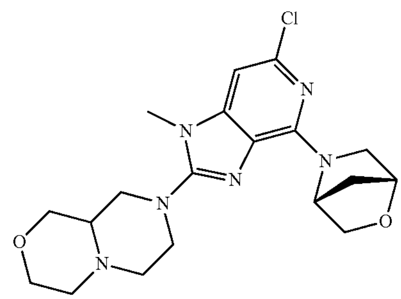 [SMILES: Cn1c(N2CCN3CCOCC3C2)nc2c(N3C[C@H]4C[C@@H]3CO4)nc(Cl)cc21] | (M + H)+ = 405; $t_{Ret.}$ = 0.80 | VAB |
| B-1a-bt | 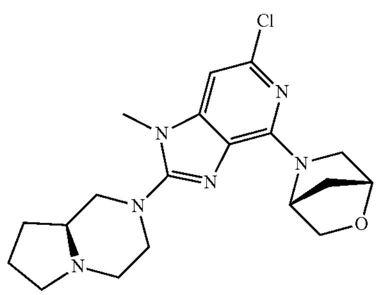 [SMILES: Cn1c(N2CCN3CCC[C@H]3C2)nc2c(N3C[C@H]4C[C@@H]3CO4)nc(Cl)cc21] | (M + H)+ = 389; $t_{Ret.}$ = 0.89 | VAB |
| B-1a-bu | 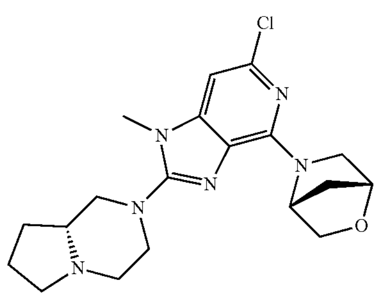 [SMILES: Cn1c(N2CCN3CCC[C@@H]3C2)nc2c(N3C[C@H]4C[C@@H]3CO4)nc(Cl)cc21] | (M + H)+ = 389; $t_{Ret.}$ = 0.89 | VAB |
| B-1a-bv | 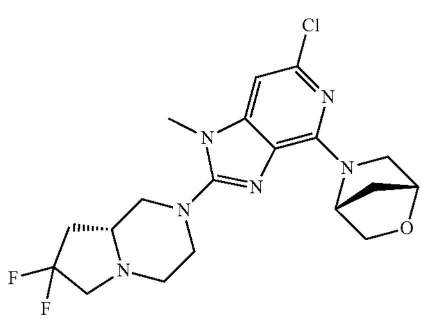 [SMILES: Cn1c(N2CCN3CC(F)(F)C[C@@H]3C2)nc2c(N3C[C@H]4C[C@@H]3CO4)nc(Cl)cc21] | (M + H)+ = 425; $t_{Ret.}$ = 0.94 | VAB |

TABLE 2-continued

| # | structure | MS (M + H)+; t_Ret. HPLC [min] | HPLC-MS method |
|---|---|---|---|
| B-1a-bw | 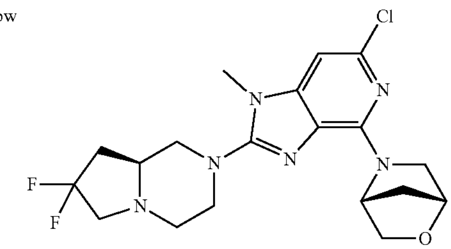 | (M + H)+ = 425; t_Ret. = 0.98 | VAB |
| B-1a-bx | 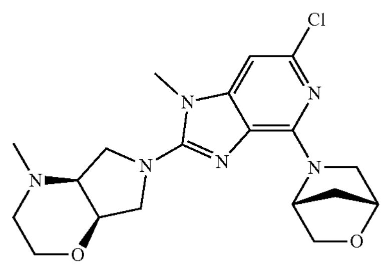 [SMILES: CN1CCO[C@@H]2CN(c3nc4c(N5C[C@H]6C[C@@H]5CO6)nc(Cl)cc4n3C)C[C@@H]21] | (M + H)+ = 405; t_Ret. = 0.77 | VAB |
| B-1a-by | 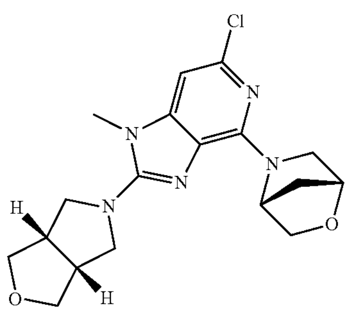 [SMILES: Cn1c(N2C[C@H]3COC[C@H]3C2)nc2c(N3C[C@H]4C[C@@H]3CO4)nc(Cl)cc21] | (M + H)+ = 376; t_Ret. = 0.83 | VAB |
| B-1a-bz | 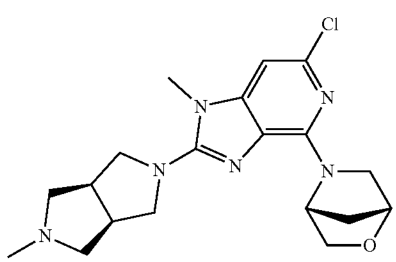 [SMILES: CN1C[C@@H]2CN(c3nc4c(N5C[C@H]6C[C@@H]5CO6)nc(Cl)cc4n3C)C[C@@H]2C1] | (M + H)+ = 389; t_Ret. = 0.83 | VAB |
| B-1a-ca | 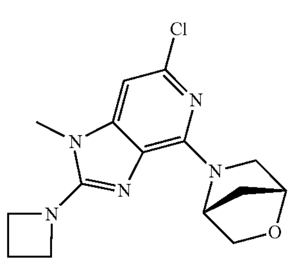 [SMILES: Cn1c(N2CCC2)nc2c(N3C[C@H]4C[C@@H]3CO4)nc(Cl)cc21] | (M + H)+ = 320; t_Ret. = 0.84 | VAB |

TABLE 2-continued

| # | structure | MS (M + H)+; t_Ret. HPLC [min] | HPLC-MS method |
|---|---|---|---|
| B-1a-cb | 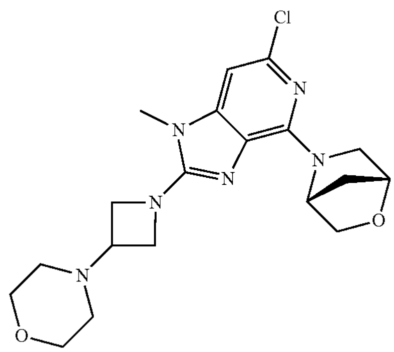 [SMILES: Cn1c(N2CC(N3CCOCC3)C2)nc2c(N3C[C@H]4C[C@@H]3CO4)nc(Cl)cc21] | (M + H)+ = 405; t_Ret. = 0.78 | VAB |
| B-1a-cc | 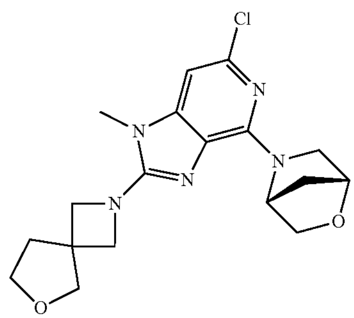 [SMILES: Cn1c(N2CC3(CCOC3)C2)nc2c(N3C[C@H]4C[C@@H]3CO4)nc(Cl)cc21] | (M + H)+ = 376; t_Ret. = 1.10 | LCMS3, basisch_1 |
| B-1a-cd | 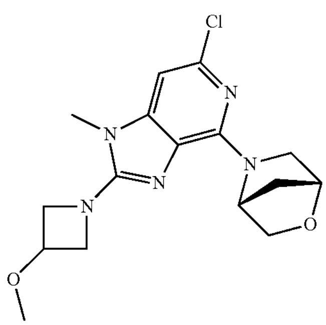 [SMILES: COC1CN(c2nc3c(N4C[C@H]5C[C@@H]4CO5)nc(Cl)cc3n2C)C1] | (M + H)+ = 350; t_Ret. = 1.11 | LCMS3, basisch_1 |
| B-1a-ce | 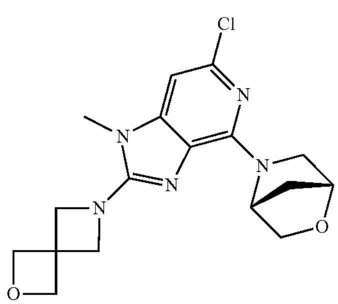 [SMILES: Cn1c(N2CC3(COC3)C2)nc2c(N3C[C@H]4C[C@@H]3CO4)nc(Cl)cc21] | (M + H)+ = 362; t_Ret. = 1.02 | LCMS3, basisch_1 |
| B-1a-cf | 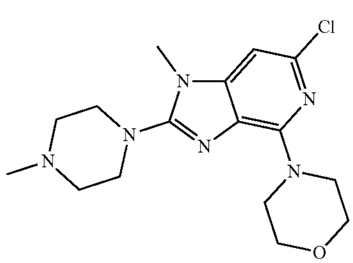 [SMILES: CN1CCN(c2nc3c(N4CCOCC4)nc(Cl)cc3n2C)CC1] | (M + H)+ = 351; t_Ret. = 0.85 | VAB |

TABLE 2-continued

| # | structure | MS (M + H)+; $t_{Ret.}$ HPLC [min] | HPLC-MS method |
|---|---|---|---|
| B-1a-cg | 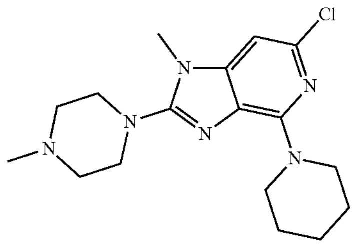 [SMILES: CN1CCN(c2nc3c(N4CCCCC4)nc(Cl)cc3n2C)CC1] | (M + H)+ = 349; $t_{Ret.}$ = 1.02 | VAB |
| B-1a-ch | 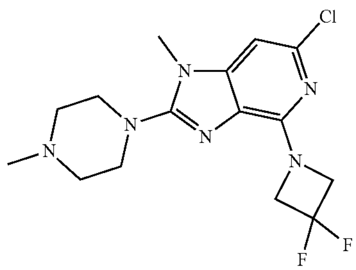 [SMILES: CN1CCN(c2nc3c(N4CC(F)(F)C4)nc(Cl)cc3n2C)CC1] | (M + H)+ = 357; $t_{Ret.}$ = 0.91 | VAB |
| B-1b-a | 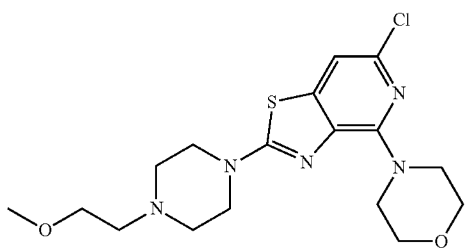 [SMILES: COCCN1CCN(c2nc3c(N4CCOCC4)nc(Cl)cc3s2)CC1] | (M + H)+ = 398; $t_{Ret.}$ = 0.981 | VAB |
| B-1b-b | 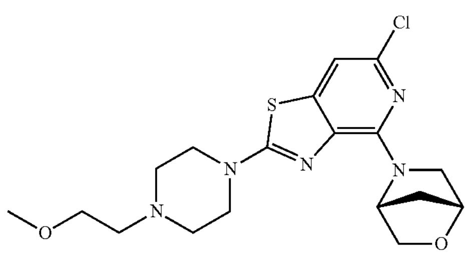 [SMILES: COCCN1CCN(c2nc3c(N4C[C@H]5C[C@@H]4CO5)nc(Cl)cc3s2)CC1] | (M + H)+ = 410; $t_{Ret.}$ = 0.963 | VAB |
| B-1b-c | 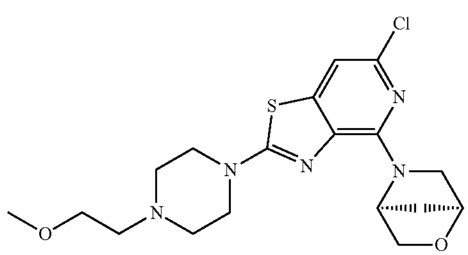 [SMILES: COCCN1CCN(c2nc3c(N4C[C@@H]5C[C@H]4CO5)nc(Cl)cc3s2)CC1] | (M + H)+ = 410; $t_{Ret.}$ = 0.963 | VAB |
| B-1b-d | 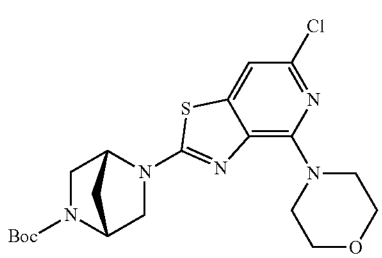 [SMILES: CC(C)(C)OC(=O)N1C[C@H]2C[C@@H]1CN2c1nc2c(N3CCOCC3)nc(Cl)cc2s1] | (M + H)+ = 452; $t_{Ret.}$ = 1.101 | VAB |

TABLE 2-continued

| # | structure | MS (M + H)+; t_Ret. HPLC [min] | HPLC-MS method |
|---|---|---|---|
| B-1b-e | 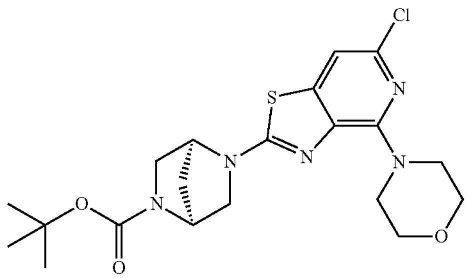 [SMILES: CC(C)(C)OC(=O)N1C[C@@H]2C[C@H]1CN2c1nc2c(N3CCOCC3)nc(Cl)cc2s1] | (M + H)+ = 452; t_Ret. = 1.101 | VAB |
| B-1b-f | 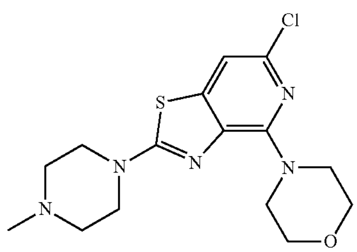 | (M + H)+ = 398; t_Ret. = 0.981 | VAB |
| B-1c*-a | 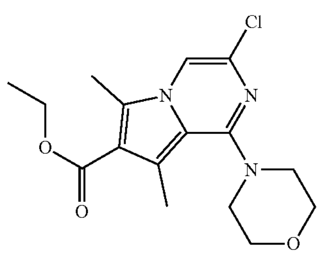 [SMILES: CCOC(=O)c1c(C)c2c(N3CCOCC3)nc(Cl)cn2c1C] | (M + H)+ = 338; t_Ret. = 1.054 | VAB |
| B-1d*-a | 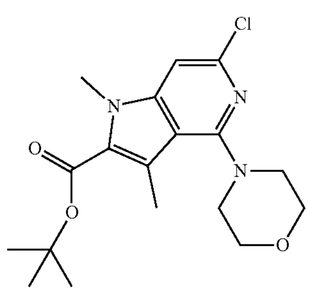 [SMILES: Cc1c(C(=O)OC(C)(C)C)n(C)c2cc(Cl)nc(N3CCOCC3)c12] | (M + H)+ = 366; t_Ret. = 1.154 | VAB |
| B-1d*-b | 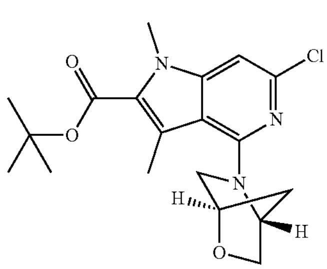 [SMILES: Cc1c(C(=O)OC(C)(C)C)n(C)c2cc(Cl)nc(N3C[C@H]4C[C@@H]3CO4)c12] | (M + H)+ = 378; t_Ret. = 1.125 | VAB |

TABLE 2-continued

| # | structure | MS (M + H)⁺; $t_{Ret.}$ HPLC [min] | HPLC-MS method |
|---|---|---|---|
| B-1d*-c | 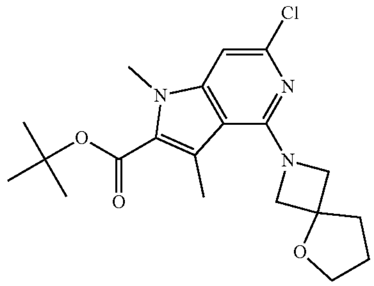 [SMILES: Cc1c(C(=O)OC(C)(C)C)n(C)c2cc(Cl)nc(N3CC4(CCCO4)C3)c12] | (M + H)⁺ = 392; $t_{Ret.}$ = 0.960 | VAB |
| B-1e*-a | 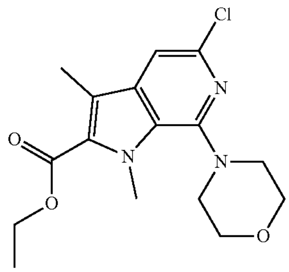 [SMILES: CCOC(=O)c1c(C)c2cc(Cl)nc(N3CCOCC3)c2n1C] | (M + H)⁺ = 338; $t_{Ret.}$ = 1.089 | VAB |

Synthesis of B-1a-s

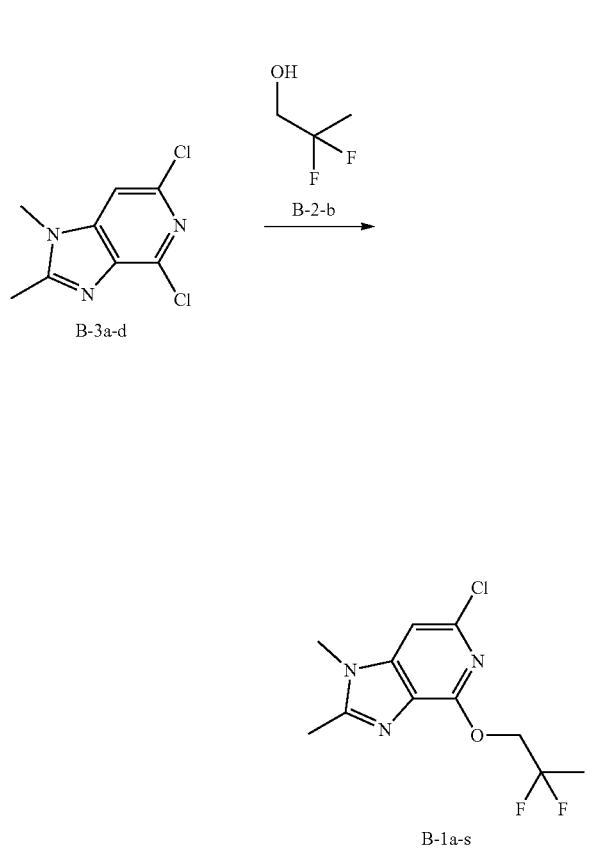

To a stirred solution of B-3a-d (100 mg; 0.44 mmol) in AcCN (0.50 mL) is added B-2-b (75.0 mg; 0.78 mmol) and Cs₂CO₃ (500 mg; 1.54 mmol). The mixture is stirred at 75° C. for 48 h. Purification via prep. HPLC 1 leads to B-1a-s.

Synthesis of B-1b-g

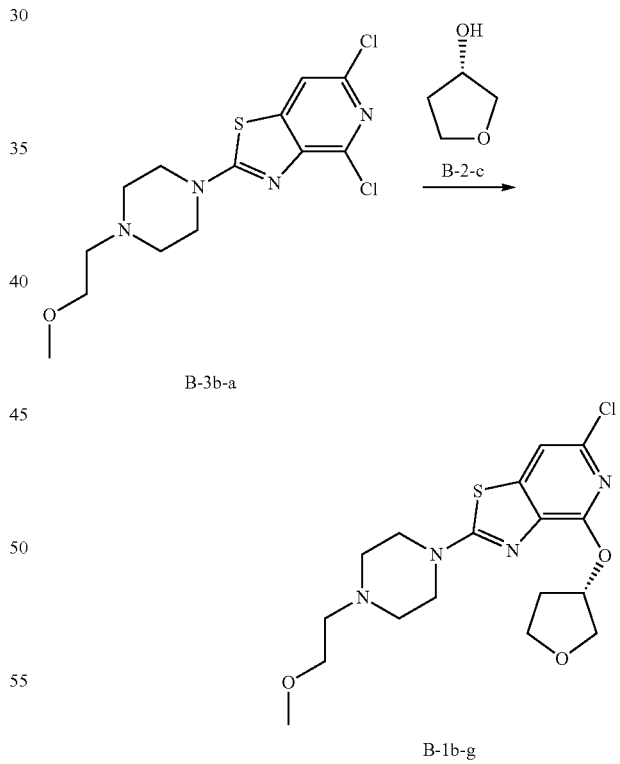

To a solution of B-2-c (75 mg; 0.20 mmol) in DMSO is added NaH (32 mg; 0.80 mmol). After stirring for 5 min at ambient temperature B-3b-a is added to the reaction mixture and stirring is continued for 3 d. Purification by prep. HPLC 1 affords the pure product B-1b-g.

The following intermediates B-1a and B-1b (table 3) are available in an analogous manner starting from different building blocks B-3a and B-3b.

TABLE 3

| # | structure | MS (M + H)+; tRet. HPLC [min] | HPLC-MS method |
|---|---|---|---|
| B-1a-s | 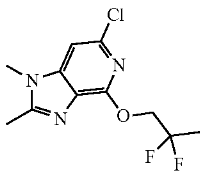 [SMILES: Cc1nc2c(OCC(C)(F)F)nc(Cl)cc2n1C] | (M + H)+ = 276; tRet. = 0.845 | VAB |
| B-1a-t | 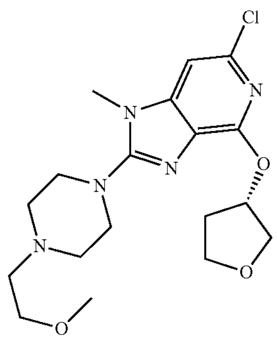 [SMILES: COCCN1CCN(c2nc3c(O[C@H]4CCOC4)nc(Cl)cc3n2C)CC1] | (M + H)+ = 396; tRet. = 0.821 | VAB |
| B-1a-u | 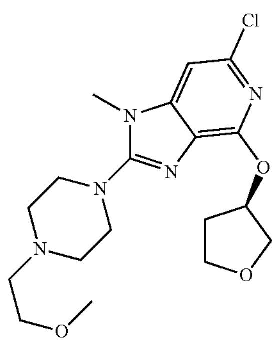 [SMILES: COCCN1CCN(c2nc3c(O[C@@H]4CCOC4)nc(Cl)cc3n2C)CC1] | (M + H)+ = 396; tRet. = 0.832 | VAB |
| B-1a-v | 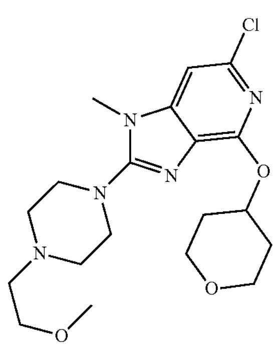 [SMILES: COCCN1CCN(c2nc3c(OC4CCOCC4)nc(Cl)cc3n2C)CC1] | (M + H)+ = 410; tRet. = 0.851 | VAB |
| B-1a-w | 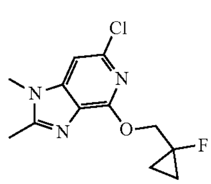 [SMILES: Cc1nc2c(OCC3(F)CC3)nc(Cl)cc2n1C] | (M + H)+ = 270; tRet. = 0.844 | VAB |

TABLE 3-continued

| # | structure | MS (M + H)+; tRet. HPLC [min] | HPLC-MS method |
|---|---|---|---|
| B-1a-x | | (M + H)+ = 286; tRet. = 0.750 | VAB |
| B-1a-y | | (M + H)+ = 212; tRet. = 0.764 | VAB |
| B-1b-g | | (M + H)+ = 399; tRet. = 0.910 | VAB |
| B-1b-h | | (M + H)+ = 453; tRet. = 1.029 | VAB |

Synthesis of B-1a-z

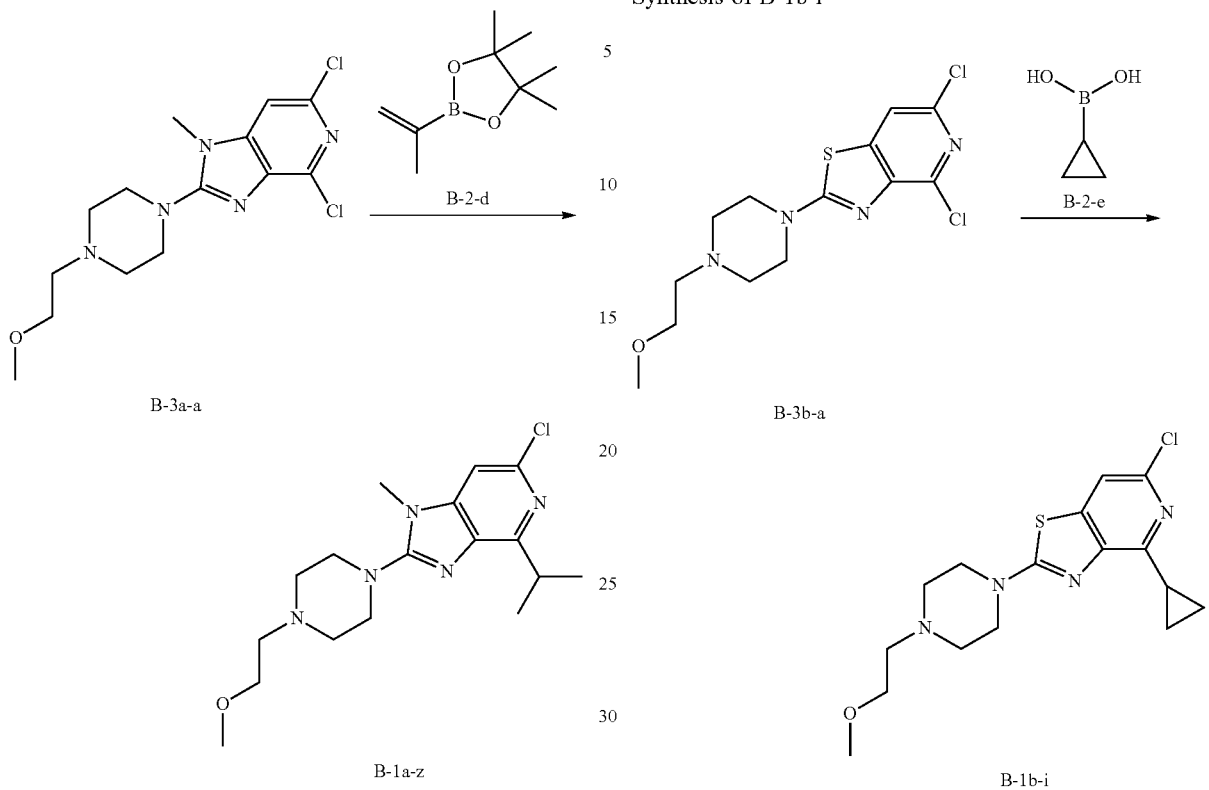

B-3a-a (250 mg, 0.73 mmol), B-2-d (141 mg; 0.80 mmol), Pd(II)dppf Cl₂*CH₂Cl₂ (61 mg; 0.07 mmol) and sodium carbonate (196 mg; 1.82 mmol) are suspended in dioxane (2.0 mL) and water (1.0 mL). The reaction mixture is stirred under microwave irradiation at 100° C. for 1 h. Purification via NP 1 yields the unsaturated intermediate which is directly used in the next step.

A BUCHI lab autoclave is charged with the unsaturated intermediate (215 mg; 0.62 mmol), EtOH (5.0 mL) and tris(triphenylphosphine)rhodium(I)chloride (113 mg; 0.12 mmol). The mixture is stirred for 16 h under 5 bar H₂ pressure. The reaction mixture is diluted with DCM and sat. aq. NaHCO₃ solution and extracted. The organic phase is dried over MgSO₄, filtered and the solvent is evaporated under reduced pressure to give B-1a-z.

Synthesis of B-1b-i

To a stirred solution of B-3b-a (130 mg; 0.37 mmol) are added Pd(II)dppf Cl₂*CH₂Cl₂ (61 mg; 0.07 mmol), sodium carbonate (196 mg; 1.82 mmol) and B-2-e (77 mg; 0.90 mmol) and the mixture is stirred for 16 h. The reaction mixture is poured into sat. aq. NaHCO₃ solution and extracted with DCM. The organic phase is dried over MgSO₄, filtered and the solvent is evaporated under reduced pressure. This crude product is purified via prep. HPLC 1 to Give B-1b-1

The following intermediates B-1a, B-1b, B-1c*, B-1d* and B-1e* (table 4) are available in an analogous manner starting from different building blocks B-3a, B-3b, B-3c*, B-3d* and B-3e*.

TABLE 4

| # | structure | MS (M + H)⁺; $t_{Ret.}$ HPLC [min] | HPLC-MS method |
|---|-----------|-------------------------------------|----------------|
| B-1a-z | 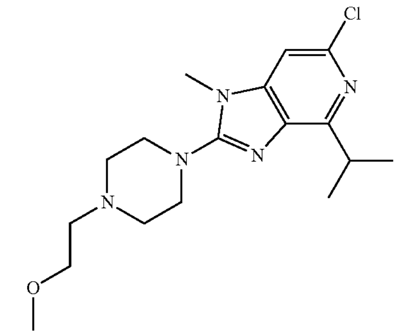 [SMILES: COCCN1CCN(c2nc3c(C(C)C)nc(Cl)cc3n2C)CC1] | (M + H)⁺ = 352; $t_{Ret.}$ = 0.879 | VAB |

TABLE 4-continued

| # | structure | MS (M + H)+; t_Ret. HPLC [min] | HPLC-MS method |
|---|---|---|---|
| B-1a-aa | 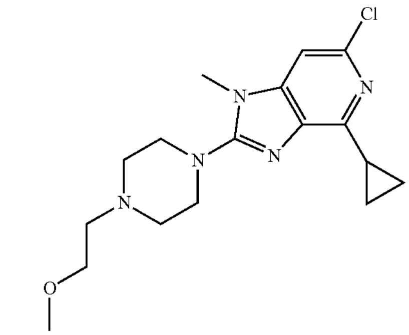 [SMILES: COCCN1CCN(c2nc3c(C4CC4)nc(Cl)cc3n2C)CC1] | (M + H)+ = 350; t_Ret. = 0.866 | VAB |
| B-1a-ab | 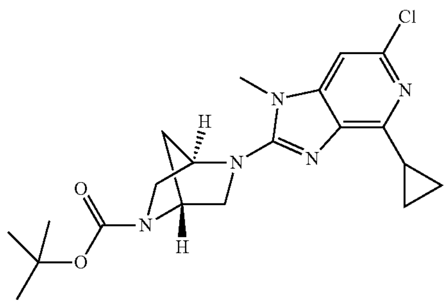 [SMILES: Cn1c(N2C[C@H]3C[C@@H]2CN3C(=O)OC(C)(C)C)nc2c(C3CC3)nc(Cl)cc21] | (M + H)+ = 404; t_Ret. = 1.015 | VAB |
| B-1a-ac | 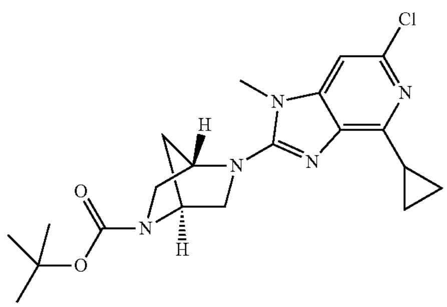 [SMILES: Cn1c(N2C[C@@H]3C[C@H]2CN3C(=O)OC(C)(C)C)nc2c(C3CC3)nc(Cl)cc21] | (M + H)+ = 404; t_Ret. = 1.001 | VAB |
| B-1a-ad | 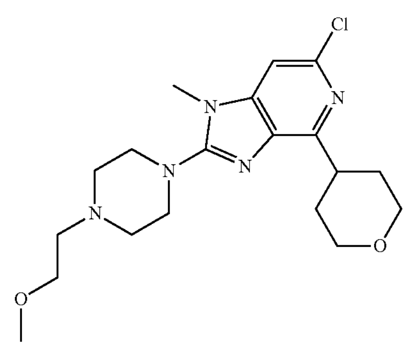 [SMILES: COCCN1CCN(c2nc3c(C4CCOCC4)nc(Cl)cc3n2C)CC1] | (M + H)+ = 394; t_Ret. = 0.809 | VAB |
| B-1a-ae | 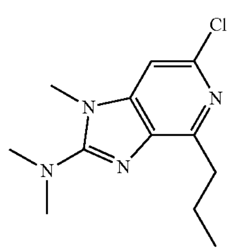 [SMILES: CCCc1nc(Cl)cc2c1nc(N(C)C)n2C] | (M + H)+ = 253; t_Ret. = 0.825 | VAB |

TABLE 4-continued

| # | structure | MS (M + H)+; t_Ret. HPLC [min] | HPLC-MS method |
|---|-----------|-------------------------------|----------------|
| B-1a-af | 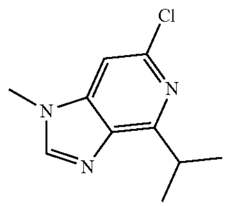 | (M + H)+ = 210; t_Ret. = 0.760 | VAB |
| B-1a-ag | 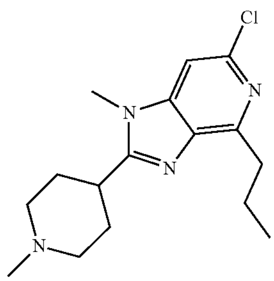 [SMILES: CCCc1nc(Cl)cc2c1nc(C1CCN(C)CC1)n2C] | (M + H)+ = 307; t_Ret. = 0.809 | VAB |
| B-1a-ah | 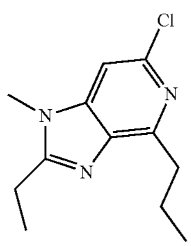 [SMILES: CCCc1nc(Cl)cc2c1nc(CC)n2C] | (M + H)+ = 238; t_Ret. = 0.806 | VAB |
| B-1a-ai | 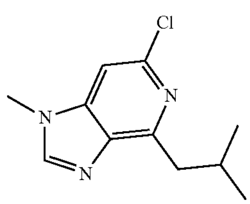 | (M + H)+ = 238; t_Ret. = 0.819 | VAB |
| B-1a-aj | 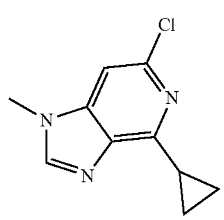 | (M + H)+ = 208; t_Ret. = 0.754 | VAB |
| B-1a-ak | 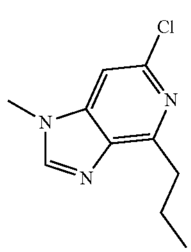 | (M + H)+ = 210; t_Ret. = 0.729 | VAB |

TABLE 4-continued

| # | structure | MS (M + H)⁺; t_Ret. HPLC [min] | HPLC-MS method |
|---|---|---|---|
| B-1a-al | 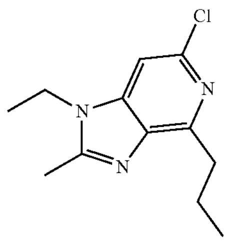 [SMILES: CCCc1nc(Cl)cc2c1nc(C)n2CC] | (M + H)⁺ = 238; t_Ret. = 0.809 | VAB |
| B-1a-am | 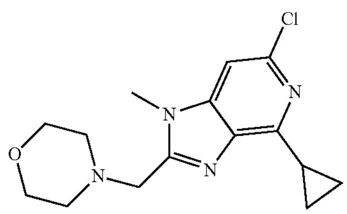 [SMILES: Cn1c(CN2CCOCC2)nc2c(C3CC3)nc(Cl)cc21] | (M + H)⁺ = 307; t_Ret. = 0.828 | VAB |
| B-1a-an | 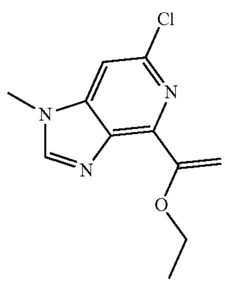 [SMILES: C=C(OCC)c1nc(Cl)cc2c1ncn2C] | (M + H)⁺ = 238; t_Ret. = 0.716 | VAB |
| B-1a-ao | 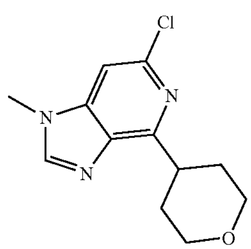 [SMILES: Cn1cnc2c(C3CCOCC3)nc(Cl)cc21] | (M + H)⁺ = 252; t_Ret. = 0 | VAB |
| B-1a-ci | 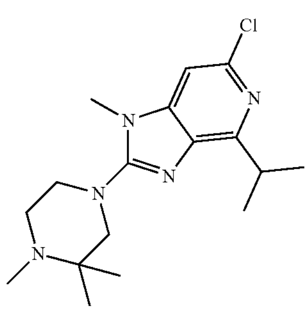 [SMILES: CC(C)c1nc(Cl)cc2c1nc(N1CCN(C)C(C)(C)C1)n2C] | (M + H)⁺ = 336; t_Ret. = 0.92 | VAB |

TABLE 4-continued

| # | structure | MS (M + H)+; t_Ret. HPLC [min] | HPLC-MS method |
|---|---|---|---|
| B-1a-cj | 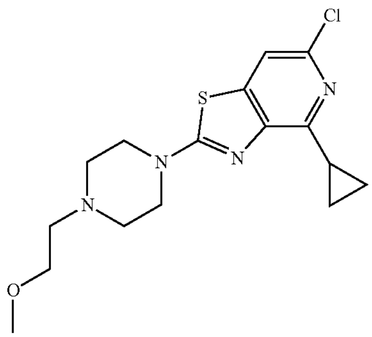 | (M + H)+ = 322; t_Ret. = 1.27 | LCMS3, basisch_1 |
| B-1a-ck | 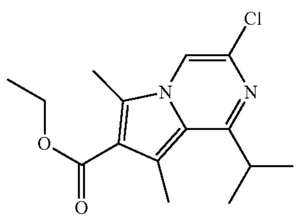 [SMILES: CCOC(=O)c1c(C)c2c(C(C)C)nc(Cl)cn2c1C] | (M + H)+ = 295; t_Ret. = 1.16 | LCMS3, basisch_1 |
| B-1a-cl | 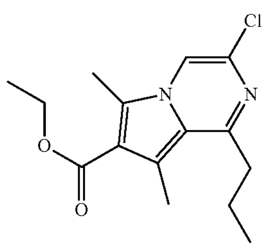 | (M + H)+ = 323; t_Ret. = 0.95 | VAB |
| B-1a-cm | 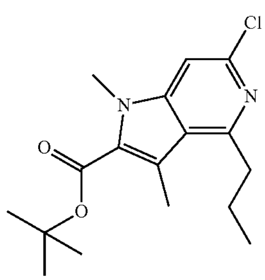 | (M + H)+ = 358; t_Ret. = 0.96 | VAB |
| B-1a-cn | 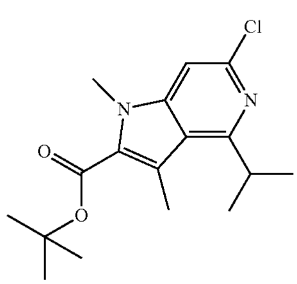 | (M + H)+ = 308; t_Ret. = 0.83 | VAB |

TABLE 4-continued

| # | structure | MS (M + H)+; t_Ret. HPLC [min] | HPLC-MS method |
|---|---|---|---|
| B-1a-co | 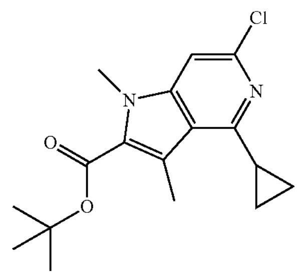 [SMILES: Cc1c(C(=O)OC(C)(C)C)n(C)c2cc(Cl)nc(C3CC3)c12] | (M + H)+ = 322; t_Ret. = 1.28 | LCMS3, basisch_1 |
| B-1a-cp | 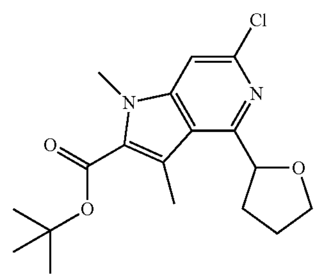 | (M + H)+ = 398; t_Ret. = 1.00 | VAB |
| B-1a-cq | 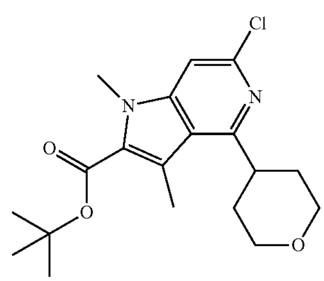 | (M + H)+ = 378; t_Ret. = 0.85 | VAB |
| B-1a-cr | 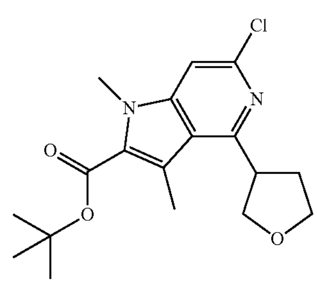 | (M + H)+ = 295; t_Ret. = 0.83 | VAB |
| B-1a-cs | 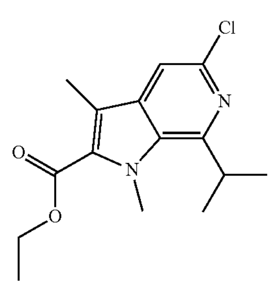 | (M + H)+ = 350; t_Ret. = 1.06 | LCMS3, basisch_1 |

TABLE 4-continued

| # | structure | MS (M + H)+; t_Ret. HPLC [min] | HPLC-MS method |
|---|---|---|---|
| B-1a-ct | 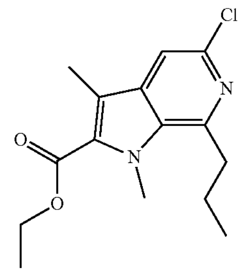 | (M + H)+ = 350; t_Ret. = 1.14 | LCMS3, basisch_1 |
| B-1a-cu | 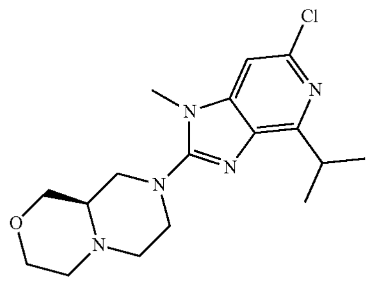 [SMILES: CC(C)c1nc(Cl)cc2c1nc(N1CCN3CCOC[C@H]3C1)n2C] | (M + H)+ = 350; t_Ret. = 0.83 | VAB |
| B-1a-cv | 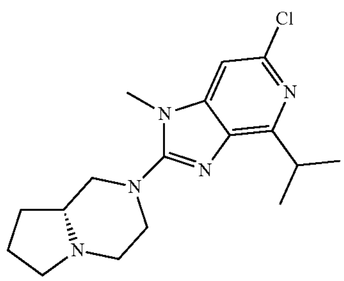 [SMILES: CC(C)c1nc(Cl)cc2c1nc(N1CCN3CCC[C@@H]3C1)n2C] | (M + H)+ = 334; t_Ret. = 0.57 | VAS |
| B-1a-cw | 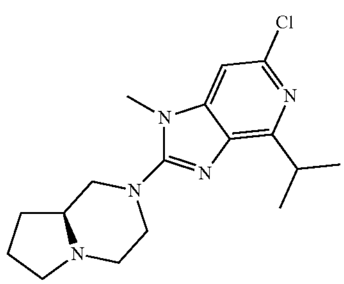 [SMILES: CC(C)c1nc(Cl)cc2c1nc(N1CCN3CCC[C@H]3C1)n2C] | (M + H)+ = 334; t_Ret. = 0.60 | VAS |
| B-1a-cx | 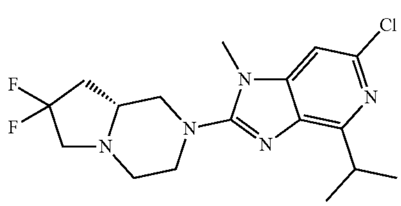 [SMILES: CC(C)c1nc(Cl)cc2c1nc(N1CCN3CC(F)(F)C[C@@H]3C1)n2C] | (M + H)+ = 370; t_Ret. = 0.97 | VAB |
| B-1a-cy | 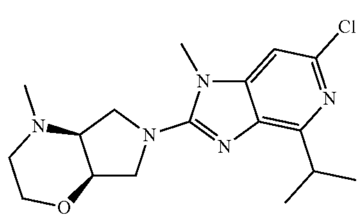 [SMILES: CC(C)c1nc(Cl)cc2c1nc(N1C[C@H]3OCCN(C)[C@H]3C1)n2C] | (M + H)+ = 350; t_Ret. = 0.79 | VAB |

TABLE 4-continued

| # | structure | MS (M + H)⁺; $t_{Ret.}$ HPLC [min] | HPLC-MS method |
|---|---|---|---|
| B-1b-i | 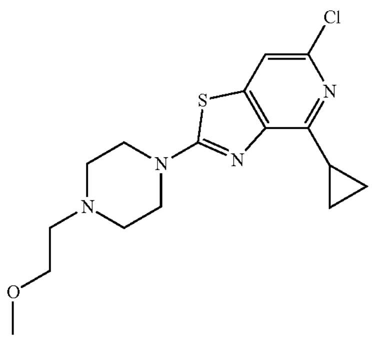 [SMILES: COCCN1CCN(c2nc3c(C4CC4)nc(Cl)cc3s2)CC1] | (M + H)⁺ = 353; $t_{Ret.}$ = 1.028 | VAB |
| B-1c*-b | 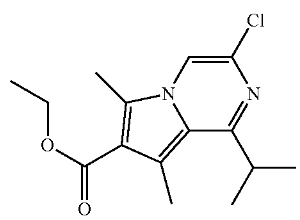 [SMILES: CCOC(=O)c1c(C)c2c(C(C)C)nc(Cl)cn2c1C] | (M + H)⁺ = 295; $t_{Ret.}$ = 1.139 | VAB |
| B-1c*-c | 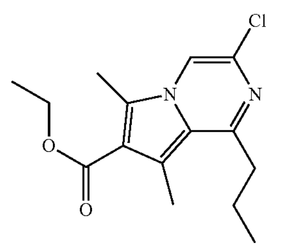 [SMILES: CCCc1nc(Cl)cn2c(C)c(C(=O)OCC)c(C)c12] | (M + H)⁺ = 295; $t_{Ret.}$ = 1.113 | VAB |
| B-1d*-d | 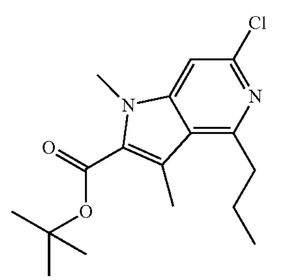 [SMILES: CCCc1nc(Cl)cc2c1c(C)c(C(=O)OC(C)(C)C)n2C] | (M + H)⁺ = 323; $t_{Ret.}$ = 1.203 | VAB |
| B-1d*-e | 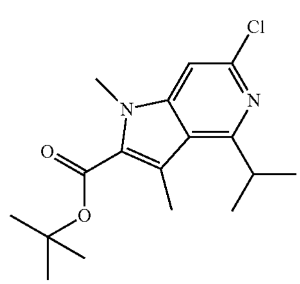 [SMILES: Cc1c(C(=O)OC(C)(C)C)n(C)c2cc(Cl)nc(C(C)C)c12] | (M + H)⁺ = 323; $t_{Ret.}$ = 1.236 | VAB |

TABLE 4-continued

| # | structure | MS (M + H)+; t_{Ret.} HPLC [min] | HPLC-MS method |
|---|---|---|---|
| B-1d*-f | 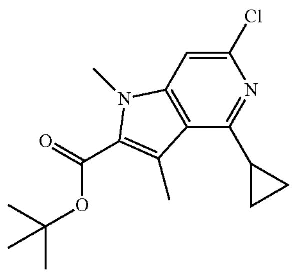 [SMILES: Cc1c(C(=O)OC(C)(C)C)n(C)c2cc(Cl)nc(C3CC3)c12] | (M + H)+ = 321; t_{Ret.} = 1.215 | VAB |
| B-1d*-g | 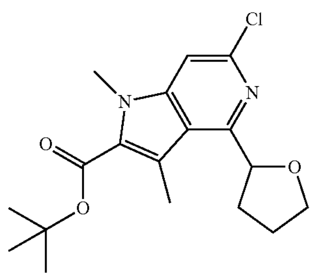 | (M + H)+ = 351; t_{Ret.} = 1.140 | VAB |
| B-1d*-h | 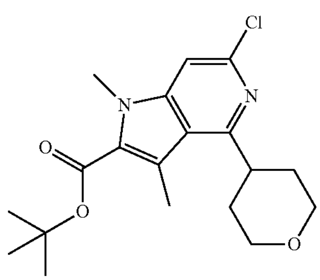 [SMILES: Cc1c(C(=O)OC(C)(C)C)n(C)c2cc(Cl)nc(C3CCOCC3)c12] | (M + H)+ = 365; t_{Ret.} = 1.129 | VAB |
| B-1d*-i | 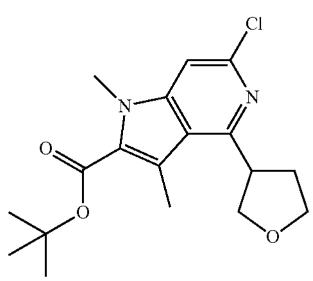 [SMILES: Cc1c(C(=O)OC(C)(C)C)n(C)c2cc(Cl)nc(C3CCOC3)c12] | (M + H)+ = 351; t_{Ret.} = 1.114 | VAB |
| B-1e*-b | 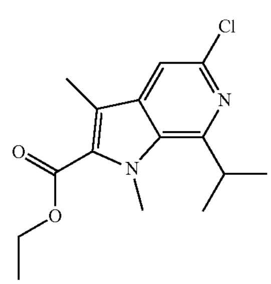 [SMILES: CCOC(=O)c1c(C)c2cc(Cl)nc(C(C)C)c2n1C] | (M + H)+ = 295; t_{Ret.} = 1.162 | VAB |

TABLE 4-continued

| # | structure | MS (M + H)+; $t_{Ret.}$ HPLC [min] | HPLC-MS method |
|---|---|---|---|
| B-1e*-c | 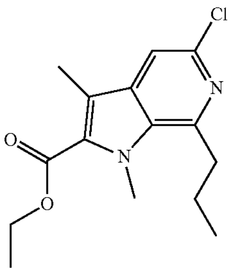 [SMILES: CCCc1nc(Cl)cc2c(C)c(C(=O)OCC)n(C)c12] | (M + H)+ = 295; $t_{Ret.}$ = 1.129 | VAB |

Synthesis of Intermediates B-3

Synthesis of B-3a-a

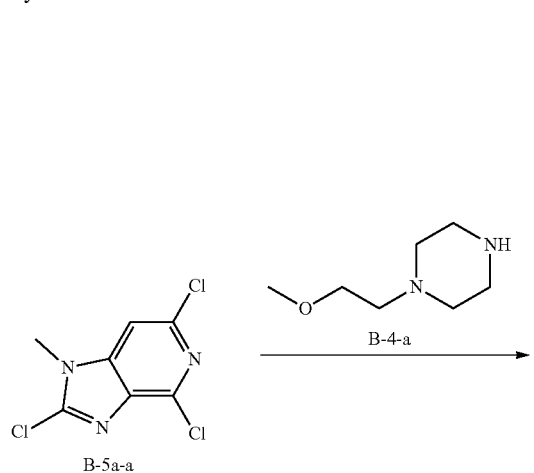

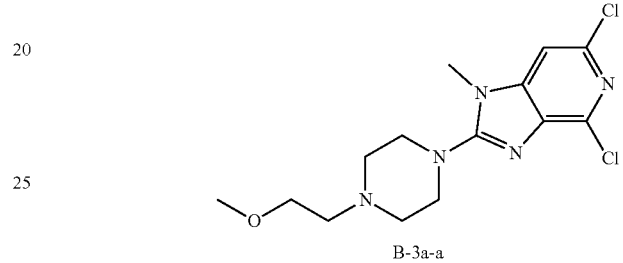

-continued

Starting materials B-5a-a (30.0 g, 126.9 mmol) and B-4-a (18.3 g, 126.9 mmol) are suspended in AcCN. The reaction mixture is stirred under microwave irradiation at 60° C. for 3 h. The reaction mixture is diluted with DCM, mixed with half statured aq. $NH_4Cl$ solution and extracted once. The organic phase is dried over $MgSO_4$, filtered and the solvent is evaporated under reduced pressure to give B-3a-a.

The following intermediates B-3a and B-3b (table 5) are available in an analogous manner starting from different building blocks B-5a and B-5b.

TABLE 5

| # | structure | MS (M + H)+; $t_{Ret.}$ HPLC [min] | HPLC-MS method |
|---|---|---|---|
| B-3a-a | 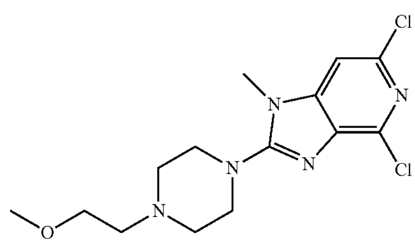 | (M + H)+ = 344; $t_{Ret.}$ = 0.762 | VAB |
| B-3a-b | 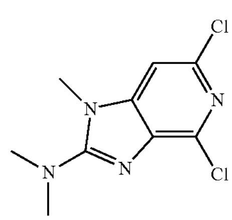 | (M + H)+ = 245; $t_{Ret.}$ = 0.719 | VAB |

TABLE 5-continued

| # | structure | MS (M + H)+; t_Ret. HPLC [min] | HPLC-MS method |
|---|---|---|---|
| B-3a-n | 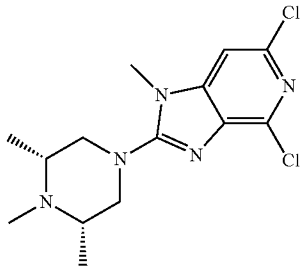 [SMILES: C[C@@H]1CN(c2nc3c(Cl)nc(Cl)cc3n2C)C[C@H](C)N1C] | (M + H)+ = 328; t_Ret. = 0.81 | VAB |
| B-3a-o | 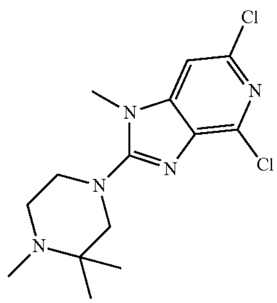 [SMILES: CN1CCN(c2nc3c(Cl)nc(Cl)cc3n2C)CC1(C)C] | (M + H)+ = 328; t_Ret. = 0.81 | VAB |
| B-3a-p | 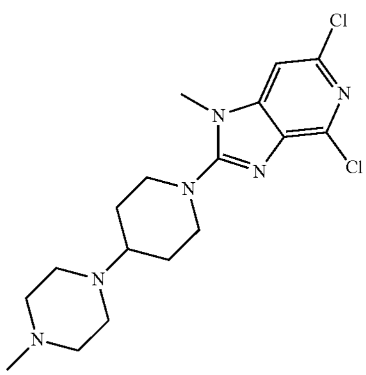 [SMILES: CN1CCN(C2CCN(c3nc4c(Cl)nc(Cl)cc4n3C)CC2)CC1] | (M + H)+ = 383; t_Ret. = 0.70 | VAB |
| B-3a-q | 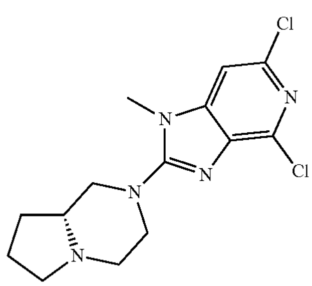 [SMILES: Cn1c(N2CCN3CCC[C@@H]3C2)nc2c(Cl)nc(Cl)cc21] | (M + H)+ = 326; t_Ret. = 0.79 | VAB |
| B-3a-r | 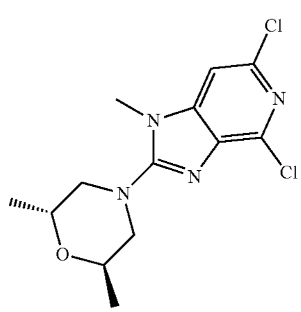 [SMILES: C[C@@H]1CN(c2nc3c(Cl)nc(Cl)cc3n2C)C[C@@H](C)O1] | (M + H)+ = 315; t_Ret. = 0.82 | VAB |

TABLE 5-continued

| # | structure | MS (M + H)+; t_Ret. HPLC [min] | HPLC-MS method |
|---|---|---|---|
| B-3a-s | 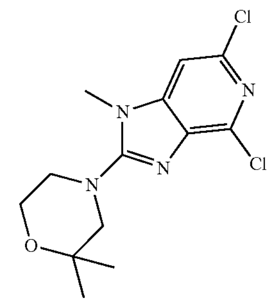 [SMILES: Cn1c(N2CCOC(C)(C)C2)nc2c(Cl)nc(Cl)cc21] | (M + H)+ = 315; t_Ret. = 0.82 | VAB |
| B-3a-t | 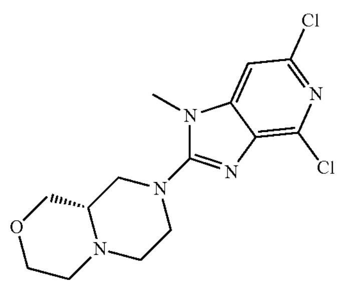 [SMILES: Cn1c(N2CCN3CCOC[C@@H]3C2)nc2c(Cl)nc(Cl)cc21] | (M + H)+ = 342; t_Ret. = 0.93 | LCMS3, basisch_1 |
| B-3a-u | 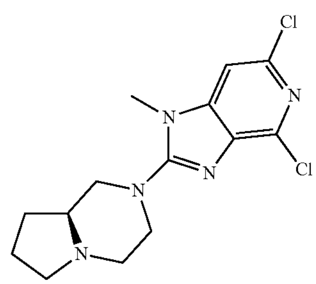 [SMILES: Cn1c(N2CCN3CCC[C@H]3C2)nc2c(Cl)nc(Cl)cc21] | (M + H)+ = 326; t_Ret. = 0.79 | VAB |
| B-3a-v | 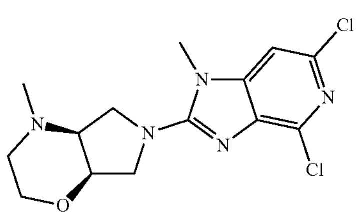 [SMILES: CN1CCO[C@@H]2CN(c3nc4c(Cl)nc(Cl)cc4n3C)C[C@@H]21] | (M + H)+ = 342; t_Ret. = 0.67 | VAB |
| B-3a-w | 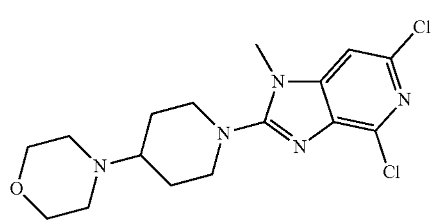 [SMILES: Cn1c(N2CCC(N3CCOCC3)CC2)nc2c(Cl)nc(Cl)cc21] | (M + H)+ = 370; t_Ret. = 0.73 | VAB |

TABLE 5-continued

| # | structure | MS (M + H)+; t_Ret. HPLC [min] | HPLC-MS method |
|---|---|---|---|
| B-3a-x | 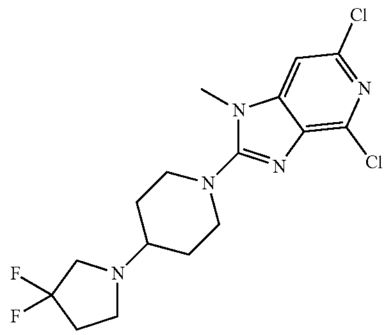 [SMILES: Cn1c(N2CCC(N3CCC(F)(F)C3)CC2)nc2c(Cl)nc(Cl)cc21] | (M + H)+ = 390; t_Ret. = 1.21 | LCMS3, basisch_1 |
| B-3a-y | 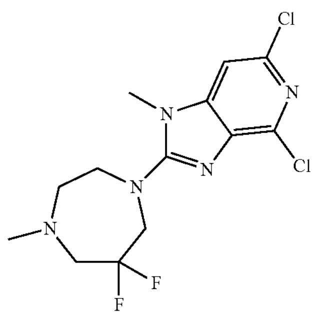 [SMILES: CN1CCN(c2nc3c(Cl)nc(Cl)cc3n2C)CC(F)(F)C1] | (M + H)+ = 350; t_Ret. = 1.16 | LCMS3, basisch_1 |
| B-3a-z | 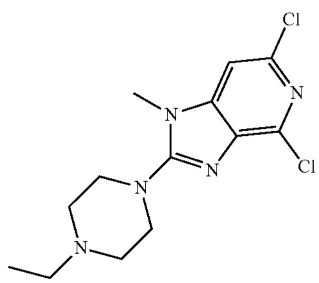 [SMILES: CCN1CCN(c2nc3c(Cl)nc(Cl)cc3n2C)CC1] | (M + H)+ = 314; t_Ret. = 0.77 | VAB |
| B-3a-aa | 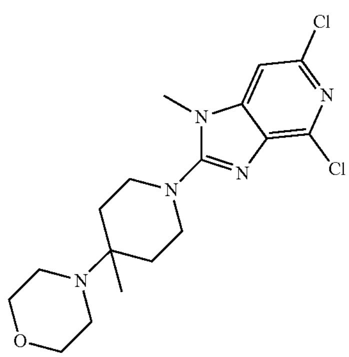 [SMILES: Cn1c(N2CCC(C)(N3CCOCC3)CC2)nc2c(Cl)nc(Cl)cc21] | (M + H)+ = 384; t_Ret. = 0.85 | VAB |
| B-3a-ab | 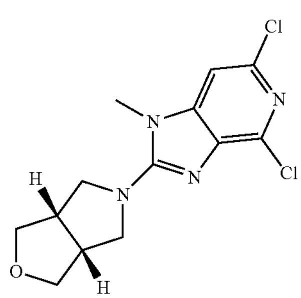 [SMILES: Cn1c(N2C[C@H]3COC[C@H]3C2)nc2c(Cl)nc(Cl)cc21] | (M + H)+ = 313; t_Ret. = 0.72 | VAB |

TABLE 5-continued

| # | structure | MS (M + H)+; t_Ret. HPLC [min] | HPLC-MS method |
|---|---|---|---|
| B-3a-ac | 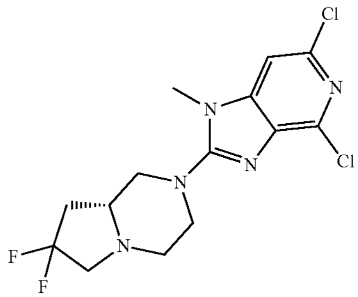 [SMILES: Cn1c(N2CCN3CC(F)(F)C[C@@H]3C2)nc2c(Cl)nc(Cl)cc21] | (M + H)+ = 362; t_Ret. = 0.85 | VAB |
| B-3a-ad | 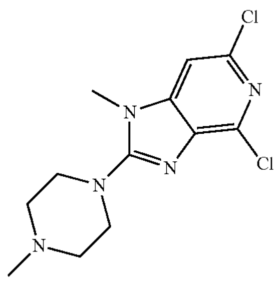 [SMILES: CN1CCN(c2nc3c(Cl)nc(Cl)cc3n2C)CC1] | (M + H)+ = 300; t_Ret. = 0.96 | LCMS3, basisch_1 |
| B-3a-ae | 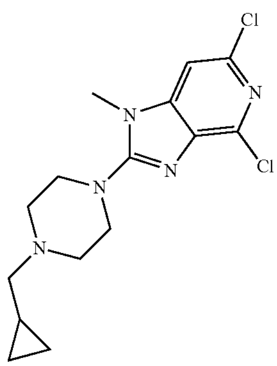 [SMILES: Cn1c(N2CCN(CC3CC3)CC2)nc2c(Cl)nc(Cl)cc21] | t_Ret. = 2.07 | XB5A |
| B-3a-af | 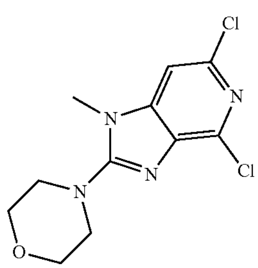 [SMILES: Cn1c(N2CCOCC2)nc2c(Cl)nc(Cl)cc21] | (M + H)+ = 287; t_Ret. = 0.72 | VAB |
| B-3a-ag | 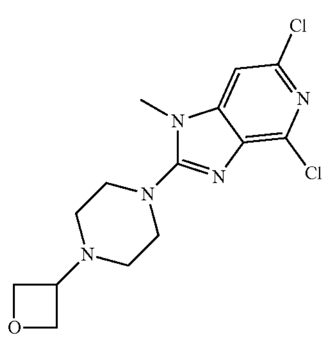 [SMILES: Cn1c(N2CCN(C3COC3)CC2)nc2c(Cl)nc(Cl)cc21] | (M + H)+ = 342; t_Ret. = 0.70 | VAB |

TABLE 5-continued

| # | structure | MS (M + H)+; $t_{Ret.}$ HPLC [min] | HPLC-MS method |
|---|---|---|---|
| B-3a-ah | 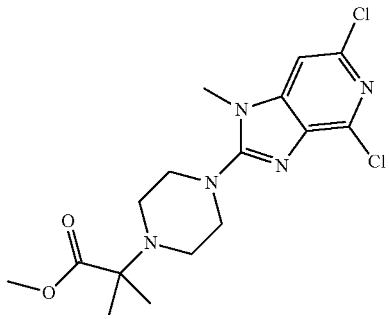 [SMILES: COC(=O)C(C)(C)N1CCN(c2nc3c(Cl)nc(Cl)cc3n2C)CC1] | (M + H)+ = 386; $t_{Ret.}$ = 1.18 | LCMS3, basisch_1 |
| B-3a-ai | 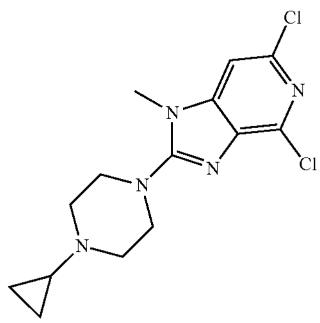 [SMILES: Cn1c(N2CCN(C3CC3)CC2)nc2c(Cl)nc(Cl)cc21] | (M + H)+ = 326; $t_{Ret.}$ = 0.83 | VAB |
| B-3a-aj | 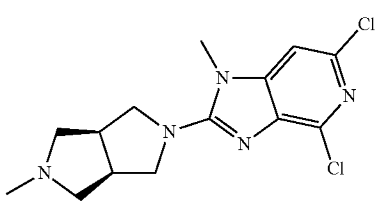 [SMILES: CN1C[C@@H]2CN(c3nc4c(Cl)nc(Cl)cc4n3C)C[C@@H]2C1] | (M + H)+ = 326; $t_{Ret.}$ = 0.74 | VAB |
| B-3a-ak | 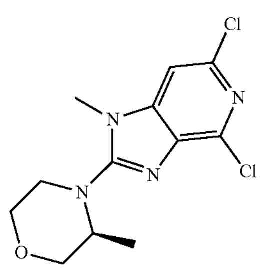 [SMILES: C[C@H]1COCCN1c1nc2c(Cl)nc(Cl)cc2n1C] | (M + H)+ = 301; $t_{Ret.}$ = 0.76 | VAB |
| B-3a-al | 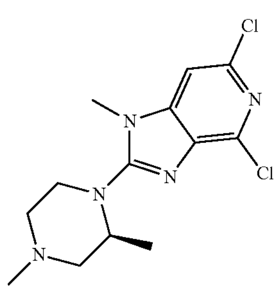 [SMILES: C[C@H]1CN(C)CCN1c1nc2c(Cl)nc(Cl)cc2n1C] | (M + H)+ = 314; $t_{Ret.}$ = 1.07 | LCMS3, basisch_1 |

TABLE 5-continued

| # | structure | MS (M + H)+; t_Ret. HPLC [min] | HPLC-MS method |
|---|---|---|---|
| B-3a-am | 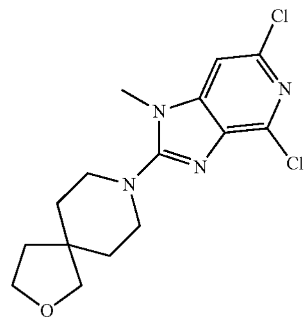 [SMILES: Cn1c(N2CCC3(CCOC3)CC2)nc2c(Cl)nc(Cl)cc21] | (M + H)+ = 341; t_Ret. = 0.82 | VAB |
| B-3a-an | 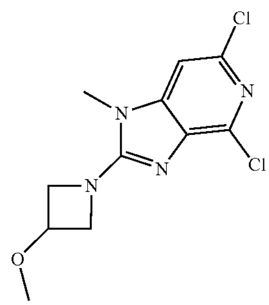 [SMILES: COC1CN(c2nc3c(Cl)nc(Cl)cc3n2C)C1] | (M + H)+ = 287; t_Ret. = 0.90 | LCMS3, basisch_1 |
| B-3a-ao | 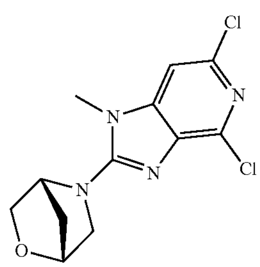 [SMILES: Cn1c(N2C[C@H]3C[C@@H]2CO3)nc2c(Cl)nc(Cl)cc21] | (M + H)+ = 299; t_Ret. = 0.70 | VAB |
| B-3a-ap | 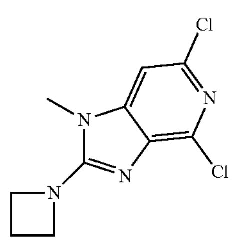 [SMILES: Cn1c(N2CCC2)nc2c(Cl)nc(Cl)cc21] | (M + H)+ = 257; t_Ret. = 0.72 | VAB |
| B-3a-aq | 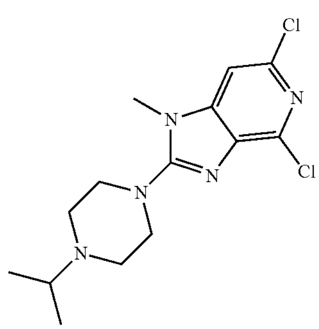 [SMILES: CC(C)N1CCN(c2nc3c(Cl)nc(Cl)cc3n2C)CC1] | (M + H)+ = 328; t_Ret. = 0.82 | VAB |

TABLE 5-continued

| # | structure | MS (M + H)+; t_{Ret.} HPLC [min] | HPLC-MS method |
|---|---|---|---|
| B-3a-ar | 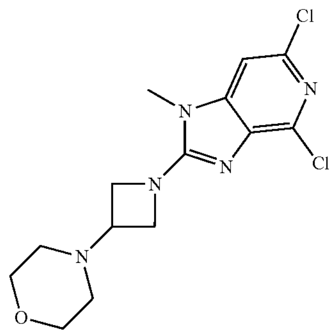 [SMILES: Cn1c(N2CC(N3CCOCC3)C2)nc2c(Cl)nc(Cl)cc21] | (M + H)+ = 342 t_{Ret.} = 0.69 | VAB |
| B-3a-as | 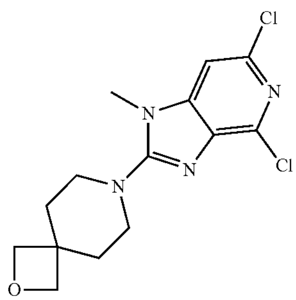 [SMILES: Cn1c(N2CCC3(CC2)COC3)nc2c(Cl)nc(Cl)cc21] | (M + H)+ = 327; t_{Ret.} = 0.77 | VAB |
| B-3a-at | 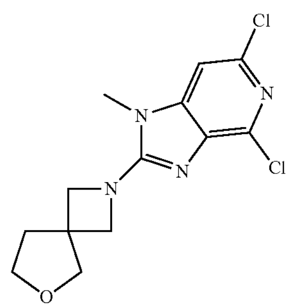 [SMILES: Cn1c(N2CC3(CCOC3)C2)nc2c(Cl)nc(Cl)cc21] | (M + H)+ = 313; t_{Ret.} = 0.92 | LCMS3, basisch_1 |
| B-3a-au | 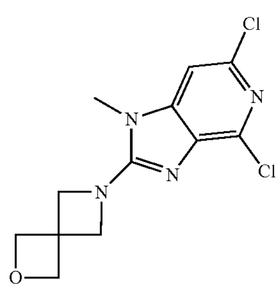 | (M + H)+ = 313; t_{Ret.} = 0.92 | LCMS3, basisch_1 |
| B-3a-av | 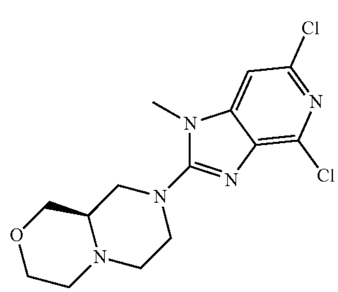 [SMILES: Cn1c(N2CCN3CCOC[C@H]3C2)nc2c(Cl)nc(Cl)cc21] | (M + H)+ = 342; t_{Ret.} = 0.93 | LCMS3, basisch_1 |

TABLE 5-continued

| # | structure | MS (M + H)+; t$_{Ret.}$ HPLC [min] | HPLC-MS method |
|---|---|---|---|
| B-3a-aw | 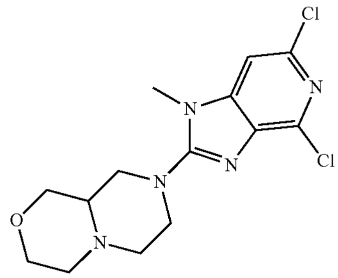 [SMILES: Cn1c(N2CCN3CCOCC3C2)nc2c(Cl)nc(Cl)cc21] | (M + H)+ = 342; t$_{Ret.}$ = 0.93 | LCMS3, basisch_1 |
| B-3a-ax | 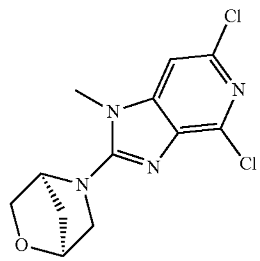 [SMILES: Cn1c(N2C[C@@H]3C[C@H]2CO3)nc2c(Cl)nc(Cl)cc21] | (M + H)+ = 299; t$_{Ret.}$ = 0.69 | VAB |
| B-3a-ay | 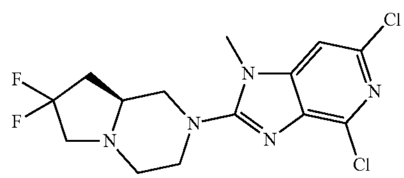 [SMILES: Cn1c(N2CCN3CC(F)(F)C[C@H]3C2)nc2c(Cl)nc(Cl)cc21] | (M + H)+ = 362; t$_{Ret.}$ = 0.86 | VAB |
| B-3a-az | 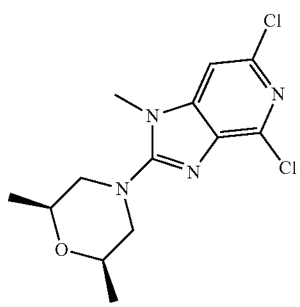 [SMILES: C[C@@H]1CN(c2nc3c(Cl)nc(Cl)cc3n2C)C[C@H](C)O1] | (M + H)+ = 315; t$_{Ret.}$ = 0.83 | VAB |
| B-3a-ba | 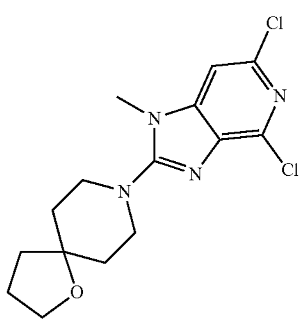 [SMILES: Cn1c(N2CCC3(CCCO3)CC2)nc2c(Cl)nc(Cl)cc21] | (M + H)+ = 341; t$_{Ret.}$ = 0.85 | VAB |
| B-3b-a | 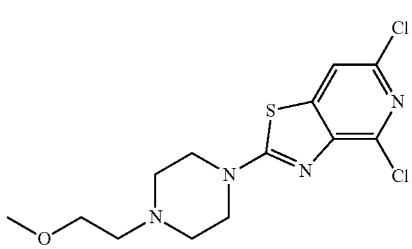 [SMILES: COCCN1CCN(c2nc3c(Cl)nc(Cl)cc3s2)CC1] | (M + H)+ = 347; t$_{Ret.}$ = 0.908 | VAB |

TABLE 5-continued

| # | structure | MS (M + H)+; $t_{Ret.}$ HPLC [min] | HPLC-MS method |
|---|---|---|---|
| B-3b-b | 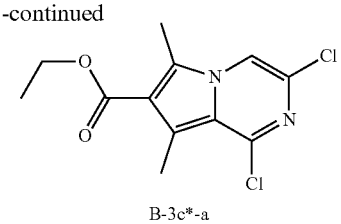 | (M + H)+ = 401; $t_{Ret.}$ = 1.024 | VAB |

Synthesis of B-3c*-a

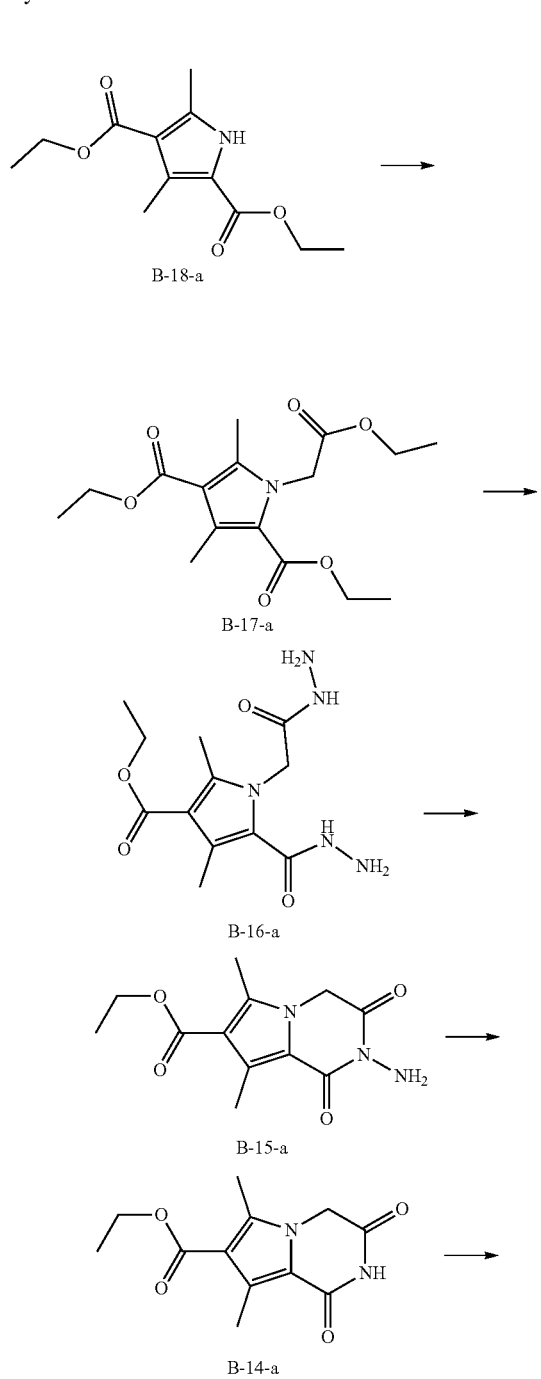

Experimental Procedure for the Synthesis of B-17-a

To a stirred solution of B-18-a (65.0 g; 271.6 mmol) in DMF (650.0 mL) is added NaH (32.46 mL; 814.98 mmol) dropwise at 0° C. The reaction mixture is stirred at 0° C. for 10 min and then chloro ethylacetate is added a 0° C. The reaction mixture is stirred at rt for 16 h. The reaction mixture is poured into ice water (2000 mL) and the precipitate is filtered and dried under vacuum to give B-17-a (HPLC-MS: (M+H)+=326, $t_{Ret.}$=1.41 min, method LCMS3, basisch_1)

Experimental Procedure for the Synthesis of B-16-a

To a stirred solution of B-17-a (75.0 g; 230.52 mmol) in EtOH (1000 mL) is added hydrazine hydrate (500 mL) at rt. The reaction mixture is stirred at 80° C. for 6 h. The reaction mixture is cooled to rt and the precipitate is filtered, washed with EtOAc and dried under vacuum to give B-16-a.

Experimental Procedure for the Synthesis of B-15-a

B-16-a (160 g; 538.15 mmol) is dissolved in acetic acid (1500 mL) and the reaction mixture is stirred at rt for 16 h. Then diethylether (2500 mL) is added to the reaction mixture and the precipitate is filtered and dried under vacuum to give B-15-a (HPLC-MS: (M+H)+=266.1, $t_{Ret.}$=0.775 min, method VAB).

Experimental Procedure for the Synthesis of B-14-a

To a stirred solution of B-15-a (35.0 g; 131.65 mmol) in 4 N aqueous HCl (1500 mL) is added a solution of sodium nitrite (45.52 g, 659.72 mmol) in water at 0° C. The reaction mixture is allowed to reach rt over a period of 16 h. The precipitate is filtered, washed with water (500 mL) and dried under vacuum to give B-14-a (HPLC-MS: (M+H)+=251.0, $t_{Ret.}$=0.92 min, method LCMS3, basisch_1)

Experimental Procedure for the Synthesis of B-3c*-a

To a stirred solution of B-14-a (23.0 g; 91.91 mmol) in toluene (100.0 mL) is added POCl₃ (400.0 mL), DIPEA (76.0 mL; 459.54 mmol), and PCl₅ (19.1 g; 91.91 mmol) at 0° C. Then the reaction mixture is stirred for 48 h under reflux. POCl₃ and toluene are removed under reduced pressure and the obtained residue is dissolved in EtOAc (1000 mL) and extracted with saturated aqueous NaHCO₃ solution (2×1000 mL), then washed with brine (500 mL). The organic layer is dried over MgSO₄, filtered and the solvent is evaporated under reduced pressure. The crude product is purified by normal phase chromatography (EtOAc/hexane 0:10) to afford the desired product B-3c*-a (HPLC-MS: (M+H)+=287.1, $t_{Ret.}$=2.40 min, method GVK_LCMS_61).
Synthesis of B-3d*-a

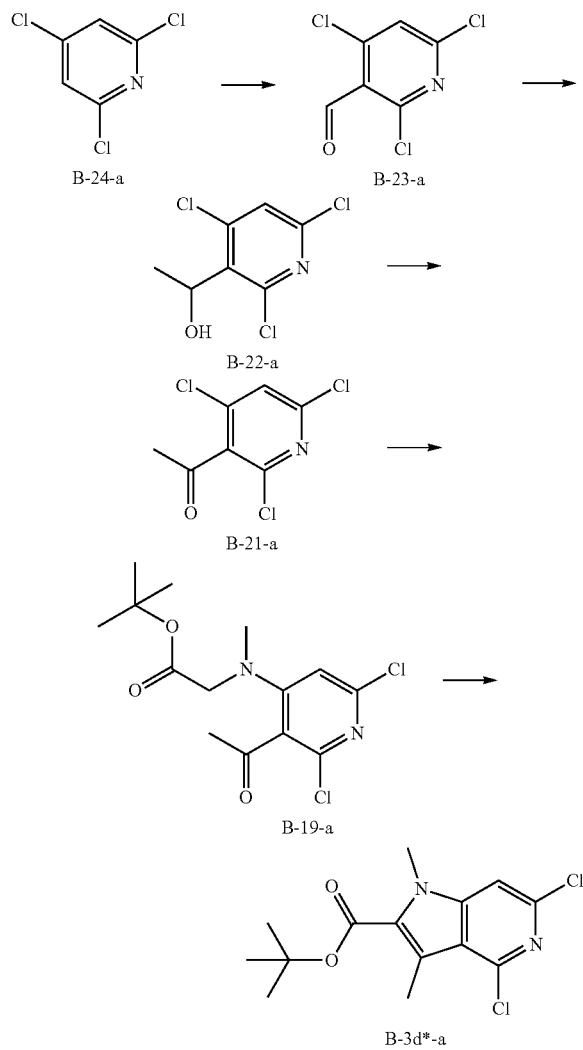

Experimental Procedure for the Synthesis of B-23-a

A stirred solution of B-24-a (500.0 g; 2.74 mol) in THF (5.0 L) is cooled to −78° C. 1.6 M n-butyllithium in hexane (1.7 L; 2.74 mol) is added under nitrogen condition. The reaction mixture is stirred at −78° C. for 60 min and then ethylformate (220.45 mL; 2.74 mol) is added dropwise at −78° C. and the reaction mixture is stirred at −78° C. for 4 h. The reaction is quenched with saturated ammonium chloride solution (200 mL) and extracted with EtOAc (2×2.0 L). The organic layer is dried over MgSO$_4$, filtered and the solvent is evaporated under reduced pressure. The crude product is purified by normal phase chromatography (EtOAc/hexane 0:10) to afford the desired product B-23-a (HPLC-MS: $t_{Ret.}$=2.11 min, method GVK_LCMS_41)

Experimental Procedure for the Synthesis of B-22-a

A stirred solution of B-23-a (170 g; 807.8 mmol) in THF (1.7 L) is cooled to −78° C. Then 2 M methylmagnesium in THF (807.8 mL, 1.62 mol) is added under nitrogen condition. The reaction mixture is stirred at −78° C. for 4 h. The reaction is quenched with saturated ammonium chloride solution (200 mL) and extracted with EtOAc (1×2.0 L). The organic layer is dried over MgSO$_4$, filtered and the solvent is evaporated under reduced pressure. The crude product is purified by normal phase chromatography (EtOAc/hexane 5:20) to afford the desired product B-22-a (HPLC-MS: $t_{Ret.}$=1.75 min, method GVK_LCMS_61).

Experimental Procedure for the Synthesis of B-21-a

To a stirred solution of B-22-a (170 g, 0.76 mol) in DCM (1.7 L) is added n-methylmorpholine (131.7 g, 1.13 mol, 1.5 eq.) at rt. The reaction mixture is stirred at rt for 30 min. Then tetrapropylammonium perruthenate (8.7 g, 24.7 mmol) is added and the reaction mixture is stirred at rt for 4 h. The reaction mixture is filtered through a pad of Celite and washed with DCM (3000 mL). The solvent is evaporated under reduced pressure. The crude product is purified by normal phase chromatography (EtOAc/hexane 10:50) to afford the desired product B-21-a (HPLC-MS: $t_{Ret.}$=2.02 min, method GVK_LCMS_61).

Experimental Procedure for the Synthesis of B-19-a

To a stirred solution of B-21-a (268 g; 1.19 mol) and tert-butyl methyl glycinate B-20-a (259.0 g; 1.43 mol) in EtOH (2.6 L) is added DIPEA (256.7 mL, 1.43 mol) at rt. The reaction mixture is stirred at 80° C. for 12 h. The reaction mixture is quenched with water (200 mL) and the solvent is removed under reduced pressure, then extracted with EtOAc (2×200 mL). The organic layer is dried over MgSO$_4$, filtered and the solvent is evaporated under reduced pressure. The crude product is purified by normal phase chromatography (EtOAc/hexane 2:5) to afford the desired product B-19-a (HPLC-MS: (M+H)+=333.0, $t_{Ret.}$=1.39 min, method LCMS3, basisch_1)

Experimental Procedure for the Synthesis of B-3d*-a

To a stirred solution of B-19-a (100 g, 0.30 mol) in DME (800 mL) is added potassium tert-butoxide (16.84 g; 0.15 mol) at −15° C. The reaction mixture is stirred at −15° C. for 6 h. The reaction mixture is quenched with ice water (2 L) and the precipitate is filtered, washed with n-pentane and dried under vacuum to give B-3d*-a (HPLC-MS: (M+H)+= 315.0, $t_{Ret.}$=1.67 min, method LCMS3, basisch_1)

Synthesis of B-3e*-a

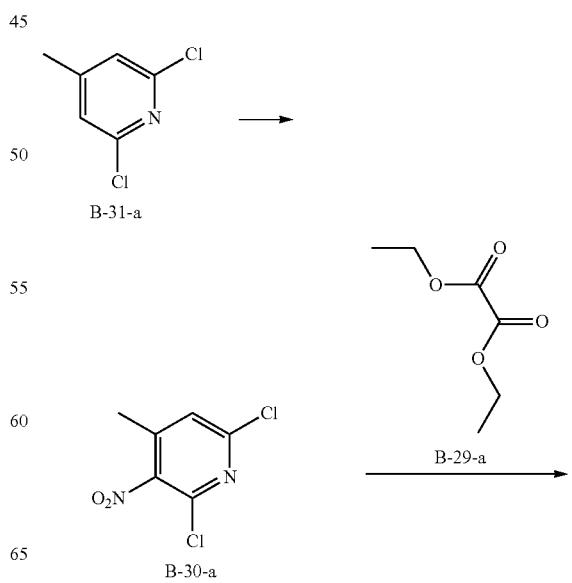

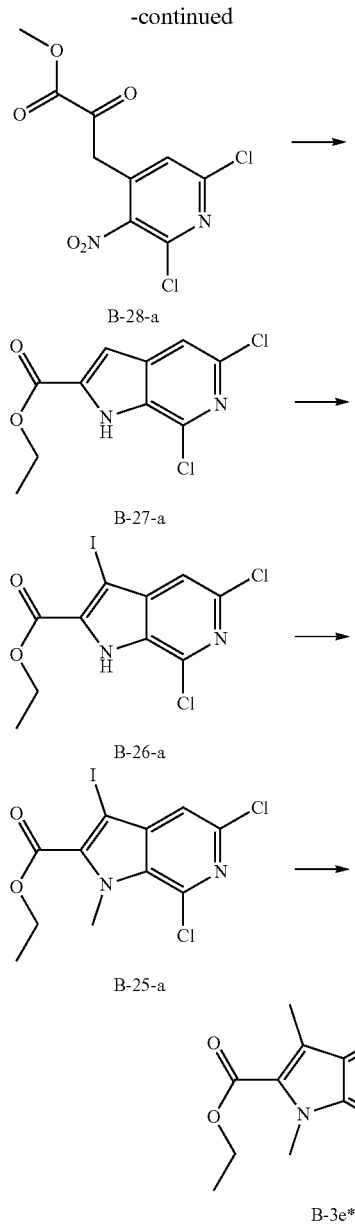

B-28-a

B-27-a

B-26-a

B-25-a

B-3e*-a

Experimental Procedure for the Synthesis of B-30-a

A stirred solution of B-31-a (350.0 g; 2.2 mol) in trifluoroacetic anhydride (1.7 L) is cooled to 0° C. Then nitric acid (285.8 g; 4.5 mol) is added dropwise at 0° C. and the reaction mixture is allowed to reach rt over a period of 18 h. The reaction mixture is quenched with sodium metabisulfite and stirred at rt for 2 h. The reaction mixture is neutralized to pH=7 by using 8 N aqueous NaOH solution and extracted with DCM (2×600 mL), washed with brine. The combined organic layers are dried over $Na_2SO_4$, filtered and the solvent is evaporated under reduced pressure to give B-30-a (HPLC-MS: $(M+H)^+$=207.0, $t_{Ret.}$=2.62 min, method GVK_LCMS_41)

Experimental Procedure for the Synthesis of B-28-a

To a stirred solution of potassium ethoxide (40.56 g; 0.48 mol) in diethyl ether (2.5 L) and EtOH (0.3 L) under argon atmosphere is added B-30-a (70.5 g; 0.48 mol) and the reaction mixture is stirred at rt for 30 min. A solution of B-29-a (100.0 g; 0.48 mol) in diethyl ether (150 mL) is added to the reaction. The reaction mixture is stirred at rt for 16 h. The solvent is removed under reduced pressure and acidified to pH=4 by using acetic acid, extracted with EtOAc (2×600 mL). The combined organic layers are dried over $Na_2SO_4$, filtered and the solvent is evaporated under reduced pressure to give B-28-a (HPLC-MS: $(M+H)^+$=307.0, $t_{Ret.}$=2.37 min, method GVK_LCMS_41)

Experimental Procedure for the Synthesis of B-27-a

To a stirred solution of B-28-a (50.0 g; 0.16 mol) in EtOH (1.75 L) and EtOH (0.75 L) is added iron (54.7 g; 0.98 mol) and an aqueous solution of ammonium chloride (750.0 mL) at rt. The reaction mixture is stirred at 90° C. for 5 h. The reaction mixture is filtered through a pad of Celite and washed with hot EtOH and THF. The solvent is diluted in water and extracted with EtOAc (2×1 L). The combined organic layers are dried over $Na_2SO_4$, filtered and the solvent is evaporated under reduced pressure to afford the desired product B-27-a (HPLC-MS: $(M+H)^+$=269, $t_{Ret.}$=2.25 min, method GVK_LCMS_41)

Experimental Procedure for the Synthesis of B-26-a

To a stirred solution of B-27-a (40.0 g; 0.15 mol) in DCM (400 mL) and DMF (200 mL) is added NIS (69.5 g; 0.31 mol) at rt and the reaction mixture is stirred at rt for 24 h. The reaction mixture is quenched with ice water and extracted with DCM (2×2 L). The combined organic layers are dried over $Na_2SO_4$, filtered and the solvent is evaporated under reduced pressure. The crude product is purified by normal phase chromatography (EtOAc/petroleum ether 50:70) to afford the desired product B-26-a (HPLC-MS: $(M+H)^+$=273.38, $t_{Ret.}$=3.12 min, method GVK_LCMS_41)

Experimental Procedure for the Synthesis of B-25-a

A stirred solution of B-26-a (50.5 g; 0.13 mol) in DMF (500 mL) is cooled to 0° C., then NaH (6.3 g; 0.26 mol) is added and the reaction mixture is stirred at rt for 30 min. The reaction mixture is cooled to 0° C. before methyl iodide (37.25 g; 0.26 mol) is added. The reaction mixture is stirred at rt for 3 h, then quenched with water. The precipitate is filtered, washed with diethyl ether and dried under vacuum to give B-25-a (HPLC-MS: $(M+H)^+$=398.90, $t_{Ret.}$=2.73 min, method GVK_LCMS_41)

Experimental Procedure for the Synthesis of B-3e*-a

To a stirred solution of B-25-a (20.0 g; 0.05 mol) in THF (400 mL) is added $Fe(acac)_3$ (1.77 g; 0.005 mol) at rt and the reaction mixture is cooled to 0° C. Then 1 N MeMgBr solution (100 mL) is added at 0° C. and the reaction mixture is allowed to reach rt over a period of 8 h. The reaction is quenched with saturated ammonium chloride solution and extracted with EtOAc (2×200 mL). The combined organic layers are dried over $Na_2SO_4$, filtered and the solvent is evaporated under reduced pressure. The crude product is purified by normal phase chromatography (EtOAc/petroleum ether 1:10) to afford the desired product B-3e*-a (HPLC-MS: $(M+H)^+$=287.19, $t_{Ret.}$=2.46 min, method GVK_LCMS_61)

Synthesis of B-3f-a and B-3f-b

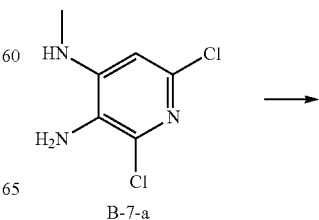

B-7-a

-continued

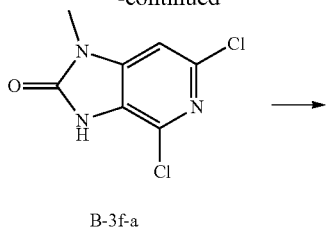

B-3f-a

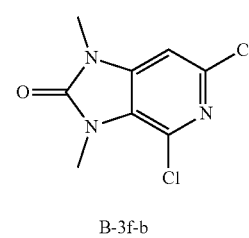

B-3f-b

Experimental Procedure for the Synthesis of B-3f-a

To a stirred solution of B-7-a (336 mg, 1.66 mmol) in DCE (6 mL) is added CDI (350 mg, 2.16 mmol) and the reaction mixture is stirred over night at 50° C. The residue is treated with AcCN (4 mL) and the precipitate is filtrated, washed with AcCN and dried over night at 45° C. in a vacuum drying oven to give B-3f-a (HPLC-MS: (M+H)$^+$ =218, $t_{Ret.}$=0.50 min, method VAB)

Experimental Procedure for the Synthesis of B-3f-b

To a stirred solution of B-3f-a (29.38 g, 134.75 mmol) in DMF (293.4 mL) at −5° C. is added sodium hydride (6.47 g, 161.69 mmol) and stirred for 10 min. Iodomethan (10.07 mL, 161.69 mmol) is added and stirred for 45 min at −5° C. The reaction mixture is quenched with saturated NH$_4$Cl (300 mL) and diluted with saturated brine (200 mL). The precipitate is filtered, washed with water and dried in a vacuum oven at 50° C. to give B-3f-b (30.06 g; 129.53 mmol) (HPLC: $t_{Ret.}$=2.42 min, method XB5A)

Synthesis of B-3g-a

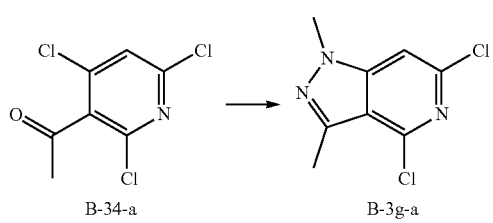

B-34-a → B-3g-a

Experimental Procedure for the Synthesis of B-3q-a

To a stirred solution of B-34-a (50.00 mg; 0.223 mmol) in MeOH (1 mL) is added methylhydrazine (0.023 mL; 0.445 mmol) and stirred at 60° C. overnight. The reaction mixture is filtered and purified by prep. HPLC 3 to afford the desired product B-3g-a (20 mg, 0.093 mmol) (HPLC-MS: (M+H)$^+$= 216, $t_{Ret.}$=1.24 min, method LCMS3, basisch_1).

The following intermediates B-3g (table 6) are available in an analogous manner starting from building blocks B-34 and corresponding hydrazine derivatives.

TABLE 6

| # | structure | MS (M + H)$^+$; $t_{Ret.}$ HPLC [min] | HPLC-MS method |
|---|---|---|---|
| B-3g-a | 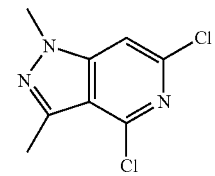 | (M + H)$^+$ = 216; $t_{Ret.}$ = 1.24 | LCMS3, basisch_1 |
| B-3g-b | 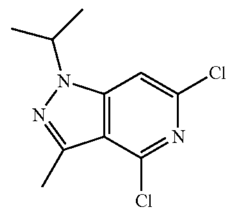 | (M + H)$^+$ = 244; $t_{Ret.}$ = 2.22 | GVK_LCMS_61 |
| B-3g-c | 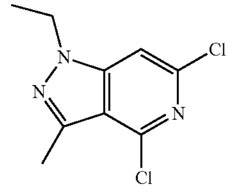 | (M + H)$^+$ = 230; $t_{Ret.}$ = 2.08 | GVK_LCMS_61 |

Synthesis of B-3h-a

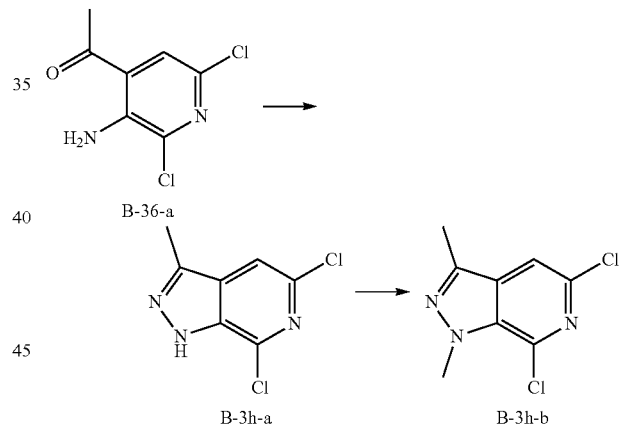

B-36-a

B-3h-a    B-3h-b

Experimental Procedure for the Synthesis of B-3h-a

A solution of B-36-a (200.0 mg; 0.975 mmol) in conc.HCl (2.0 mL) is stirred for 10 min at rt and cooled to 0° C., then NaNO$_2$ (79.594 mg; 1.170 mmol) in water is added dropwise at −5° C. and stirred for 15 min at 0 to −5° C. SnCl$_2$*2 H$_2$O (511.507 mg; 2.243 mmol) in conc. HCl is added dropwise and the resulting reaction mixture is stirred for 30 min. Then the reaction mixture is filtered and washed with water, aq. NaHCO$_3$ solution and air dried. The obtained crude material is purified by flash column chromatography using 0-30% EtOAc/PE as eluent affording desired product B-3h-a (50.0 mg, 0.247 mmol) (HPLC-MS: (M+H)$^+$=202, $t_{Ret.}$=1.93 min, method GVK_LCMS_41).

Experimental Procedure for the Synthesis of B-3h-b

To a stirred solution of B-3h-a (50.00 mg, 0.247 mmol) and potassium carbonate (100.00 mg, 0.716 mmol) in AcCN (2 mL), sulfuric acid dimethyl ester (25.0 µL, 0.258 mmol)

is added dropwise and stirred for 30 min at rt. The reaction mixture is filtered and the solvent is removed under reduced pressure. The residue is purified by prep. HPLC 1 to get B-3h-b (22.00 mg, 0.102 mmol) (HPLC-MS: (M+H)$^+$=216, $t_{Ret.}$=1.23 min, method LCMS3, basisch_1)

Synthesis of B-3a-c

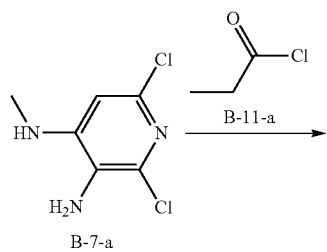

is extracted with DCM. The organic layer is concentrated to dryness. The crude compound is purified (normal phase chromatography) to afford the desired product B-10-a (HPLC-MS: (M+H)$^+$=248.0, $t_{Ret.}$=1.46 min, method TCG_LCMS, basisch_1).

Experimental Procedure for the Synthesis of B-3a-c

To B-10-a (500 mg, 2.0 mmol) are added 1,4-dioxane (10 mL) and acetic acid (1.0 mL, 15.5 mmol, 8.7 eq.). The reaction mixture is heated to 110° C. After full conversion the solvents are evaporated. The residue is basified with sodium bicarbonate (saturated aqueous solution). The aqueous layer is extracted with EtOAc. The solvent is evaporated and the residue is purified (normal phase chromatography, mobile phase cyclohexane/EtOAc) to afford B-3a-c.

The following intermediates B-10 (table 7) are also available in analogy to the synthesis of B-10-a starting from different building blocks B-7 and B-11.

TABLE 7

| # | structure | MS (M + H)$^+$; tRet. HPLC [min] | HPLC-MS method |
|---|---|---|---|
| B-10-a | 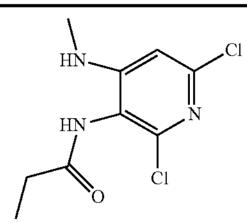 | (M + H)$^+$ = 248; $t_{Ret.}$ = 1.46 | TCG_LCMS, basisch_1 |
| B-10-b | 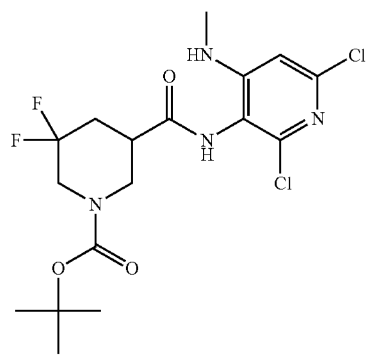 [SMILES: CNc1cc(Cl)nc(Cl)c1NC(=O)C1CN(C(=O)OC(C)(C)C)CC(F)(F)C1] | (M + H)$^+$ = 439.1; $t_{Ret.}$ = 0.942 | VAB |

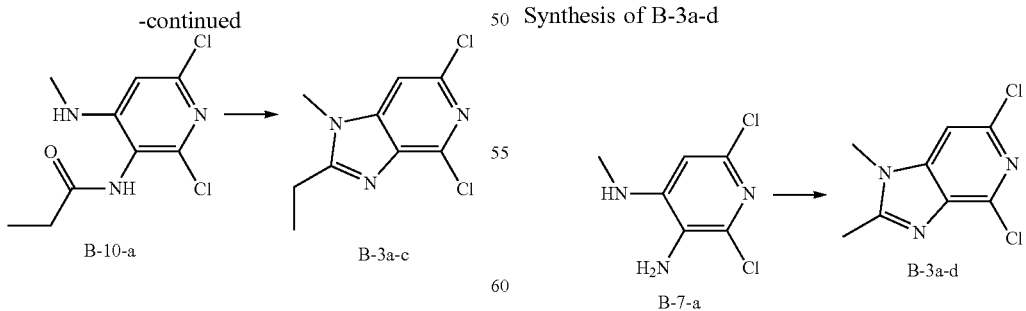

Experimental Procedure for the Synthesis of B-10-a

A stirred solution of B-7-a (200 mg, 1.04 mmol) in DCM (10 mL) is cooled to −20° C. B-11-a (120 mg, 1.25 mmol, 1.2 eq.) is added and the reaction mixture is stirred for 2 h at −20° C. The reaction mixture is basified with sodium carbonate (saturated aqueous solution). The aqueous phase Synthesis of B-3a-d To B-7-a (34.7 g, 174.8 mmol, 1 eq.) are added acetic acid (100 mL, 1740 mmol, 10 eq.) and polyphosphoric acid (135 mL, 2320 mmol, 13.3 eq.). The reaction mixture is stirred at 100° C. for 3 h. The reaction mixture is cooled to rt, diluted with water and basified with 6 N aqueous sodium hydroxide to pH 8. The aqueous phase is extracted with DCM. The organic layer is concentrated to dryness, the residue is purified (normal phase chromatography, mobile phase cyclohexane/EtOAc 35% to 95%) to afford B-3a-d.

Synthesis of B-3a-e

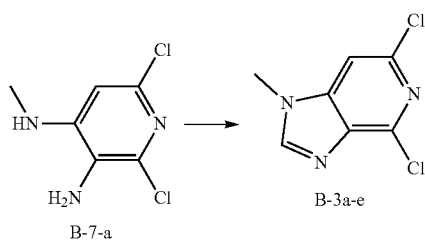

B-7-a (2.8 g, 14.58 mmol, 1 eq.), trimethyl orthoformate (30 mL, 274 mmol, 18.8 eq.) and acetic acid (3 mL, 52 mmol, 3.6 eq.) are charged to a pressure reactor. The reaction mixture is stirred at 100° C. for 16 h. After cooling, the reaction mixture is basified with an aqueous solution of sodium bicarbonate. The aqueous phase is extracted with EtOAc. The organic phase is washed with brine, dried over sodium sulfate and concentrated to dryness. The residue is purified by normal phase chromatography (mobile phase cyclohexene/EtOAc) to afford B-3a-e.

Synthesis of B-3a-g

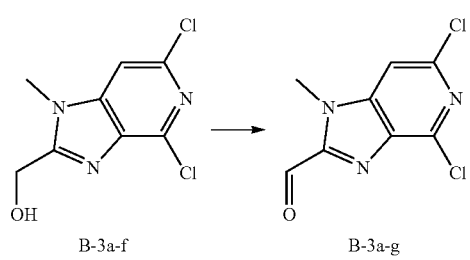

A solution of B-3a-f (18.0 g, 77.56 mmol) in DCM (270.0 mL) is added DESS-MARTIN reagent (39.46 g, 93.08 mmol, 1.2 eq.) at 0° C. and stirred for 12 h at rt. The reaction mixture is diluted with sat. NaHCO$_3$ solution (500.0 mL) and extracted with DCM (2×500 mL). The combined organic layers are dried over Na$_2$SO$_4$ and concentrated under reduced pressure. The crude material is purified by normal phase chromatography (mobile phase cyclohexene/EtOAc 30-80%) to afford B-3a-g (HPLC-MS: (M+H)$^+$= 248.0, t$_{Ret.}$=0.64 min, method VAB). Starting material B-3a-f can be obtained analogously to the synthesis as described for B-3a-d using hydroxy acetic acid as the carboxylic acid.

Synthesis of B-3a-h

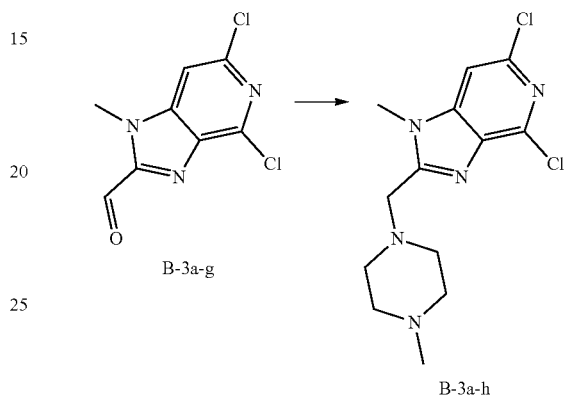

A solution of B-3a-g (75.00 mg, 0.267 mmol) and 1-methylpiperazine (53.52 mg, 0.534 mmol) in DCM (1 mL) are shaked for 10 min at rt. Acetic acid (7.640 µL; 0.134 mmol) and sodium triacetoxyborohydride (141.565 mg; 0.668 mmol) are added and the reaction mixture is shaked for 2 h at rt. The mixture is concentrated under reduced pressure and dissolved in DMF and water, filtered and purified by prep. HPLC 1 to get B-3a-h (41.00 mg, 0.112 mmol).

The following intermediates B-3a (table 8) are available in an analogous manner as described for intermediates B-3a-c to B-3a-e, B-3a-g and B-3a-h.

The following intermediates B-3a (table 8) are available in an analogous manner starting from different building blocks B-7, and B-14.

TABLE 8

| # | structure | MS (M + H)$^+$; t$_{Ret.}$ HPLC [min] | HPLC-MS method |
|---|---|---|---|
| B-3a-c | 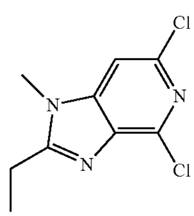 | (M + H)$^+$ = 230; t$_{Ret.}$ = 2.88 | TCG_LCMS, basisch_2 |
| B-3a-d | 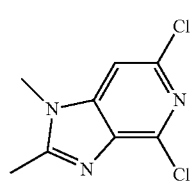 | (M + H)$^+$ = 216; t$_{Ret.}$ = 0.76 | LCMS3, basisch_1 |

TABLE 8-continued
| # | structure | MS (M + H)+; $t_{Ret.}$ HPLC [min] | HPLC-MS method |
|---|---|---|---|
| B-3a-e | 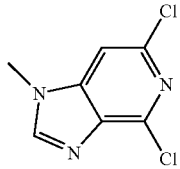 | (M + H)+ = 202.0; $t_{Ret.}$ = 0.56 | VAB |
| B-3a-f | 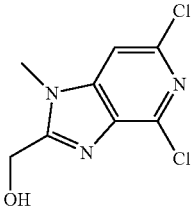 | (M + H)+ = 232; $t_{Ret.}$ = 0.60 | LCMS3, basisch_1 |
| B-3a-g | 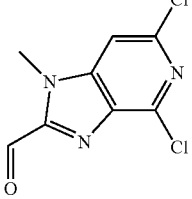 | (M + H)+ = 248; $t_{Ret.}$ = 0.61 | VAB |
| B-3a-h | 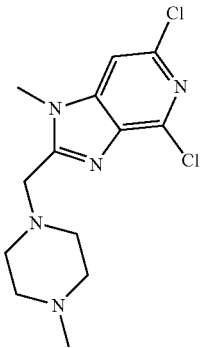 [SMILES: CN1CCN(Cc2nc3c(Cl)nc(Cl)cc3n2C)CC1] | (M + H)+ = 314; $t_{Ret.}$ = 0.91 | LCMS3, basisch_1 |
| B-3a-i | 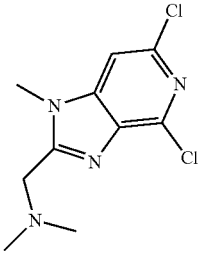 [SMILES: CN(C)Cc1nc2c(Cl)nc(Cl)cc2n1C] | (M + H)+ = 259; $t_{Ret.}$ = 0.95 | LCMS3, basisch_1 |
| B-3a-j | 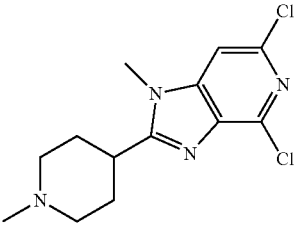 [SMILES: CN1CCC(c2nc3c(Cl)nc(Cl)cc3n2C)CC1] | (M + H)+ = 299; $t_{Ret.}$ = 0.735 | VAB |

TABLE 8-continued

| # | structure | MS (M + H)+; $t_{Ret.}$ HPLC [min] | HPLC-MS method |
|---|---|---|---|
| B-3a-k | 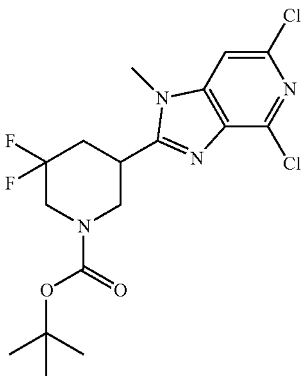 [SMILES: Cn1c(C2CN(C(=O)OC(C)(C)C)CC(F)(F)C2)nc2c(Cl)nc(Cl)cc21] | (M + H)+ = 421.1; $t_{Ret.}$ = 1.01 | VAB |
| B-3a-l | 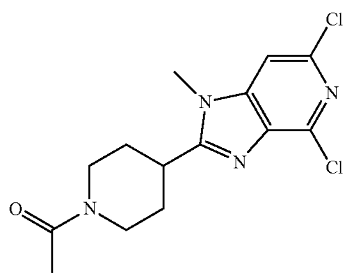 [SMILES: CC(=O)N1CCC(c2nc3c(Cl)nc(Cl)cc3n2C)CC1] | (M + H)+ = 327.0; $t_{Ret.}$ = 0.699 | VAB |
| B-3a-m | 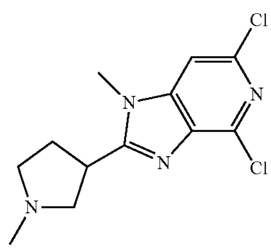 [SMILES: CN1CCC(c2nc3c(Cl)nc(Cl)cc3n2C)C1] | (M + H)+ = 285.0; $t_{Ret.}$ = 0.97 | LCMS3, basisch_1 |

Synthesis of Intermediates 8-5
Synthesis of B-5a-a

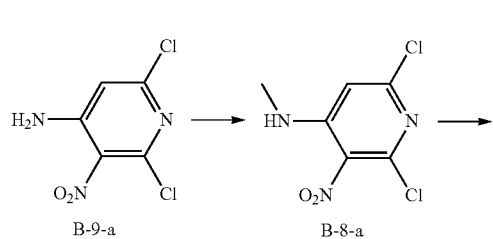

B-9-a   B-8-a

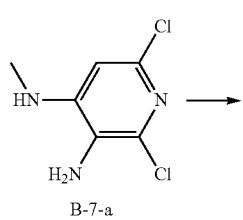

B-7-a

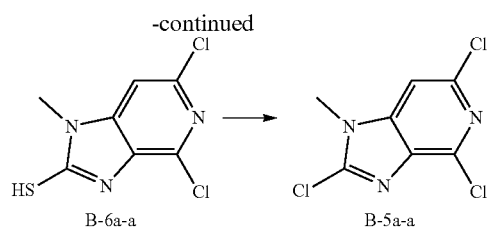

B-6a-a   B-5a-a

Experimental Procedure for the Synthesis of B-8-a

To a stirred solution of B-9-a (100.0 g; 0.480 mol) in AcCN (1500 mL) is added $K_2CO_3$ (165.9 g; 1.20 mol) at 0° C. and stirred for 15 min. Then MeI (186.2 mL; 2.90 mol) is added at same temperature and the reaction is heated to 80° C. for 16 h. The solvent is removed under reduced pressure and the obtained crude material is portioned between ice cold water and EtOAc. The separated organic layer is dried over $Na_2SO_4$ and concentrated under reduced pressure. The obtained crude material is purified by flash column chromatography using EtOAc/petroleum ether as eluent giving the desired product B-8-a (HPLC-MS: (M+H)+=222.0; $t_{Ret.}$=1.11 min, method LCMS3, basisch_1).

Experimental Procedure for the Synthesis of B-7-a

To a stirred solution of B-8-a (85.0 g; 0.383 mol) in EtOH (750 mL) are added $NH_4Cl$ (101.5 g; 1.91 mol) and water (100.0 mL) and stirred for 10 min before iron (105.3 g; 1.91 mol) is added. The reaction mixture is stirred at 90° C. for 16 h. After complete conversion the reaction mixture is evaporated under vacuum and taken up in EtOAc and water and filtered through a Celite pad. The organic layer is dried over anhydrous $Na_2SO_4$ and concentrated under vacuum to get crude product. This crude product is triturated with 5% EtOAc/petroleum ether, stirred for 30 min, filtered and dried under vacuum to get B-7-a (HPLC-MS: $(M+H)^+$=192.0; $t_{Ret.}$=0.81 min, method LCMS3, basisch_1).

Experimental Procedure for the Synthesis of B-6a-a

To a stirred solution of B-7-a (75.0 g; 0.391 mol) in THF (600 mL) is added 1,1'-thiocarbonyldiimidazole (139.0 g; 0.781 mol). The reaction mixture is stirred at 80° C. for 24 h, then cooled to rt and evaporated to dryness. EtOAc is added to the residue and the mixture is extracted with water. The organic layer is washed with water, dried over anhydrous $Na_2SO_4$ and concentrated under vacuum to get crude product, which is triturated with diethyl ether, stirred for 30 min, filtered and dried under vacuum to get B-6a-a (HPLC-MS: $(M+H)^+$=234.3, $t_{Ret.}$=1.93 min, method GVK_LCMS_41).

Experimental Procedure for the Synthesis of B-5a-a

A solution of B-6a-a (60.0 g; 0.256 mol) in thionyl chloride (600 mL) and DMF (120 mL) is stirred at 80° C. for 30 min. The reaction mixture is evaporated under vacuum, diluted with EtOAc and extracted with saturated $NaHCO_3$ solution. The organic layer is dried over anhydrous $Na_2SO_4$ and concentrated under vacuum to get crude product. This crude product is purified by normal phase chromatography using DCM/petroleum ether to get B-5a-a (HPLC-MS: $(M+H)^+$=236.0, $t_{Ret.}$=2.03 min, method GVK_LCMS_41).

Alternative Synthesis of B-5a-a

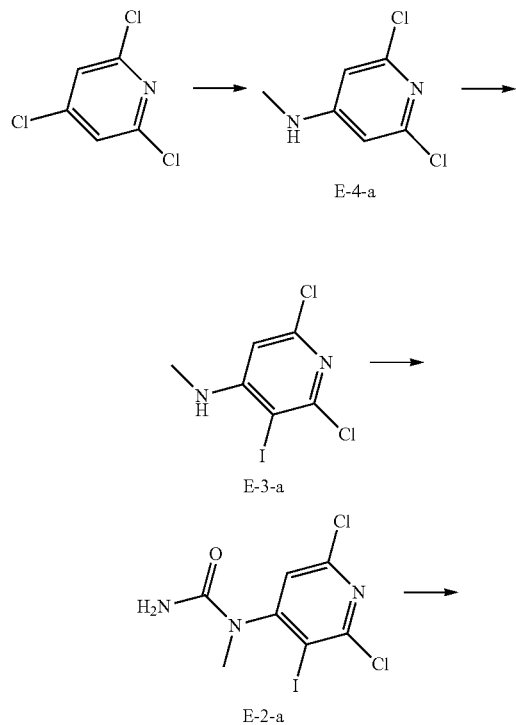

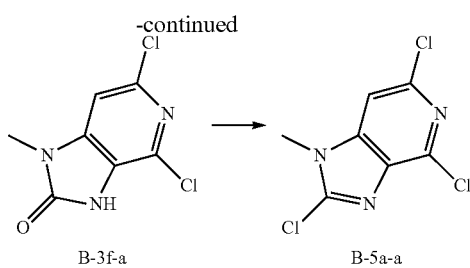

Experimental Procedure for the Synthesis of E-4-a

To a suspension of 2,4,6-trichloropyridine (2.5 g, 13.7 mmol, 1.0 eq.) in EtOH (2.5 mL) at 80° C. is added methylamine in EtOH (33 wt %, 10.0 mL, 73.04 mmol, 5.33 eq.) over 4 h. The mixture is stirred at 80° C. for 4 h, then is cooled to rt over 2 h. The mixture is stirred at rt for 1 h, then filtered. The solid is rinsed sequentially with water (5.0 mL), heptane (2.5 mL), and MTBE (2.5 mL). The solid is dried under vacuum at 50° C., then is slurried with MTBE (10.0 mL) for 1 h at rt. The mixture is filtered, then rinsed with MTBE (2.5 mL). The solid is dried under vacuum at 55° C. to give E-4-a ($^1$H-NMR (500 MHz, DMSO-d6) δ 7.35 (d, J=5 Hz, 1H), 6.51 (s, 2H), 2.72 (d, J=5 Hz, 3H)).

Experimental Procedure for the Synthesis of E-3-a

A suspension of E-4-a (5.0 g, 27.715 mmol, 1.0 eq.) and N-iodosuccinimide (6.55 g, 29.101 mmol, 1.05 eq.) in acetonitrile (30 mL) is heated to 80° C. for 8 h. The mixture is cooled to rt over 1 h, then water (20 mL) is added over 1 h. The mixture is cooled to rt, and stirred at rt for 1 h. The mixture is filtered, then the solid rinsed with water (13 mL). The solid is dried at 55° C. under vacuum to give E-3-a ($^1$H-NMR (500 MHz, DMSO-d6) δ 6.58 (d, J=4 Hz, 1H), 6.45 (s, 1H), 2.82 (d, J=4 Hz, 3H)).

Experimental Procedure for the Synthesis of E-2-a

To a solution of chlorosulfonyl isocyanate (2.32 g, 25.107 mmol, 1.3 eq.) in 2-methyltetrahydrofuran (6 mL) at −15° C. is added E-3-a (5.97 g, 19.313 mmol, 1.0 eq.) in 2-methyl-tetrahydrofuran (30 mL) to keep the temperature below −5° C. The mixture is stirred at −10° C. for 1 h, then 2.0 M sodium hydroxide solution (3.92 eq.) is added at a rate to keep the temperature below 18° C. The mixture is cooled to 0° C., then stirred at that temperature for 1 h, then filtered. The solid is rinsed with water (12 mL) and isopropyl acetate (12 mL). The solid is then dried at 55° C. under vacuum to give E-2-a ($^1$H-NMR (400 MHz, DMSO-d6) δ 7.58 (s, 1H), 6.25 (s, 2H), 3.05 (s, 3H)).

Experimental Procedure for the Synthesis of B-3f-a

To a suspension of E-2-a (10.0 g, 26.883 mmol, 1.0 eq.), copper(I) iodide (57.5 mg, 0.5 mmol, 0.02 eq.), and 1,10-phenanthroline (48.5 mg, 0.269 mmol, 0.01 eq.) in acetonitrile (100 mL) is added N,N-diisopropylethylamine (9.37 mL, 53.765 mmol, 2.0 eq.). The mixture is heated at 80° C. for 18 h, then cooled to rt. The mixture is filtered and rinsed with acetonitrile (10 mL). The filtrate is then vacuum distilled until 50 mL of solution remain. The mixture is then filtered to collect a second crop of solid. The combined crops of solid are treated with acetonitrile (5 mL) and 10 wt % ammonium chloride (aq, 10 mL) at 40° C. The mixture is stirred at 40° C. for 2 h, then cooled to rt, and filtered. The solid is dried at 55° C. under vacuum to give B-3f-a ($^1$H-NMR (400 MHz, DMSO-d6) δ 11.86 (br s, 1H), 7.40 (s, 1H), 3.30 (s, 3H)).

Experimental Procedure for the Synthesis of B-5a-a

A suspension of B-3f-a (2.54 g, 11.16 mmol, 1.0 eq.) and benzyltriethylammonium chloride (5.08 g, 22.32 mmol, 2.0 eq.) in phosphorus oxychloride (9.41 g, 61.386 mmol, 5.5 eq.) is heated at 105° C. for 24 h. Toluene (25.4 mL) is added, and the mixture is cooled to rt. Water (12.7 mL) is added at a rate to keep the temperature below 50° C. The mixture is cooled to 25° C., then 30 wt % sodium hydroxide is added (22 eq.) to bring the pH to 7.4. The mixture is then filtered and rinsed with toluene (5 mL). The aqueous phase is removed, and the organic phase is washed with water (13 mL). The aqueous phase is removed, and toluene is removed by vacuum distillation until 7.5 mL remain. The mixture is cooled to rt, heptane (7.6 mL) is added, and the mixture is stirred at rt for 1 h before filtering. The solid is rinsed with water (5 mL), then the solid is dried at 50° C. to give B-5a-a ($^1$H-NMR (500 MHz, DMSO-d6) δ 7.99 (s, 1H), 3.82 (s, 3H)).

Synthesis of B-5b-a

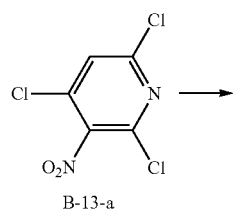

B-13-a

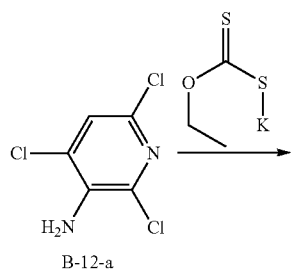

B-12-a

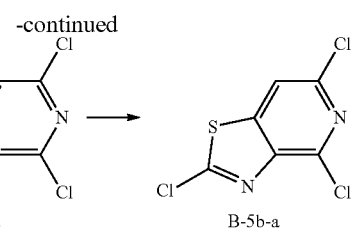

B-6b-a → B-5b-a

Experimental Procedure for the Synthesis of B-12-a

To a stirred solution of B-13-a (150.0 g; 0.66 mol) in EtOH (1200 mL) are added water (300 mL) and NH$_4$Cl (178.1 g; 3.30 mol). Then iron powder (181.4 g; 3.30 mol) is added slowly and the reaction mixture is stirred at 80° C. for 6 h. The reaction mixture is filtered through a Celite pad and the solvent is evaporated under vacuum. The remaining residue is dissolved in EtOAc and extracted with water. The organic layer is dried over anhydrous Na$_2$SO$_4$ and concentrated under vacuum to get crude material. This crude material is stirred with petroleum ether for 1 h, filtered and washed with petroleum ether to get B-12-a (HPLC-MS: (M+H)$^+$=197.0, t$_{Ret.}$=0.817 min, method VAB).

Experimental Procedure for the Synthesis of B-6b-a

To a stirred solution of B-12-a (2.46 g; 12.5 mmol) in AcCN (50 mL) is added potassium O-ethyl carbonodithioate (3.00 g; 18.7 mmol). The reaction mixture is stirred at 80° C. for 3 d. The mixture is diluted with water and extracted with DCM. The product containing aqueous phase is acidified with 1 N aq. HCl and extracted with DCM. The organic layer is dried over anhydrous MgSO$_4$ and concentrated under vacuum to get B-6b-a (HPLC-MS: (M+H)$^+$=237.1, t$_{Ret.}$=0.562 min, method VAB).

Experimental Procedure for the Synthesis of B-5b-a

To a stirred solution of B-6b-a (1.10 g; 4.64 mmol) in 1,2-dichloroethane is added oxalyl chloride (0.5 mL; 5.80 mmol). Thereafter DMF (0.36 mL; 4.64 mmol) is added dropwise and the mixture is stirred at 80° C. for 16 h. The reaction mixture is cooled to rt, diluted with DCM and water and extracted. The organic layer is dried over anhydrous MgSO$_4$ and concentrated under vacuum to get B-5b-a (HPLC-MS: (M+H)$^+$=252.1, t$_{Ret.}$=0.909 min, method VAB).

Synthesis of Compounds (I) According to the Invention

Synthesis of I-001

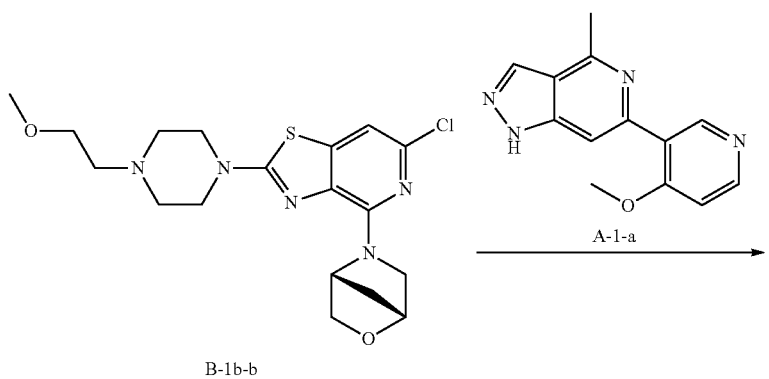

B-1b-b

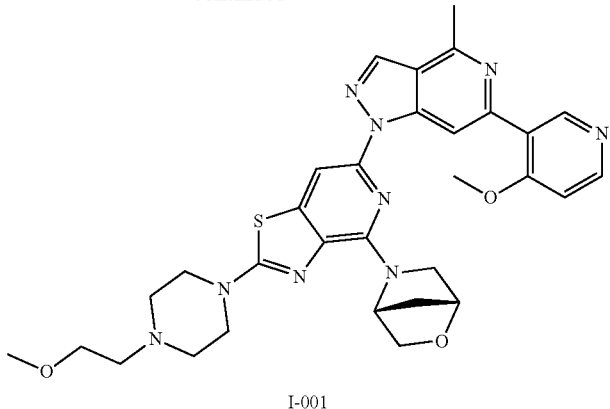

I-001

B-1b-b (80 mg, 0.2 mmol, 1 eq.), A-1-a (50 mg, 0.2 mmol, 1 eq.), tris(dibenzylidene-acetone)dipalladium(0) (18 mg, 0.02 mmol, 0.1 eq.) and tert-butyl XPhos (18 mg, 0.04 mmol, 0.2 eq.) are charged to a pressure vessel. Toluene (1 mL) and 1,4-dioxane (1 mL) are added and the reaction mixture is purged with argon. Sodium tert-butoxide (2 M in THF; 155 µL, 0.34 mmol, 1.75 eq.) are added and the reaction mixture is heated (microwave irradiation) to 125° C. for 20 min. The reaction mixture is purified (normal phase chromatography, mobile phase DCM/MeOH) to afford I-001.

Synthesis of I-002, I-003 and I-004

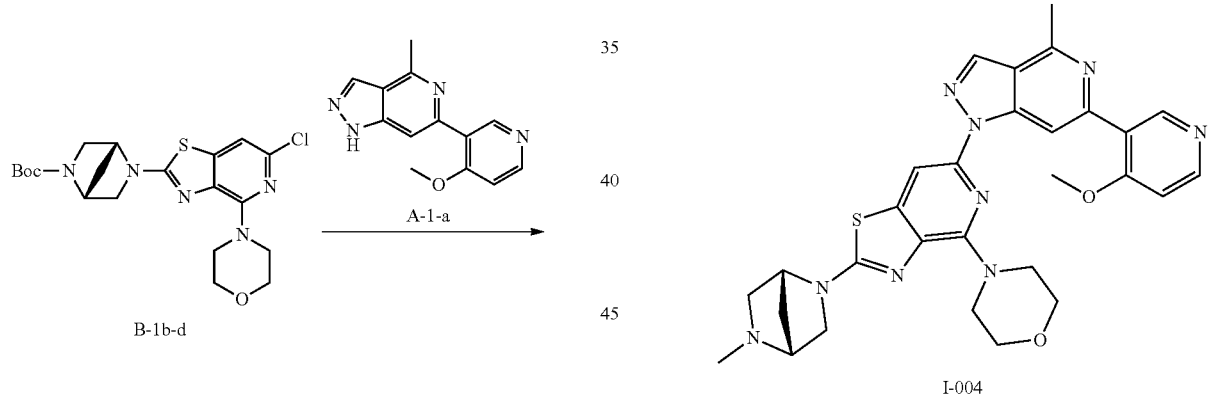

I-003

I-004

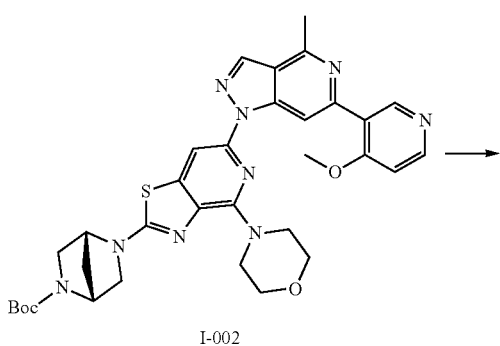

I-002

Step 1

B-1b-d (180 mg, 0.4 mmol), A-1-a (100 mg, 0.4 mmol, 1 eq.), tris-(dibenzylideneacetone)-dipalladium(0) (36 mg, 0.04 mmol, 0.1 eq.) and tert-butyl XPhos (36 mg, 0.04 mmol, 0.2 eq.) are charged to a pressure vessel. Toluene (1 mL) and 1,4-dioxane (1 mL) are added and the reaction mixture is purged with argon. Sodium tert-butoxide (2 M in THF; 320 µL, 0.7 mmol, 1.75 eq.) are added and the reaction mixture is heated (microwave irradiation) to 125° C. for 20 min. The reaction mixture is purified (normal phase chromatography, mobile phase DCM/MeOH) to afford I-002.

Step 2

I-002 (140 mg, 0.21 mmol) is dissolved in DCM (2.5 mL). Trifluoroacetic acid (0.5 mL, 6.5 mmol, 30 eq.) is added and the reaction mixture is stirred at rt for 4 h. An aqueous solution of potassium bicarbonate is added, the basified aqueous layer is extracted with DCM. The organic phase is dried over sodium sulfate and filtered off. The filtrate is reduced to dryness to afford I-003.

Step 3

I-003 (40 mg, 0.07 mmol) is dissolved in a mixture of DCM (1 mL) and MeOH (1 mL). Glacial acetic acid (8.3 µL, 0.14 mmol, 2 eq.) and formaldehyde (37% in water; 16 µL, 0.21 mmol, 3 eq.) are added and the reaction mixture is stirred at rt for 10 min. Sodium cyanoborohydride (23.8 mg, 0.36 mmol, 5 eq.) is added and the reaction mixture is stirred at rt for 1 h. The reaction mixture is diluted with water, the aqueous phase is extracted with DCM. The solvent is evaporated, the residue is purified (normal phase chromatography, mobile phase DCM/MeOH) to afford I-004.

Synthesis of I-069, I-070 and I-071

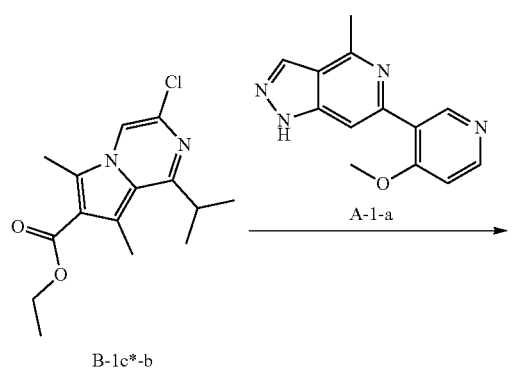

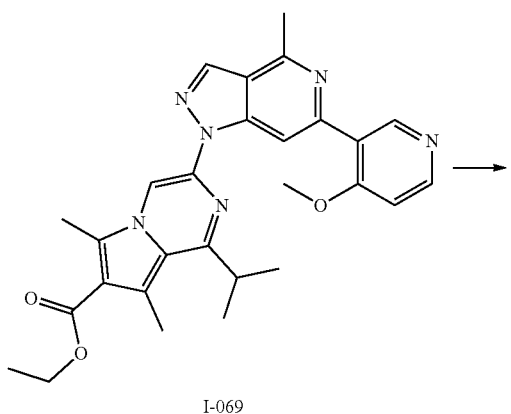

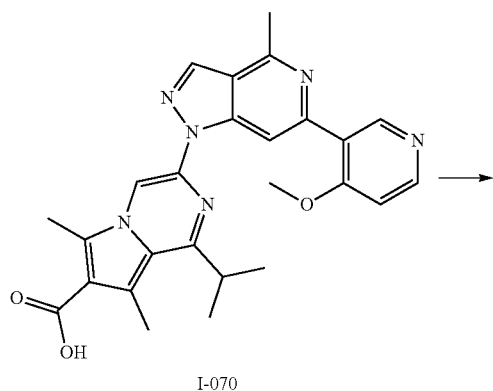

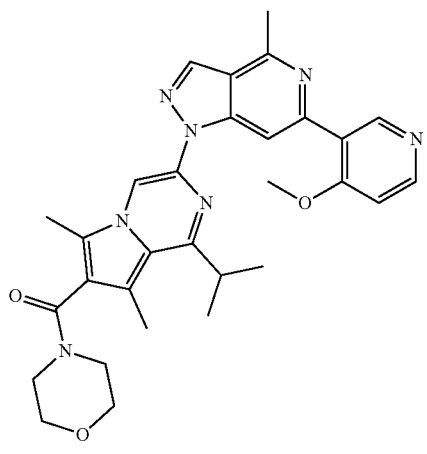

Step 1

B-1c*-b (3.80 g; 12.63 mmol), A-1-1 (3.25 g; 12.85 mmol), tris-(dibenzylideneacetone)-dipalladium(0) (750 mg, 0.80 mmol) and tert-butyl XPhos (750 mg, 1.68 mmol) are charged to a flask. Toluene (100 mL) is added and the reaction mixture is purged with argon. Sodium tert-butoxide (2 M in THF; 12.5 mL, 25.0 mmol) is added and the reaction mixture is stirred at 80° C. for 6 h. The reaction mixture is purified (normal phase chromatography, mobile phase DCM/MeOH) to afford I-069.

Step 2

I-069 (1.56 g; 2.97 mmol) is dissolved in EtOH (15.0 mL) and water (5 mL) and LiOH (0.5 g; 20.5 mmol) is added and the reaction mixture is stirred for 6.5 h under reflux. The mixture is evaporated to dryness, slurried with water and acidified with aq. 1N HCl to pH 5. The resulting residue is filtered, washed with water and freeze-dried to afford I-070.

Step 3

I-070 (1.10 g; 2.22 mmol) is dissolved in AcCN (15.0 mL) and DIPEA (1.00 mL; 5.70 mmol). To the solution HATU (1.50 g; 3.75 mmol) is added and the mixture is stirred for 30 min at rt. Morpholine (0.35 mL; 4.05 mmol) is added and stirring at rt is continued for 17 h. The reaction mixture is purified (normal phase chromatography, mobile phase DCM/MeOH/NH₄OH) to afford I-071.

Synthesis of I-082, I-083 and I-084

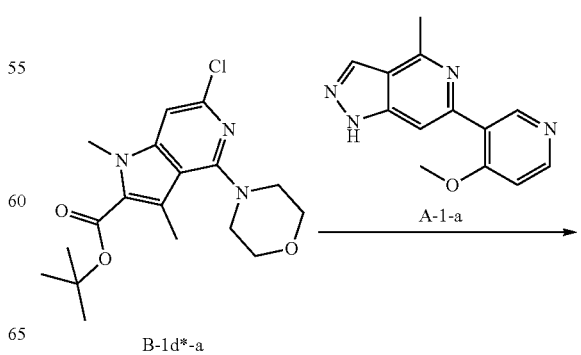

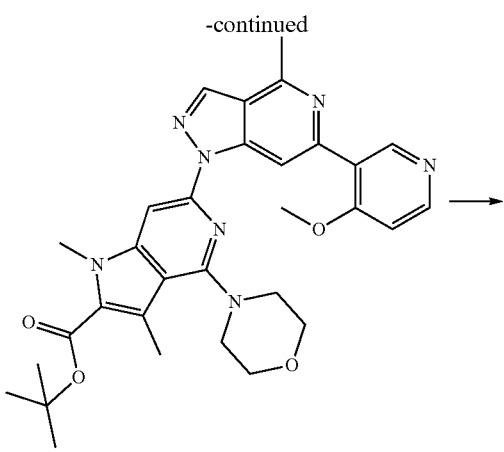

I-082

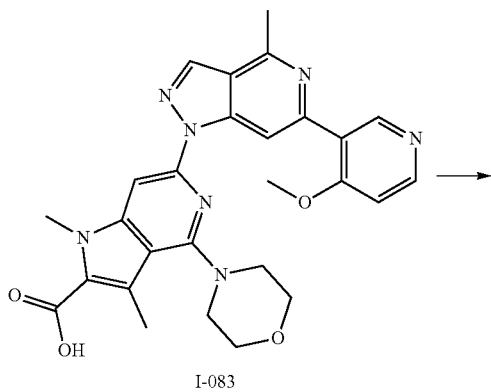

I-083

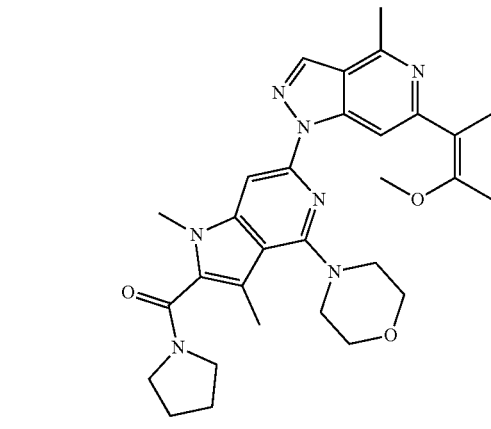

I-084

Step 1

B-1d*-a (1.80 g, 4.67 mmol), A-1-a (1.40 g, 5.54 mmol), tris-(dibenzylideneacetone)-dipalladium(0) (350 mg, 0.38 mmol) and tert-butyl XPhos (330 mg, 0.74 mmol) are charged to a flask. Toluene (45 mL) is added and the reaction mixture is purged with argon. Sodium tert-butoxide (2 M in THF; 4.5 mL, 9.00 mmol) is added and the reaction mixture is stirred at 100° C. for 1 h. The reaction mixture is purified (prep HPLC 1) to afford I-082.

Step 2

I-082 (1.18 g; 2.07 mmol) is dissolved in 1,4-dioxane (16.0 mL) and 4 N hydrogen chloride in 1,4-dioxane (4.0 mL; 46.67 mmol) is added. The reaction mixture is stirred for 3.5 h at 65° C. and afterwards cooled to rt. The resulting precipitate is filtered off, washed with 1,4-dioxane and dried in vacuum to afford I-083.

Step 3

I-083 (1.10 g; 1.90 mmol) is dissolved in NMP (10.0 mL) and DIPEA (1.75 mL; 10.24 mmol). To the solution HATU (1.00 g; 2.50 mmol) is added and the mixture is stirred for 30 min at 30° C. Pyrrolidine (0.20 mL; 2.32 mmol) is added and stirring at 30° C. is continued for 1 h. The mixture is diluted with water and extracted with DCM. The solvent is evaporated, the residue is purified (normal phase chromatography, mobile phase DCM/MeOH/NH$_4$OH) to afford I-084.

Synthesis of I-126

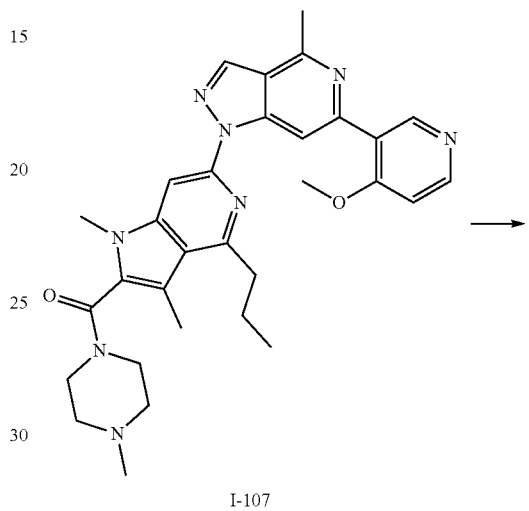

I-107

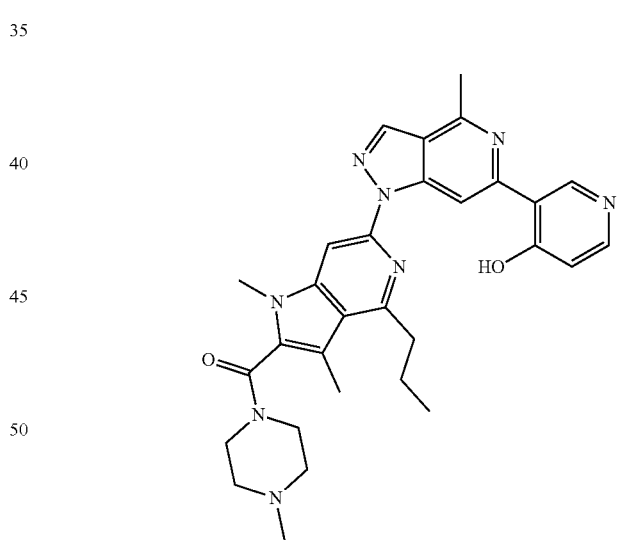

I-126

In a pressure vessel I-107 (150 mg; 0.27 mmol), p-toluenesulfonic acid (467 mg; 2.71 mmol) and lithium chloride (115 mg; 2.71 mmol) are suspended in NMP and stirred for 25 min at 180° C. under microwave irradiation. The reaction mixture is purified with prep HPLC 1 to afford I-126.

The following compounds (I) (table 9 and 10) are available in an analogous manner as described for compounds I-001 to I-004, I-069 to I-071, I-082 to I-084 and I-126 or by further derivatization of compounds (I) initially obtained in such a manner.

TABLE 9

| # | structure | IC$_{50}$ [nM] | MS (M + H)$^+$ t$_{Ret}$ HPLC [min] | HPLC-MS method |
|---|---|---|---|---|
| I-001 | 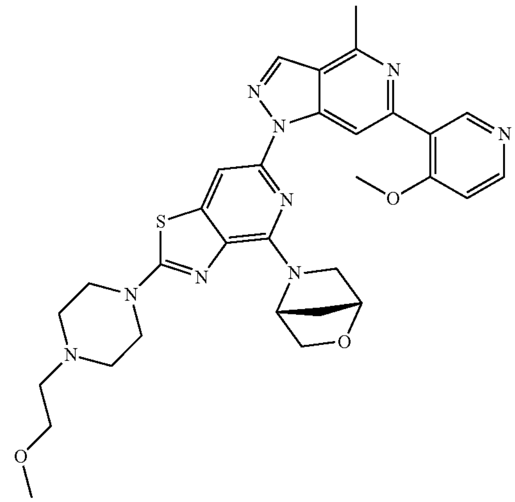 [SMILES: COCCN1CCN(c2nc3c(N4C[C@H]5C[C@@H]4CO5)nc(-n4ncc5c(C)nc(-c6cnccc6OC)cc54)cc3s2)CC1] | 1.4 | (M + H)$^+$ = 614; t$_{Ret.}$ = 1.33 | LCMS3, basisch_1 |
| I-002 | 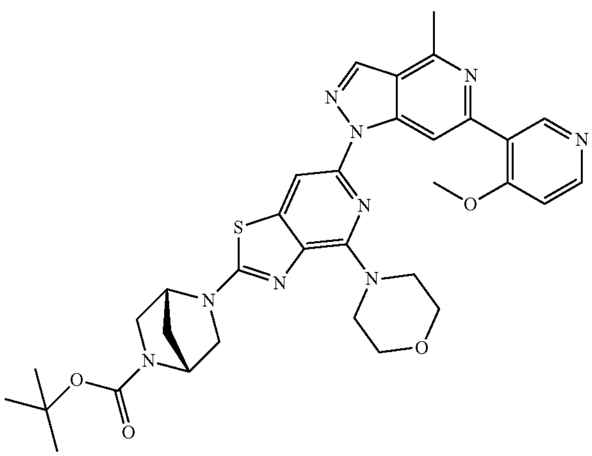 [SMILES: COc1ccncc1-c1cc2c(cnn2-c2cc3sc(N4C[C@H]5C[C@@H]4CN5C(=O)OC(C)(C)C)nc3c(N3CCOCC3)n2)c(C)n1] | | n.a. | n.a. |
| I-003 | 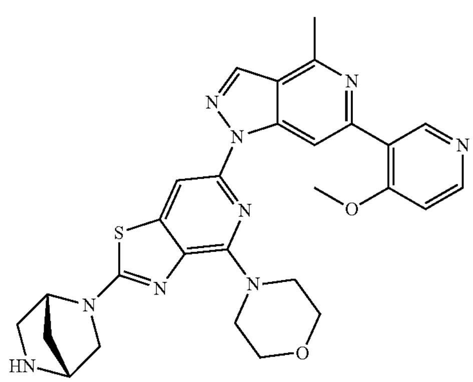 [SMILES: COc1ccncc1-c1cc2c(cnn2-c2cc3sc(N4C[C@H]5C[C@@H]4CN5)nc3c(N3CCOCC3)n2)c(C)n1] | | (M + H)$^+$ = 556 t$_{Ret.}$ = 0.84 | VAB |

TABLE 9-continued

| # | structure | IC$_{50}$ [nM] | MS (M + H)$^+$ t$_{Ret}$ HPLC [min] | HPLC-MS method |
|---|---|---|---|---|
| I-004 | 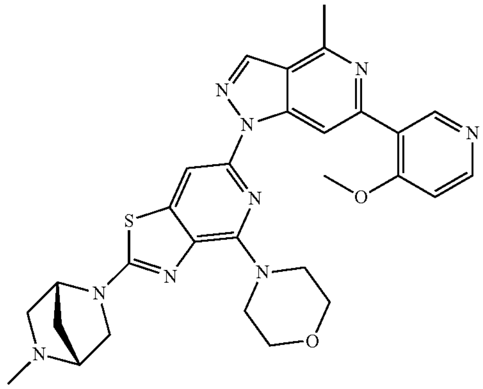 [SMILES: COc1ccncc1-c1cc2c(cnn2-c2cc3sc(N4C[C@H]5C[C@@H]4CN5C)nc3c(N3CCOCC3)n2)c(C)n1] | 1.4 | (M + H)$^+$ = 570 t$_{Ret.}$ = 1.25 | LCMS3, basisch_1 |
| I-005 | 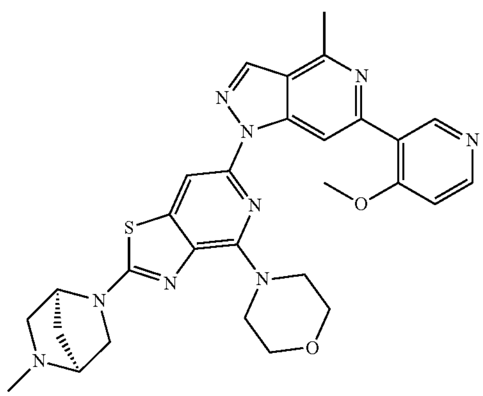 [SMILES: COc1ccncc1-c1cc2c(cnn2-c2cc3sc(N4C[C@@H]5C[C@H]4CN5C)nc3c(N3CCOCC3)n2)c(C)n1] | 1.6 | (M + H)$^+$ = 570 t$_{Ret.}$ = 1.25 | LCMS3, basisch_1 |
| I-006 | 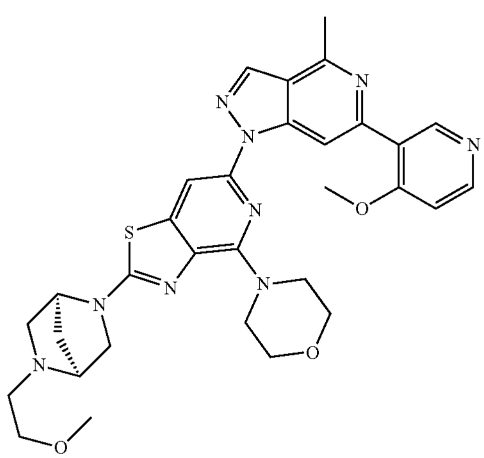 [SMILES: COCCN1C[C@@H]2C[C@H]1CN2c1nc2c(N3CCOCC3)nc(-n3ncc4c(C)nc(-c5cnccc5OC)cc43)cc2s1] | 1.9 | (M + H)$^+$ = 614 t$_{Ret.}$ = 1.29 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-007 | 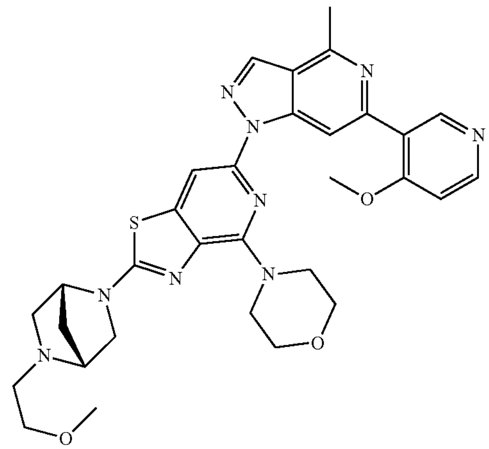 [SMILES: COCCN1C[C@H]2C[C@@H]1CN2c1nc2c(N3CCOCC3)nc(-n3ncc4c(C)nc(-c5cnccc5OC)cc43)cc2s1] | 2.1 | (M + H)$^+$ = 614<br>t$_{Ret.}$ = 1.29 | LCMS3, basisch_1 |
| I-008 | 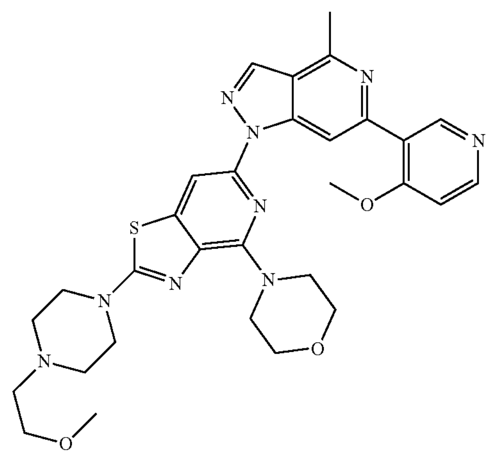 [SMILES: COCCN1CCN(c2nc3c(N4CCOCC4)nc(-n4ncc5c(C)nc(-c6cnccc6OC)cc54)cc3s2)CC1] | 2.6 | (M + H)$^+$ = 602<br>t$_{Ret.}$ = 1.34 | LCMS3, basisch_1 |
| I-009 | 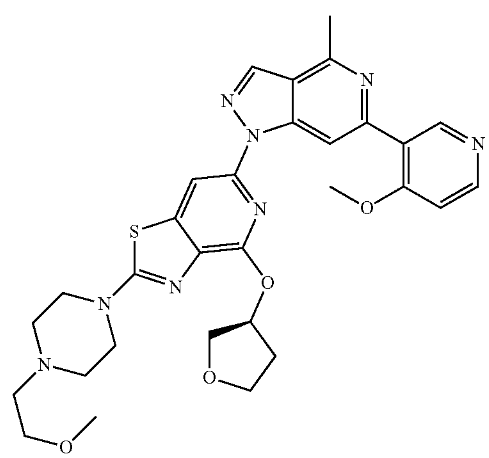 [SMILES: COCCN1CCN(c2nc3c(O[C@H]4CCOC4)nc(-n4ncc5c(C)nc(-c6cnccc6OC)cc54)cc3s2)CC1] | 3.9 | (M + H)$^+$ = 603<br>t$_{Ret.}$ = 1.22 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-010 | 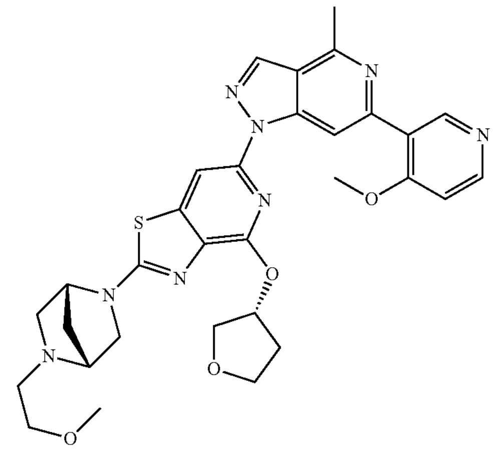 [SMILES: COCCN1C[C@H]2C[C@@H]1CN2c1nc2c(O[C@@H]3CCOC3)nc(-n3ncc4c(C)nc(-c5cnccc5OC)cc43)cc2s1] | 5.8 | (M + H)$^+$ = 615 t$_{Ret.}$ = 1.18 | LCMS3, basisch_1 |
| I-011 | 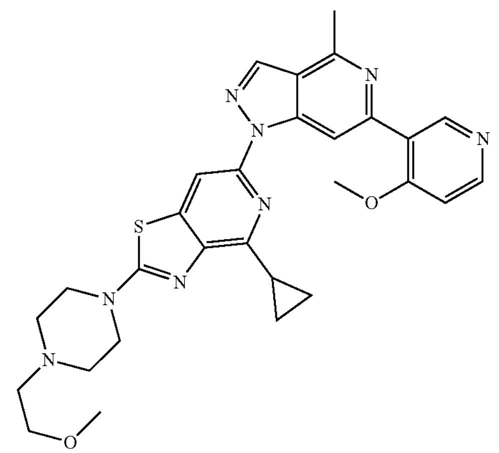 [SMILES: COCCN1CCN(c2nc3c(C4CC4)nc(-n4ncc5c(C)nc(-c6cnccc6OC)cc54)cc3s2)CC1] | 6.1 | (M + H)$^+$ = 557 t$_{Ret.}$ = 1.41 | LCMS3, basisch_1 |
| I-012 | 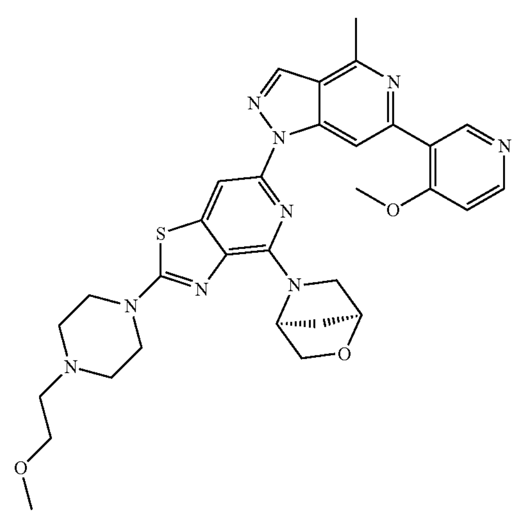 [SMILES: COCCN1CCN(c2nc3c(N4C[C@@H]5C[C@H]4CO5)nc(-n4ncc5c(C)nc(-c6cnccc6OC)cc54)cc3s2)CC1] | 31 | (M + H)$^+$ = 614 t$_{Ret.}$ = 1.33 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-013 | 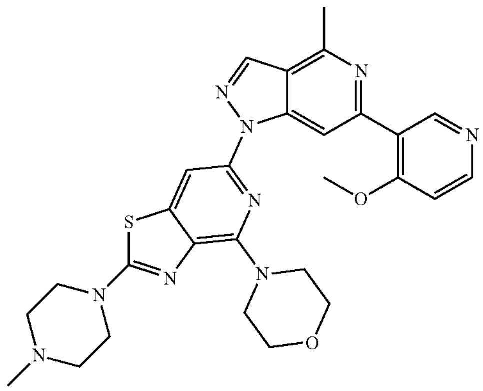 [SMILES: COc1ccncc1-c1cc2c(cnn2-c2cc3sc(N4CCN(C)CC4)nc3c(N3CCOCC3)n2)c(C)n1] | 43 | (M + H)$^+$ = 558<br>t$_{Ret.}$ = 1.32 | LCMS3, basisch_1 |
| I-014 | 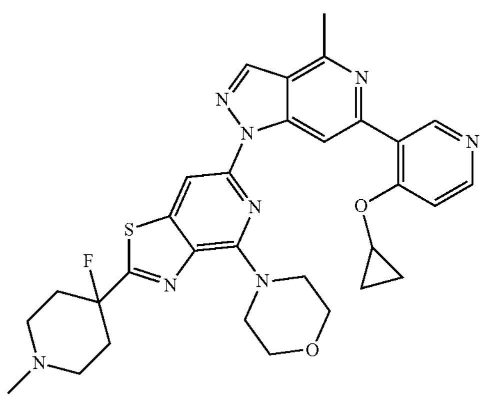 [SMILES: Cc1nc(-c2cnccc2OC2CC2)cc2c1cnn2-c1cc2sc(C3(F)CCN(C)CC3)nc2c(N2CCOCC2)n1] | 16 | (M + H)$^+$ = 601<br>t$_{Ret.}$ = 1.55 | LCMS3, basisch_1 |
| I-015 | 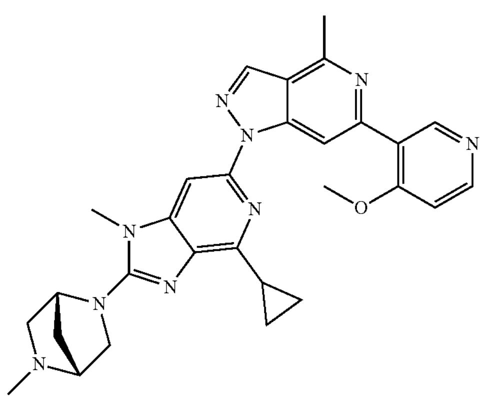 [SMILES: COc1ccncc1-c1cc2c(cnn2-c2cc3c(nc(N4C[C@H]5C[C@@H]4CN5C)n3C)c(C3CC3)n2)c(C)n1] | 1.5 | (M + H)$^+$ = 522<br>t$_{Ret.}$ = 1.13 | LCMS3, basisch_1 |

TABLE 9-continued

| # | structure | IC$_{50}$ [nM] | MS (M + H)$^+$ t$_{Ret.}$ HPLC [min] | HPLC-MS method |
|---|---|---|---|---|
| I-016 | 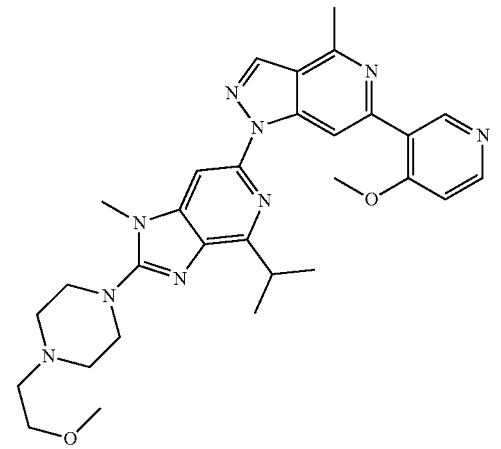 [SMILES: COCCN1CCN(c2nc3c(C(C)C)nc(-n4ncc5c(C)nc(-c6cnccc6OC)cc54)cc3n2C)CC1] | 1.5 | (M + H)$^+$ = 556 t$_{Ret.}$ = 1.25 | LCMS3, basisch_1 |
| I-017 | 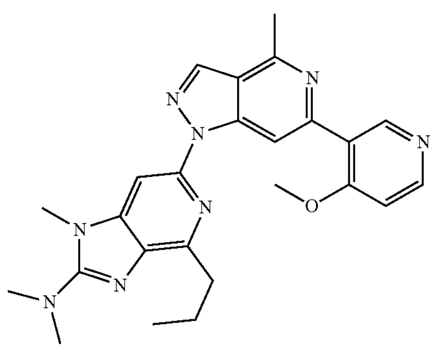 [SMILES: CCCc1nc(-n2ncc3c(C)nc(-c4cnccc4OC)cc32)cc2c1nc(N(C)C)n2C] | 1.9 | (M + H)$^+$ = 457 t$_{Ret.}$ = 1.28 | LCMS3, basisch_1 |
| I-018 | 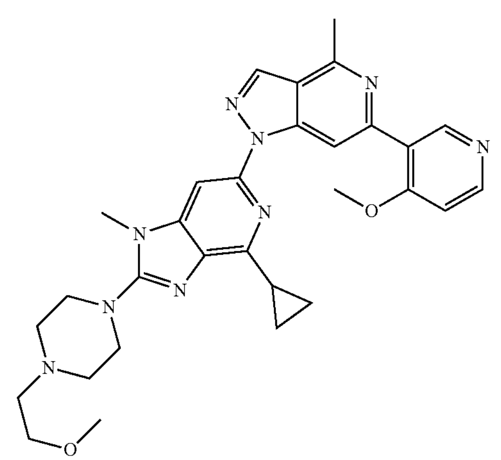 [SMILES: COCCN1CCN(c2nc3c(C4CC4)nc(-n4ncc5c(C)nc(-c6cnccc6OC)cc54)cc3n2C)CC1] | 2.0 | (M + H)$^+$ = 554 t$_{Ret.}$ = 1.21 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-019 | 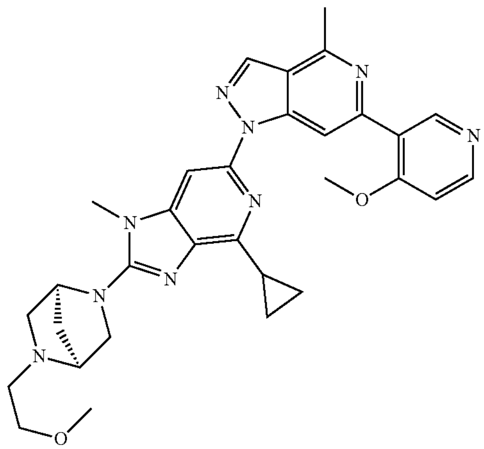 [SMILES: COCCN1C[C@@H]2C[C@H]1CN2c1nc2c(C3CC3)nc(-n3ncc4c(C)nc(-c5cnccc5OC)cc43)cc2n1C] | 2.8 | (M + H)$^+$ = 566 t$_{Ret.}$ = 1.17 | LCMS3, basisch_1 |
| I-020 | 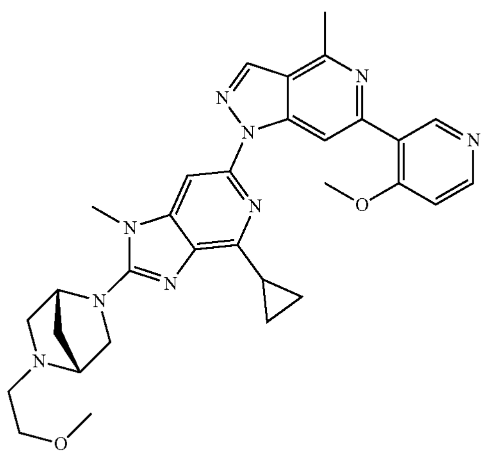 [SMILES: COCCN1C[C@H]2C[C@@H]1CN2c1nc2c(C3CC3)nc(-n3ncc4c(C)nc(-c5cnccc5OC)cc43)cc2n1C] | 3.1 | (M + H)$^+$ = 566 t$_{Ret.}$ = 1.17 | LCMS3, basisch_1 |
| I-021 | 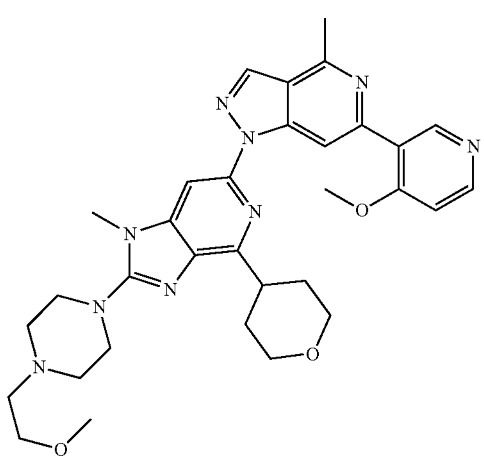 [SMILES: COCCN1CCN(c2nc3c(C4CCOCC4)nc(-n4ncc5c(C)nc(-c6cnccc6OC)cc54)cc3n2C)CC1] | 7.4 | (M + H)$^+$ = 598 t$_{Ret.}$ = 1.18 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-022 | 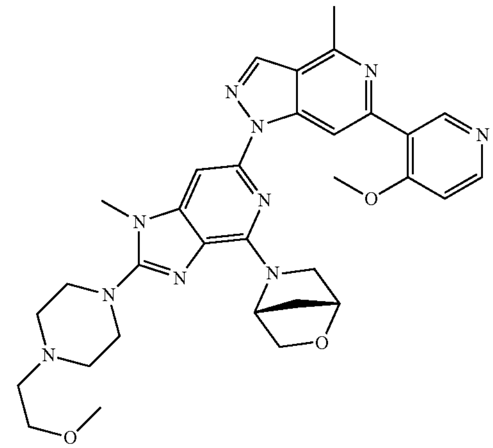 [SMILES: COCCN1CCN(c2nc3c(N4C[C@H]5C[C@@H]4CO5)nc(-n4ncc5c(C)nc(-c6cnccc6OC)cc54)cc3n2C)CC1] | 1.0 | (M + H)$^+$ = 611<br>t$_{Ret.}$ = 1.21 | LCMS3, basisch_1 |
| I-023 | 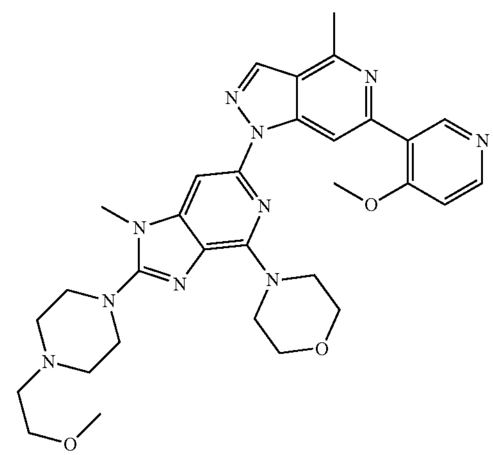 | 2.5 | (M + H)$^+$ = 599<br>t$_{Ret.}$ = 1.21 | LCMS3, basisch_1 |
| I-024 | 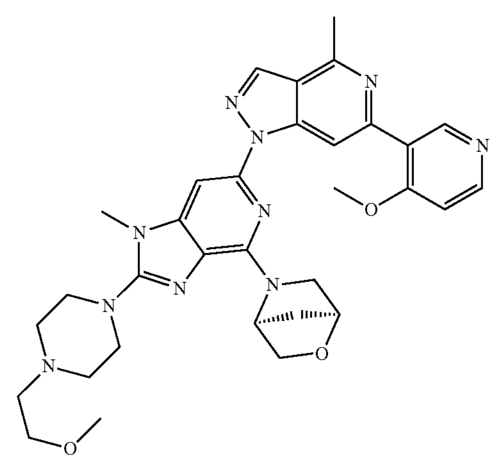 [SMILES: COCCN1CCN(c2nc3c(N4C[C@@H]5C[C@H]4CO5)nc(-n4ncc5c(C)nc(-c6cnccc6OC)cc54)cc3n2C)CC1] | 3.5 | (M + H)$^+$ = 611<br>t$_{Ret.}$ = 1.21 | LCMS3, basisch_1 |

TABLE 9-continued
| # | structure | IC$_{50}$ [nM] | MS (M + H)$^+$ t$_{Ret}$ HPLC [min] | HPLC-MS method |
|---|---|---|---|---|
| I-025 | 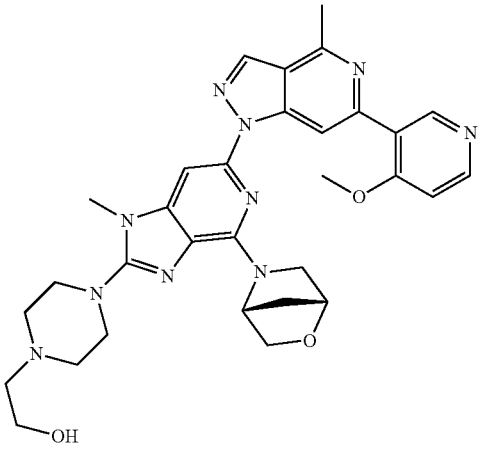 [SMILES: COc1ccncc1-c1cc2c(cnn2-c2cc3c(nc(N4CCN(CCO)CC4)n3C)c(N3C[C@H]4C[C@@H]3CO4)n2)c(C)n1] | 1.1 | (M − H)$^−$ = 595 t$_{Ret.}$ = 1.06 | LCMS3, basisch_1 |
| I-026 | 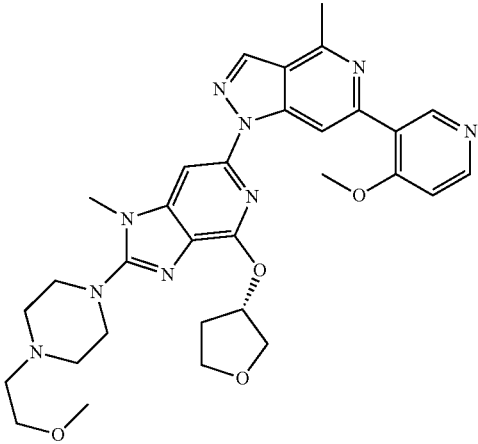 [SMILES: COCCN1CCN(c2nc3c(O[C@H]4CCOC4)nc(-n4ncc5c(C)nc(-c6cnccc6OC)cc54)cc3n2C)CC1] | 6.7 | (M + H)$^+$ = 600 t$_{Ret.}$ = 1.12 | LCMS3, basisch_1 |
| I-027 | 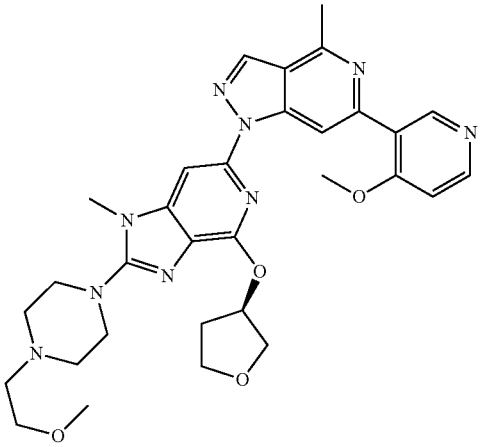 [SMILES: COCCN1CCN(c2nc3c(O[C@@H]4CCOC4)nc(-n4ncc5c(C)nc(-c6cnccc6OC)cc54)cc3n2C)CC1] | 7.8 | (M + H)$^+$ = 600 t$_{Ret.}$ = 1.12 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-028 | 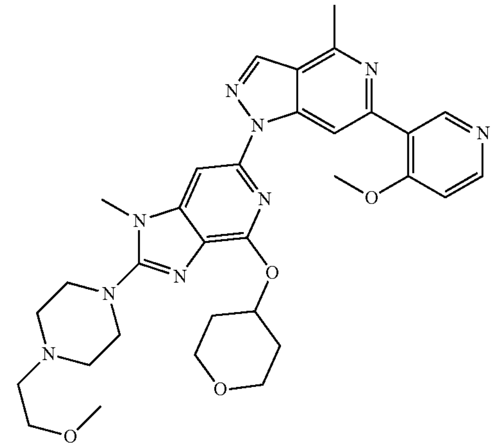 [SMILES: COCCN1CCN(c2nc3c(OC4CCOCC4)nc(-n4ncc5c(C)nc(-c6cnccc6OC)cc54)cc3n2C)CC1] | 6.8 | (M + H)$^+$ = 614<br>t$_{Ret.}$ = 1.13 | LCMS3, basisch_1 |
| I-029 | 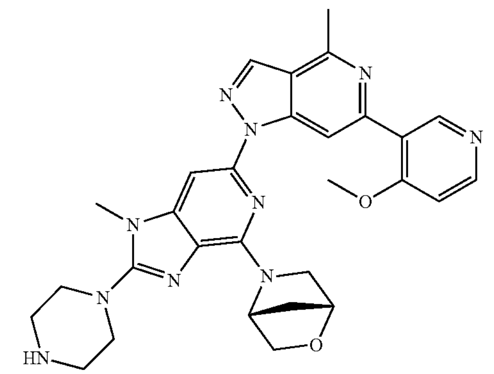 [SMILES: COc1ccncc1-c1cc2c(cnn2-c2cc3c(nc(N4CCNCC4)n3C)c(N3C[C@H]4C[C@@H]3CO4)n2)c(C)n1] | 0.9 | (M + H)$^+$ = 553<br>t$_{Ret.}$ = 1.15 | LCMS3, basisch_1 |
| I-030 | 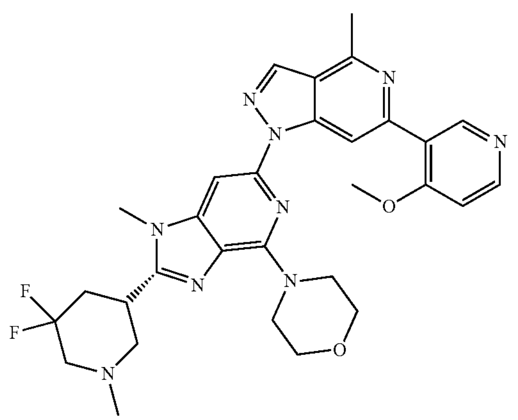 | 0.5 | (M + H)$^+$ = 590<br>t$_{Ret.}$ = 1.26 | LCMS3. basisch_1 |
| I-031 | 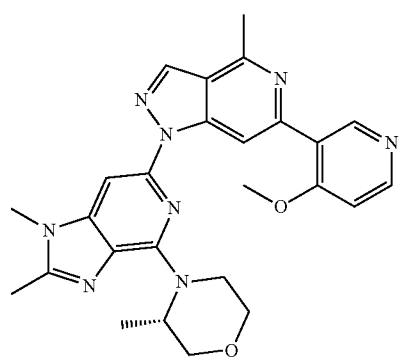 [SMILES: COc1ccncc1-c1cc2c(cnn2-c2cc3c(nc(C)n3C)c(N3CCOC[C@@H]3C)n2)c(C)n1] | 1.2 | (M + H)$^+$ = 485<br>t$_{Ret.}$ = 1.14 | LCMS3. basisch_1 |

TABLE 9-continued

| # | structure | IC$_{50}$ [nM] | MS (M + H)$^+$ $t_{Ret}$ HPLC [min] | HPLC-MS method |
|---|---|---|---|---|
| I-032 | 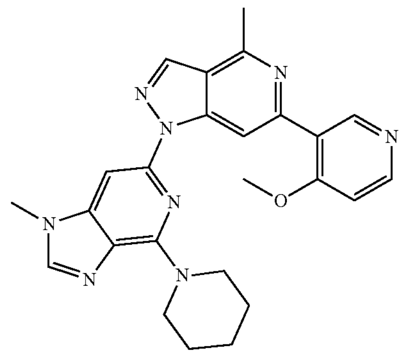 [SMILES: COc1ccncc1-c1cc2c(cnn2-c2cc3c(ncn3C)c(N3CCCCC3)n2)c(C)n1] | 1.0 | (M + H)$^+$ = 455 $t_{Ret.}$ = 1.28 | LCMS3. basisch_1 |
| I-033 | 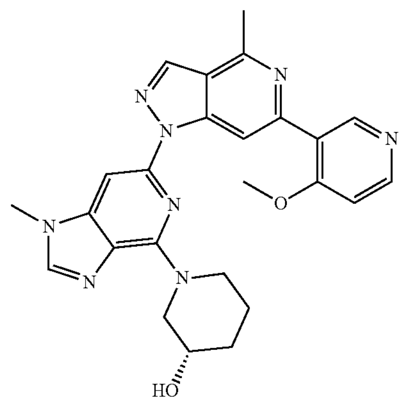 [SMILES: COc1ccncc1-c1cc2c(cnn2-c2cc3c(ncn3C)c(N3CCC[C@H](O)C3)n2)c(C)n1] | 1.9 | (M + H)$^+$ = 471 $t_{Ret.}$ = 1.04 | LCMS3. basisch_1 |
| I-034 | 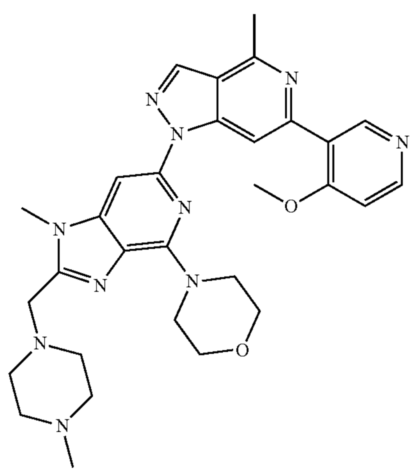 [SMILES: COc1ccncc1-c1cc2c(cnn2-c2cc3c(nc(CN4CCN(C)CC4)n3C)c(N3CCOCC3)n2)c(C)n1] | 2.3 | (M + H)$^+$ = 569 $t_{Ret.}$ = 1.15 | LCMS3. basisch_1 |
| I-035 | 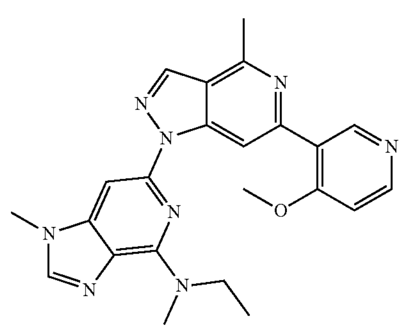 [SMILES: CCN(C)c1nc(-n2ncc3c(C)nc(-c4cnccc4OC)cc32)cc2c1ncn2C] | 2.4 | (M + H)$^+$ = 429 $t_{Ret.}$ = 1.22 | LCMS3. basisch_1 |

TABLE 9-continued

| # | structure | IC$_{50}$ [nM] | MS (M + H)$^+$ t$_{Ret.}$ HPLC [min] | HPLC-MS method |
|---|---|---|---|---|
| I-036 | 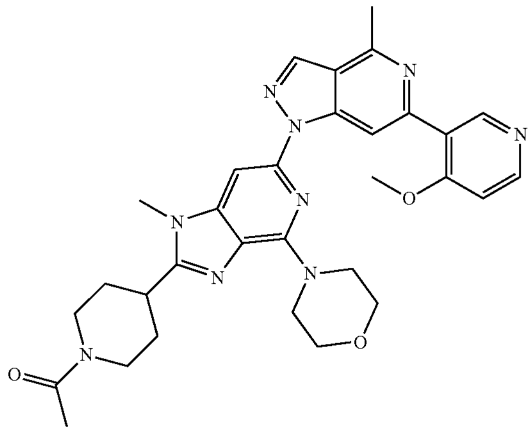 [SMILES: COc1ccncc1-c1cc2c(cnn2-c2cc3c(nc(C4CCN(C(C)=O)CC4)n3C)c(N3CCOCC3)n2)c(C)n1] | 2.5 | (M + H)$^+$ = 582<br>t$_{Ret.}$ = 1.09 | LCMS3.<br>basisch_1 |
| I-037 | 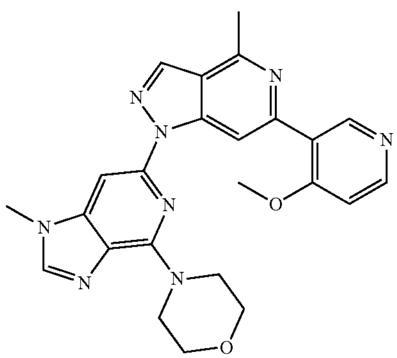 [SMILES: COc1ccncc1-c1cc2c(cnn2-c2cc3c(ncn3C)c(N3CCOCC3)n2)c(C)n1] | 2.8 | (M + H)$^+$ = 457<br>t$_{Ret.}$ = 1.11 | LCMS3.<br>basisch_1 |
| I-038 | 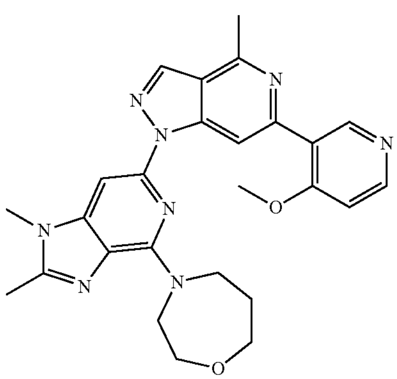 [SMILES: COc1ccncc1-c1cc2c(cnn2-c2cc3c(nc(C)n3C)c(N3CCCOCC3)n2)c(C)n1] | 2.8 | (M + H)$^+$ = 485<br>t$_{Ret.}$ = 1.14 | LCMS3.<br>basisch_1 |
| I-039 | 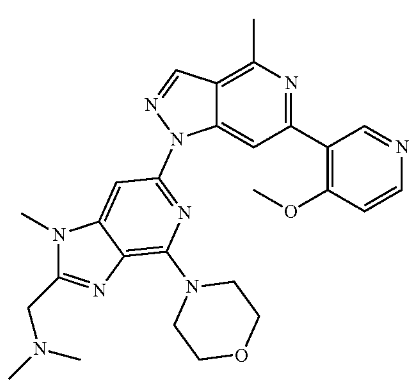 [SMILES: COc1ccncc1-c1cc2c(cnn2-c2cc3c(nc(CN(C)C)n3C)c(N3CCOCC3)n2)c(C)n1] | 3.4 | (M + H)$^+$ = 514<br>t$_{Ret.}$ = 1.18 | LCMS3.<br>basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-040 | 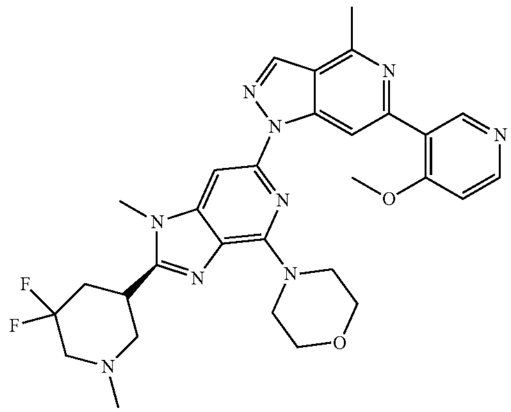 | 3.6 | (M + H)$^+$ = 590 t$_{Ret.}$ = 1.26 | LCMS3. basisch_1 |
| I-041 | 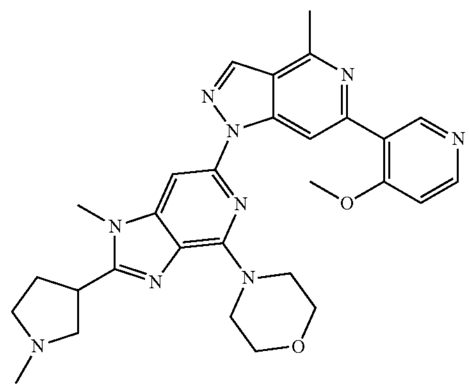 [SMILES: COc1ccncc1-c1cc2c(cnn2-c2cc3c(nc(C4CCN(C)C4)n3C)c(N3CCOCC3)n2)c(C)n1] | 3.7 | (M + H)$^+$ = 540 t$_{Ret.}$ = 1.21 | LCMS3. basisch_1 |
| I-042 | 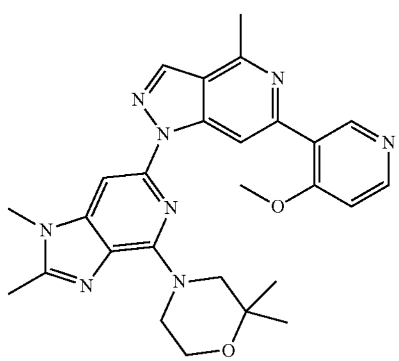 [SMILES: COc1ccncc1-c1cc2c(cnn2-c2cc3c(nc(C)n3C)c(N3CCOC(C)(C)C3)n2)c(C)n1] | 4.2 | (M + H)$^+$ = 499 t$_{Ret.}$ = 1.18 | LCMS3. basisch_1 |
| I-043 | 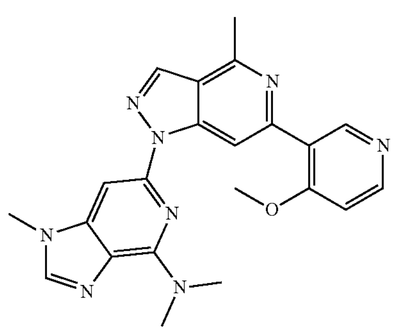 [SMILES: COc1ccncc1-c1cc2c(cnn2-c2cc3c(ncn3C)c(N(C)C)n2)c(C)n1] | 4.5 | (M + H)$^+$ = 415 t$_{Ret.}$ = 1.15 | LCMS3. basisch_1 |

TABLE 9-continued
| # | structure | IC$_{50}$ [nM] | MS (M + H)$^+$ t$_{Ret}$ HPLC [min] | HPLC-MS method |
|---|---|---|---|---|
| I-044 | 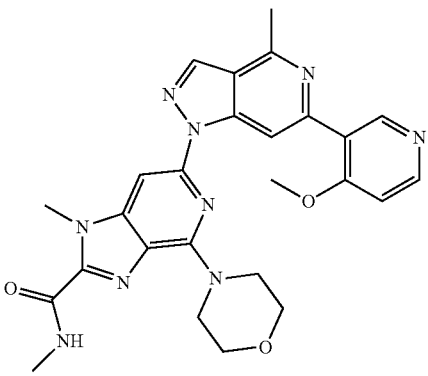 [SMILES: CNC(=O)c1nc2c(N3CCOCC3)nc(-n3ncc4c(C)nc(-c5cnccc5OC)cc43)cc2n1C] | 4.7 | (M + H)$^+$ = 514<br>t$_{Ret.}$ = 1.15 | LCMS3.<br>basisch_1 |
| I-045 | 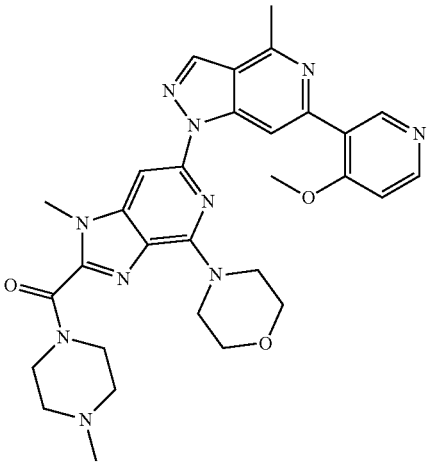 [SMILES: COc1ccncc1-c1cc2c(cnn2-c2cc3c(nc(C(=O)N4CCN(C)CC4)n3C)c(N3CCOCC3)n2)c(C)n1] | 5.1 | (M + H)$^+$ = 583<br>t$_{Ret.}$ = 1.11 | LCMS3.<br>basisch_1 |
| I-046 | 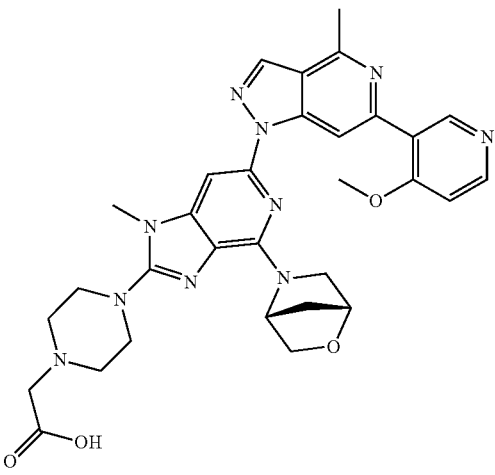 [SMILES: COc1ccncc1-c1cc2c(cnn2-c2cc3c(nc(N4CCN(CC(=O)O)CC4)n3C)c(N3C[C@H]4C[C@@H]3CO4)n2)c(C)n1] | 9.6 | (M + H)$^+$ = 611<br>t$_{Ret.}$ = 0.86 | LCMS3,<br>basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-047 | 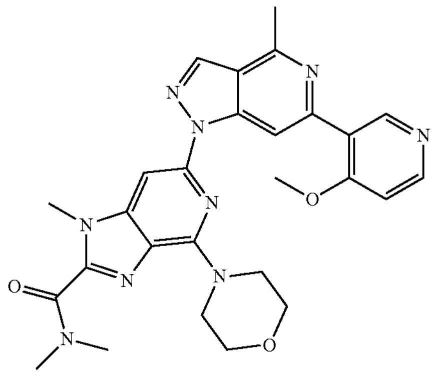 [SMILES: COc1ccncc1-c1cc2c(cnn2-c2cc3c(nc(C(=O)N(C)C)n3C)c(N3CCOCC3)n2)c(C)n1] | 5.3 | (M + H)$^+$ = 528<br>t$_{Ret.}$ = 1.12 | LCMS3.<br>basisch_1 |
| I-048 | 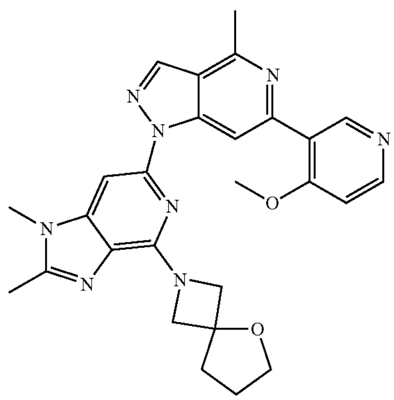 [SMILES: COc1ccncc1-c1cc2c(cnn2-c2cc3c(nc(C)n3C)c(N3CC4(CCCO4)C3)n2)c(C)n1] | 6.7 | (M + H)$^+$ = 497<br>t$_{Ret.}$ = 1.12 | LCMS3.<br>basisch_1 |
| I-049 | 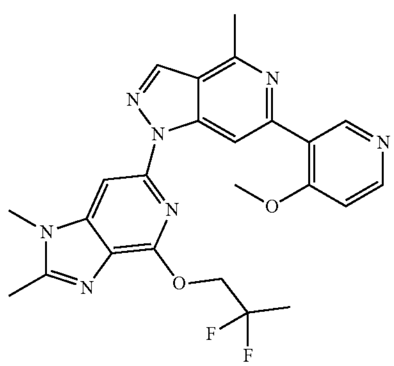 [SMILES: COc1ccncc1-c1cc2c(cnn2-c2cc3c(nc(C)n3C)c(OCC(C)(F)F)n2)c(C)n1] | 2.5 | (M + H)$^+$ = 480<br>t$_{Ret.}$ = 1.11 | LCMS3.<br>basisch_1 |
| I-050 | 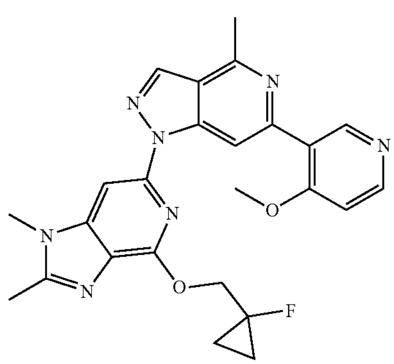 [SMILES: COc1ccncc1-c1cc2c(cnn2-c2cc3c(nc(C)n3C)c(OCC3(F)CC3)n2)c(C)n1] | 5.8 | (M + H)$^+$ = 474<br>t$_{Ret.}$ = 1.11 | LCMS3.<br>basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-051 | 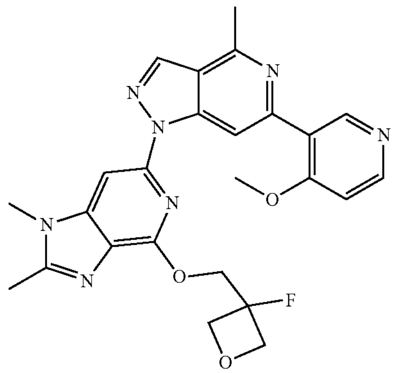 [SMILES: COc1ccncc1-c1cc2c(cnn2-c2cc3c(nc(C)n3C)c(OCC3(F)COC3)n2)c(C)n1] | 32 | (M + H)$^+$ = 490<br>t$_{Ret.}$ = 1.13 | LCMS3. basisch_1 |
| I-052 | 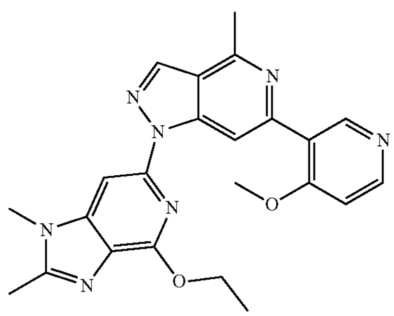 | 8 | (M + H)$^+$ = 416<br>t$_{Ret.}$ = 1.08 | LCMS3. basisch_1 |
| I-053 | 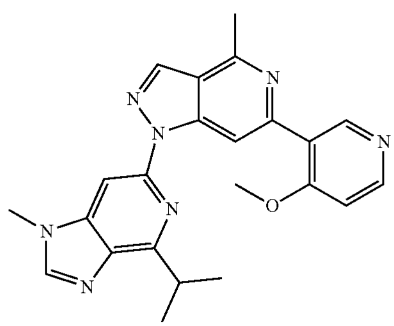 [SMILES: COc1ccncc1-c1cc2c(cnn2-c2cc3c(ncn3C)c(C(C)C)n2)c(C)n1] | 1.1 | (M + H)$^+$ = 414<br>t$_{Ret.}$ = 1.16 | LCMS3. basisch_1 |
| I-054 | 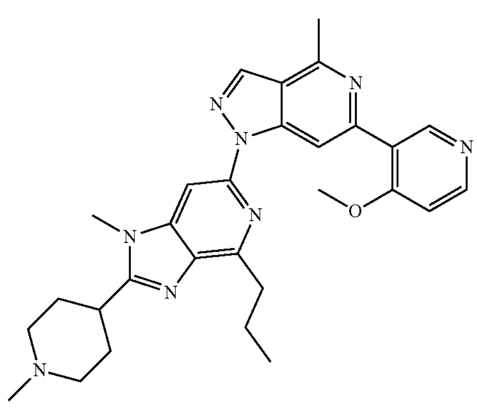 [SMILES: CCCc1nc(-n2ncc3c(C)nc(-c4cnccc4OC)cc32)cc2c1nc(C1CCN(C)CC1)n2C] | 1.4 | (M + H)$^+$ = 511<br>t$_{Ret.}$ = 1.18 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-055 | 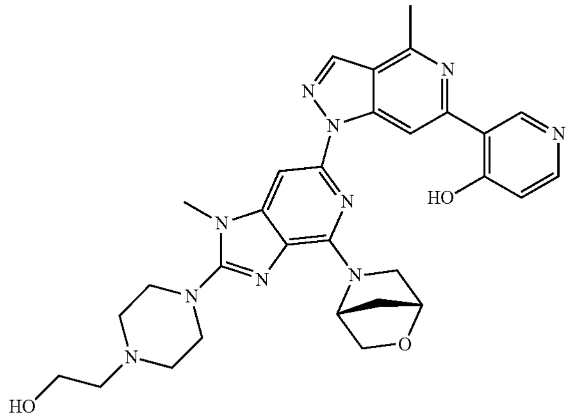 [SMILES: Cc1nc(-c2cnccc2O)cc2c1cnn2-c1cc2c(nc(N3CCN(CCO)CC3)n2C)c(N2C[C@H]3C[C@@H]2CO3)n1] | | n.a. | n.a. |
| I-056 | 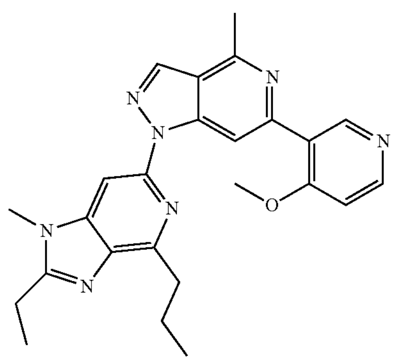 [SMILES: CCCc1nc(-n2ncc3c(C)nc(-c4cnccc4OC)cc32)cc2c1nc(CC)n2C] | 1.8 | (M + H)$^+$ = 442<br>t$_{Ret.}$ = 1.22 | LCMS3.<br>basisch_1 |
| I-057 | 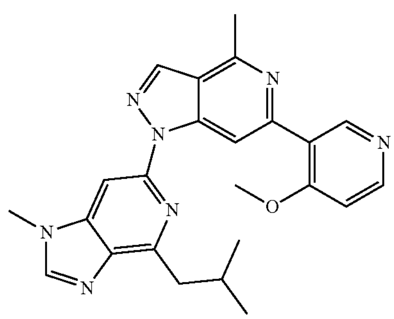 [SMILES: COc1ccncc1-c1cc2c(cnn2-c2cc3c(ncn3C)c(CC(C)C)n2)c(C)n1] | 2.1 | (M + H)$^+$ = 428<br>t$_{Ret.}$ = 1.20 | LCMS3.<br>basisch_1 |
| I-058 | 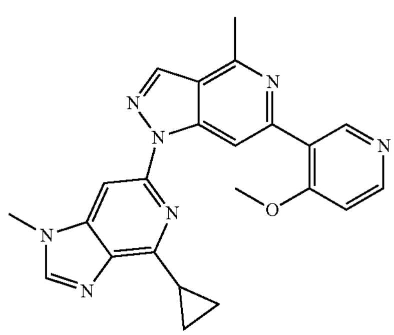 [SMILES: COc1ccncc1-c1cc2c(cnn2-c2cc3c(ncn3C)c(C3CC3)n2)c(C)n1] | 2.3 | (M + H)$^+$ = 412<br>t$_{Ret.}$ = 1.12 | LCMS3.<br>basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-059 | 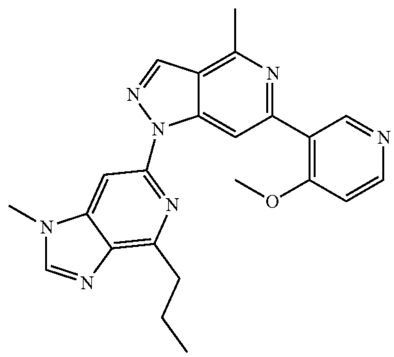 [SMILES: CCCc1nc(-n2ncc3c(C)nc(-c4cnccc4OC)cc32)cc2c1ncn2C] | 2.9 | (M + H)$^+$ = 414<br>t$_{Ret.}$ = 1.15 | LCMS3.<br>basisch_1 |
| I-060 | 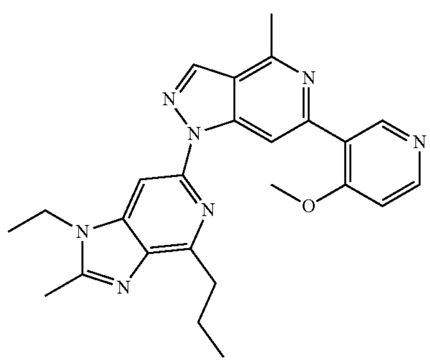 [SMILES: CCCc1nc(-n2ncc3c(C)nc(-c4cnccc4OC)cc32)cc2c1nc(C)n2CC] | 3.3 | (M + H)$^+$ = 442<br>t$_{Ret.}$ = 1.24 | LCMS3.<br>basisch_1 |
| I-061 | 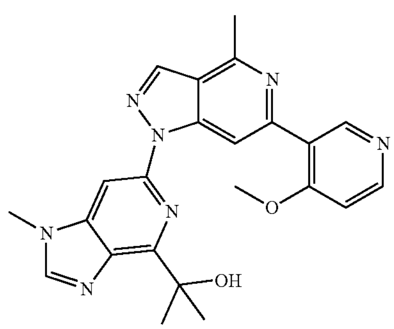 [SMILES: COc1ccncc1-c1cc2c(cnn2-c2cc3c(ncn3C)c(C(C)(C)O)n2)c(C)n1] | 3.3 | (M + H)$^+$ = 430<br>t$_{Ret.}$ = 1.07 | LCMS3.<br>basisch_1 |
| I-062 | 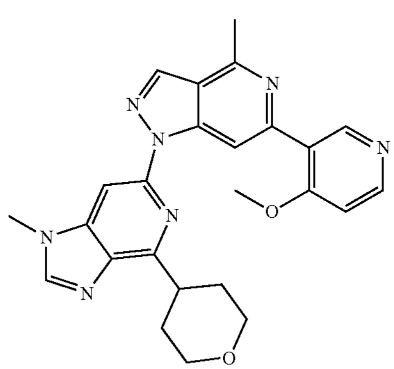 [SMILES: COc1ccncc1-c1cc2c(cnn2-c2cc3c(ncn3C)c(C3CCOCC3)n2)c(C)n1] | 3.9 | (M + H)$^+$ = 456<br>t$_{Ret.}$ = 1.08 | LCMS3.<br>basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-063 | 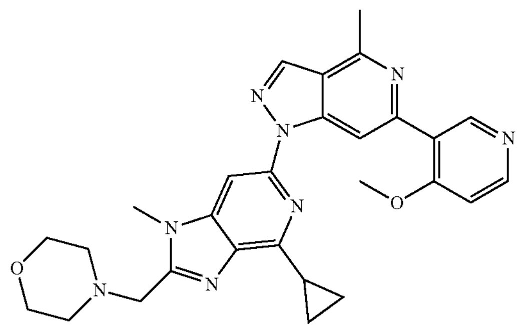 [SMILES: COc1ccncc1-c1cc2c(cnn2-c2cc3c(nc(CN4CCOCC4)n3C)c(C3CC3)n2)c(C)n1] | 4.3 | (M + H)$^+$ = 511<br>t$_{Ret.}$ = 1.16 | LCMS3.<br>basisch_1 |
| I-064 | 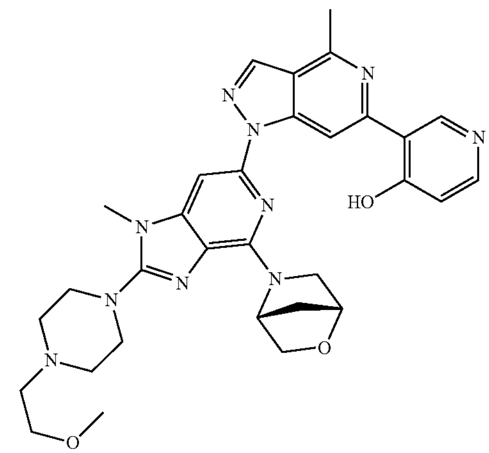 [SMILES: COCCN1CCN(c2nc3c(N4C[C@H]5C[C@@H]4CO5)nc(-n4ncc5c(C)nc(-c6cnccc6O)cc54)cc3n2C)CC1] | 27 | (M + H)$^+$ = 597<br>t$_{Ret.}$ = 1.11 | LCMS3.<br>basisch_1 |
| I-065 | 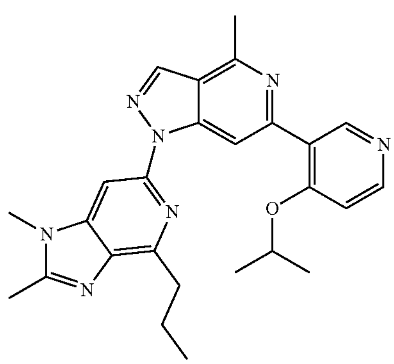 [SMILES: CCCc1nc(-n2ncc3c(C)nc(-c4cnccc4OC(C)C)cc32)cc2c1nc(C)n2C] | 65 | (M + H)$^+$ = 456<br>t$_{Ret.}$ = 1.25 | LCMS3.<br>basisch_1 |
| I-066 | 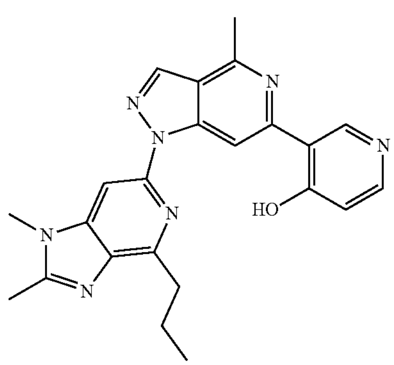 | 81 | (M + H)$^+$ = 454<br>t$_{Ret.}$ = 1.20 | LCMS3.<br>basisch_1 |

TABLE 9-continued
| # | structure | IC$_{50}$ [nM] | MS (M + H)$^+$ t$_{Ret}$ HPLC [min] | HPLC-MS method |
|---|---|---|---|---|
| I-067 | 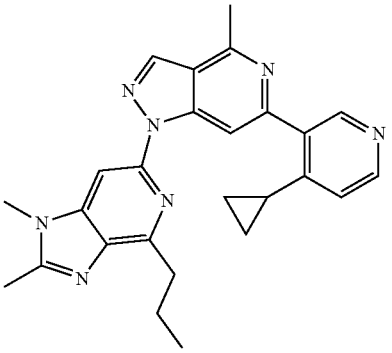 [SMILES: CCCc1nc(-n2ncc3c(C)nc(-c4cnccc4C4CC4)cc32)cc2c1nc(C)n2C] | 135 | (M + H)$^+$ = 438 t$_{Ret.}$ = 1.25 | LCMS3. basisch_1 |
| I-068 | 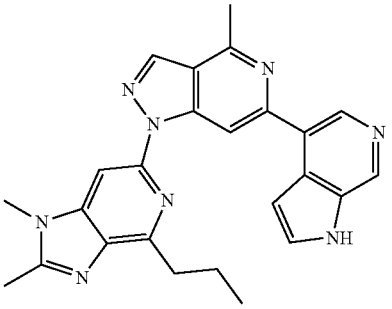 [SMILES: CCCc1nc(-n2ncc3c(C)nc(-c4cncc5[nH]ccc45)cc32)cc2c1nc(C)n2C] | 60 | (M + H)$^+$ = 437 t$_{Ret.}$ = 1.12 | LCMS3, basisch_1 |
| I-069 | 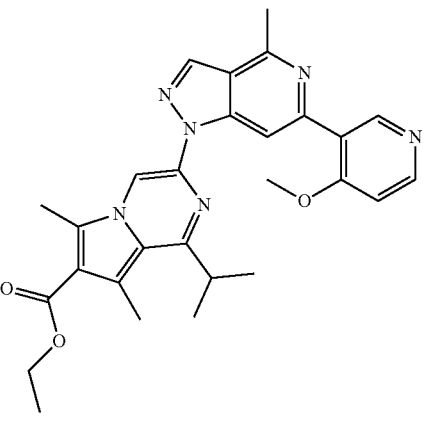 [SMILES: CCOC(=O)c1c(C)c2c(C(C)C)nc(-n3ncc4c(C)nc(-c5cnccc5OC)cc43)cn2c1C] | n.a. | | n.a. |
| I-070 | 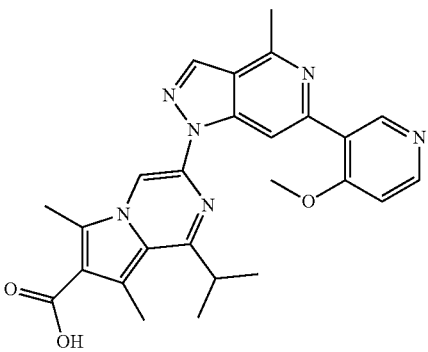 [SMILES: COc1ccncc1-c1cc2c(cnn2-c2cn3c(C)c(C(=O)O)c(C)c3c(C(C)C)n2)c(C)n1] | n.a. | | n.a. |

TABLE 9-continued
| # | structure | IC$_{50}$ [nM] | MS (M + H)$^+$ $t_{Ret}$ HPLC [min] | HPLC-MS method |
|---|---|---|---|---|
| I-071 | 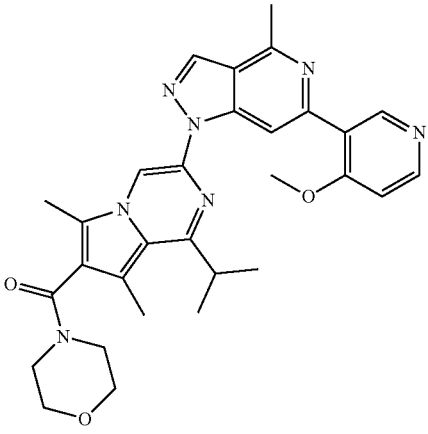 [SMILES: COc1ccncc1-c1cc2c(cnn2-c2cn3c(C)c(C(=O)N4CCOCC4)c(C)c3c(C(C)C)n2)c(C)n1] | 2.3 | (M + H)$^+$ = 540 $t_{Ret.}$ = 1.21 | LCMS3. basisch_1 |
| I-072 | 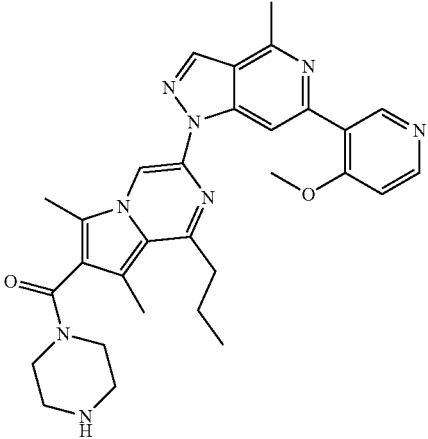 [SMILES: CCCc1nc(-n2ncc3c(C)nc(-c4cnccc4OC)cc32)cn2c(C)c(C(=O)N3CCNCC3)c(C)c12] | 21 | (M + H)$^+$ = 539 $t_{Ret.}$ = 1.10 | LCMS3. basisch_1 |
| I-073 | 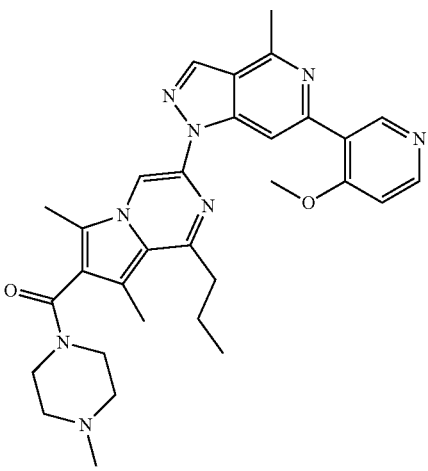 [SMILES: CCCc1nc(-n2ncc3c(C)nc(-c4cnccc4OC)cc32)cn2c(C)c(C(=O)N3CCN(C)CC3)c(C)c12] | 72 | (M + H)$^+$ = 553 $t_{Ret.}$ = 1.20 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-074 | 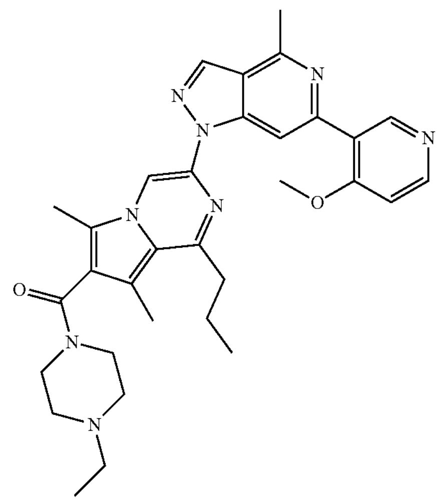 [SMILES: CCCc1nc(-n2ncc3c(C)nc(-c4cnccc4OC)cc32)cn2c(C)c(C(=O)N3CCN(CC)CC3)c(C)c12] | 64 | (M + H)$^+$ = 567 t$_{Ret.}$ = 1.29 | LCMS3. basisch_1 |
| I-075 | 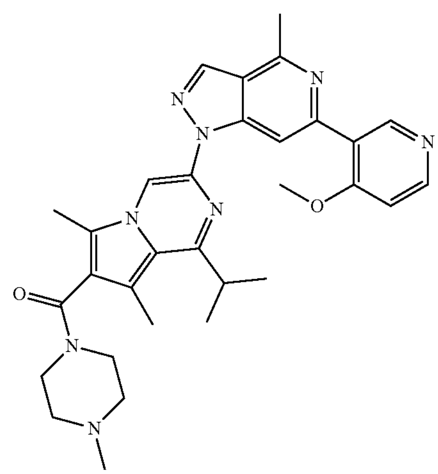 [SMILES: COc1ccncc1-c1cc2c(cnn2-c2cn3c(C)c(C(=O)N4CCN(C)CC4)c(C)c3c(C(C)C)n2)c(C)n1] | 3 | (M + H)$^+$ = 553 t$_{Ret.}$ = 1.19 | LCMS3. basisch_1 |
| I-076 | 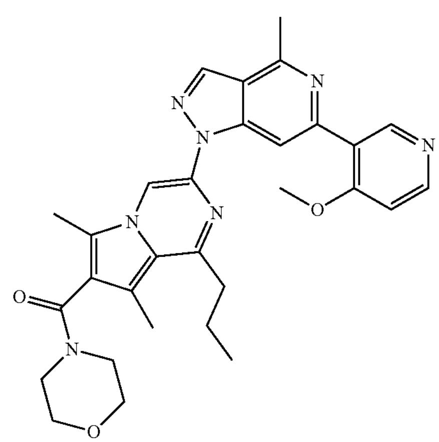 [SMILES: CCCc1nc(-n2ncc3c(C)nc(-c4cnccc4OC)cc32)cn2c(C)c(C(=O)N3CCOCC3)c(C)c12] | 20 | (M + H)$^+$ = 540 t$_{Ret.}$ = 1.24 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-077 | 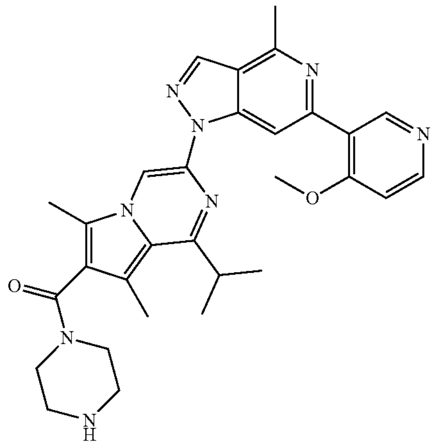 [SMILES: COc1ccncc1-c1cc2c(cnn2-c2cn3c(C)c(C(=O)N4CCNCC4)c(C)c3c(C(C)C)n2)c(C)n1] | 3 | (M + H)$^+$ = 539<br>t$_{Ret.}$ = 1.05 | LCMS3.<br>basisch_1 |
| I-078 | 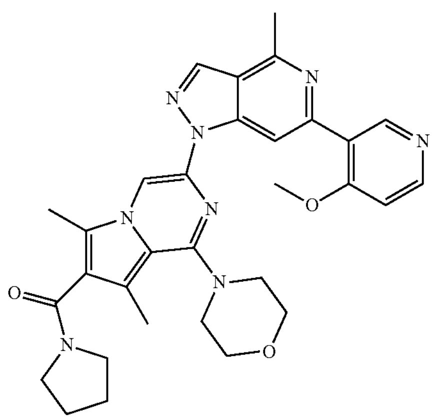 [SMILES: COc1ccncc1-c1cc2c(cnn2-c2cn3c(C)c(C(=O)N4CCCC4)c(C)c3c(N3CCOCC3)n2)c(C)n1] | 3.1 | (M + H)$^+$ = 567<br>t$_{Ret.}$ = 1.19 | LCMS3.<br>basisch_1 |
| I-079 | 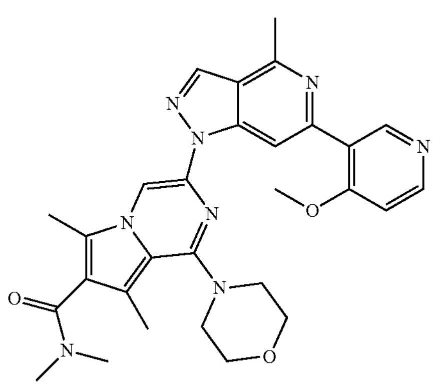 [SMILES: COc1ccncc1-c1cc2c(cnn2-c2cn3c(C)c(C(=O)N(C)C)c(C)c3c(N3CCOCC3)n2)c(C)n1] | 5.4 | (M + H)$^+$ = 541<br>t$_{Ret.}$ = 1.12 | LCMS3.<br>basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-080 | 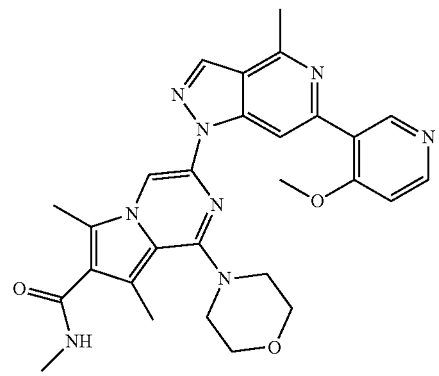 [SMILES: CNC(=O)c1c(C)c2c(N3CCOCC3)nc(-n3ncc4c(C)nc(-c5cnccc5OC)cc43)cn2c1C] | 1.1 | (M + H)$^+$ = 527<br>t$_{Ret.}$ = 1.08 | LCMS3.basisch_1 |
| I-081 | 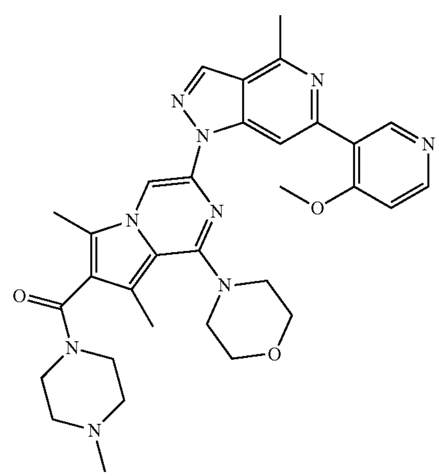 [SMILES: COc1ccncc1-c1cc2c(cnn2-c2cn3c(C)c(C(=O)N4CCN(C)CC4)c(C)c3c(N3CCOCC3)n2)c(C)n1] | 1.1 | (M + H)$^+$ = 596<br>t$_{Ret.}$ = 1.12 | LCMS3.basisch_1 |
| I-082 | 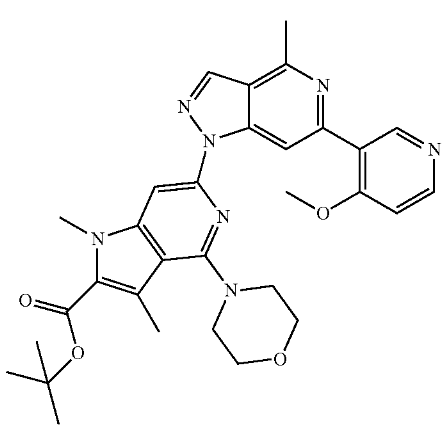 [SMILES: COc1ccncc1-c1cc2c(cnn2-c2cc3c(c(N4CCOCC4)n2)c(C)c(C(=O)OC(C)(C)C)n3C)c(C)n1] | | (M + H)$^+$ = 570<br>t$_{Ret.}$ = 1.64 | LCMS3.basisch_1 |

TABLE 9-continued
| # | structure | IC₅₀ [nM] | MS (M + H)⁺ t_Ret HPLC [min] | HPLC-MS method |
|---|---|---|---|---|
| I-083 | 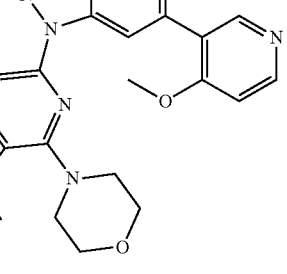 | 24 | (M + H)⁺ = 514<br>t_Ret. = 0.80 | LCMS3.basisch_1 |
| I-084 | 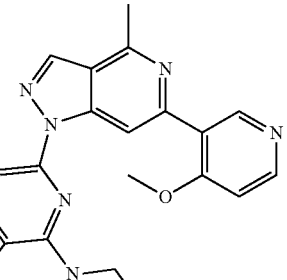 | 1.2 | (M + H)⁺ = 567<br>t_Ret. = 1.20 | LCMS3.basisch_1 |
| I-085 | 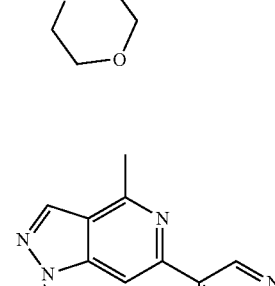 | 1.3 | (M + H)⁺ = 553<br>t_Ret. = 1.15 | LCMS3.basisch_1 |
| I-086 | 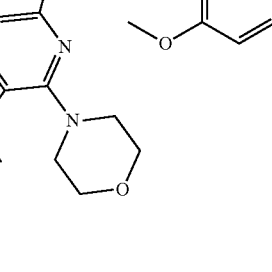 | 1.3 | (M + H)⁺ = 541<br>t_Ret. = 1.14 | LCMS3.basisch_1 |

TABLE 9-continued
| # | structure | IC$_{50}$ [nM] | MS (M + H)$^+$ t$_{Ret}$ HPLC [min] | HPLC-MS method |
|---|---|---|---|---|
| I-087 | 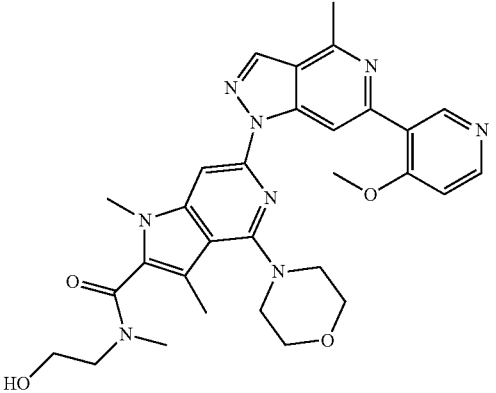 [SMILES: COc1ccncc1-c1cc2c(cnn2-c2cc3c(c(N4CCOCC4)n2)c(C)c(C(=O)N(C)CCO)n3C)c(C)n1] | 1.6 | (M + H)$^+$ = 571 t$_{Ret.}$ = 1.03 | LCMS3. basisch_1 |
| I-088 | 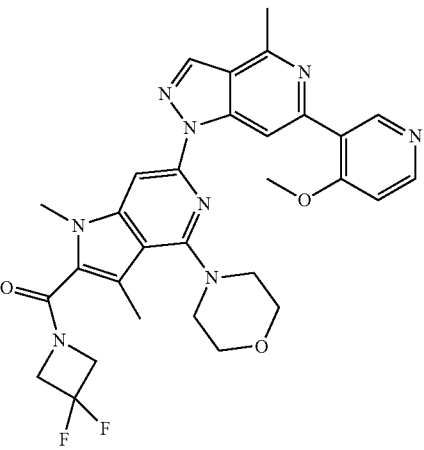 [SMILES: COc1ccncc1-c1cc2c(cnn2-c2cc3c(c(N4CCOCC4)n2)c(C)c(C(=O)N2CC(F)(F)C2)n3C)c(C)n1] | 2.4 | (M + H)$^+$ = 589 t$_{Ret.}$ = 1.26 | LCMS3. basisch_1 |
| I-089 | 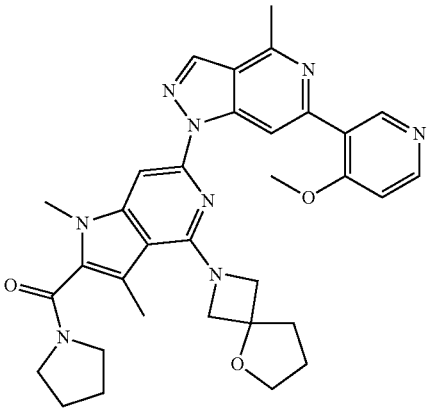 [SMILES: COc1ccncc1-c1cc2c(cnn2-c2cc3c(c(N4CC5(CCCO5)C4)n2)c(C)c(C(=O)N2CCCC2)n3C)c(C)n1] | 3.8 | (M + H)$^+$ = 593 t$_{Ret.}$ = 1.24 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-090 | 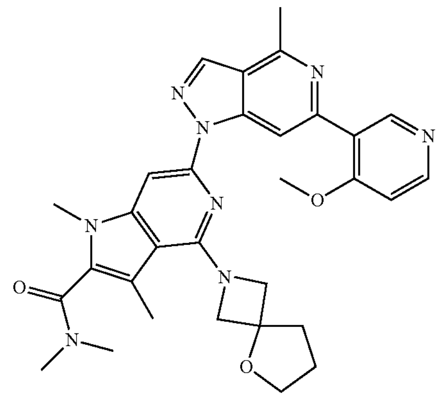 [SMILES: COc1ccncc1-c1cc2c(cnn2-c2cc3c(c(N4CC5(CCCO5)C4)n2)c(C)c(C(=O)N(C)C)n3C)c(C)n1] | 3.8 | (M + H)$^+$ = 567 t$_{Ret.}$ = 1.18 | LCMS3. basisch_1 |
| I-091 | 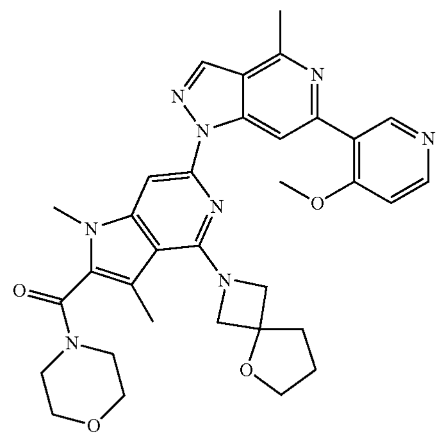 [SMILES: COc1ccncc1-c1cc2c(cnn2-c2cc3c(c(N4CC5(CCCO5)C4)n2)c(C)c(C(=O)N2CCOCC2)n3C)c(C)n1] | 4.3 | (M + H)$^+$ = 609 t$_{Ret.}$ = 1.16 | LCMS3. basisch_1 |
| I-092 | 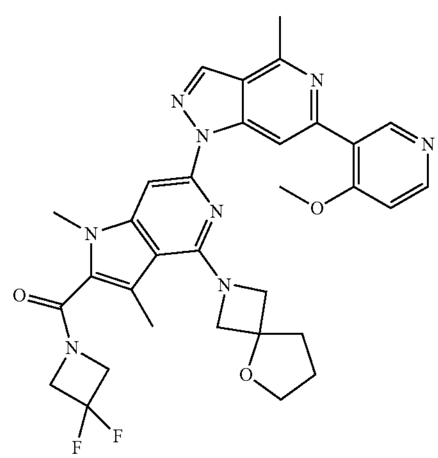 [SMILES: COc1ccncc1-c1cc2c(cnn2-c2cc3c(c(N4CC5(CCCO5)C4)n2)c(C)c(C(=O)N2CC(F)(F)C2)n3C)c(C)n1] | 6.7 | (M + H)$^+$ = 615 t$_{Ret.}$ = 1.29 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-093 | 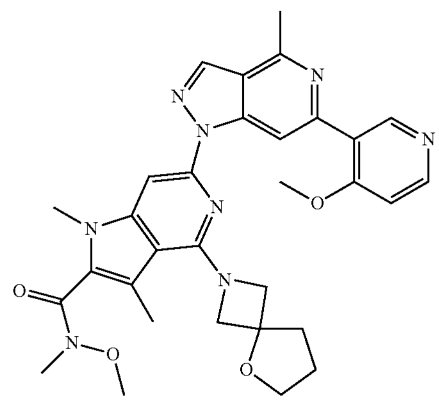 [SMILES: COc1ccncc1-c1cc2c(cnn2-c2cc3c(c(N4CC5(CCCO5)C4)n2)c(C)c(C(=O)N(C)OC)n3C)c(C)n1] | 6.9 | (M + H)$^+$ = 583 t$_{Ret.}$ = 1.21 | LCMS3. basisch_1 |
| I-094 | 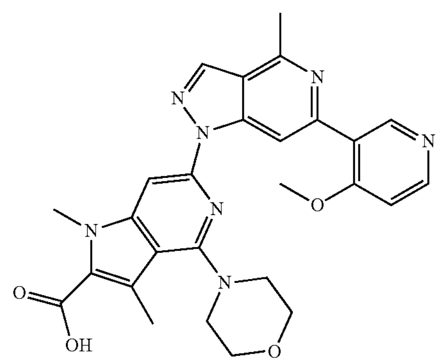 [SMILES: COc1ccncc1-c1cc2c(cnn2-c2cc3c(c(N4CCOCC4)n2)c(C)c(C(=O)O)n3C)c(C)n1] | 24 | (M + H)$^+$ = 514 t$_{Ret.}$ = 0.80 | LCMS3. basisch_1 |
| I-095 | 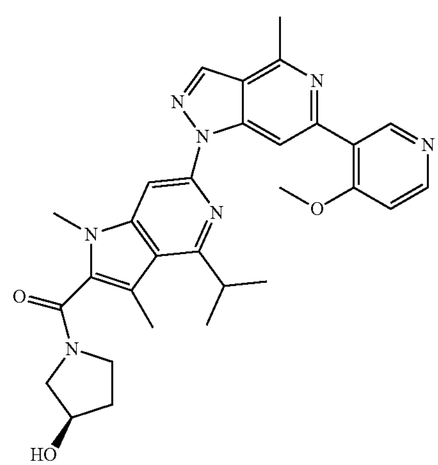 [SMILES: COc1ccncc1-c1cc2c(cnn2-c2cc3c(c(C(C)C)n2)c(C)c(C(=O)N2CC[C@@H](O)C2)n3C)c(C)n1] | 0.6 | (M + H)$^+$ = 540 t$_{Ret.}$ = 1.10 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-096 | 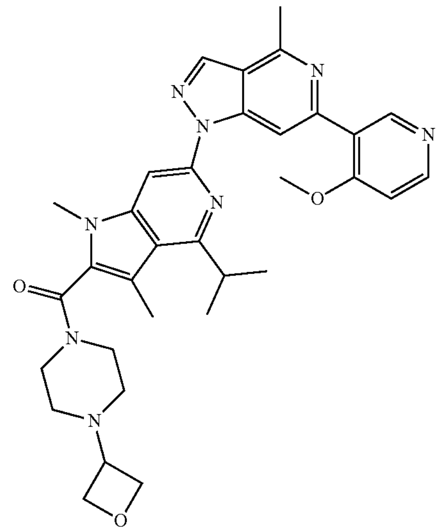 [SMILES: COc1ccncc1-c1cc2c(cnn2-c2cc3c(c(C(C)C)n2)c(C)c(C(=O)N2CCN(C4COC4)CC2)n3C)c(C)n1] | 0.6 | (M + H)$^+$ = 595<br>t$_{Ret.}$ = 1.16 | LCMS3. basisch_1 |
| I-097 | 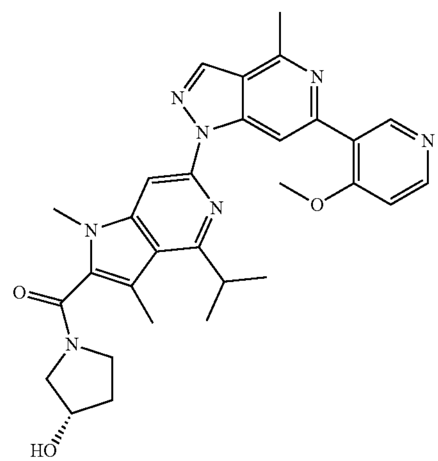 [SMILES: COc1ccncc1-c1cc2c(cnn2-c2cc3c(c(C(C)C)n2)c(C)c(C(=O)N2CC[C@H](O)C2)n3C)c(C)n1] | 0.7 | (M + H)$^+$ = 540<br>t$_{Ret.}$ = 1.10 | LCMS3. basisch_1 |
| I-098 | 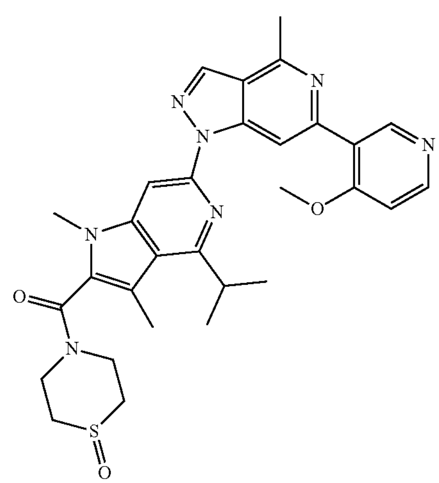 [SMILES: COc1ccncc1-c1cc2c(cnn2-c2cc3c(c(C(C)C)n2)c(C)c(C(=O)N2CCS(=O)CC2)n3C)c(C)n1] | 0.9 | (M + H)$^+$ = 572<br>t$_{Ret.}$ = 1.08 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-099 | 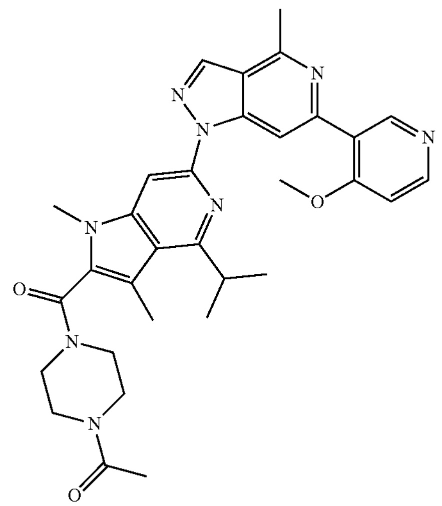 [SMILES: COc1ccncc1-c1cc2c(cnn2-c2cc3c(c(C(C)C)n2)c(C)c(C(=O)N2CCN(C(C)=O)CC2)n3C)c(C)n1] | 1.0 | (M + H)$^+$ = 581<br>t$_{Ret.}$ = 1.14 | LCMS3.<br>basisch_1 |
| I-100 | 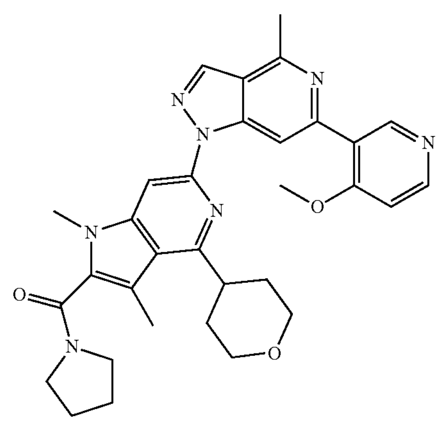 [SMILES: COc1ccncc1-c1cc2c(cnn2-c2cc3c(c(C4CCOCC4)n2)c(C)c(C(=O)N2CCCC2)n3C)c(C)n1] | 1.1 | (M + H)$^+$ = 566<br>t$_{Ret.}$ = 1.20 | LCMS3.<br>basisch_1 |
| I-101 | 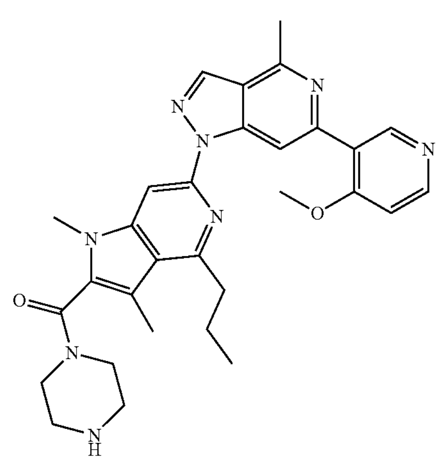 [SMILES: CCCc1nc(-n2ncc3c(C)nc(-c4cnccc4OC)cc32)cc2c1c(C)c(C(=O)N1CCNCC1)n2C] | 1.1 | (M + H)$^+$ = 539<br>t$_{Ret.}$ = 1.08 | LCMS3.<br>basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-102 | 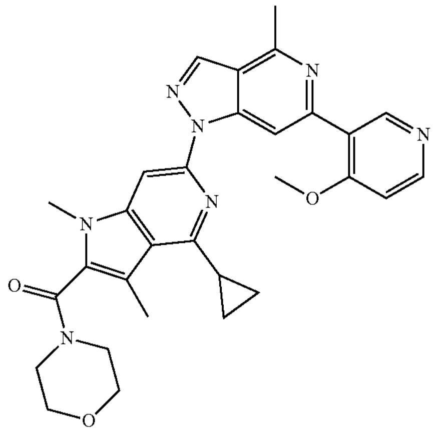 [SMILES: COc1ccncc1-c1cc2c(cnn2-c2cc3c(c(C4CC4)n2)c(C)c(C(=O)N2CCOCC2)n3C)c(C)n1] | 1.1 | (M + H)$^+$ = 538 t$_{Ret.}$ = 1.20 | LCMS3. basisch_1 |
| I-103 | 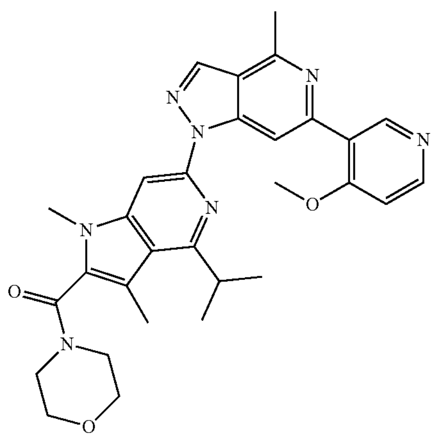 [SMILES: COc1ccncc1-c1cc2c(cnn2-c2cc3c(c(C(C)C)n2)c(C)c(C(=O)N2CCOCC2)n3C)c(C)n1] | 1.2 | (M + H)$^+$ = 540 t$_{Ret.}$ = 1.23 | LCMS3. basisch_1 |
| I-104 | 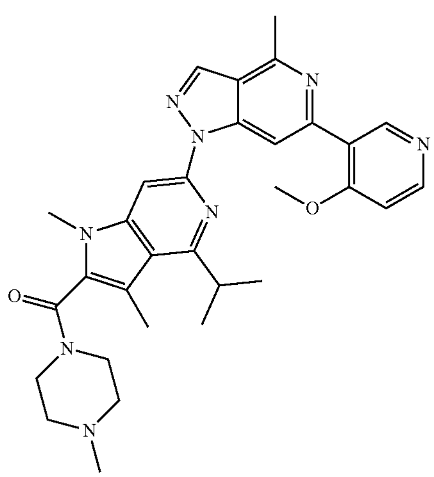 [SMILES: COc1ccncc1-c1cc2c(cnn2-c2cc3c(c(C(C)C)n2)c(C)c(C(=O)N2CCN(C)CC2)n3C)c(C)n1] | 1.2 | (M + H)$^+$ = 553 t$_{Ret.}$ = 1.22 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-105 | 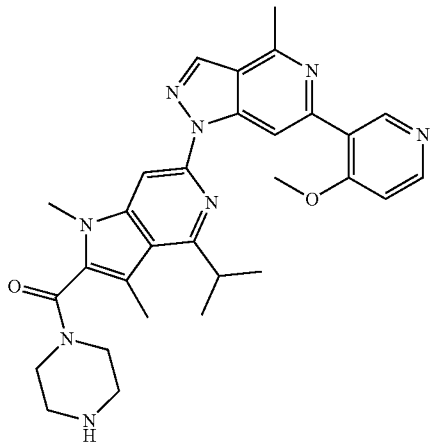 [SMILES: COc1ccncc1-c1cc2c(cnn2-c2cc3c(c(C(C)C)n2)c(C)c(C(=O)N2CCNCC2)n3C)c(C)n1] | 1.3 | (M + H)$^+$ = 539 t$_{Ret.}$ = 1.07 | LCMS3. basisch_1 |
| I-106 | 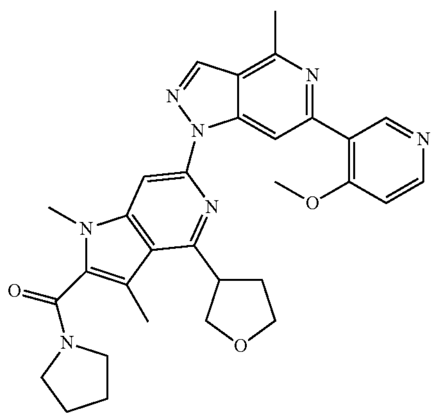 [SMILES: COc1ccncc1-c1cc2c(cnn2-c2cc3c(c(C4CCOC4)n2)c(C)c(C(=O)N2CCCC2)n3C)c(C)n1] | 1.4 | (M + H)$^+$ = 552 t$_{Ret.}$ = 1.17 | LCMS3. basisch_1 |
| I-107 | 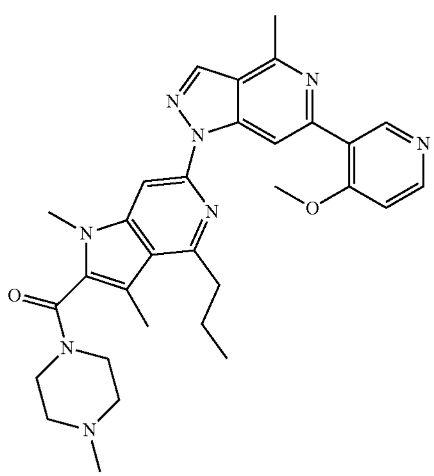 [SMILES: CCCc1nc(-n2ncc3c(C)nc(-c4cnccc4OC)cc32)cc2c1c(C)c(C(=O)N1CCN(C)CC1)n2C] | 1.6 | (M + H)$^+$ = 553 t$_{Ret.}$ = 1.22 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-108 | 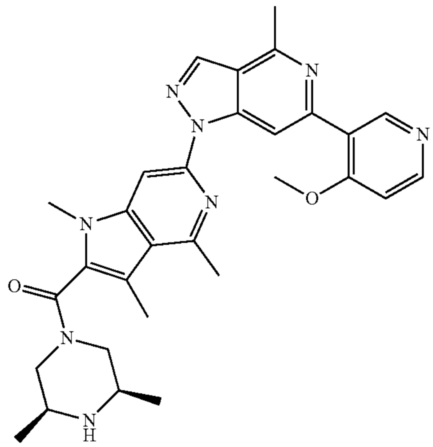 | 1.7 | (M + H)$^+$ = 567 t$_{Ret.}$ = 1.21 | LCMS3. basisch_1 |
| I-109 | 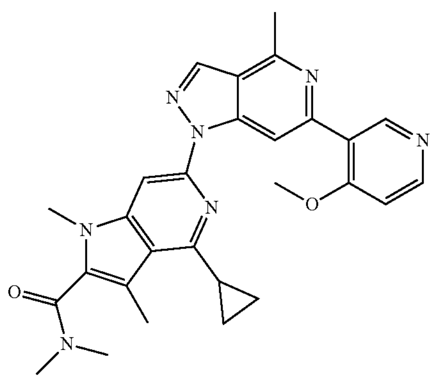 [SMILES: COc1ccncc1-c1cc2c(cnn2-c2cc3c(c(C4CC4)n2)c(C)c(C(=O)N(C)C)n3C)c(C)n1] | 1.9 | (M + H)$^+$ = 496 t$_{Ret.}$ = 1.18 | LCMS3. basisch_1 |
| I-110 | 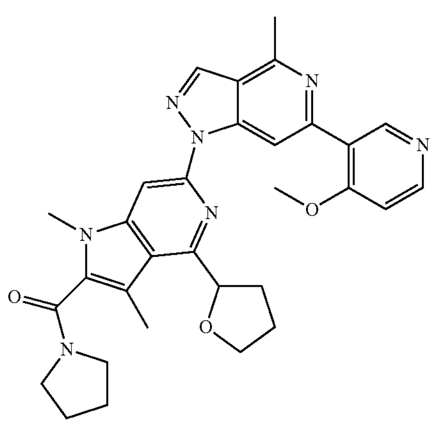 [SMILES: COc1ccncc1-c1cc2c(cnn2-c2cc3c(c(C4CCCO4)n2)c(C)c(C(=O)N2CCCC2)n3C)c(C)n1] | 1.9 | (M + H)$^+$ = 552 t$_{Ret.}$ = 1.18 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-111 | 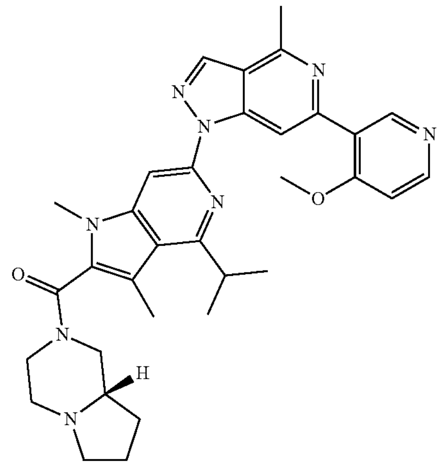 [SMILES: COc1ccncc1-c1cc2c(cnn2-c2cc3c(c(C(C)C)n2)c(C)c(C(=O)N2CCN4CCC[C@H]4C2)n3C)c(C)n1] | 2 | (M + H)$^+$ = 579 t$_{Ret.}$ = 1.31 | LCMS3. basisch_1 |
| I-112 | 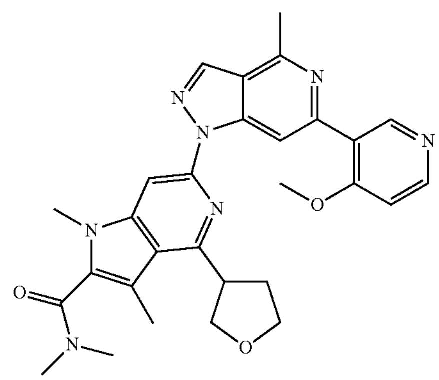 [SMILES: COc1ccncc1-c1cc2c(cnn2-c2cc3c(c(C4CCOC4)n2)c(C)c(C(=O)N(C)C)n3C)c(C)n1] | 2 | (M + H)$^+$ = 526 t$_{Ret.}$ = 1.11 | LCMS3. basisch_1 |
| I-113 | 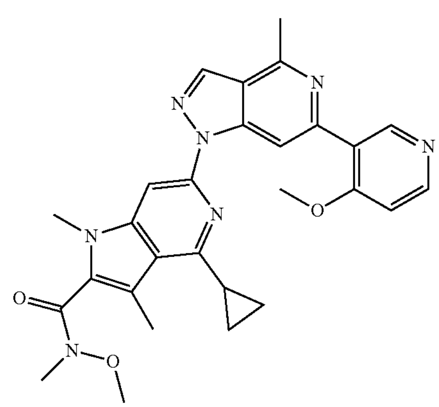 [SMILES: COc1ccncc1-c1cc2c(cnn2-c2cc3c(c(C4CC4)n2)c(C)c(C(=O)N(C)OC)n3C)c(C)n1] | 2 | (M + H)$^+$ = 512 t$_{Ret.}$ = 1.25 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-114 | 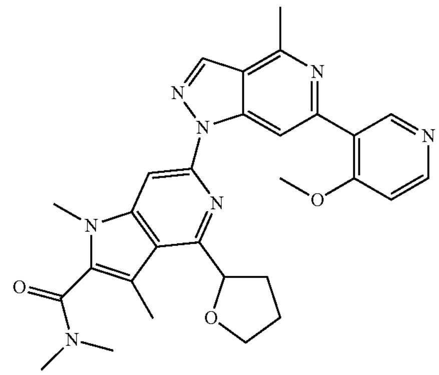 [SMILES: COc1ccncc1-c1cc2c(cnn2-c2cc3c(c(C4CCCO4)n2)c(C)c(C(=O)N(C)C)n3C)c(C)n1] | 2.2 | (M + H)$^+$ = 526 t$_{Ret.}$ = 1.12 | LCMS3. basisch_1 |
| I-115 | 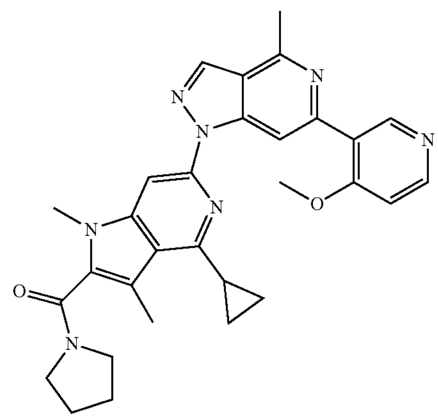 [SMILES: COc1ccncc1-c1cc2c(cnn2-c2cc3c(c(C4CC4)n2)c(C)c(C(=O)N2CCCC2)n3C)c(C)n1] | 2.8 | (M + H)$^+$ = 522 t$_{Ret.}$ = 1.27 | LCMS3. basisch_1 |
| I-116 | 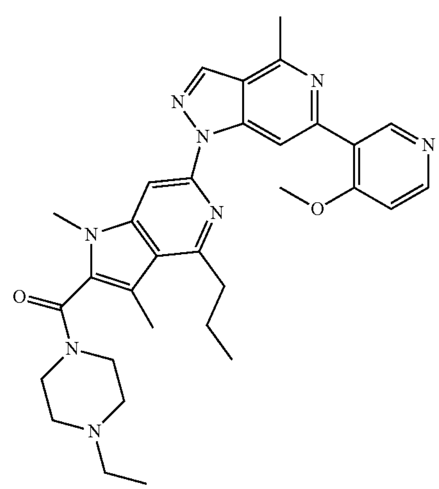 | 2.9 | (M + H)$^+$ = 553 t$_{Ret.}$ = 1.18 | LCMS3. basisch_1 |

TABLE 9-continued
| # | structure | IC$_{50}$ [nM] | MS (M + H)$^+$ t$_{Ret}$ HPLC [min] | HPLC-MS method |
|---|---|---|---|---|
| I-117 | 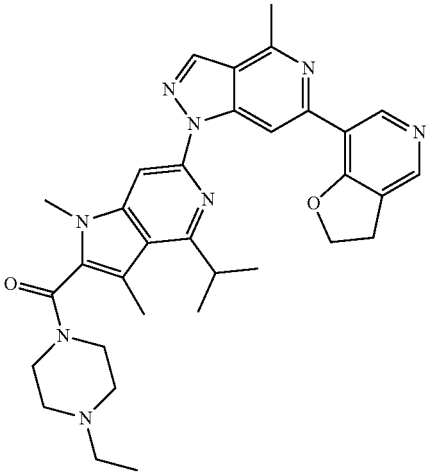 [SMILES: CCN1CCN(C(=O)c2c(C)c3c(C(C)C)nc(-n4ncc5c(C)nc(-c6cncc7c6OCC7)cc54)cc3n2C)CC1] | 2.9 | (M + H)$^+$ = 579 t$_{Ret.}$ = 1.34 | LCMS3. basisch_1 |
| I-118 | 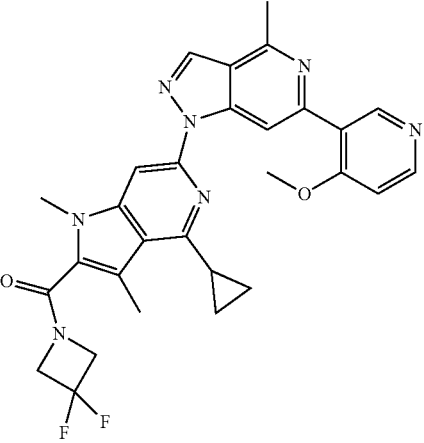 [SMILES: COc1ccncc1-c1cc2c(cnn2-c2cc3c(c(C4CC4)n2)c(C)c(C(=O)N2CC(F)(F)C2)n3C)c(C)n1] | 3 | (M + H)$^+$ = 544 t$_{Ret.}$ = 1.32 | LCMS3. basisch_1 |
| I-119 | 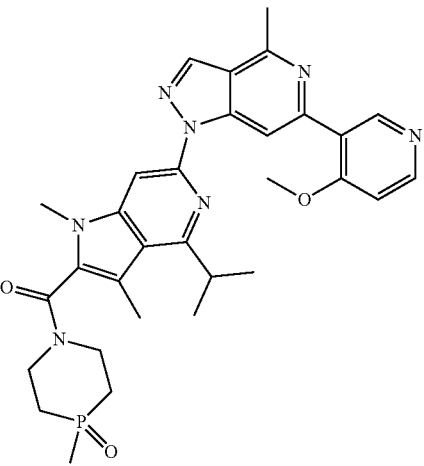 [SMILES: COc1ccncc1-c1cc2c(cnn2-c2cc3c(c(C(C)C)n2)c(C)c(C(=O)N2CCP(C)(=O)CC2)n3C)c(C)n1] | 5.6 | (M + H)$^+$ = 586 t$_{Ret.}$ = 1.04 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-120 | 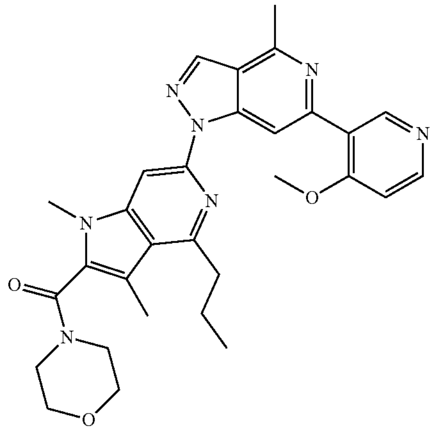 [SMILES: CCCc1nc(-n2ncc3c(C)nc(-c4cnccc4OC)cc32)cc2c1c(C)c(C(=O)N1CCOCC1)n2C] | 5.7 | (M + H)$^+$ = 540 t$_{Ret.}$ = 1.23 | LCMS3. basisch_1 |
| I-121 | 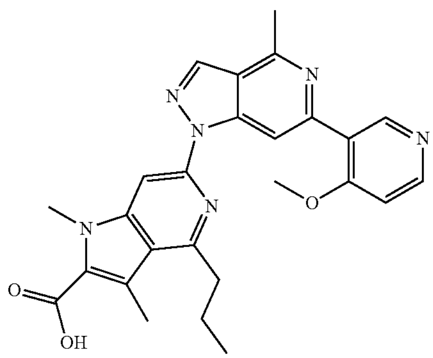 [SMILES: CCCc1nc(-n2ncc3c(C)nc(-c4cnccc4OC)cc32)cc2c1c(C)c(C(=O)O)n2C] | 40 | (M + H)$^+$ = 471 t$_{Ret.}$ = 0.84 | LCMS3. basisch_1 |
| I-122 | 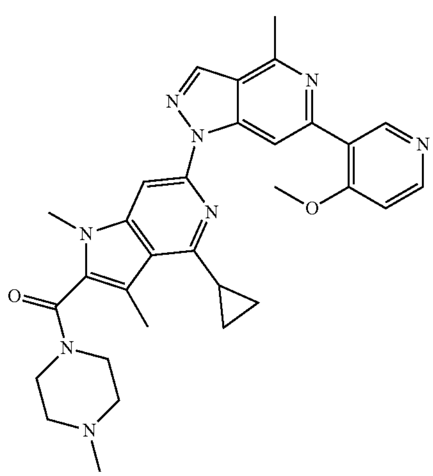 [SMILES: COc1ccncc1-c1cc2c(cnn2-c2cc3c(c(C4CC4)n2)c(C)c(C(=O)N2CCN(C)CC2)n3C)c(C)n1] | 4.0 | (M + H)$^+$ = 551 t$_{Ret.}$ = 1.19 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-123 | 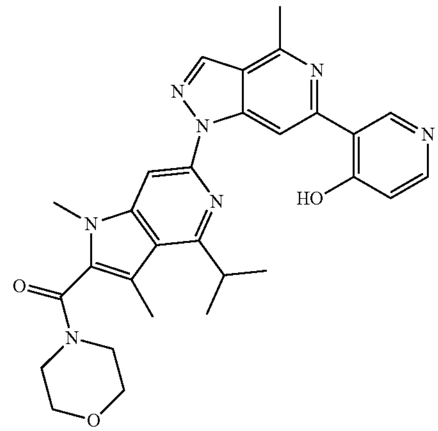 [SMILES: Cc1nc(-c2cnccc2O)cc2c1cnn2-c1cc2c(c(C(C)C)n1)c(C)c(C(=O)N1CCOCC1)n2C] | 16 | (M + H)$^+$ = 526 t$_{Ret.}$ = 1.16 | LCMS3. basisch_1 |
| I-124 | 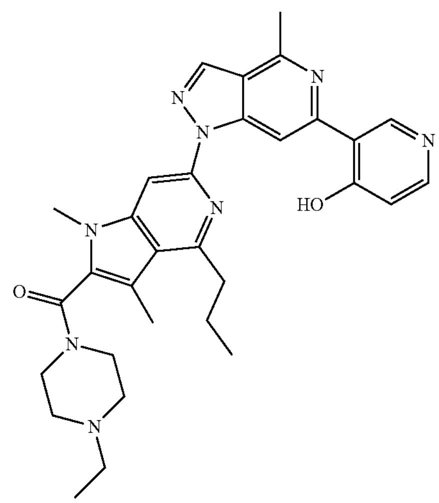 | 48 | (M + H)$^+$ = 567 t$_{Ret.}$ = 1.27 | LCMS3. basisch_1 |
| I-125 | 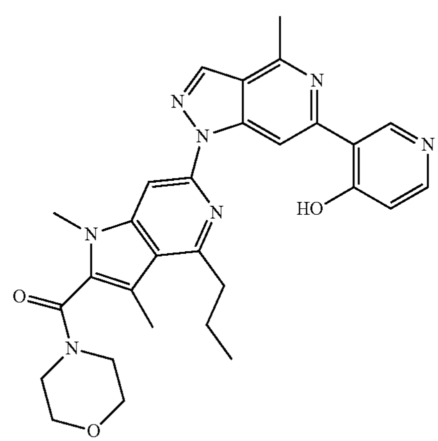 [SMILES: CCCc1nc(-n2ncc3c(C)nc(-c4cnccc4O)cc32)cc2c1c(C)c(C(=O)N1CCOCC1)n2C] | | (M + H)$^+$ = 526 t$_{Ret.}$ = 1.10 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-126 | 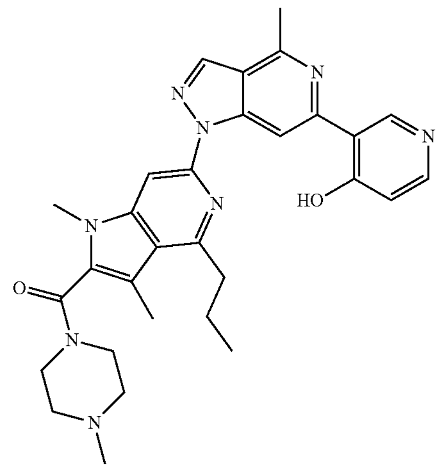 [SMILES: CCCc1nc(-n2ncc3c(C)nc(-c4cnccc4O)cc32)cc2c1c(C)c(C(=O)N1CCN(C)CC1)n2C] | 205 | (M + H)$^+$ = 539 t$_{Ret.}$ = 1.09 | LCMS3. basisch_1 |
| I-127 | 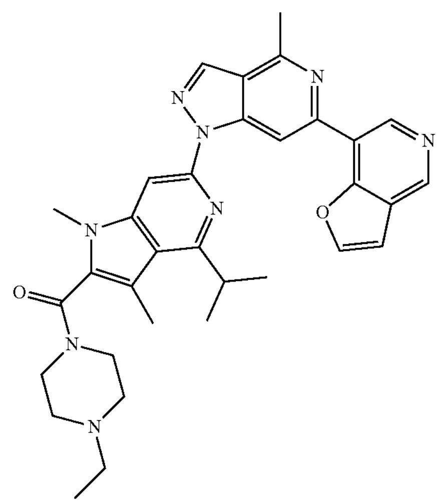 [SMILES: CCN1CCN(C(=O)c2c(C)c3c(C(C)C)nc(-n4ncc5c(C)nc(-c6cncc7ccoc67)cc54)cc3n2C)CC1] | 5.2 | (M + H)$^+$ = 577 t$_{Ret.}$ = 1.40 | LCMS3. basisch_1 |
| I-128 | 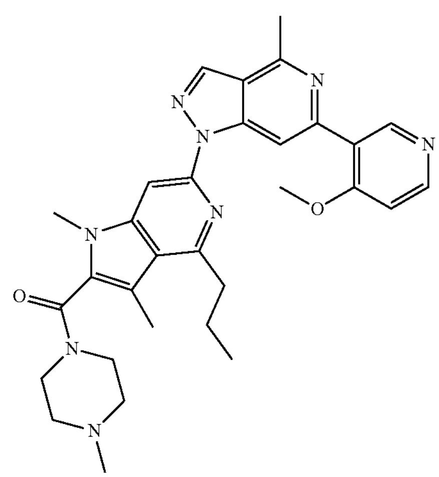 [SMILES: CCCc1nc(-n2ncc3c(C)nc(-c4cnccc4OC)cc32)cc2c1c(C)c(C(=O)N1CCN(C)CC1)n2C] | 1.4 | (M + H)$^+$ = 553 t$_{Ret.}$ = 1.17 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-129 | 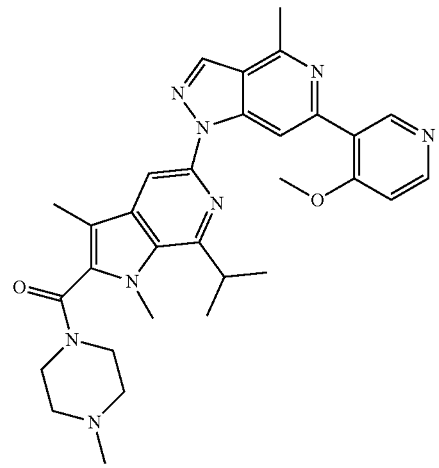 [SMILES: COc1ccncc1-c1cc2c(cnn2-c2cc3c(C)c(C(=O)N4CCN(C)CC4)n(C)c3c(C(C)C)n2)c(C)n1] | 5.3 | (M + H)$^+$ = 553 t$_{Ret.}$ = 1.22 | LCMS3. basisch_1 |
| I-130 | 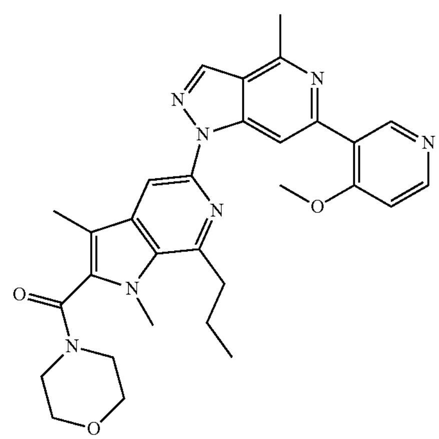 [SMILES: CCCc1nc(-n2ncc3c(C)nc(-c4cnccc4OC)cc32)cc2c(C)c(C(=O)N3CCOCC3)n(C)c12] | | (M + H)$^+$ = 540 t$_{Ret.}$ = 1.20 | LCMS3. basisch_1 |
| I-131 | 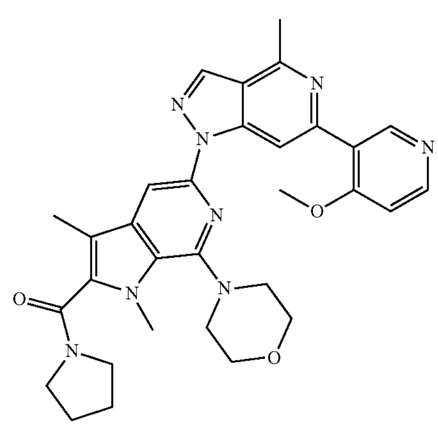 [SMILES: COc1ccncc1-c1cc2c(cnn2-c2cc3c(C)c(C(=O)N4CCCC4)n(C)c3c(N3CCOCC3)n2)c(C)n1] | 1.9 | (M + H)$^+$ = 567 t$_{Ret.}$ = 1.24 | LCMS3. basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-132 | 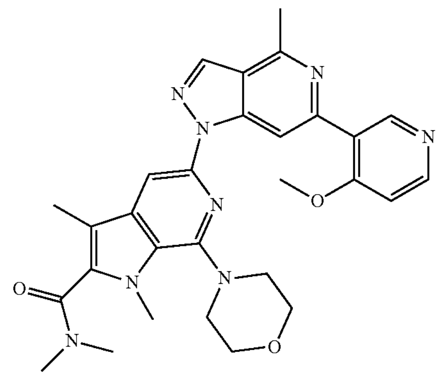 [SMILES: COc1ccncc1-c1cc2c(cnn2-c2cc3c(C)c(C(=O)N(C)C)n(C)c3c(N3CCOCC3)n2)c(C)n1] | 2.3 | (M + H)$^+$ = 541 t$_{Ret.}$ = 1.17 | LCMS3. basisch_1 |
| I-133 | 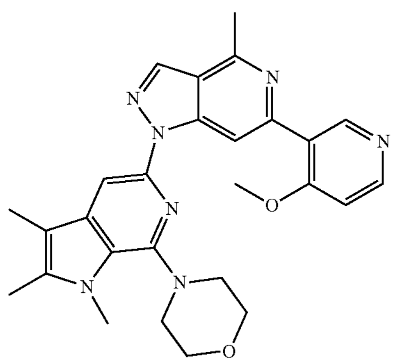 [SMILES: COc1ccncc1-c1cc2c(cnn2-c2cc3c(C)c(C)n(C)c3c(N3CCOCC3)n2)c(C)n1] | 11 | (M + H)$^+$ = 484 t$_{Ret.}$ = 1.43 | LCMS3. basisch_1 |
| I-134 | 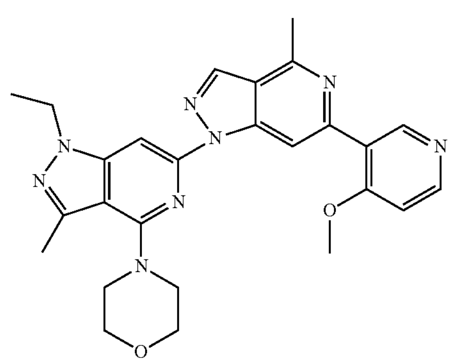 [SMILES: CCn1nc(C)c2c(N3CCOCC3)nc(-n3ncc4c(C)nc(-c5cnccc5OC)cc43)cc21] | 4.5 | (M + H)$^+$ = 485 t$_{Ret.}$ = 1.26 | LCMS3, basisch_1 |
| I-135 | 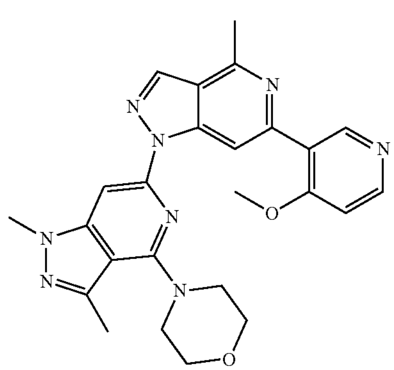 [SMILES: COc1ccncc1-c1cc2c(cnn2-c2cc3c(c(C)nn3C)c(N3CCOCC3)n2)c(C)n1] | 1.5 | (M + H)$^+$ = 471 t$_{Ret.}$ = 1.18 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-136 | 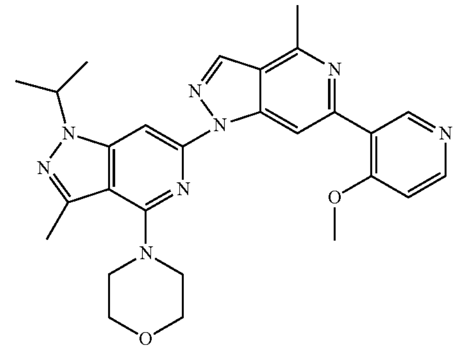 [SMILES: COc1ccncc1-c1cc2c(cnn2-c2cc3c(c(C)nn3C(C)C)c(N3CCOCC3)n2)c(C)n1] | 3.8 | (M + H)$^+$ = 499 t$_{Ret.}$ = 2.06 | LCMS3, basisch_1 |
| I-137 | 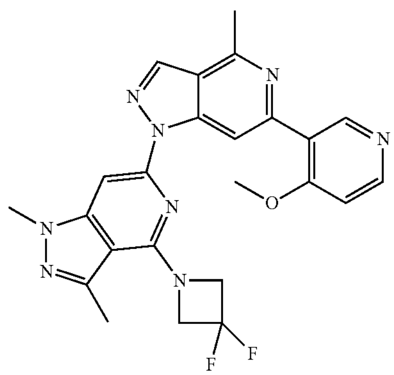 [SMILES: COc1ccncc1-c1cc2c(cnn2-c2cc3c(c(C)nn3C)c(N3CC(F)(F)C3)n2)c(C)n1] | 5.5 | (M + H)$^+$ = 477 t$_{Ret.}$ = 1.27 | LCMS3, basisch_1 |
| I-138 | 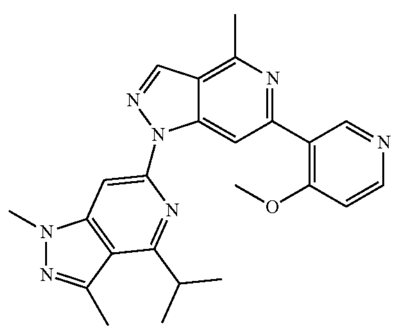 [SMILES: COc1ccncc1-c1cc2c(cnn2-c2cc3c(c(C)nn3C)c(C(C)C)n2)c(C)n1] | 7.8 | (M + H)$^+$ = 428 t$_{Ret.}$ = 1.33 | LCMS3, basisch_1 |
| I-139 | 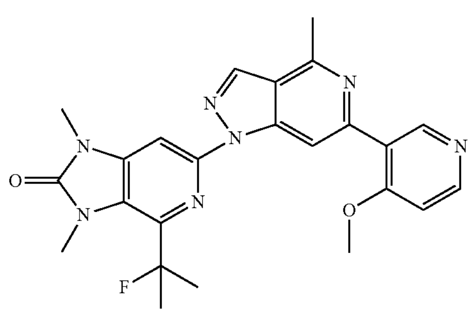 [SMILES: COc1ccncc1-c1cc2c(cnn2-c2cc3c(c(C(C)(C)F)n2)n(C)c(=O)n3C)c(C)n1] | 6.4 | (M + H)$^+$ = 462 t$_{Ret.}$ = 1.21 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-140 | 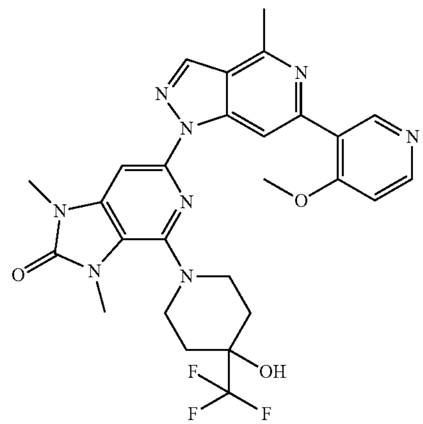 [SMILES: COc1ccncc1-c1cc2c(cnn2-c2cc3c(c(N4CCC(O)(C(F)(F)F)CC4)n2)n(C)c(=O)n3C)c(C)n1] | 11 | (M + H)$^+$ = 569 t$_{Ret.}$ = 1.19 | LCMS3, basisch_1 |
| I-141 | 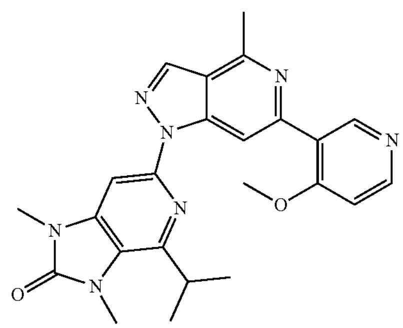 [SMILES: COc1ccncc1-c1cc2c(cnn2-c2cc3c(c(C(C)C)n2)n(C)c(=O)n3C)c(C)n1] | 1.6 | (M + H)$^+$ = 444 t$_{Ret.}$ = 1.17 | LCMS3, basisch_1 |
| I-142 | 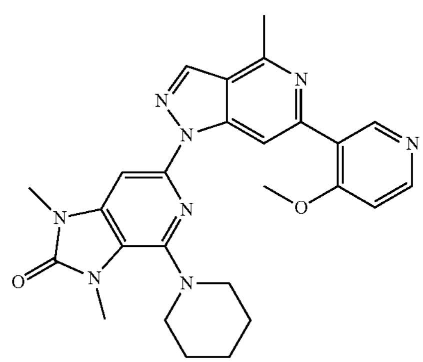 [SMILES: COc1ccncc1-c1cc2c(cnn2-c2cc3c(c(N4CCCCC4)n2)n(C)c(=O)n3C)c(C)n1] | 2.1 | (M + H)$^+$ = 485 t$_{Ret.}$ = 1.27 | LCMS3, basisch_1 |
| I-143 | 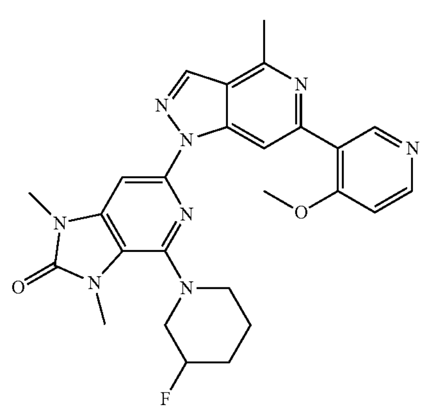 [SMILES: COc1ccncc1-c1cc2c(cnn2-c2cc3c(c(N4CCCC(F)C4)n2)n(C)c(=O)n3C)c(C)n1] | 2.8 | (M + H)$^+$ = 503 t$_{Ret.}$ = 1.19 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-144 | 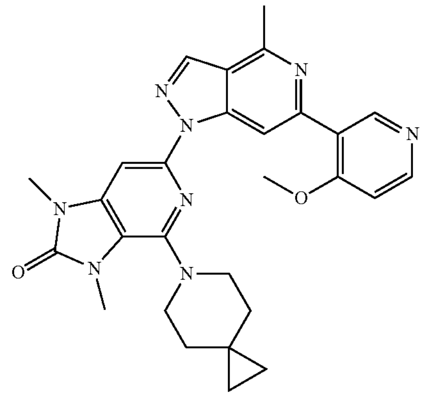 [SMILES: COc1ccncc1-c1cc2c(cnn2-c2cc3c(c(N4CCC5(CC4)CC5)n2)n(C)c(=O)n3C)c(C)n1] | 2.9 | (M + H)$^+$ = 511<br>t$_{Ret.}$ = 1.33 | LCMS3, basisch_1 |
| I-145 | 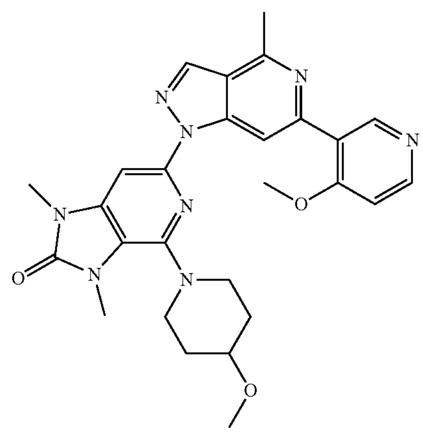 [SMILES: COc1ccncc1-c1cc2c(cnn2-c2cc3c(c(N4CCC(OC)CC4)n2)n(C)c(=O)n3C)c(C)n1] | 3.3 | (M + H)$^+$ = 515<br>t$_{Ret.}$ = 1.15 | LCMS3, basisch_1 |
| I-146 | 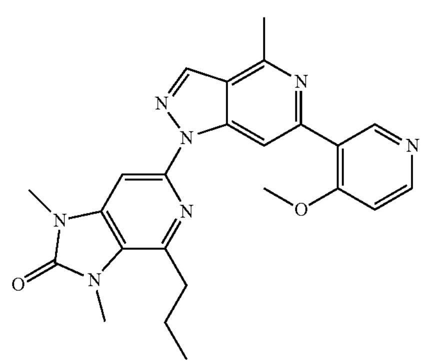 [SMILES: CCCc1nc(-n2ncc3c(C)nc(-c4cnccc4OC)cc32)cc2c1n(C)c(=O)n2C] | 3.9 | (M + H)$^+$ = 444<br>t$_{Ret.}$ = 1.17 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-147 | 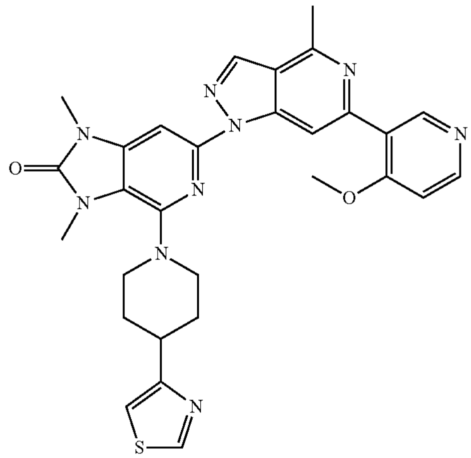 [SMILES: COc1ccncc1-c1cc2c(cnn2-c2cc3c(c(N4CCC(c5cscn5)CC4)n2)n(C)c(=O)n3C)c(C)n1] | 4.9 | (M + H)$^+$ = 568 t$_{Ret.}$ = 1.21 | LCMS3, basisch_1 |
| I-148 | 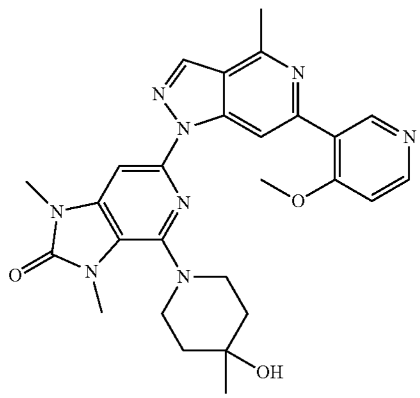 [SMILES: COc1ccncc1-c1cc2c(cnn2-c2cc3c(c(N4CCC(C)(O)CC4)n2)n(C)c(=O)n3C)c(C)n1] | 6.5 | (M + H)$^+$ = 515 t$_{Ret.}$ = 1.08 | LCMS3, basisch_1 |
| I-149 | 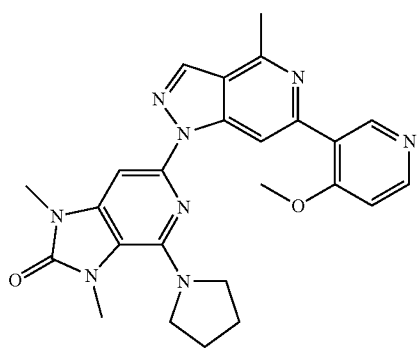 [SMILES: COc1ccncc1-c1cc2c(cnn2-c2cc3c(c(N4CCCC4)n2)n(C)c(=O)n3C)c(C)n1] | 6.6 | (M + H)$^+$ = 471 t$_{Ret.}$ = 1.17 | LCMS3, basisch_1 |
| I-150 | 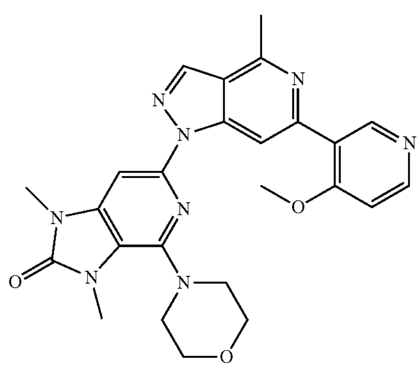 [SMILES: COc1ccncc1-c1cc2c(cnn2-c2cc3c(c(N4CCOCC4)n2)n(C)c(=O)n3C)c(C)n1] | 7.5 | (M + H)$^+$ = 487 t$_{Ret.}$ = 1.07 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-151 | 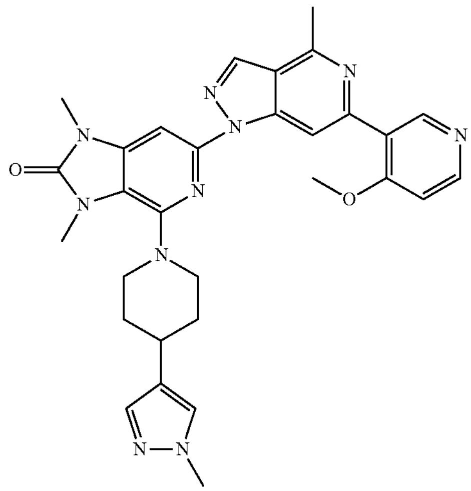 [SMILES: COc1ccncc1-c1cc2c(cnn2-c2cc3c(c(N4CCC(c5cnn(C)c5)CC4)n2)n(C)c(=O)n3C)c(C)n1] | 7.7 | (M + H)$^+$ = 565<br>t$_{Ret.}$ = 1.15 | LCMS3, basisch_1 |
| I-152 | 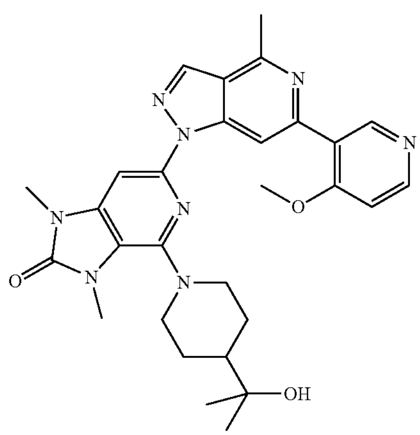 [SMILES: COc1ccncc1-c1cc2c(cnn2-c2cc3c(c(N4CCC(C(C)(C)O)CC4)n2)n(C)c(=O)n3C)c(C)n1] | 13 | (M + H)$^+$ = 543<br>t$_{Ret.}$ = 1.80 | LCMS3, basisch_1 |
| I-153 | 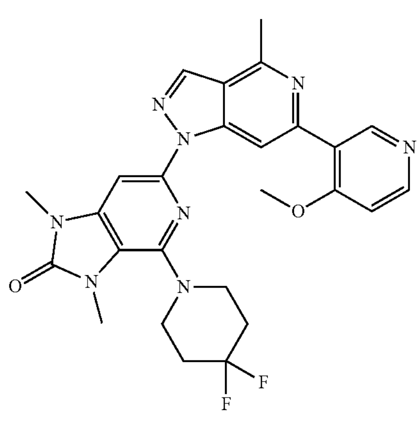 [SMILES: COc1ccncc1-c1cc2c(cnn2-c2cc3c(c(N4CCC(F)(F)CC4)n2)n(C)c(=O)n3C)c(C)n1] | 18 | (M + H)$^+$ = 521<br>t$_{Ret.}$ = 1.22 | LCMS3, basisch_1 |

TABLE 9-continued

| # | structure | IC$_{50}$ [nM] | MS (M + H)$^+$ t$_{Ret}$ HPLC [min] | HPLC-MS method |
|---|---|---|---|---|
| I-154 | 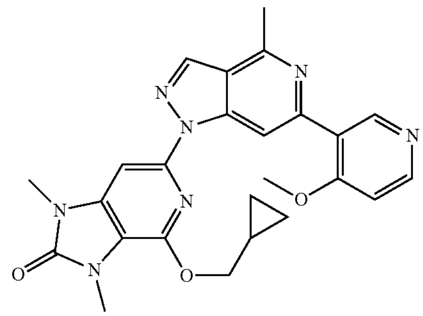 [SMILES: COc1ccncc1-c1cc2c(cnn2-c2cc3c(c(OCC4CC4)n2)n(C)c(=O)n3C)c(C)n1] | 18 | (M + H)$^+$ = 472 t$_{Ret.}$ = 1.20 | LCMS3, basisch_1 |
| I-155 | 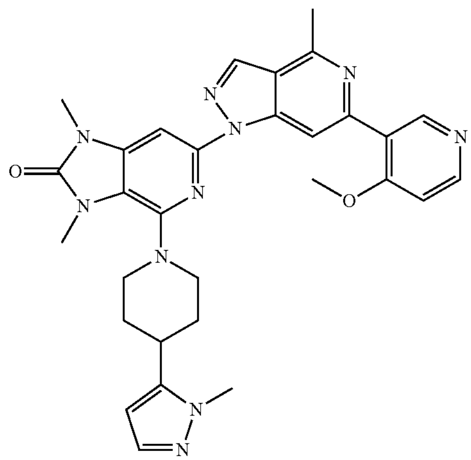 [SMILES: COc1ccncc1-c1cc2c(cnn2-c2cc3c(c(N4CCC(c5ccnn5C)CC4)n2)n(C)c(=O)n3C)c(C)n1] | 18 | (M + H)$^+$ = 565 t$_{Ret.}$ = 1.15 | LCMS3, basisch_1 |
| I-156 | 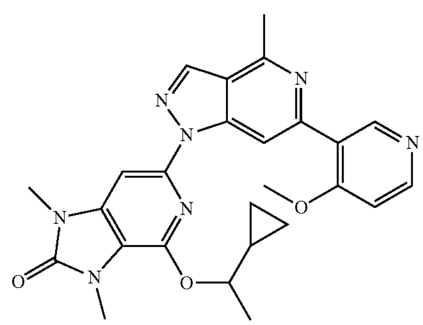 [SMILES: COc1ccncc1-c1cc2c(cnn2-c2cc3c(c(OC(C)C4CC4)n2)n(C)c(=O)n3C)c(C)n1] | 19 | (M + H)$^+$ = 486 t$_{Ret.}$ = 1.24 | LCMS3, basisch_1 |
| I-157 | 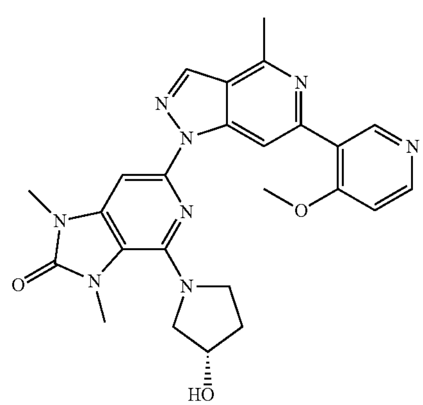 [SMILES: COc1ccncc1-c1cc2c(cnn2-c2cc3c(c(N4CC[C@H](O)C4)n2)n(C)c(=O)n3C)c(C)n1] | 21 | (M + H)$^+$ = 487 t$_{Ret.}$ = 0.98 | LCMS3, basisch_1 |

TABLE 9-continued
| # | structure | IC$_{50}$ [nM] | MS (M + H)$^+$ t$_{Ret}$ HPLC [min] | HPLC-MS method |
|---|---|---|---|---|
| I-158 | 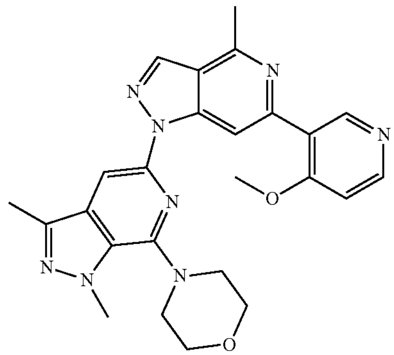 [SMILES: COc1ccncc1-c1cc2c(cnn2-c2cc3c(C)nn(C)c3c(N3CCOCC3)n2)c(C)n1] | 2.9 | (M + H)$^+$ = 471 t$_{Ret.}$ = 1.22 | LCMS3, basisch_1 |
TABLE 10
| # | structure | IC$_{50}$ [nM] | MS (M + H)$^+$ t$_{Ret}$ HPLC [min] | HPLC-MS method |
|---|---|---|---|---|
| I-159 | 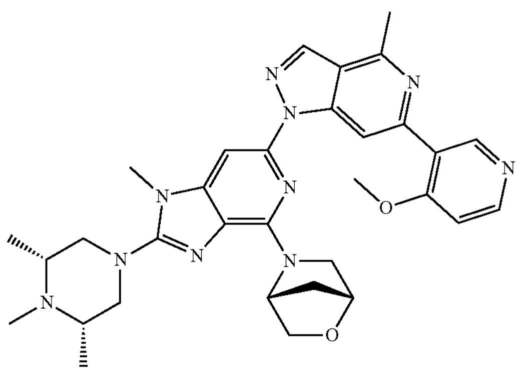 [SMILES: COc1ccncc1-c1cc2c(cnn2-c2cc3c(nc(N4C[C@@H](C)N(C)[C@@H](C)C4)n3C)c(N3C[C@H]4C[C@@H]3CO4)n2)c(C)n1] | 6 | (M + H)$^+$ = 595 t$_{Ret.}$ = 1.29 | LCMS3, basisch_1 |
| I-160 | 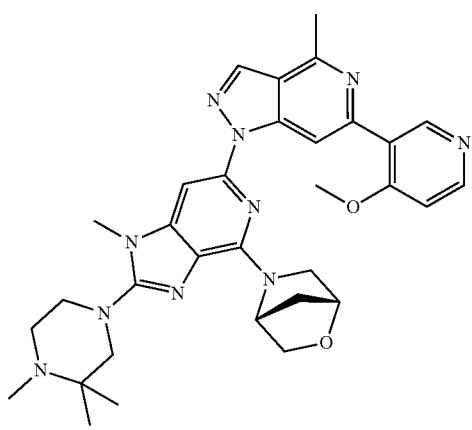 [SMILES: COc1ccncc1-c1cc2c(cnn2-c2cc3c(nc(N4CCN(C)C(C)(C)C4)n3C)c(N3C[C@H]4C[C@@H]3CO4)n2)c(C)n1] | 6.9 | (M + H)$^+$ = 595 t$_{Ret.}$ = 1.31 | LCMS3, basisch_1 |

TABLE 10-continued

| # | structure | IC$_{50}$ [nM] | MS (M + H)$^+$ t$_{Ret.}$ HPLC [min] | HPLC-MS method |
|---|---|---|---|---|
| I-161 | 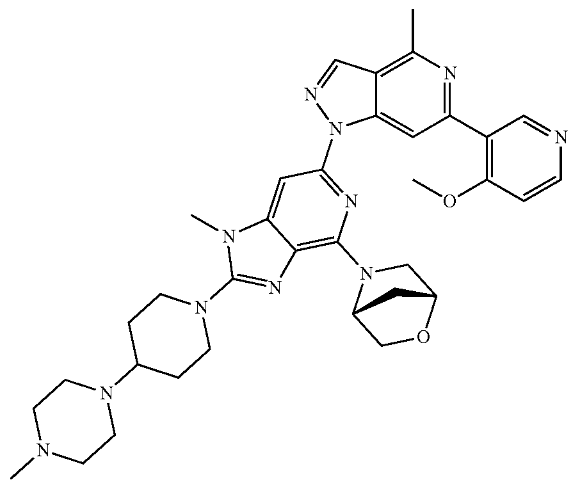 [SMILES: COc1ccncc1-c1cc2c(cnn2-c2cc3c(nc(N4CCC(N5CCN(C)CC5)CC4)n3C)c(N3C[C@H]4C[C@@H]3CO4)n2)c(C)n1] | 8.1 | (M + H)$^+$ = 650<br>t$_{Ret.}$ = 1.23 | LCMS3, basisch_1 |
| I-162 | 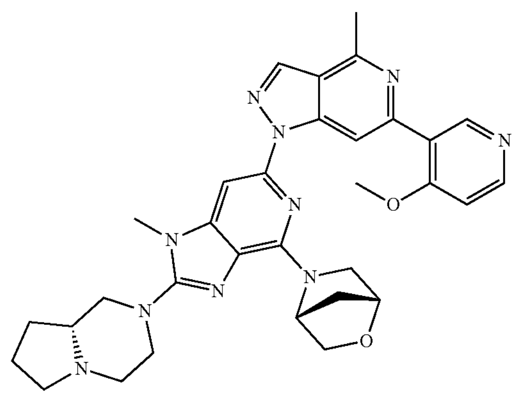 [SMILES: COc1ccncc1-c1cc2c(cnn2-c2cc3c(nc(N4CCN5CCC[C@@H]5C4)n3C)c(N3C[C@H]4C[C@@H]3CO4)n2)c(C)n1] | 12 | (M + H)$^+$ = 593<br>t$_{Ret.}$ = 1.28 | LCMS3, basisch_1 |
| I-163 | 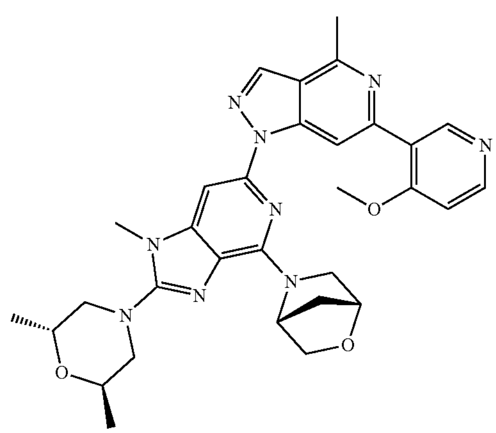 [SMILES: COc1ccncc1-c1cc2c(cnn2-c2cc3c(nc(N4C[C@@H](C)O[C@H](C)C4)n3C)c(N3C[C@H]4C[C@@H]3CO4)n2)c(C)n1] | 12 | (M + H)$^+$ = 582<br>t$_{Ret.}$ = 1.35 | LCMS3, basisch_1 |

TABLE 10-continued
| # | structure | IC$_{50}$ [nM] | MS (M + H)$^+$ t$_{Ret}$ HPLC [min] | HPLC-MS method |
|---|---|---|---|---|
| I-164 | 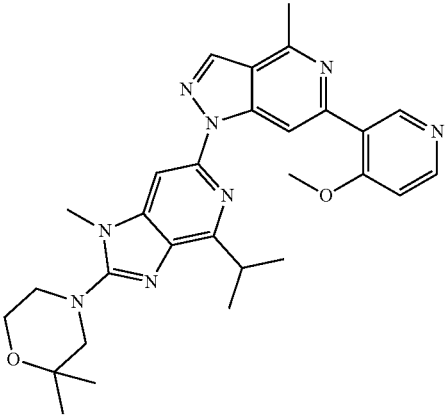 [SMILES: COc1ccncc1-c1cc2c(cnn2-c2cc3c(nc(N4CCOC(C)(C)C4)n3C)c(C(C)C)n2)c(C)n1] | 13 | (M + H)$^+$ = 527 t$_{Ret.}$ = 1.96 | LCMS3, basisch_1 |
| I-165 | 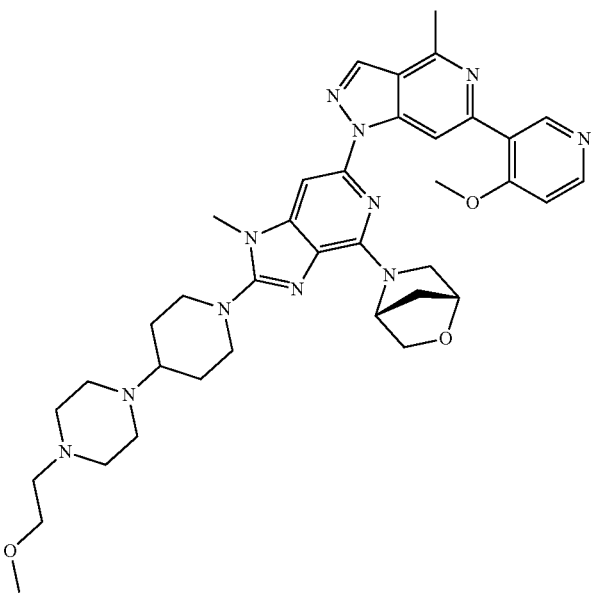 [SMILES: COCCN1CCN(C2CCN(c3nc4c(N5C[C@H]6C[C@@H]5CO6)nc(-n5ncc6c(C)nc(-c7cnccc7OC)cc65)cc4n3C)CC2)CC1] | 14 | (M + H)$^+$ = 694 t$_{Ret.}$ = 1.19 | LCMS3, basisch_1 |
| I-166 | 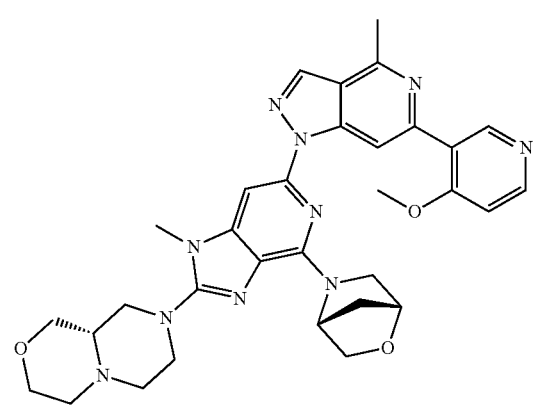 [SMILES: COc1ccncc1-c1cc2c(cnn2-c2cc3c(nc(N4CCN5CCOC[C@@H]5C4)n3C)c(N3C[C@H]4C[C@@H]3CO4)n2)c(C)n1] | 14 | (M + H)$^+$ = 609 t$_{Ret.}$ = 1.14 | LCMS3, basisch_1 |

TABLE 10-continued

| # | structure | IC$_{50}$ [nM] | MS (M + H)$^+$ t$_{Ret.}$ HPLC [min] | HPLC-MS method |
|---|---|---|---|---|
| I-167 | 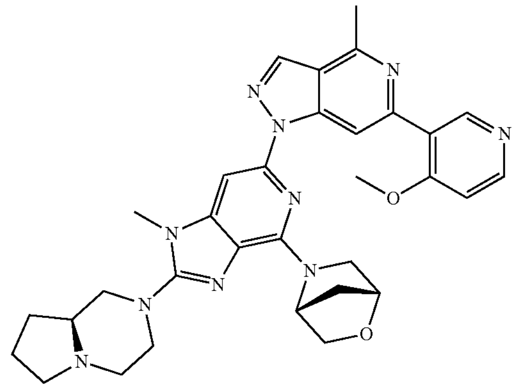 [SMILES: COc1ccncc1-c1cc2c(cnn2-c2cc3c(nc(N4CCN5CCC[C@H]5C4)n3C)c(N3C[C@H]4C[C@@H]3CO4)n2)c(C)n1] | 18 | (M + H)$^+$ = 593 t$_{Ret.}$ = 1.28 | LCMS3, basisch_1 |
| I-168 | 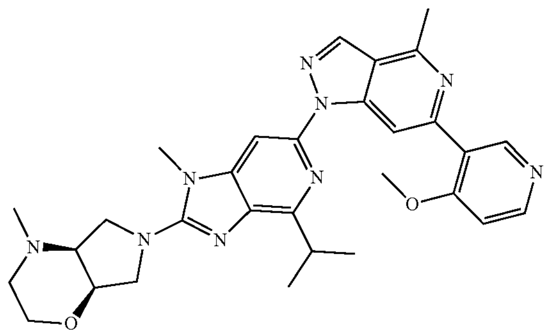 [SMILES: COc1ccncc1-c1cc2c(cnn2-c2cc3c(nc(N4C[C@H]5OCCN(C)[C@H]5C4)n3C)c(C(C)C)n2)c(C)n1] | 18 | (M + H)$^+$ = 554 t$_{Ret.}$ = 1.16 | LCMS3, basisch_1 |
| I-169 | 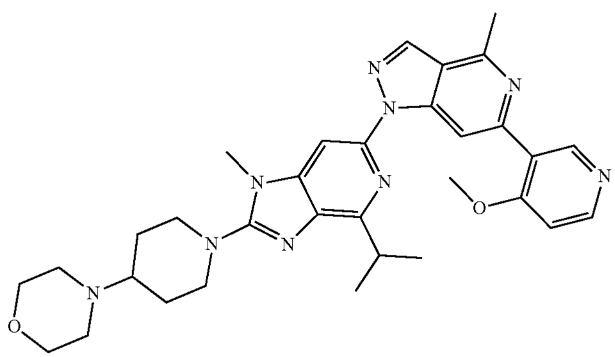 [SMILES: COc1ccncc1-c1cc2c(cnn2-c2cc3c(nc(N4CCC(N5CCOCC5)CC4)n3C)c(C(C)C)n2)c(C)n1] | 19 | (M + H)$^+$ = 582 t$_{Ret.}$ = 1.23 | LCMS3, basisch_1 |
| I-170 | 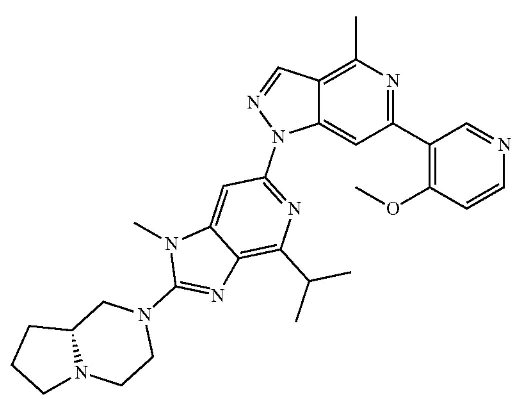 [SMILES: COc1ccncc1-c1cc2c(cnn2-c2cc3c(nc(N4CCN5CCC[C@@H]5C4)n3C)c(C(C)C)n2)c(C)n1] | 20 | (M + H)$^+$ = 538 t$_{Ret.}$ = 1.33 | LCMS3, basisch_1 |

TABLE 10-continued

| # | structure | IC$_{50}$ [nM] | MS (M + H)$^+$ t$_{Ret}$ HPLC [min] | HPLC-MS method |
|---|---|---|---|---|
| I-171 | 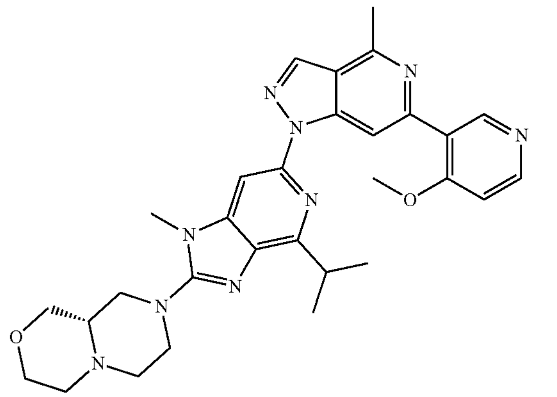 [SMILES: COc1ccncc1-c1cc2c(cnn2-c2cc3c(nc(N4CCN5CCOC[C@@H]5C4)n3C)c(C(C)C)n2)c(C)n1] | 20 | (M + H)$^+$ = 554<br>t$_{Ret.}$ = 1.20 | LCMS3, basisch_1 |
| I-172 | 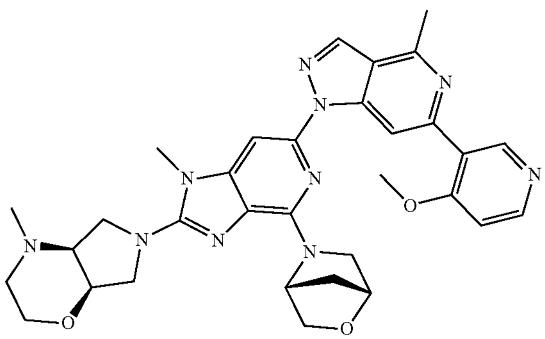 [SMILES: COc1ccncc1-c1cc2c(cnn2-c2cc3c(nc(N4C[C@H]5OCCN(C)[C@H]5C4)n3C)c(N3C[C@H]4C[C@@H]3CO4)n2)c(C)n1] | 20 | (M + H)$^+$ = 609<br>t$_{Ret.}$ = 1.12 | LCMS3, basisch_1 |
| I-173 | 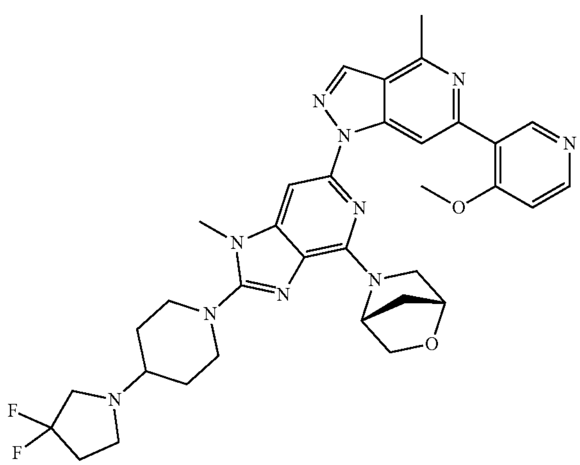 [SMILES: COc1ccncc1-c1cc2c(cnn2-c2cc3c(nc(N4CCC(N5CCC(F)(F)C5)CC4)n3C)c(N3C[C@H]4C[C@@H]3CO4)n2)c(C)n1] | 21 | (M + H)$^+$ = 657<br>t$_{Ret.}$ = 1.38 | LCMS3, basisch_1 |
| I-174 | 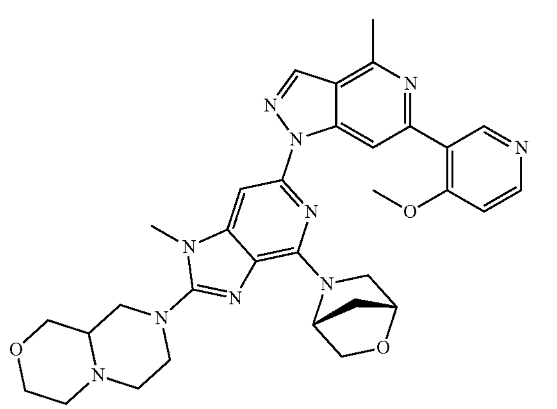 | 21 | (M + H)$^+$ = 609<br>t$_{Ret.}$ = 1.14 | LCMS3, basisch_1 |

TABLE 10-continued

| # | structure | IC$_{50}$ [nM] | MS (M + H)$^+$ $t_{Ret.}$ HPLC [min] | HPLC-MS method |
|---|---|---|---|---|
| I-175 | 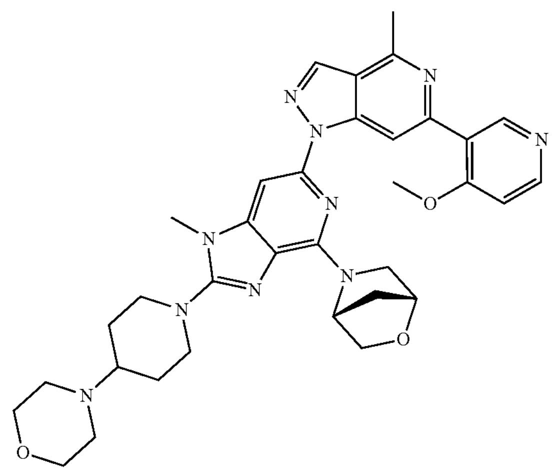 [SMILES: COc1ccncc1-c1cc2c(cnn2-c2cc3c(nc(N4CCC(N5CCOCC5)CC4)n3C)c(N3C[C@H]4C[C@@H]3CO4)n2)c(C)n1] | 22 | (M + H)$^+$ = 637 $t_{Ret.}$ = 1.20 | LCMS3, basisch_1 |
| I-176 | 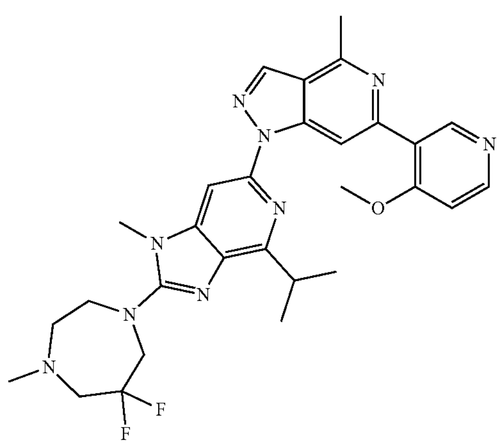 [SMILES: COc1ccncc1-c1cc2c(cnn2-c2cc3c(nc(N4CCN(C)CC(F)(F)C4)n3C)c(C(C)C)n2)c(C)n1] | 24 | (M + H)$^+$ = 562 $t_{Ret.}$ = 1.37 | LCMS3, basisch_1 |
| I-177 | 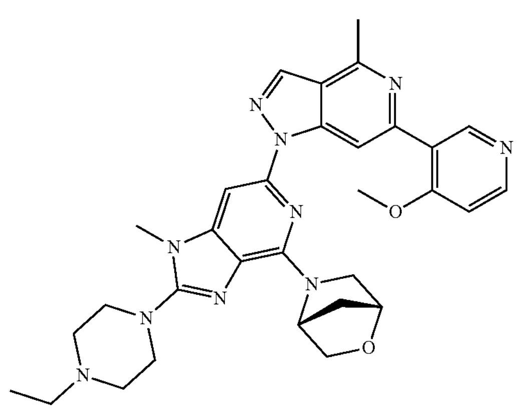 [SMILES: CCN1CCN(c2nc3c(N4C[C@H]5C[C@@H]4CO5)nc(-n4ncc5c(C)nc(-c6cnccc6OC)cc54)cc3n2C)CC1] | 26 | (M + H)$^+$ = 581 $t_{Ret.}$ = 1.30 | LCMS3, basisch_1 |

TABLE 10-continued

| # | structure | IC$_{50}$ [nM] | MS (M + H)$^+$ t$_{Ret.}$ HPLC [min] | HPLC-MS method |
|---|---|---|---|---|
| I-178 | 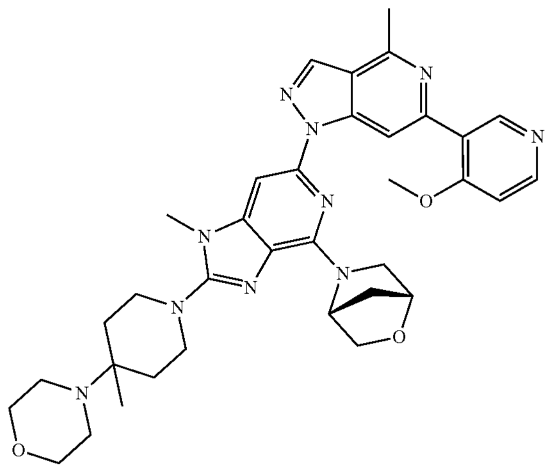 [SMILES: COc1ccncc1-c1cc2c(cnn2-c2cc3c(nc(N4CCC(C)(N5CCOCC5)CC4)n3C)c(N3C[C@H]4C[C@@H]3CO4)n2)c(C)n1] | 27 | (M + H)$^+$ = 651 t$_{Ret.}$ = 1.36 | LCMS3, basisch_1 |
| I-179 | 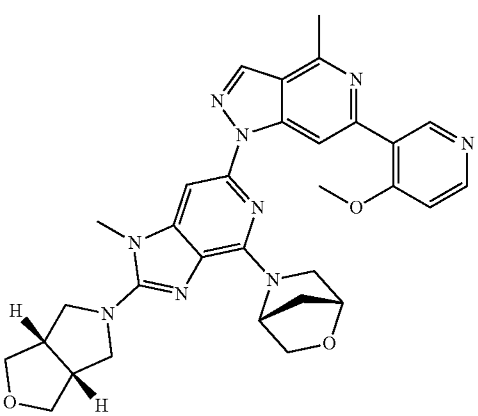 [SMILES: COc1ccncc1-c1cc2c(cnn2-c2cc3c(nc(N4C[C@H]5COC[C@H]5C4)n3C)c(N3C[C@H]4C[C@@H]3CO4)n2)c(C)n1] | 29 | (M + H)$^+$ = 580 t$_{Ret.}$ = 1.18 | LCMS3, basisch_1 |
| I-180 | 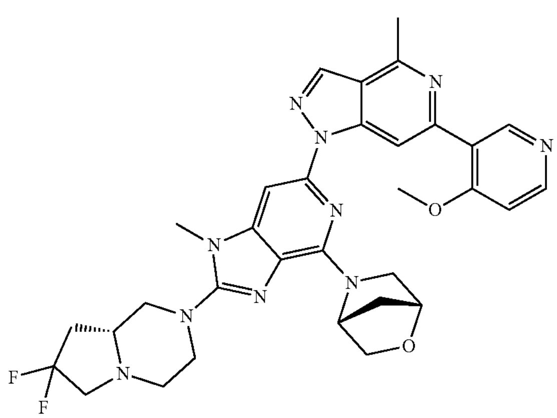 [SMILES: COc1ccncc1-c1cc2c(cnn2-c2cc3c(nc(N4CCN5CC(F)(F)C[C@@H]5C4)n3C)c(N3C[C@H]4C[C@@H]3CO4)n2)c(C)n1] | 30 | (M + H)$^+$ = 629 t$_{Ret.}$ = 1.34 | LCMS3, basisch_1 |

TABLE 10-continued

| # | structure | IC$_{50}$ [nM] | MS (M + H)$^+$ $t_{Ret}$ HPLC [min] | HPLC-MS method |
|---|---|---|---|---|
| I-181 | 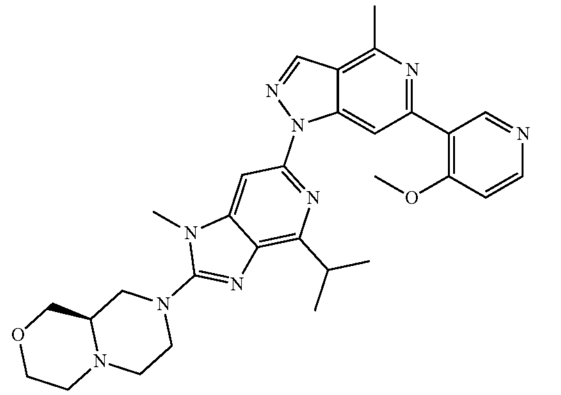 [SMILES: COc1ccncc1-c1cc2c(cnn2-c2cc3c(nc(N4CCN5CCOC[C@H]5C4)n3C)c(C(C)C)n2)c(C)n1] | 30 | (M + H)$^+$ = 554 $t_{Ret.}$ = 1.19 | LCMS3, basisch_1 |
| I-182 | 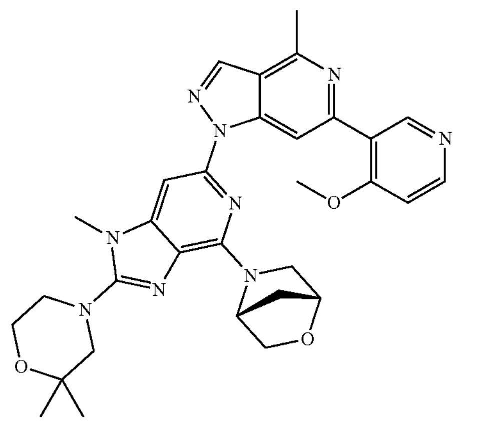 [SMILES: COc1ccncc1-c1cc2c(cnn2-c2cc3c(nc(N4CCOC(C)(C)C4)n3C)c(N3C[C@H]4C[C@@H]3CO4)n2)c(C)n1] | 31 | (M + H)$^+$ = 582 $t_{Ret.}$ = 1.32 | LCMS3, basisch_1 |
| I-183 | 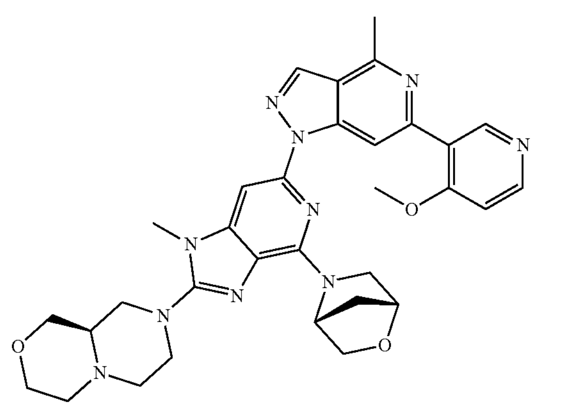 [SMILES: COc1ccncc1-c1cc2c(cnn2-c2cc3c(nc(N4CCN5CCOC[C@H]5C4)n3C)c(N3C[C@H]4C[C@@H]3CO4)n2)c(C)n1] | 33 | (M + H)$^+$ = 609 $t_{Ret.}$ = 1.14 | LCMS3, basisch_1 |

TABLE 10-continued
| # | structure | IC$_{50}$ [nM] | MS (M + H)$^+$ t$_{Ret.}$ HPLC [min] | HPLC-MS method |
|---|---|---|---|---|
| I-184 | 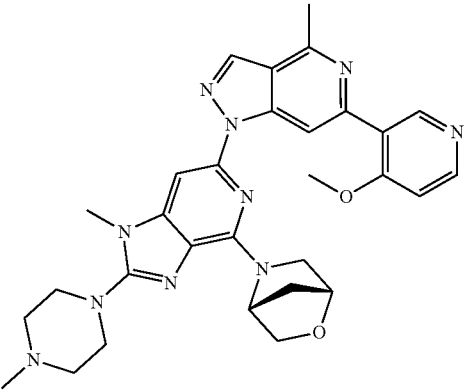 [SMILES: COc1ccncc1-c1cc2c(cnn2-c2cc3c(nc(N4CCN(C)CC4)n3C)c(N3C[C@H]4C[C@@H]3CO4)n2)c(C)n1] | 34 | (M + H)$^+$ = 567 t$_{Ret.}$ = 1.19 | LCMS3, basisch_1 |
| I-185 | 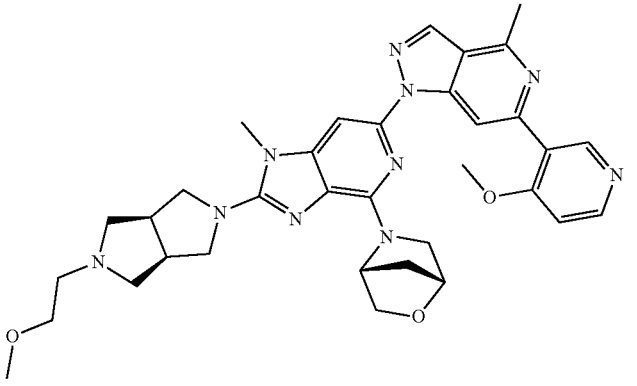 [SMILES: COCCN1C[C@@H]2CN(c3nc4c(N5C[C@H]6C[C@@H]5CO6)nc(-n5ncc6c(C)nc(-c7cnccc7OC)cc65)cc4n3C)C[C@@H]2C1] | 34 | (M + H)$^+$ = 637 t$_{Ret.}$ = 1.25 | LCMS3, basisch_1 |
| I-186 | 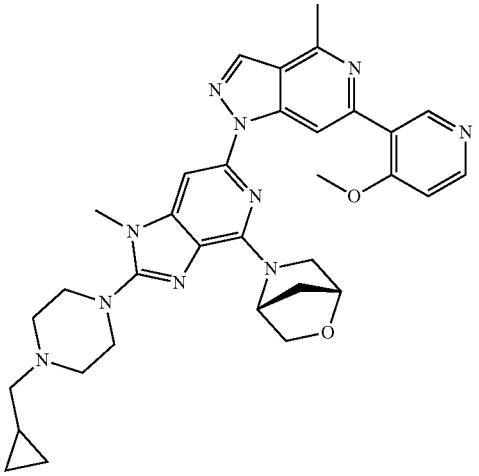 [SMILES: COc1ccncc1-c1cc2c(cnn2-c2cc3c(nc(N4CCN(CC5CC5)CC4)n3C)c(N3C[C@H]4C[C@@H]3CO4)n2)c(C)n1] | 35 | (M + H)$^+$ = 607 t$_{Ret.}$ = 1.36 | LCMS3, basisch_1 |

TABLE 10-continued
| # | structure | IC$_{50}$ [nM] | MS (M + H)$^+$ t$_{Ret.}$ HPLC [min] | HPLC-MS method |
|---|---|---|---|---|
| I-187 | 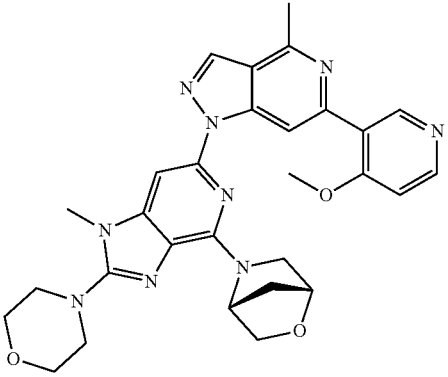 [SMILES: COc1ccncc1-c1cc2c(cnn2-c2cc3c(nc(N4CCOCC4)n3C)c(N3C[C@H]4C[C@@H]3CO4)n2)c(C)n1] | 35 | (M + H)$^+$ = 554<br>t$_{Ret.}$ = 1.18 | LCMS3, basisch_1 |
| I-188 | 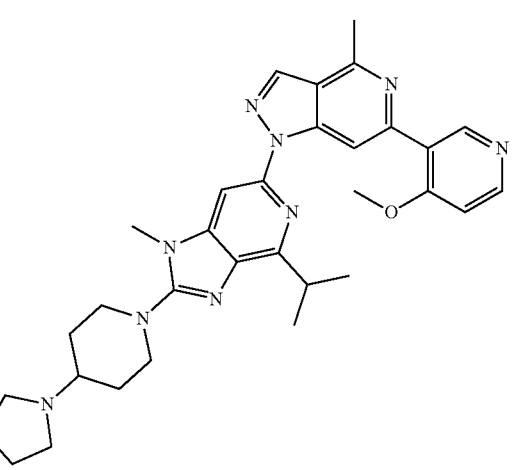 | 36 | (M + H)$^+$ = 602<br>t$_{Ret.}$ = 1.43 | LCMS3, basisch_1 |
| I-189 | 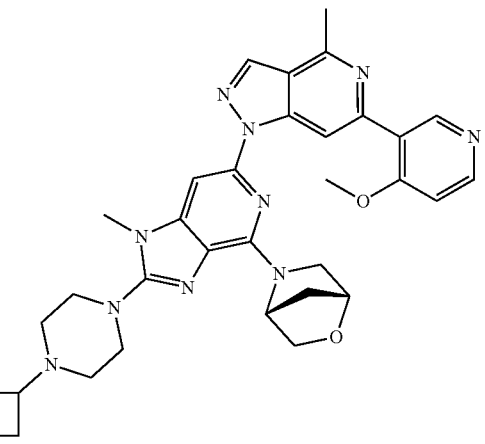 | 36 | (M + H)$^+$ = 609<br>t$_{Ret.}$ = 1.11 | LCMS3, basisch_1 |
| I-190 | 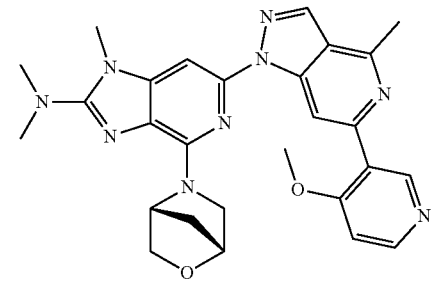 [SMILES: COc1ccncc1-c1cc2c(cnn2-c2cc3c(nc(N(C)C)n3C)c(N3C[C@H]4C[C@@H]3CO4)n2)c(C)n1] | 36 | (M + H)$^+$ = 512<br>t$_{Ret.}$ = 1.24 | LCMS3, basisch_1 |

TABLE 10-continued

| # | structure | IC$_{50}$ [nM] | MS (M + H)$^+$ $t_{Ret.}$ HPLC [min] | HPLC-MS method |
|---|---|---|---|---|
| I-191 | 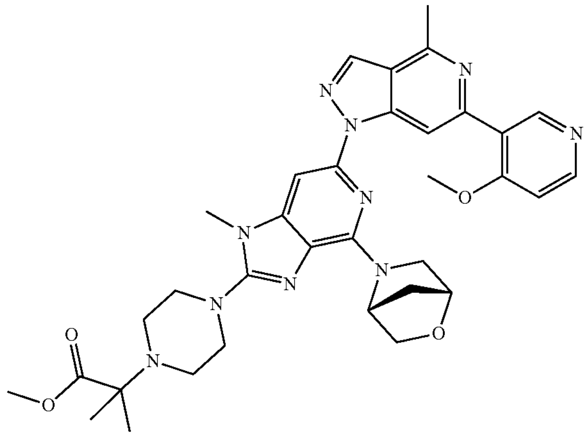 [SMILES: COC(=O)C(C)(C)N1CCN(c2nc3c(N4C[C@H]5C[C@@H]4CO5)nc(-n4ncc5c(C)nc(-c6cnccc6OC)cc54)cc3n2C)CC1] | 39 | (M + H)$^+$ = 653 $t_{Ret.}$ = 1.35 | LCMS3, basisch_1 |
| I-192 | 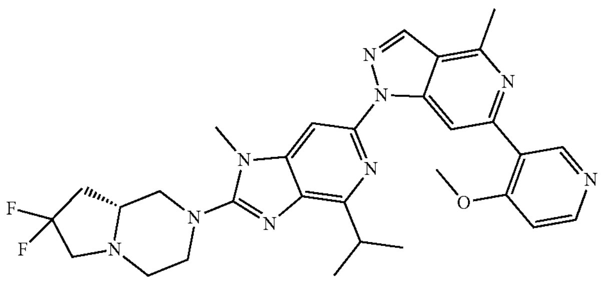 [SMILES: COc1ccncc1-c1cc2c(cnn2-c2cc3c(nc(N4CCN5CC(F)(F)C[C@@H]5C4)n3C)c(C(C)C)n2)c(C)n1] | 39 | (M + H)$^+$ = 574 $t_{Ret.}$ = 1.38 | LCMS3, basisch_1 |
| I-193 | 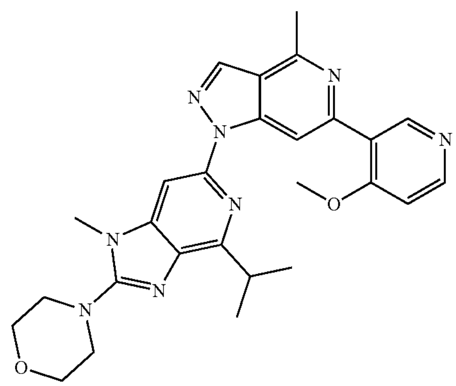 [SMILES: COc1ccncc1-c1cc2c(cnn2-c2cc3c(nc(N4CCOCC4)n3C)c(C(C)C)n2)c(C)n1] | 40 | (M + H)$^+$ = 499 $t_{Ret.}$ = 1.22 | LCMS3, basisch_1 |
| I-194 | 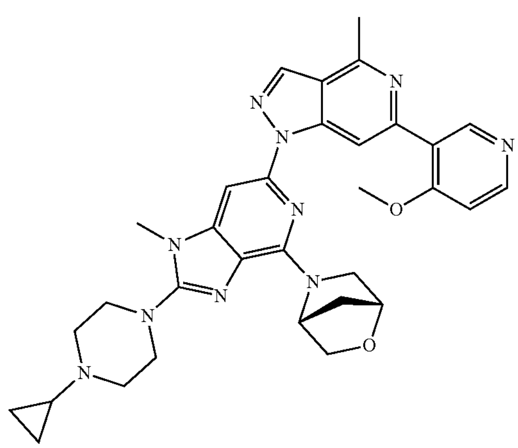 [SMILES: COc1ccncc1-c1cc2c(cnn2-c2cc3c(nc(N4CCN(C5CC5)CC4)n3C)c(N3C[C@H]4C[C@@H]3CO4)n2)c(C)n1] | 41 | (M + H)$^+$ = 593 $t_{Ret.}$ = 1.37 | LCMS3, basisch_1 |

TABLE 10-continued
| # | structure | IC$_{50}$ [nM] | MS (M + H)$^+$ t$_{Ret.}$ HPLC [min] | HPLC-MS method |
|---|---|---|---|---|
| I-195 | 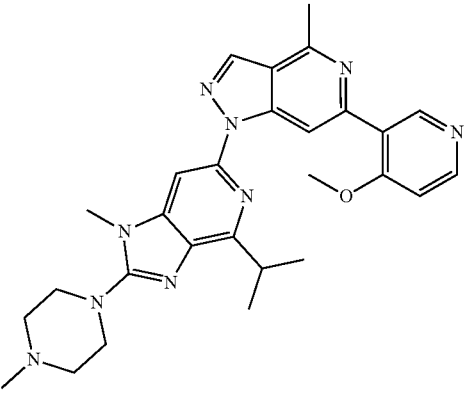 [SMILES: COc1ccncc1-c1cc2c(cnn2-c2cc3c(nc(N4CCN(C)CC4)n3C)c(C(C)C)n2)c(C)n1] | 42 | (M + H)$^+$ = 512<br>t$_{Ret.}$ = 1.23 | LCMS3, basisch_1 |
| I-196 | 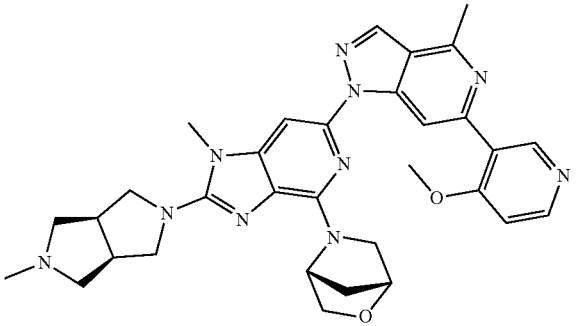 [SMILES: COc1ccncc1-c1cc2c(cnn2-c2cc3c(nc(N4C[C@H]5CN(C)C[C@H]5C4)n3C)c(N3C[C@H]4C[C@@H]3CO4)n2)c(C)n1] | 43 | (M + H)$^+$ = 593<br>t$_{Ret.}$ = 1.21 | LCMS3, basisch_1 |
| I-197 | 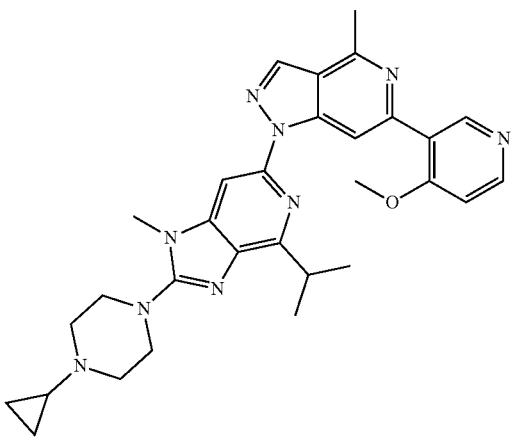 [SMILES: COc1ccncc1-c1cc2c(cnn2-c2cc3c(nc(N4CCN(C5CC5)CC4)n3C)c(C(C)C)n2)c(C)n1] | 44 | (M + H)$^+$ = 538<br>t$_{Ret.}$ = 1.40 | LCMS3, basisch_1 |
| I-198 | 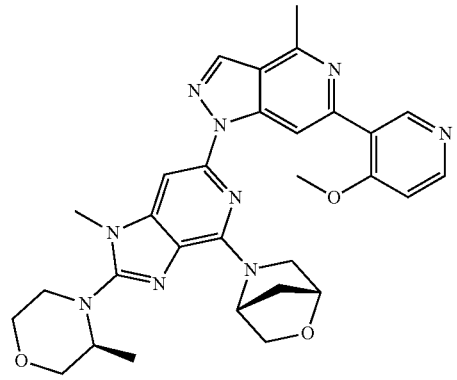 [SMILES: COc1ccncc1-c1cc2c(cnn2-c2cc3c(nc(N4CCOC[C@@H]4C)n3C)c(N3C[C@H]4C[C@@H]3CO4)n2)c(C)n1] | 50 | (M + H)$^+$ = 568<br>t$_{Ret.}$ = 1.27 | LCMS3, basisch_1 |

TABLE 10-continued

| # | structure | IC$_{50}$ [nM] | MS (M + H)$^+$ t$_{Ret.}$ HPLC [min] | HPLC-MS method |
|---|---|---|---|---|
| I-199 | 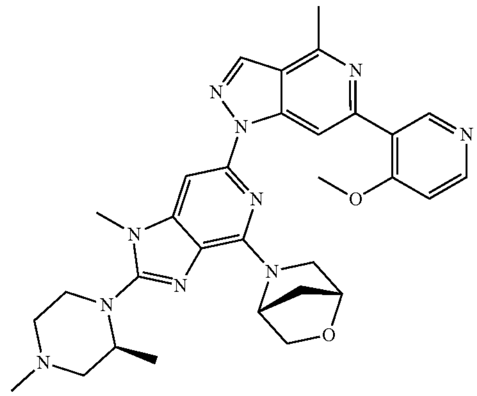 [SMILES: COc1ccncc1-c1cc2c(cnn2-c2cc3c(nc(N4CCN(C)C[C@@H]4C)n3C)c(N3C[C@H]4C[C@@H]3CO4)n2)c(C)n1] | 51 | (M + H)$^+$ = 581 t$_{Ret.}$ = 1.29 | LCMS3, basisch_1 |
| I-200 | 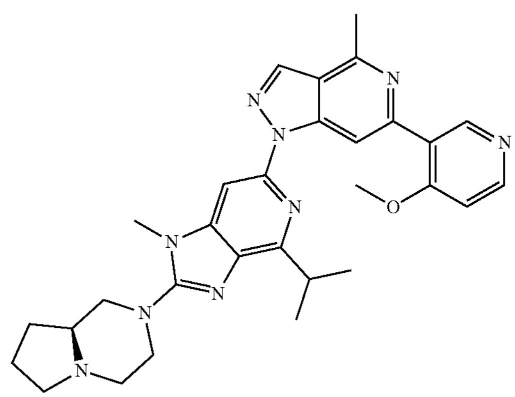 [SMILES: COc1ccncc1-c1cc2c(cnn2-c2cc3c(nc(N4CCN5CCC[C@H]5C4)n3C)c(C(C)C)n2)c(C)n1] | 51 | (M + H)$^+$ = 538 t$_{Ret.}$ = 1.34 | LCMS3, basisch_1 |
| I-201 | 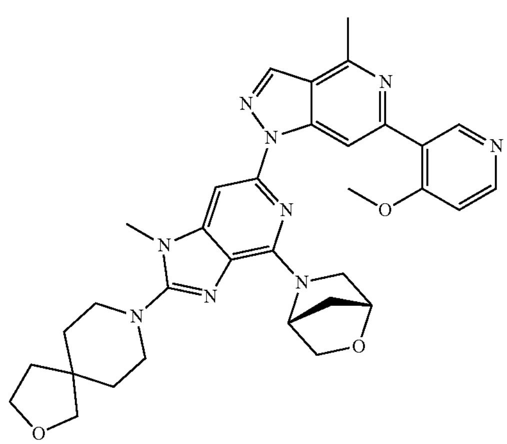 [SMILES: COc1ccncc1-c1cc2c(cnn2-c2cc3c(nc(N4CCC5(CCOC5)CC4)n3C)c(N3C[C@H]4C[C@@H]3CO4)n2)c(C)n1] | 51 | (M + H)$^+$ = 608 t$_{Ret.}$ = 1.31 | LCMS3, basisch_1 |

TABLE 10-continued

| # | structure | IC$_{50}$ [nM] | MS (M + H)$^+$ t$_{Ret}$ HPLC [min] | HPLC-MS method |
|---|---|---|---|---|
| I-202 | 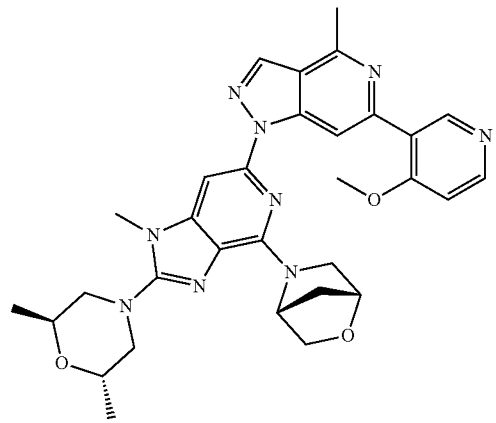 [SMILES: COc1ccncc1-c1cc2c(cnn2-c2cc3c(nc(N4C[C@H](C)O[C@@H](C)C4)n3C)c(N3C[C@H]4C[C@@H]3CO4)n2)c(C)n1] | 51 | (M + H)$^+$ = 582<br>t$_{Ret.}$ = 1.35 | LCMS3, basisch_1 |
| I-203 | 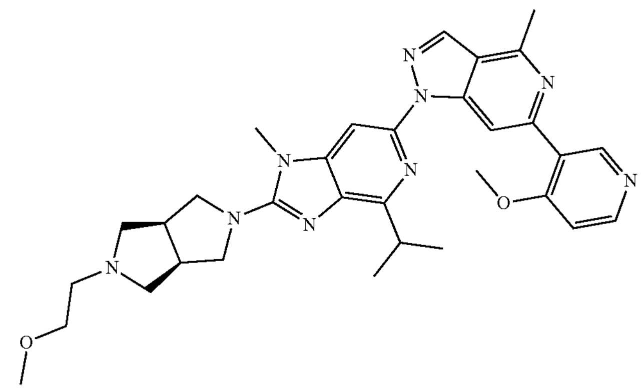 [SMILES: COCCN1C[C@@H]2CN(c3nc4c(C(C)C)nc(-n5ncc6c(C)nc(-c7cnccc7OC)cc65)cc4n3C)C[C@@H]2C1] | 51 | (M + H)$^+$ = 582<br>t$_{Ret.}$ = 1.27 | LCMS3, basisch_1 |
| I-204 | 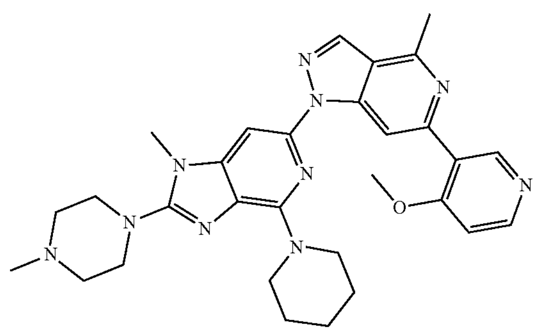 [SMILES: COc1ccncc1-c1cc2c(cnn2-c2cc3c(nc(N4CCN(C)CC4)n3C)c(N3CCCCC3)n2)c(C)n1] | 52 | (M + H)$^+$ = 553<br>t$_{Ret.}$ = 1.37 | LCMS3, basisch_1 |
| I-205 | 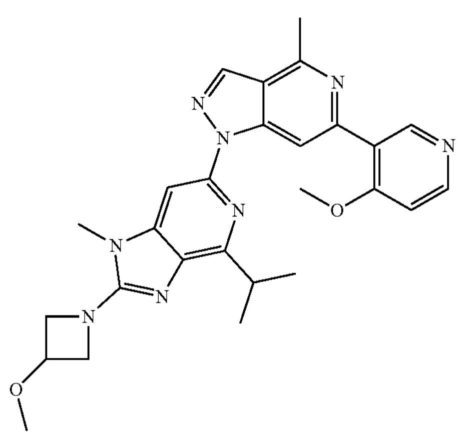 [SMILES: COc1ccncc1-c1cc2c(cnn2-c2cc3c(nc(N4CC(OC)C4)n3C)c(C(C)C)n2)c(C)n1] | 52 | (M + H)$^+$ = 499<br>t$_{Ret.}$ = 1.20 | LCMS3, basisch_1 |

TABLE 10-continued

| # | structure | IC$_{50}$ [nM] | MS (M + H)$^+$ t$_{Ret.}$ HPLC [min] | HPLC-MS method |
|---|---|---|---|---|
| I-206 | 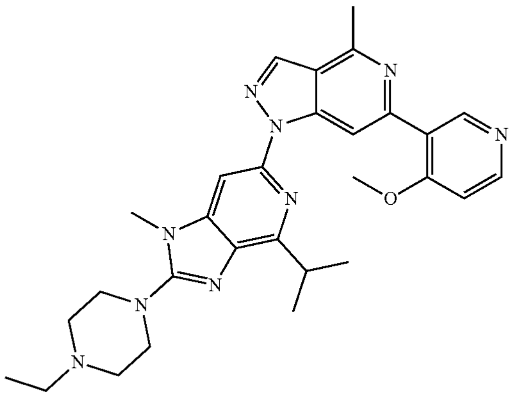 [SMILES: CCN1CCN(c2nc3c(C(C)C)nc(-n4ncc5c(C)nc(-c6cnccc6OC)cc54)cc3n2C)CC1] | 53 | (M + H)$^+$ = 526<br>t$_{Ret.}$ = 1.33 | LCMS3,<br>basisch_1 |
| I-207 | 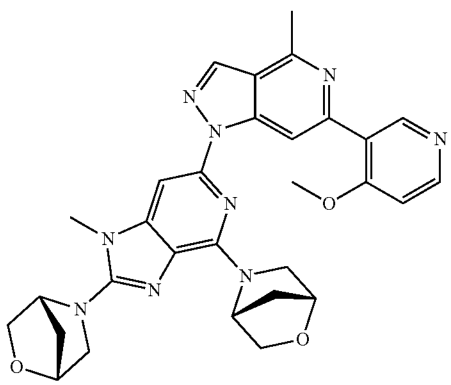 [SMILES: COc1ccncc1-c1cc2c(cnn2-c2cc3c(nc(N4C[C@H]5C[C@@H]4CO5)n3C)c(N3C[C@H]4C[C@@H]3CO4)n2)c(C)n1] | 55 | (M + H)$^+$ = 566<br>t$_{Ret.}$ = 1.15 | LCMS3,<br>basisch_1 |
| I-208 | 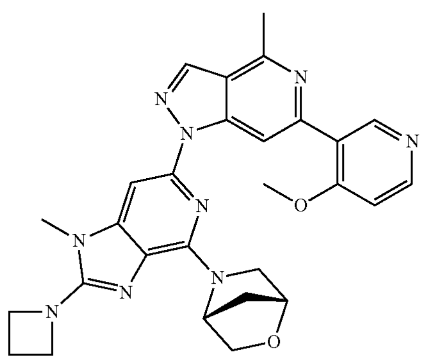 [SMILES: COc1ccncc1-c1cc2c(cnn2-c2cc3c(nc(N4CCC4)n3C)c(N3C[C@H]4C[C@@H]3CO4)n2)c(C)n1] | 56 | (M + H)$^+$ = 524<br>t$_{Ret.}$ = 1.21 | LCMS3,<br>basisch_1 |
| I-209 | 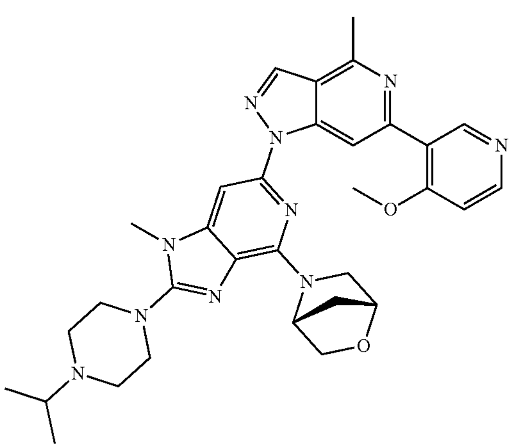 [SMILES: COc1ccncc1-c1cc2c(cnn2-c2cc3c(nc(N4CCN(C(C)C)CC4)n3C)c(N3C[C@H]4C[C@@H]3CO4)n2)c(C)n1] | 57 | (M + H)$^+$ = 595<br>t$_{Ret.}$ = 1.35 | LCMS3,<br>basisch_1 |

TABLE 10-continued

| # | structure | IC$_{50}$ [nM] | MS (M + H)$^+$ t$_{Ret.}$ HPLC [min] | HPLC-MS method |
|---|---|---|---|---|
| I-210 | 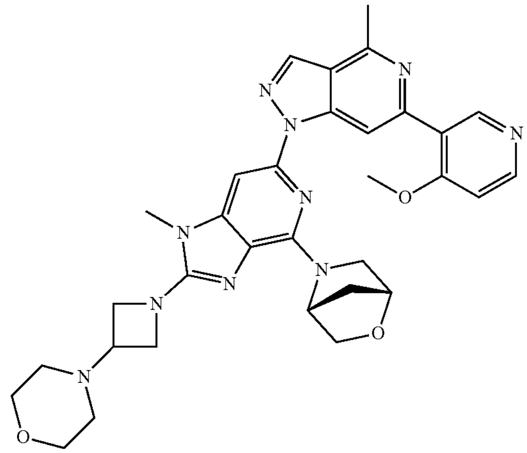 [SMILES: COc1ccncc1-c1cc2c(cnn2-c2cc3c(nc(N4CC(N5CCOCC5)C4)n3C)c(N3C[C@H]4C[C@@H]3CO4)n2)c(C)n1] | 62 | (M + H)$^+$ = 609 t$_{Ret.}$ = 1.10 | LCMS3, basisch_1 |
| I-211 | 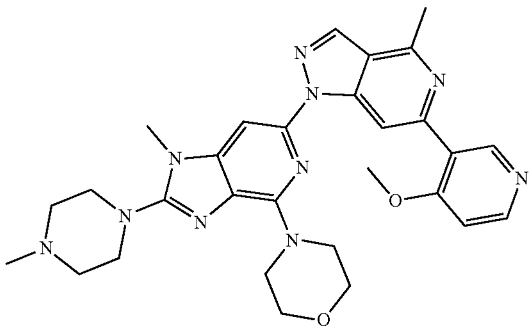 [SMILES: COc1ccncc1-c1cc2c(cnn2-c2cc3c(nc(N4CCN(C)CC4)n3C)c(N3CCOCC3)n2)c(C)n1] | 64 | (M + H)$^+$ = 555 t$_{Ret.}$ = 1.18 | LCMS3, basisch_1 |
| I-212 | 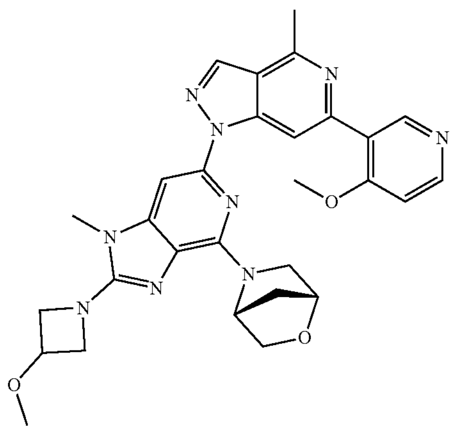 [SMILES: COc1ccncc1-c1cc2c(cnn2-c2cc3c(nc(N4CC(OC)C4)n3C)c(N3C[C@H]4C[C@@H]3CO4)n2)c(C)n1] | 64 | (M + H)$^+$ = 554 t$_{Ret.}$ = 1.17 | LCMS3, basisch_1 |
| I-213 | 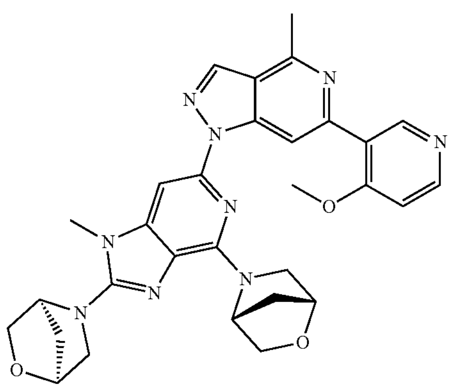 [SMILES: COc1ccncc1-c1cc2c(cnn2-c2cc3c(nc(N4C[C@@H]5C[C@H]4CO5)n3C)c(N3C[C@H]4C[C@@H]3CO4)n2)c(C)n1] | 65 | (M + H)$^+$ = 566 t$_{Ret.}$ = 1.16 | LCMS3, basisch_1 |

TABLE 10-continued
| # | structure | IC$_{50}$ [nM] | MS (M + H)$^+$ t$_{Ret}$ HPLC [min] | HPLC-MS method |
|---|---|---|---|---|
| I-214 | 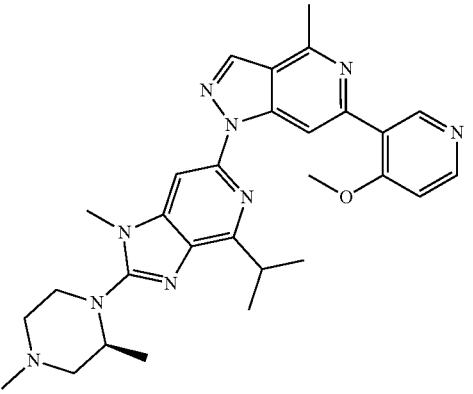 [SMILES: COc1ccncc1-c1cc2c(cnn2-c2cc3c(nc(N4CCN(C)C[C@@H]4C)n3C)c(C(C)C)n2)c(C)n1] | 67 | (M + H)$^+$ = 526 t$_{Ret.}$ = 1.32 | LCMS3, basisch_1 |
| I-215 | 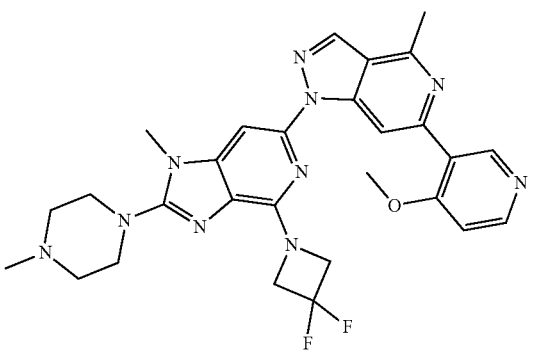 [SMILES: COc1ccncc1-c1cc2c(cnn2-c2cc3c(nc(N4CCN(C)CC4)n3C)c(N3CC(F)(F)C3)n2)c(C)n1] | 71 | (M + H)$^+$ = 561 t$_{Ret.}$ = 1.31 | LCMS3, basisch_1 |
| I-216 | 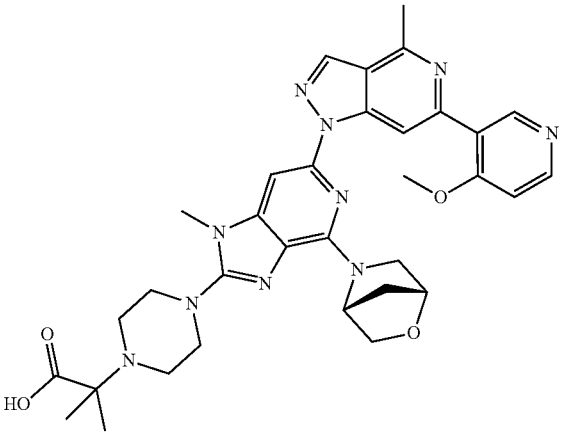 [SMILES: COc1ccncc1-c1cc2c(cnn2-c2cc3c(nc(N4CCN(C(C)(C)C(=O)O)CC4)n3C)c(N3C[C@H]4C[C@@H]3CO4)n2)c(C)n1] | 71 | (M + H)$^+$ = 639 t$_{Ret.}$ = 0.91 | LCMS3, basisch_1 |

TABLE 10-continued

| # | structure | IC$_{50}$ [nM] | MS (M + H)$^+$ t$_{Ret.}$ HPLC [min] | HPLC-MS method |
|---|---|---|---|---|
| I-217 | 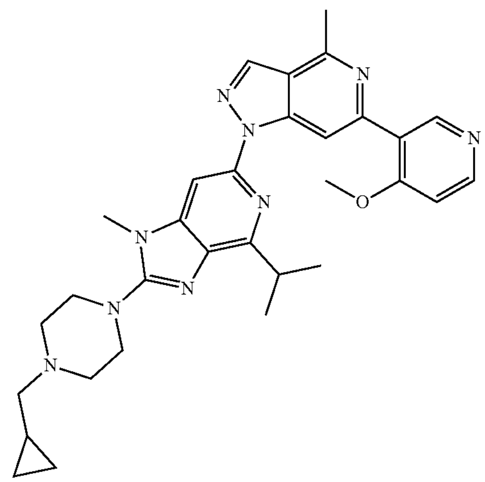 [SMILES: COc1ccncc1-c1cc2c(cnn2-c2cc3c(nc(N4CCN(CC5CC5)CC4)n3C)c(C(C)C)n2)c(C)n1] | 75 | (M + H)$^+$ = 552 t$_{Ret.}$ = 1.40 | LCMS3, basisch_1 |
| I-218 | 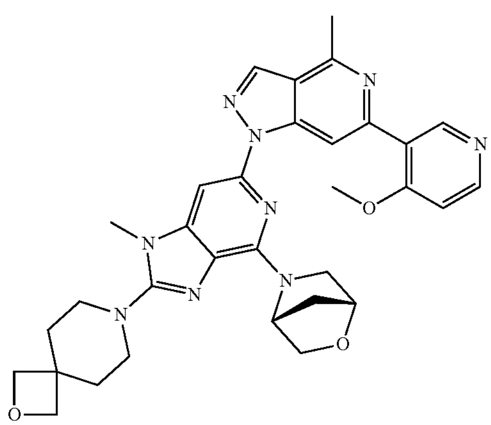 [SMILES: COc1ccncc1-c1cc2c(cnn2-c2cc3c(nc(N4CCC5(CC4)COC5)n3C)c(N3C[C@H]4C[C@@H]3CO4)n2)c(C)n1] | 76 | (M + H)$^+$ = 594 t$_{Ret.}$ = 1.23 | LCMS3, basisch_1 |
| I-219 | 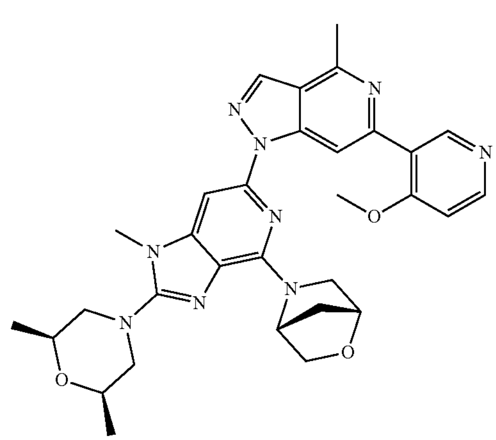 [SMILES: COc1ccncc1-c1cc2c(cnn2-c2cc3c(nc(N4C[C@@H](C)O[C@@H](C)C4)n3C)c(N3C[C@H]4C[C@@H]3CO4)n2)c(C)n1] | 80 | (M + H)$^+$ = 582 t$_{Ret.}$ = 1.34 | LCMS3, basisch_1 |

TABLE 10-continued

| # | structure | IC$_{50}$ [nM] | MS (M + H)$^+$ t$_{Ret.}$ HPLC [min] | HPLC-MS method |
|---|---|---|---|---|
| I-220 | 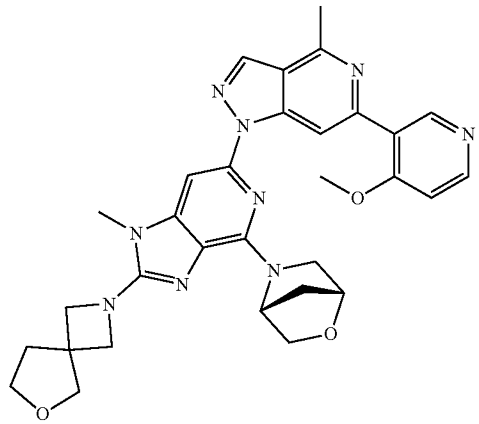 [SMILES: COc1ccncc1-c1cc2c(cnn2-c2cc3c(nc(N4CC5(CCOC5)C4)n3C)c(N3C[C@H]4C[C@@H]3CO4)n2)c(C)n1] | 81 | (M + H)$^+$ = 580 t$_{Ret.}$ = 1.15 | LCMS3, basisch_1 |
| I-221 | 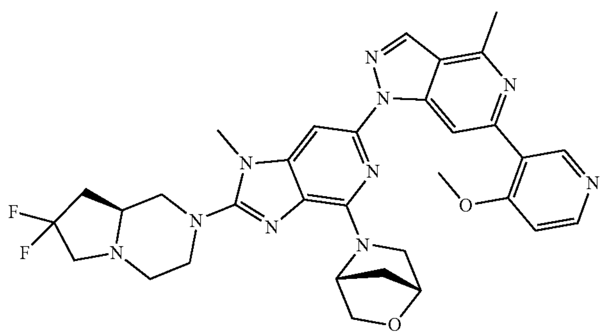 [SMILES: COc1ccncc1-c1cc2c(cnn2-c2cc3c(nc(N4CCN5CC(F)(F)C[C@H]5C4)n3C)c(N3C[C@H]4C[C@@H]3CO4)n2)c(C)n1] | 87 | (M + H)$^+$ = 629 t$_{Ret.}$ = 1.34 | LCMS3, basisch_1 |
| I-222 | 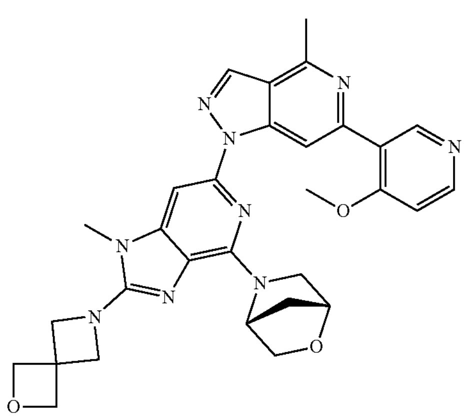 [SMILES: COc1ccncc1-c1cc2c(cnn2-c2cc3c(nc(N4CC5(COC5)C4)n3C)c(N3C[C@H]4C[C@@H]3CO4)n2)c(C)n1] | 87 | (M + H)$^+$ = 566 t$_{Ret.}$ = 1.09 | LCMS3, basisch_1 |

TABLE 10-continued

| # | structure | IC$_{50}$ [nM] | MS (M + H)$^+$ t$_{Ret}$ HPLC [min] | HPLC-MS method |
|---|---|---|---|---|
| I-223 | 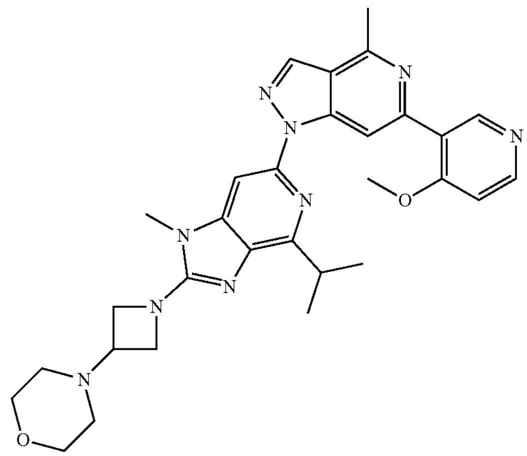 [SMILES: COc1ccncc1-c1cc2c(cnn2-c2cc3c(nc(N4CC(N5CCOCC5)C4)n3C)c(C(C)C)n2)c(C)n1] | 95 | (M + H)$^+$ = 554 t$_{Ret.}$ = 1.13 | LCMS3, basisch_1 |
| I-224 | 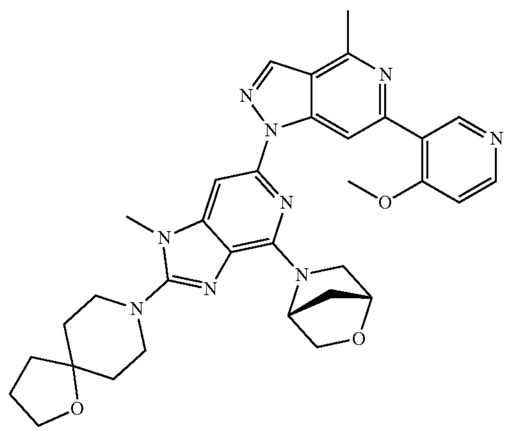 [SMILES: COc1ccncc1-c1cc2c(cnn2-c2cc3c(nc(N4CCC5(CCCO5)CC4)n3C)c(N3C[C@H]4C[C@@H]3CO4)n2)c(C)n1] | 97 | (M + H)$^+$ = 608 t$_{Ret.}$ = 1.39 | LCMS3, basisch_1 |
| I-225 | 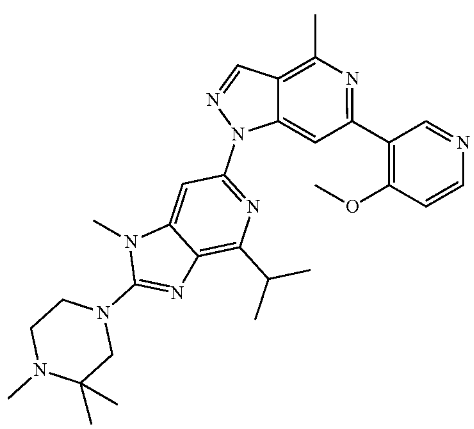 [SMILES: COc1ccncc1-c1cc2c(cnn2-c2cc3c(nc(N4CCN(C)C(C)(C)C4)n3C)c(C(C)C)n2)c(C)n1] | 100 | (M + H)$^+$ = 540 t$_{Ret.}$ = 1.35 | LCMS3, basisch_1 |

The following Examples describe the biological activity of the compounds according to the invention, without restricting the invention to these Examples:

Ba/F3 Cell Model Generation and Proliferation Assays

Ba/F3 cells were ordered from DSMZ (ACC300, Lot17) and grown in RPMI-1640 (ATCC 30-2001)+10% FCS+10 ng/ml IL-3 at 37° C. in 5% CO$_2$ atmosphere. Plasmids containing EGFR mutants were obtained from GeneScript. To generate EGFR-dependent Ba/F3 models, Ba/F3 cells were transduced with retroviruses containing vectors that harbor EGFR isoforms. Platinum-E cells (Cell Biolabs) were used for retrovirus packaging. Retrovirus was added to Ba/F3 cells. To ensure infection, 4 µg/mL polybrene was added and cells were spinfected. Infection efficiency was confirmed by measuring GFP-positive cells using a cell analyzer. Cells with an infection efficiency of 10% to 20% were further cultivated and puromycin selection with 1 µg/mL was initiated. As a control, parental Ba/F3 cells were used to show selection status. Selection was considered successful when parental Ba/F3 cells cultures died. To evaluate the transforming potential of EGFR mutations, the growth medium was no longer supplemented with IL-3. Ba/F3 cells harboring the empty vector were used as a control. A switch from IL-3 to EGF was performed for Ba/F3 cells with the wildtype EGFR known for its dependency on EGF ligand. Approximately ten days before conducting the experiments, puromycin was left out. For proliferation assays (data in table 13), Ba/F3 cells were seeded into 96-well plates at $5 \times 10^3$ cells/100 µL in growth media. Compounds were added by using a HP D3000 Digital Dispenser. All treatments were performed in technical triplicates. Treated cells were incubated for 72 h at 37° C. with 5% $CO_2$. CellTiter-Glo® Luminescent Cell Viability Assay (Promega) was performed and chemoluminescence was measured by using the multilabel Plate Reader VICTOR X4. The raw data were imported into and analyzed with the Boehringer Ingelheim proprietary software MegaLab (curve fitting based on the program PRISM, GraphPad Inc.).

TABLE A

Viability $IC_{50}$ values in nM of Ba/F3 cell lines driven by the indicated EGFR alleles and treated with the indicated compounds (average data of two independent biological experiments with three technical replicates are shown).

| drug | $IC_{50}$ EGFR-indep. + IL-3 [nM] | $IC_{50}$ EGFR wt + EGFR [nM] | $IC_{50}$ EGFR del19 [nM] |
|---|---|---|---|
| erlotinib | >5000 | 38.9 | 2.0 |
| gefitinib | >5000 | 37.0 | 1.8 |
| afatinib | 1055.7 | 0.60 | 0.02 |
| dacomitinib | 977.9 | 0.64 | 0.01 |
| osimertinib | 960.3 | 26.7 | 0.5 |
| nazartinib | >5000 | 95.1 | 1.1 |
| I-107 | 632.89 | 249.26 | 5.45 |
| I-022 | 2941.2 | 2708.3 | 3.7 |
| I-204 | 816.1 | 334.3 | 2.7 |
| I-162 | 1367.3 | 356.2 | 1.1 |
| I-161 | 3798.5 | 764.2 | 2.4 |
| I-186 | 1627.8 | 449.6 | 2.0 |

| drug | $IC_{50}$ EGFR del19 T790M [nM] | $IC_{50}$ EGFR del19 C797S [nM] | $IC_{50}$ EGFR del19 T790M C797S [nM] (*) |
|---|---|---|---|
| erlotinib | 1039.8 | 3.0 | 3562.5 |
| gefitinib | 852.7 | 2.6 | 2091.2 |
| afatinib | 31.2 | 1.9 | 807.3 |
| dacomitinib | 56.3 | 1.6 | 1170.3 |
| osimertinib | 1.6 | 628.4 | 729.6 |
| nazartinib | 4.1 | 744.8 | 455.2 |
| I-107 | 6.06 | 7.07 | 5.42 |
| I-022 | 7.8 | 5.0 | 7.4 |
| I-204 | 8.3 | 3.5 | 7.3 |
| I-162 | 3.2 | 1.1 | 2.6 |
| I-161 | 9.3 | 3.0 | 8.4 |
| I-186 | 5.2 | 2.6 | 4.2 |

| drug | $IC_{50}$ EGFR L858R [nM] | $IC_{50}$ EGFR L858R T790M [nM] | $IC_{50}$ EGFR L858R C797S [nM] |
|---|---|---|---|
| erlotinib | 4.6 | >5000 | 11.1 |
| gefitinib | 5.8 | 3399.6 | 11.5 |
| afatinib | 0.02 | 34.8 | 7.2 |
| dacomitinib | 0.03 | 61.4 | 6.9 |
| osimertinib | 1.1 | 1.9 | 768.7 |
| nazartinib | 5.1 | 7.3 | 1985.2 |
| I-107 | 26.38 | 29.68 | 52.22 |
| I-022 | 19.0 | 12.4 | 33.9 |

TABLE A-continued

Viability $IC_{50}$ values in nM of Ba/F3 cell lines driven by the indicated EGFR alleles and treated with the indicated compounds (average data of two independent biological experiments with three technical replicates are shown).

| | | | |
|---|---|---|---|
| I-204 | 13.5 | 15.7 | 26.9 |
| I-162 | 4.6 | 7.2 | 10.6 |
| I-161 | 11.5 | 13.3 | 23.5 |
| I-186 | 11.3 | 10.8 | 19.0 |

| drug | cell model $IC_{50}$ EGFR L858R T790M C797S [nM] |
|---|---|
| erlotinib | >5000 |
| gefitinib | >5000 |
| afatinib | 1145.4 |
| dacomitinib | 1602.4 |
| osimertinib | 1082.3 |
| nazartinib | 758.8 |
| I-107 | 24.34 |
| I-022 | 14.2 |
| I-204 | 19.2 |
| I-162 | 7.8 |
| I-161 | 14.6 |
| I-186 | 12.9 |

Ba/F3 EGFR del19 T790M C797S Proliferation Assay

Further compounds measured with the assay described above indicated with (*)

| # | $IC_{50}$ EGFR del19 T790M C797S [nM] |
|---|---|
| I-017 | 9 |
| I-022 | 7.4 |
| I-023 | 4 |
| I-031 | 4 |
| I-032 | 9 |
| I-033 | 13 |
| I-034 | 44 |
| I-036 | 13 |
| I-038 | 9 |
| I-044 | 15 |
| I-048 | 53 |
| I-053 | 9 |
| I-054 | 10 |
| I-096 | 3 |
| I-135 | 8 |
| I-141 | 7 |
| I-142 | 8 |
| I-145 | 7 |
| I-150 | 65 |
| I-158 | 7 | pEGFR Assay

This assay quantifies the phosphorylation of EGFR at Tyr1068 and was used to measure the inhibitory effect of compounds on the transgenic EGFR del19 T790M C797S protein in Ba/F3 cells. Murine Ba/F3 cells were grown in RPMI-1640 (ATCC 30-2001)+10% FCS+10 ng/mL IL-3 at 37° C. in 5% $CO_2$ atmosphere and transduced with a retroviral vector encoding EGFR del19 T790M C797S. Transduced cells were selected using puromycin. Following selection, IL-3 was withdrawn and IL-3 independent cells cultured. p-EGFR Tyr1068 was determined using the AlphaScreen Surefire pEGF Receptor (Tyr1068) Assay (PerkinElmer, TGRERS). For the assay, Ba/F3 EGFR del19 T790M C797S cells were seeded in DMEM medium with 10% FCS. 60 nL compound dilutions were added to each well of Greiner TC 384 plates using the Echo platform. Subsequently, 60.000 cells/well in 60 µL were added. Cells were incubated with compound for 4 h at 37° C. Following centrifugation and removal of the medium supernatant, 20 µL of 1.6-fold lysis buffer from TGR/Perkin Elmer kit with protease inhibitors was added. The mixture was incubated at room temperature with shaking (700 rpm) for 20 min. After centrifugation, 4 µL of the lysate were transferred to Proxiplates. 5 µL of Acceptor Mix (Activation Buffer diluted 1:25 in combined Reaction Buffer 1 and Reaction Buffer 2 (TGRERS Assay Kit, PerkinElmer) plus 1:50 of Protein A Acceptor Beads 6760137) were added to each well. Plates were shaken for 1 min (1400 rpm) and incubated for 2 h at room temperature in the dark. 3 µL of donor mix (AlphaScreen Streptavidin-coated Donor Beads (6760002, PerkinElmer) 1:50 diluted in Dilution Buffer (TGRERS Assay Kit, PerkinElmer) were added to each well. Plates were shaken for 1 min (1400 rpm) and incubated for 2 h at room temperature in the dark. Plates were subsequently analyzed using an Envision reader platform. Results were computed in the following way: The ratio of the value of the test compound and the value of the negative control (DMSO) was calculated. $IC_{50}$ values are computed from these values in the MEGASTAR $IC_{50}$ application using a 4 parametric logistic model.

This cellular phospho-EGFR (pEGFR) compound dose-response assay quantifies the phosphorylation of EGFR at Tyr1068 in Ba/F3 cells expressing the EGFR variant del19 T790M C797S. The results of the assay are provided as $IC_{50}$ values (see table 9). The lower the reported pEGFR $IC_{50}$ values for a given compound, the more potent the compound inhibits the EGFR del19 T790M C797S target protein in Ba/F3 cells.

PC-9 EGFR Del19 T790M C797S Proliferation Assay

This assay quantifies the antiproliferative effect of compounds of Table 10 in PC-9 EGFR del19 T790M C797S cells. PC-9 is a non-small cell lung cancer cell line obtained from the European Collection of Authenticated Cell Cultures (ECACC #90071810; lot: 14A030) that expresses an oncogenic variant of EGFR called EGFR del19. To generate the PC-9_TMCS_10 clones that expresses EGFR del19 T790M C797S, respectively, the mutations T790M and C797S are introduced into exon 20 of the genomic EGFR locus in PC-9 parental cells using genome engineering. Successful introduction of the mutations is verified using sequencing. Cells are seeded into 96-well plates (150 µL) in growth medium (RPMI-1640 (Gibco #12633012)+10% FCS (HyClone #SH30071)). Compounds are added by using a HP D3000 Digital Dispenser one day after plating the cells. All treatments are performed in technical triplicates. Treated cells are incubated for 96 h at 37° C. with 5% CO2. CellTiter-Glo® Luminescent Cell Viability Assay (Promega) is performed and chemoluminescence is measured by using the multilabel Plate Reader VICTOR X4. The raw data are imported into and analysed with the Boehringer Ingelheim proprietary software MegaLab (curve fitting based on R (library DLC)). The quantifications of viable cells are calculated by normalization of compound treated cells to DMSO. The 4-Parameter logistic regression model was utilized to calculate dose-response curves. The relative IC50 value is defined as the drug concentration at the inflection point of the dose response curve.

The results of the assay are provided as $IC_{50}$ values (see table 10). The lower the reported $IC_{50}$ values on the above mentioned cells for a given compound, the more potent is the antiproliferative effect of the compounds.

The formulation examples which follow illustrate the present invention without restricting its scope:
Examples of Pharmaceutical Formulations

| A) Tablets | per tablet |
|---|---|
| active substance according to formula (I) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formulae (I) | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C)Tablets | per tablet |
|---|---|
| active substance according to formulae (I) | 25 mg |
| lactose | 50 mg |
| microcrystalline cellulose | 24 mg |
| magnesium stearate | 1 mg |
| | 100 mg |

The active substance, lactose and cellulose are mixed together. The mixture is screened, then either moistened with water, kneaded, wet-granulated and dried or dry-granulated or directly final blend with the magnesium stearate and compressed to tablets of suitable shape and size. When wet-granulated, additional lactose or cellulose and magnesium stearate is added and the mixture is compressed to produce tablets of suitable shape and size.

| D) Ampoule solution | |
|---|---|
| active substance according to formulae (I) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free

The invention claimed is:
1. A compound of the formula (I)

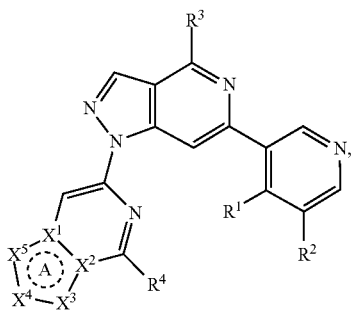

(I)

wherein
R¹ is selected from the group consisting of hydrogen, $C_{1-6}$alkyl, $C_{1-6}$haloalkyl, $C_{1-6}$alkoxy, $C_{1-6}$haloalkoxy, halogen, —OH, —NH$_2$, —NH($C_{1-6}$alkyl), —N($C_{1-6}$alkyl)$_2$, $C_{3-6}$cycloalkyl, $C_{3-6}$cycloalkoxy, 3-6 membered heterocyclyloxy and 3-6 membered heterocyclyl;
R² is selected from the group consisting of hydrogen, $C_{1-6}$alkyl, $C_{1-6}$haloalkyl, $C_{1-6}$alkoxy, $C_{1-6}$haloalkoxy, halogen, —OH, —NH$_2$, —NH($C_{1-6}$alkyl), —N($C_{1-6}$alkyl)$_2$, $C_{3-6}$cycloalkyl, $C_{3-6}$cycloalkoxy, 3-6 membered heterocyclyloxy and 3-6 membered heterocyclyl; or
R¹ and R² together with the carbon atoms they are attached form a 5-6 membered heterocyle or a 5-6 membered heteroaromatic ring;
R³ is selected from the group consisting of hydrogen, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, halogen, —CN, —OH, —NH$_2$, —NH($C_{1-6}$alkyl), —N($C_{1-6}$alkyl)$_2$, $C_{3-6}$cycloalkyl, $C_{3-6}$cycloalkoxy, 3-6 membered heterocyclyloxy and 3-6 membered heterocyclyl;
R⁴ is selected from the group consisting of $R^{a1}$ and $R^{b1}$;
  $R^{a1}$ is selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b1}$ and/or $R^{c1}$;
  each $R^{b1}$ is independently selected from the group consisting of —$OR^{c1}$, —$N(R^{c1})R^{c1}$, halogen, —CN, —C(=O)$R^{c1}$, —C(=O)$OR^{c1}$, —C(=O)N($R^{c1}$)$R^{c1}$, —C(=O)N(H)$OR^{c1}$, —C(=O)N($C_{1-4}$alkyl)$OR^{c1}$, —S(=O)$_2R^{c1}$, —S(=O)$_2$N($R^{c1}$)$R^{c1}$, —N(H)C(=O)$R^{c1}$, —N($C_{1-4}$alkyl)C(=O)$R^{c1}$, —N(H)C(=O)$OR^{c1}$, —N($C_{1-4}$alkyl)C(=O)$OR^{c1}$, —N(H)S(=O)$_2R^{c1}$, —N($C_{1-4}$alkyl)S(=O)$_2R^{c1}$ and the bivalent substituent =O;
  each $R^{c1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d1}$ and/or $R^{e1}$;
  each $R^{d1}$ is independently selected from the group consisting of —$OR^{e1}$, —$N(R^{e1})R^{e1}$, halogen, —CN, —C(=O)$R^{e1}$, —C(=O)$OR^{e1}$, —C(=O)N($R^{e1}$)$R^{e1}$, —C(=O)N(H)$OR^{e1}$, —C(=O)N($C_{1-4}$alkyl)$OR^{e1}$, —S(=O)$_2R^{e1}$, —S(=O)$_2$N($R^{e1}$)$R^{e1}$, —N(H)C(=O)$R^{e1}$, —N($C_{1-4}$alkyl)C(=O)$R^{e1}$, —N(H)C(=O)$OR^{e1}$, —N($C_{1-4}$alkyl)C(=O)$OR^{e1}$, —N(H)S(=O)$_2R^{c1}$, —N($C_{1-4}$alkyl)S(=O)$_2R^{c1}$ and the bivalent substituent =O;
  each $R^{e1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —NH$_2$, —C(=O)$C_{1-4}$alkyl, —NH($C_{1-4}$alkyl), —N($C_{1-4}$alkyl)$_2$ and the bivalent substituent =O;
X¹ is selected from the group consisting of carbon (C) and nitrogen (N);
X² is selected from the group consisting of carbon (C) and nitrogen (N);
at least one of X¹ and X² is carbon (C);
X³ is selected from the group consisting of nitrogen (N), C(R⁵), N(R⁶), C(R⁵)(R⁵), oxygen (O), sulphur (S), S(=O), S(=O)$_2$, and C(=O);
X⁴ is selected from the group consisting of nitrogen (N), C(R⁷), N(R⁸), C(R⁷)(R⁷), oxygen (O), sulphur (S), S(=O), S(=O)$_2$, and C(=O);
X⁵ is selected from the group consisting of nitrogen (N), C(R⁹), N(R¹⁰), C(R⁹)(R⁹), oxygen (O), sulphur (S), S(=O), S(=O)$_2$, and C(=O);
each bond between ring members in ring A is independently selected from a single bond, a double bond or a (hetero)aromatic bond;
each R⁵ is independently selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-4}$alkyl, $C_{1-6}$haloalkoxy-$C_{1-6}$alkyl, halogen, —NH$_2$, —NH($C_{1-6}$alkyl), —N($C_{1-6}$alkyl)$_2$, $C_{3-6}$cycloalkyl and 3-6 membered heterocyclyl;
each R⁶ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;
each R⁷ is independently selected from the group consisting of $R^{a2}$ and $R^{b2}$;

$R^{a2}$ is selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of —$OR^{c2}$, —$N(R^{c2})R^{c2}$, halogen, —CN, —C(=O)$R^{c2}$, —C(=O)O$R^{c2}$, —C(=O)N($R^{c2}$)$R^{c2}$, —C(=O)N(H)O$R^{c2}$, —C(=O)N($C_{1-4}$alkyl)O$R^{c2}$, —S(=O)$_2R^{c2}$, —S(=O)$_2$N($R^{c2}$)$R^{c2}$, —N(H)C(=O)$R^{c2}$, —N($C_{1-4}$alkyl)C(=O)$R^{c2}$, —N(H)C(=O)O$R^{c2}$, —N($C_{1-4}$alkyl)C(=O)O$R^{c2}$, —N(H)S(=O)$_2R^{c2}$, —N($C_{1-4}$alkyl)S(=O)$_2R^{c2}$ and the bivalent substituent =O;

each $R^{c2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d2}$ and/or $R^{e2}$;

each $R^{d2}$ is independently selected from the group consisting of —$OR^{e2}$, —$N(R^{e2})R^{e2}$, halogen, —CN, —C(=O)$R^{e2}$, —C(=O)O$R^{e2}$, —C(=O)N($R^{e2}$)$R^{e2}$, —C(=O)N(H)O$R^{e2}$, —C(=O)N($C_{1-4}$alkyl)O$R^{e2}$, —S(=O)$_2R^{e2}$, —S(=O)$_2$N($R^{e2}$)$R^{e2}$, —N(H)C(=O)$R^{e2}$, —N($C_{1-4}$alkyl)C(=O)$R^{e2}$, —N(H)C(=O)O$R^{e2}$, —N($C_{1-4}$alkyl)C(=O)O$R^{e2}$, —N(H)S(=O)$_2R^{e2}$, —N($C_{1-4}$alkyl)S(=O)$_2R^{e2}$ and the bivalent substituent =O;

each $R^{e2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —$NH_2$, —C(=O)$C_{1-4}$alkyl, —NH($C_{1-4}$alkyl), —N($C_{1-4}$alkyl)$_2$ and the bivalent substituent =O;

each $R^8$ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

each $R^9$ is independently selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-6}$alkyl, $C_{1-6}$haloalkoxy-$C_{1-6}$alkyl, halogen, —$NH_2$, —NH($C_{1-6}$alkyl), —N($C_{1-6}$alkyl)$_2$, $C_{3-6}$cycloalkyl and 3-6 membered heterocyclyl;

each $R^{10}$ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

or a salt thereof.

2. The compound or salt according to claim 1, wherein $R^1$ is selected from the group consisting of hydrogen, $C_{1-6}$alkyl, $C_{1-6}$haloalkyl, $C_{1-6}$alkoxy, $C_{1-6}$haloalkoxy, halogen, —OH, —$NH_2$, —NH($C_{1-6}$alkyl), —N($C_{1-6}$alkyl)$_2$, $C_{3-6}$cycloalkyl, $C_{3-6}$cycloalkoxy, 3-6 membered heterocyclyloxy and 3-6 membered heterocyclyl;

$R^2$ is selected from the group consisting of hydrogen, $C_{1-6}$alkyl, $C_{1-6}$haloalkyl, $C_{1-6}$alkoxy, $C_{1-6}$haloalkoxy, halogen, —OH, —$NH_2$, —NH($C_{1-6}$alkyl), —N($C_{1-6}$alkyl)$_2$, $C_{3-6}$cycloalkyl, $C_{3-6}$cycloalkoxy, 3-6 membered heterocyclyloxy and 3-6 membered heterocyclyl.

3. The compound or salt according to claim 1, wherein $R^1$ and $R^2$ together with the carbon atoms they are attached form a 5-6 membered heterocyle or a 5-6 membered heteroaromatic ring.

4. The compound or salt according to claim 1, wherein $R^3$ is selected from the group consisting of hydrogen, $C_{1-6}$alkyl, $C_{1-6}$haloalkyl, $C_{1-6}$alkoxy, $C_{1-6}$haloalkoxy and halogen.

5. The compound or salt according to claim 1, wherein $R^4$ is selected from the group consisting of $R^{a1}$ and $R^{b1}$;

$R^{a1}$ is selected from the group consisting of $C_{1-6}$alkyl, $C_{3-10}$cycloalkyl, 3-11 membered heterocyclyl, phenyl and 5-6 membered heteroaryl, wherein the $C_{1-6}$alkyl, $C_{3-10}$cycloalkyl, 3-11 membered heterocyclyl, phenyl and 5-6 membered heteroaryl are all optionally substituted with one or more, identical or different $R^{b1}$ and/or $R^{c1}$;

each $R^{b1}$ is independently selected from the group consisting of —$OR^{c1}$, —$N(R^{c1})R^{c1}$, halogen and the bivalent substituent =O;

each $R^{c1}$ is independently selected from the group consisting of hydrogen, $C_{1-6}$alkyl, $C_{1-6}$haloalkyl, $C_{3-10}$cycloalkyl, 3-11 membered heterocyclyl, phenyl and 5-6 membered heteroaryl, wherein the $C_{1-6}$alkyl, $C_{1-6}$haloalkyl, $C_{3-10}$cycloalkyl, 3-11 membered heterocyclyl, phenyl and 5-6 membered heteroaryl are all optionally substituted with one or more, identical or different $R^{d1}$ and/or $R^{e1}$;

each $R^{d1}$ is independently selected from the group consisting of —$OR^{e1}$, —$N(R^{e1})R^{e1}$, halogen and the bivalent substituent =O;

each $R^{e1}$ is independently selected from the group consisting of hydrogen, $C_{1-6}$alkyl, $C_{1-16}$haloalkyl, $C_{3-10}$cycloalkyl, 3-11 membered heterocyclyl, phenyl and 5-6 membered heteroaryl, wherein the $C_{1-6}$alkyl, $C_{1-6}$haloalkyl, $C_{3-10}$cycloalkyl, 3-11 membered heterocyclyl, phenyl and 5-6 membered heteroaryl are all optionally substituted with one or more, identical or different substituent(s) selected from the group consisting of halogen and the bivalent substituent =O.

6. The compound or salt according to claim 5, wherein $R^4$ is selected from the group consisting of $R^{a1}$ and $R^{b1}$;

$R^{a1}$ is selected from the group consisting of $C_{1-6}$alkyl, $C_{3-10}$cycloalkyl and 3-11 membered heterocyclyl, wherein the $C_{1-6}$alkyl, $C_{3-10}$cycloalkyl, 3-11 membered heterocyclyl are all optionally substituted with one or more, identical or different $R^{b1}$ and/or $R^{c1}$;

each $R^{b1}$ is independently selected from the group consisting of —$OR^{c1}$, —$N(R^{c1})R^{c1}$ and halogen;

each $R^{c1}$ is independently selected from the group consisting of hydrogen, $C_{1-6}$alkyl, $C_{1-6}$haloalkyl, 3-11 membered heterocyclyl and 5-6 membered heteroaryl, wherein the $C_{1-6}$alkyl, $C_{1-6}$haloalkyl, 3-11 membered heterocyclyl and 5-6 membered heteroaryl are all optionally substituted with one or more, identical or different $R^{d1}$ and/or $R^{e1}$;

each $R^{d1}$ is independently selected from the group consisting of —$OR^{e1}$, —$N(R^{e1})R^{e1}$ and halogen;

each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

7. The compound or salt according to claim 6, wherein $R^4$ is $R^{a1}$;

$R^{a1}$ is 3-11 membered heterocyclyl optionally substituted with one or more, identical or different $R^{b1}$ and/or $R^{c1}$;

each $R^{b1}$ is independently selected from the group consisting of —$OR^{c1}$, —$N(R^{c1})R^{c1}$ and halogen;

each $R^{c1}$ is independently selected from the group consisting of hydrogen, $C_{1-6}$alkyl, $C_{1-6}$haloalkyl, 3-11 membered heterocyclyl and 5-6 membered heteroaryl, wherein the $C_{1-6}$alkyl, $C_{1-6}$haloalkyl, 3-11 membered heterocyclyl and 5-6 membered heteroaryl are all optionally substituted with one or more, identical or different $R^{d1}$ and/or $R^{e1}$;

each $R^{d1}$ is independently selected from the group consisting of —$OR^{e1}$, —$N(R^{e1})R^{e1}$ and halogen;

each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

8. The compound or salt according to claim 1, wherein $R^4$ is selected from the group consisting of —$NH_2$, —$NH(C_{1-4}alkyl)$ and —$N(C_{1-4}alkyl)_2$.

9. The compound or salt according to claim 1, wherein $R^4$ is —$OR^{c1}$;

$R^{c1}$ is independently selected from the group consisting of hydrogen, $C_{1-6}$alkyl, $C_{1-6}$haloalkyl, 3-11 membered heterocyclyl and 5-6 membered heteroaryl, wherein the $C_{1-6}$alkyl, $C_{1-6}$haloalkyl, 3-11 membered heterocyclyl and 5-6 membered heteroaryl are all optionally substituted with one or more, identical or different $R^{d1}$ and/or $R^{e1}$;

each $R^{d1}$ is independently selected from the group consisting of —$OR^{e1}$, —$N(R^{e1})R^{e1}$ and halogen;

each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

10. The compound or salt according to claim 1, wherein $R^4$ is selected from the group consisting $C_{1-6}$alkyl, $C_{3-10}$cycloalkyl and 3-11 membered heterocyclyl, wherein the $C_{1-6}$alkyl, $C_{3-10}$cycloalkyl, 3-11 membered heterocyclyl are all optionally substituted with one or more, identical or different $R^{b1}$ and/or $R^{c1}$;

each $R^{b1}$ is independently selected from the group consisting of —$OR^{c1}$, —$N(R^{c1})R^{c1}$ and halogen;

each $R^{c1}$ is independently selected from the group consisting of hydrogen, $C_{1-6}$alkyl, $C_{1-6}$haloalkyl, 3-11 membered heterocyclyl and 5-6 membered heteroaryl, wherein the $C_{1-6}$alkyl, $C_{1-6}$haloalkyl, 3-11 membered heterocyclyl and 5-6 membered heteroaryl are all optionally substituted with one or more, identical or different $R^{d1}$ and/or $R^{e1}$;

each $R^{d1}$ is independently selected from the group consisting of —$OR^{e1}$, —$N(R^{e1})R^{e1}$ and halogen;

each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different halogen.

11. The compound or salt according to claim 1, wherein

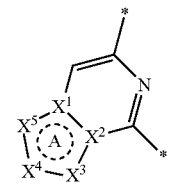

is selected from the group consisting of

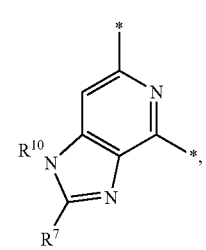

(i)

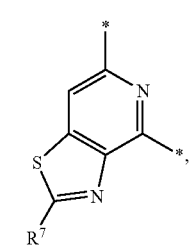

(ii)

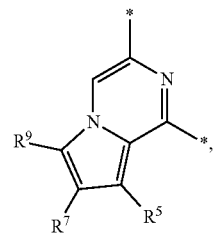

(iii)

-continued
(iv)
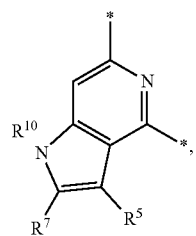
(v)
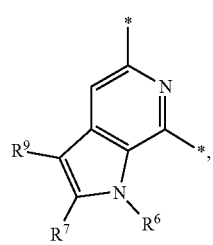
(vi)
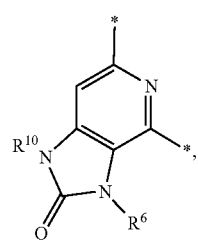
(vii)
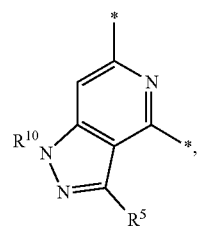
(viii)
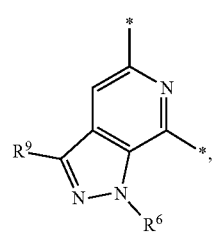
(ix)
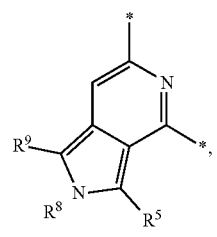
-continued
(x)
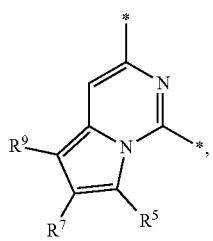
(xi)
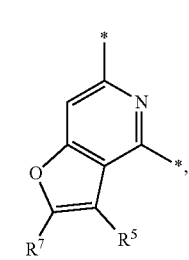
(xii)
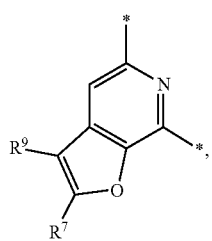
(xiii)
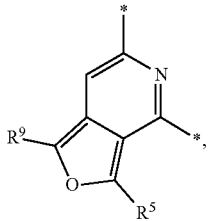
(xiv)
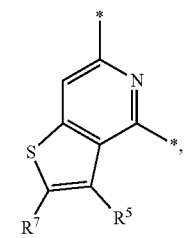
(xv)
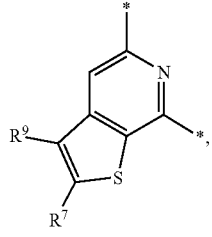

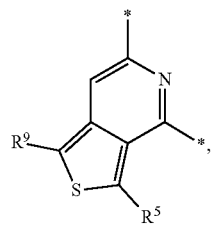
(xvi)
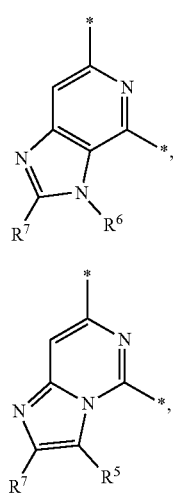
(xvii)
(xviii)
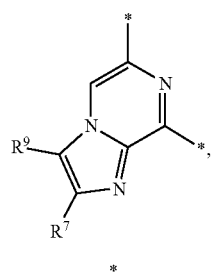
(xix)
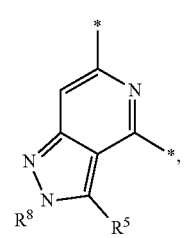
(xx)
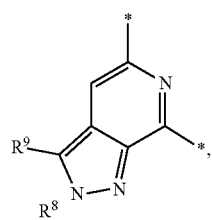
(xxi)
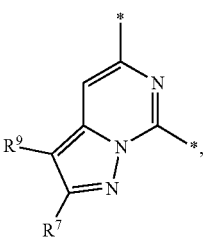
(xxii)
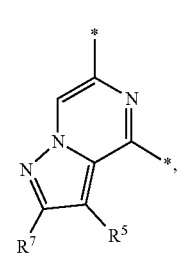
(xxiii)
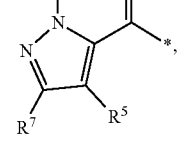
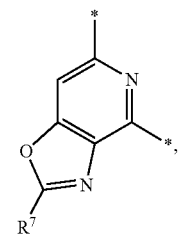
(xxiv)
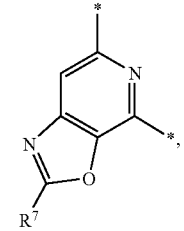
(xxv)
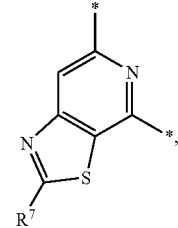
(xxvi)
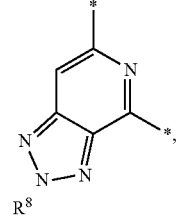
(xxvii)

-continued

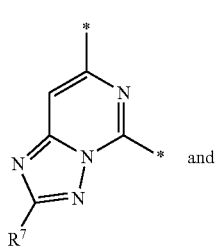

(xxviii)

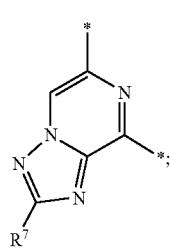

(xxix)

each $R^5$ is independently selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-4}$alkyl, $C_{1-6}$haloalkoxy-$C_{1-6}$alkyl, halogen, —NH$_2$, —NH(C$_{1-6}$alkyl), —N(C$_{1-6}$ alkyl)$_2$, $C_{3-6}$cycloalkyl and 3-6 membered heterocyclyl;

each $R^6$ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

each $R^7$ is independently selected from the group consisting of $R^{a2}$ and $R^{b2}$;
  each $R^{a2}$ is selected from the group consisting of hydrogen, $C_{1-6}$alkyl, $C_{1-6}$haloalkyl,
    $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b2}$ and/or $R^{c2}$;
  each $R^{b2}$ is independently selected from the group consisting of —OR$^{c2}$, —N(R$^{c2}$)R$^{c2}$,
    halogen, —CN, —C(=O)R$^{c2}$, —C(=O)OR$^{c2}$, —C(=O)N(R$^2$)R$^{c2}$, —C(=O)N(H)OR$^{e2}$, —C(=O)N(C$_{1-4}$alkyl)OR$^{c2}$, —S(=O)$_2$R$^{c2}$, —S(=O)$_2$N(R$^{c2}$)R$^{c2}$, —N(H)C(=O)R$^{c2}$, —N(C$_{1-4}$alkyl)C(=O)R$^{c2}$, —N(H)C(=O)OR$^{c2}$, —N(C$_{1-4}$alkyl)C(=O)OR$^{c2}$, —N(H)S(=O)$_2$R$^{c2}$, —N(C$_{1-4}$alkyl)S(=O)$_2$R$^{c2}$ and the bivalent substituent =O;
  each $R^{c2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl,
    $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d2}$ and/or $R^{e2}$;
  each $R^{d2}$ is independently selected from the group consisting of —OR$^{e2}$, —N(R$^{e2}$)R$^{e2}$, halogen, —CN, —C(=O)R$^{e2}$, —C(=O)OR$^{e2}$, —C(=O)N(R$^{e2}$)R$^{e2}$, —C(=O)N(H)OR$^{e2}$, —C(=O)N(C$_{1-4}$alkyl)OR$^{e2}$, —S(=O)$_2$R$^{e2}$, —S(=O)$_2$N(R$^{e2}$)R$^{e2}$, —N(H)C(=O)R$^{e2}$, —N(C$_{1-4}$alkyl)C(=O)R$^{e2}$, —N(H)C(=O)OR$^{e2}$, —N(C$_{1-4}$alkyl)C(=O)OR$^{e2}$, —N(H)S(=O)$_2$R$^{e2}$, —N(C$_{1-4}$alkyl)S(=O)$_2$R$^{e2}$ and the bivalent substituent =O;
  each $R^{e2}$ is independently selected from the group consisting of hydrogen, $C_{1-6}$ alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —NH$_2$, —C(=O)C$_{1-4}$alkyl, —NH(C$_{1-4}$alkyl), —N(C$_{1-4}$alkyl)$_2$ and the bivalent substituent =O;

each $R^8$ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl;

each $R^9$ is independently selected from the group consisting of hydrogen, $C_{1-6}$alkyl, $C_{1-6}$haloalkyl, $C_{1-6}$alkoxy, $C_{1-6}$haloalkoxy, $C_{1-6}$alkoxy-$C_{1-6}$alkyl, $C_{1-6}$haloalkoxy-$C_{1-6}$alkyl, halogen, —NH$_2$, —NH(C$_{1-6}$alkyl), —N(C$_{1-6}$ alkyl)$_2$, $C_{3-6}$cycloalkyl and 3-6 membered heterocyclyl;

each $R^{10}$ is independently selected from the group consisting of hydrogen, $C_{1-6}$alkyl, $C_{1-6}$haloalkyl, $C_{1-6}$alkoxy-$C_{1-6}$alkyl, $C_{1-6}$haloalkoxy-$C_{1-6}$alkyl, $C_{3-6}$cycloalkyl and 3-6 membered heterocyclyl.

12. The compound or salt according to claim 1, wherein each $R^7$ is independently selected from the group consisting of $R^{a2}$ and $R^{b2}$;
  $R^{a2}$ is selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different $R^{b2}$ and/or $R^{c2}$;
  each $R^{b2}$ is independently selected from the group consisting of —OR$^2$, —N(R$^{c2}$)R$^{e2}$,
    halogen, —C(=O)R$^{c2}$, —C(=O)OR$^{c2}$, —C(=O)N(R$^{c2}$)R$^{c2}$, —C(=O)N(H)OR$^{c2}$ and —C(=O)N(C$_{1-4}$alkyl)OR$^{c2}$;
  each $R^{c2}$ is independently selected from the group consisting of hydrogen, $C_{1-6}$alkyl, $C_{3-6}$cycloalkyl and 3-11 membered heterocyclyl, wherein the $C_{1-6}$alkyl and 3-11 membered heterocyclyl are all optionally substituted with one or more, identical or different $R^{d2}$ and/or $R^{e2}$;
  each $R^{d2}$ is independently selected from the group consisting of —OR$^{e2}$, —N(R$^{e2}$)R$^{e2}$, halogen, —C(=O)R$^{e2}$, —C(=O)OR$^{e2}$ and the bivalent substituent =O;
  each $R^{e2}$ is independently selected from the group consisting of hydrogen, $C_{1-6}$alkyl, $C_{3-6}$cycloalkyl and 3-11 membered heterocyclyl, wherein the $C_{1-6}$alkyl and 3-11 membered heterocyclyl are all optionally substituted with one or more, identical or different halogen.

13. The compound or salt according to claim 12, wherein each $R^7$ is independently selected from the group consisting of $R^{a2}$ and $R^{b2}$;
- $R^{a2}$ is selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different $R^{b2}$ and/or $R^{c2}$;
- each $R^{b2}$ is independently selected from the group consisting of —$N(R^{c2})R^{c2}$, halogen, —$C(=O)R^{c2}$ and —$C(=O)OR^{c2}$;
- each $R^{c2}$ is independently selected from the group consisting of hydrogen, $C_{1-6}$alkyl, $C_{3-6}$cycloalkyl and 3-11 membered heterocyclyl, wherein the $C_{1-6}$alkyl, $C_{3-6}$cycloalkyl and 3-11 membered heterocyclyl are all optionally substituted with one or more, identical or different $R^{d2}$ and/or $R^{e2}$;
- each $R^{12}$ is independently selected from the group consisting of —$OR^{e2}$ and —$C(=O)OR^{e2}$;
- each $R^{e2}$ is independently selected from the group consisting of hydrogen, $C_{3-6}$cycloalkyl and $C_{1-6}$alkyl.

14. The compound or salt according to claim 13, wherein each $R^7$ is $R^{a2}$;
- $R^{a2}$ is 3-11 membered heterocyclyl optionally substituted with one or more, identical or different $R^{b2}$ and/or $R^{c2}$;
- each $R^{b2}$ is independently selected from the group consisting of halogen, —$C(=O)R^{c2}$ and —$C(=O)OR^{c2}$;
- each $R^{c2}$ is $C_{1-6}$alkyl optionally substituted with one or more, identical or different $R^{d2}$ and/or $R^{e2}$;
- each $R^{d2}$ is independently selected from the group consisting of —$OR^{e2}$ and —$C(=O)OR^{e2}$;
- each $R^{e2}$ is independently selected from the group consisting of hydrogen and $C_{1-6}$alkyl.

15. The compound or salt according to claim 12, wherein each $R^7$ is $R^{b2}$;
- each $R^{b2}$ is independently selected from the group consisting of —$C(=O)R^{c2}$, —$C(=O)OR^{c2}$, —$C(=O)N(R^2)R^{c2}$, —$C(=O)N(H)OR^{c2}$ and —$C(=O)N(C_{1-4}alkyl)OR^{c2}$;
- each $R^{c2}$ is independently selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different $R^{d2}$ and/or $R^{e2}$;
- each $R^{d2}$ is independently selected from the group consisting of —$OR^{e2}$, —$N(R^{e2})R^{e2}$, halogen, —$C(=O)R^{e2}$, —$C(=O)OR^{e2}$ and the bivalent substituent =O;
- each $R^{e2}$ is independently selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different halogen.

16. A method for the treatment or prevention of a disease or condition mediated by mutant EGFR comprising administering a therapeutically effective amount of a compound according to claim 1, or a pharmaceutically acceptable salt thereof, to a human being.

17. A method for the treatment or prevention of cancer comprising administering a therapeutically effective amount of a compound according to claim 1, or a pharmaceutically acceptable salt thereof, to a human being.

18. A method for treating a cancer having tumor cells harbouring a mutant EGFR gene comprising administering a therapeutically effective amount of a compound according to claim 1, or a pharmaceutically acceptable salt thereof, to a human being.

19. The method according to claim 16, wherein the compound, or a pharmaceutically acceptable salt thereof, is administered before, after or together with one or more other pharmacologically active substance(s).

20. The method according to claim 16, wherein the compound, or a pharmaceutically acceptable salt thereof, is administered in combination with a therapeutically effective amount of one or more other pharmacologically active substance(s).

21. The method according to claim 17, wherein the cancer is selected from the group consisting of lung cancer, brain cancers, colorectal cancer, bladder cancer, urothelial cancer, breast cancer, prostate cancer, ovarian cancer, head and neck cancer, pancreatic cancer, gastric cancer and mesothelioma, including metastasis of all such cancers.

22. A pharmaceutical composition comprising a compound according to claim 1, or a pharmaceutically acceptable salt thereof, and one or more pharmaceutically acceptable excipient(s).

23. A pharmaceutical composition comprising a compound according to claim 1, or a pharmaceutically acceptable salt thereof, and one or more other pharmacologically active substance(s).

* * * * *